United States Patent [19]

Ley et al.

[11] Patent Number: 5,663,143

[45] Date of Patent: Sep. 2, 1997

[54] ENGINEERED HUMAN-DERIVED KUNITZ DOMAINS THAT INHIBIT HUMAN NEUTROPHIL ELASTASE

[75] Inventors: Arthur Charles Ley, Newton, Mass.; Robert Charles Ladner, Ijamsville, Md.; Sonia Kosow Guterman, Belmont, Mass.; Bruce Lindsay Roberts; William Markland, both of Milford, Mass.; Rachel Baribault Kent, Boxborough, Mass.

[73] Assignee: Dyax Corp., Cambridge, Mass.

[21] Appl. No.: 358,160

[22] Filed: Dec. 16, 1994

Related U.S. Application Data

[63] Continuation-in-part of Ser. No. 133,031, Oct. 13, 1993, abandoned, and Ser. No. 9,319, Jan. 26, 1993, Pat. No. 5,403,484, which is a division of Ser. No. 664,989, Mar. 1, 1991, Pat. No. 5,223,409, which is a continuation-in-part of Ser. No. 487,063, Mar. 2, 1990, abandoned, which is a continuation-in-part of Ser. No. 240,160, Sep. 2, 1988, abandoned.

[51] Int. Cl.$^6$ ............................. A61K 37/00; A61K 38/55
[52] U.S. Cl. ............................................................. 514/12
[58] Field of Search ..................................................... 514/12

[56] References Cited

U.S. PATENT DOCUMENTS

| 5,407,915 | 4/1995 | Fritz et al. ................ | 514/12 |
| 5,409,895 | 4/1995 | Morishita et al. ............ | 514/12 |

FOREIGN PATENT DOCUMENTS

| 0401508 | 12/1990 | European Pat. Off. ........ | C12P 21/02 |
| 0486001 | 5/1992 | European Pat. Off. ........ | C12N 15/15 |
| 0643075 | 3/1995 | European Pat. Off. ........ | C07K 7/10 |
| 9215605 | 9/1992 | WIPO . | |

OTHER PUBLICATIONS

Keystone Symposium on Structural and Molecular Biology of Protease Function and Inhibition, Santa Fe, New Mexico, USA, Mar. 5–12, 1994, Journal of Cellular Biochemistry Supplement O (18d). 1994. 157. Markland W et al: "Selection for protease inhibitors using the bacteriophage–display technology".

Proc Natl Acad Sci USA 89 (6). 1992. 2429–2433. Roberts B L et al: "Directed Evolution of a Protein Selection of Potent Neutrophil Elastase Inhibitors Displayed on M13 Fusion Phage".

Biochemistry, vol. 29, No. 33, 21 Aug. 1990, pp. 7539–7546, Broze Jr G J et al: "Regulation of Coagulation by a Multivalent Kunitz-Type Inhibitor".

*Primary Examiner*—Edward J. Cain
*Attorney, Agent, or Firm*—Iver P. Cooper

[57] ABSTRACT

Certain Kunitz domain derived proteins which bind and inhibit human neutrophil elastase with a $K_i$ of less than 10 picomolar are described.

9 Claims, No Drawings

ENGINEERED HUMAN-DERIVED KUNITZ DOMAINS THAT INHIBIT HUMAN NEUTROPHIL ELASTASE

CROSS-REFERENCE TO RELATED APPLICATIONS

This application is a continuation in part of application Ser. No. 08.133,031 filed 13 Oct. 1993, now abandoned and a continuation in part of Ser. No. 08/009,319 filed 26 Jan. 1993, now U.S. Pat. No. 5,403,484 which is a division of application filed Mar. 1, 1991 of Ladner, Guterman, Roberts, Markland, Ley and Kent Ser. No. 07/664,989 now U.S. Pat. No. 5,223,409 which is a continuation in part of Ladner, Guterman, Roberts and Markland, Ser. No. 07/487,063, file Mar. 2, 1990, now abandoned, which is a continuation in part of Ladner and Guterman, Ser. No. 07/240,160, filed Sep. 2, 1988, now abandoned. All of the foregoing applications are hereby incorporated by reference.

The following related and commonly-owned applications are also incorporated by reference:

Robert Charles Ladner, Sonia Kosow Guterman, Rachel Baribault Kent, and Arthur Charles Ley are named as joint inventors on U.S. Ser. No. 07/293,980, filed Jan. 8, 1989, and entitled GENERATION AND SELECTION OF NOVEL DNA-BINDING PROTEINS AND POLYPEPTIDES. This application has been assigned to Protein Engineering Corporation.

Robert Charles Ladner, Sonia Kosow Guterman, and Bruce Lindsay Roberts are named as a joint inventors on a U.S. Ser. No. 07/470,651 fled 26 Jan. 1990 (now abandoned), entitled "PRODUCTION OF NOVEL SEQUENCE-SPECIFIC DNA-ALTERING ENZYMES", likewise assigned to Protein Engineering Corp.

Ladner, Guterman, Kent, Ley, and Markland, Ser. No. 07/558,011 is also assigned to Protein Engineering Corporation.

Ladner filed an application on May 17, 1991, Ser. No. 07/715,834 that is hereby incorporated by reference.

BACKGROUND OF THE INVENTION

Field of the Invention

This invention relates to novel proteins that inhibit human neutrophil elastase (hNE). A large fraction of the sequence of each of these proteins is identical to a known human protein which has very little or no inhibitory activity with respect to hNE.

Information Disclosure Statement 1. hNE, its natural inhibitors, and pathologies Human Neutrophil Elastase (hNE, also known as Human Leukocyte Elastase (xhLE); EC 3.4.21.11) is a 29 Kd protease with a wide spectrum of activity against extracellular matrix components (CAMP82, CAMP88, MCWH89, and references therein). The enzyme is one of the major neutral proteases of the azurophil granules of polymorphonuclear leucocytes and is involved in the elimination of pathogens and in connective tissue restructuring (TRAV88). In cases of hereditary reduction of the circulating $\alpha$-1-antiprotease inhibitor (API, formerly known as $\alpha$1 antitrypsin), the principal systemic physiological inhibitor of hNE (HEID86), or the inactivation of API by oxidation ("smoker's emphysema"), extensive destruction of lung tissue may result from uncontrolled elastolytic activity of hNE (CANT89). Several human respiratory disorders, including cystic fibrosis and emphysema, are characterized by an increased neutrophil burden on the epithelial surface of the lungs (SNID91, MCEL91, GOLD86) and hNE release by neutrophils is implicated in the progress of these disorders (MCEL91, WEIS89). A preliminary study of aerosol administration of API to cystic fibrosis patients indicates that such treatment can be effective both in prevention of respiratory tissue damage and in augmentation of host antimicrobial defenses (MCEL91).

API presents some practical problems to large-scale routine use as a pulmonary anti-elastolytic agent. These include the relatively large size of the molecule (394 residues, 51 Kd), the lack of intramolecular stabilizing disulfide bridges, and specific post translational modifications of the protein by glycosylation at three sites. Perhaps of even greater importance is the sensitivity of API to oxidation, such as those released by activated neutrophils. Hence a small stable nontoxic highly efficacious inhibitor of hNE would be of great therapeutic value.

2. ITI domain 1 and ITI domain 2 as an initial protein binding domains (IPBD)

Inter-$\alpha$-trypsin inhibitor (ITI) is a large ($M_r$ ca 240,000) circulating protease inhibitor found in the plasma of many mammalian species (for recent reviews see ODOM90, SALI90, GEBH90, GEBH86). The intact inhibitor is a glycoprotein and is currently believed to consist of three glycosylated subunits that interact through a strong glycosaminoglycan linkage (ODOM90, SALI90, ENGH89, SELL87). The anti-trypsin activity of ITI is located on the smallest subunit (ITI light chain, unglycosylated $M_r$ ca 15,000) which is identical in amino acid sequence to an acid stable inhibitor found in urine (UTI) and serum (STI) (GEBH86, GEBH90). The amino-acid sequence of the ITI light chain is shown in Table 400. The mature light chain consists of a 21 residue N-terminal sequence, glycosylated at $Ser_{10}$, followed by two tandem Kunitz-type domains the first of which is glycosylated at $Asn_{45}$ (ODOM90). In the human protein, the second Kunitz-type domain has been shown to inhibit trypsin, chymotrypsin, and plasmin (ALBR83a, ALBR83b, SELL87, SWAI88). The first domain lacks these activities but has been reported to inhibit leukocyte elastase ($\approx 1$ $\mu M > K_i > \approx 1$ nM) (ALBR83a,b, ODOM90). cDNA encoding the ITI light chain also codes for $\alpha$-1-microglobulin (TRAB86, KAUM86, DIAR90); the proteins are separated post-translationally by proteolysis.

The two Kunitz domains of the ITI light chain (ITI-D1 and ITI-D2) possesses a number of characteristics that make them useful as IPBDs. ITI-D1 comprises at least residues 26 to 76 of the UTI sequence shown in FIG. 1 of GEBH86. The Kunitz domain could be thought of as comprising residues from as early as residue 22 to as far as residue 79. Residues 22 through 79 constitute a 58-amino-acid domain having the same length as BPTI and having the cysteines aligned. ITI-D2 comprises at least residues 82 through 132; residues as early as 78 and as later as 135 could be included to give domains closer to the classical 58-amino-acid length. As the space between the last cysteine of ITI-D1 (residue 76 of ITI light chain) and the first cysteine of ITI-D2 (residue 82 of ITI light chain) is only 5 residues, one can not assign 58 amino acids to each domain without some overlap. Unless otherwise stated, herein, we have taken the second domain to begin at residue 78 of the ITI light chain. Each of the domains are highly homologous to both BPTI and the EpiNE series of proteins described in U.S. Pat. No. 5,223,409. Although x-ray structures of the isolated domains ITI-D1 and ITI-D2 are not available, crystallographic studies of the related Kunltz-type domain isolated from the Alzheimer's amyloid β-protein (AAβP) precursor show that this polypeptide assumes a 3D structure almost identical to that of BPTI (HYNE90).

The three-dimensional structure of alpha-dendrotoxin from the green mamba venom has been determined (SKAR92) and the overall structure is highly similar to that of BPTI.

"The three-dimensional structure of alpha-dendrotoxin (alpha-DTX) from the green mamba (*Dendroaspis angusticeps*) venom has been determined crystallographically using the method of isomorphous replacement and refined at 2.2 Å resolution using a restrained least-squares method. The crystallographic R-factor is 0.169 for all 3451 measured reflections between 7.0 and 2.2 Å. Although the main-chain fold of alpha-DTX is similar to that of homologous bovine pancreatic trypsin inhibitor (BPTI), there are significant differences involving segments of the polypeptide chain close to the 'antiprotease site' of BPTI. Comparison of the structure of alpha-DTX with the existing models of BPTI and its complexes with trypsin and kallikrein reveals structural differences that explain the inability of alpha-DTX to inhibit trypsin and chymotrypsin."

The structure of the black mamba K venom has been determined by NMR spectroscopy and has a 3D structure that is highly similar to that of BPTI despite 32 amino-acid sequence differences between residues 5 and 55 (the first and last cysteines)(BERN93). "The solution structure of Toxin K is very similar to the solution structure of the basic pancreatic trypsin inhibitor (BPTI) and the X-ray crystal structure of the alpha-dendrotoxin from Dendroaspis angusticeps (alpha-DTX), with r.m.s.d. values of 1.31 Å and 0.92 Å, respectively, for the backbone atoms of residues 2 to 56. Some local structural differences between Toxin K and BPTI are directly related to the fact that intermolecular interactions with two of the four internal molecules of hydration water in BPTI are replaced by intramolecular hydrogen bonds in Toxin K." Thus, it is likely that the solution 3D structure of either of the isolated ITI-D1 domain or of the isolated ITI-D2 domain will be highly similar to the structures of BPTI, AAβP, and black mamba K venom. In this case, the advantages described previously for use of BPTI as an IPBD apply to ITI-D1 and to ITI-D2. ITI-D1 and ITI-D2 provide additional advantages as an IPBD for the development of specific anti-elastase inhibitory activity. First, the ITI-D1 domain has been reported to inhibit both leukocyte elastase (ALBR83a,b, ODOM90) and Cathepsin-G (SWAI88, ODOM90); activities which BPTI lacks. Second, ITI-D1 lacks affinity for the related serine proteases trypsin, chymotrypsin, and plasmin (ALBR83a,b, SWAI88), an advantage for the development of specificity in inhibition. ITI-D2 has the advantage of not being glycosylated. Additionally, ITI-D1 and ITI-D2 are human-derived polypeptides so that derivatives are anticipated to show minimal antigenicity in clinical applications.

3. Secretion of heterologous proteins from *Pichia pastoris*

Others have produced a number of proteins in the yeast *Pichia pastoris*. For example, Vedvick et al. (VEDV91) and Wagner et al. (WAGN92) produced aprotinin from the alcohol oxidase promoter with induction by methanol as a secreted protein in the culture medium at ≈1 mg/ml. Gregg et al. (GREG93) have reviewed production of a number of proteins in *P. pastoris*. Table 1 of GREG93 shows proteins that have been produced in *P. pastoris* and the yields.

No admission is made that any cited reference is prior art or pertinent prior art, and the dates given are those appearing on the reference and may not be identical to the actual publication date. The descriptions of the teachings of any cited reference are based on our present reading thereof, and we reserve the right to revise the description if an error comes to our attention, and to challenge whether the description accurately reflects the actual work reported. We reserve the right to challenge the interpretation of cited works, particularly in light of new or contradictory evidence. All references, including prior applications of any of the inventors, cited in this specification are hereby incorporated by reference.

SUMMARY OF THE INVENTION

The present invention describes a series of small potent proteinaceous inhibitors of human neutrophil elastase (hNE). One group of inhibitors are derived from one of two Kunitz-type inhibitory domain found in a protein of human origin, namely, the light chain of human Inter-α-trypsin inhibitor (ITI). The domains are designated ITI-D1 and ITI-D2. The present invention also comprises modifications to the ITI-D2 sequence that facilitate its production in the yeast *Pichia pastoris* and that are highly potent inhibitors of hNE. The invention also comprises derivatives of bovine pancreatic trypsin inhibitor that inhibit hNE. The invention also relates to methods of transferring segments of sequence from one Kunitz domain to another and to methods of production.

The invention is presented as a series of examples that describe discovery, production, and testing of actual inhibitors and additional examples describing how other inhibitors could be discovered.

BRIEF DESCRIPTION OF THE DRAWINGS

FIG. 1 shows a restriction map of plasmid pHIL-D2. Radial lines are drawn at 1000 base intervals. Two NotI sites, two BstBI sites, and a number of unique restriction sites are shown. The map shows genetic elements: a) aox1 5' segment (dark grey), b) a portion of the 3' region of aox1 (cross hatched) running clockwise from EcoRI, c) his4 (medium grey) running clockwise from near 3 o'clock to just after 6 o'clock, d) a second part of aox1 3' segment (cross hatched) running clockwise from just after the unique SphI to just before the unique AatII site (about 8 o'clock), e) bla (β lactamase, to allow selection for the plasmid in *E. coli*) in light grey from about 8:30 to about 9:30, and f) the f1 origin of replication (hatched) from about 10 o'clock to about 10:30.

NOMENCLATURE and ABBREVIATIONS

| Term | Meaning |
| --- | --- |
| x::y | Fusion of gene x to gene y in frame. |
| X::Y | Fusion protein expressed from x::y fusion gene. |
| μM | Micromolar, $10^{-6}$ molar. |
| nM | Nanomolar, $10^{-9}$ molar. |
| pM | Picomolar, $10^{-12}$ molar. |

DESCRIPTION OF THE INVENTION

The invention is presented by the following Examples and Tables. The examples contain numerous examples of amino-acid sequences accompanied by DNA sequences that encode them. It is to be understood that the invention is not limited to the particular DNA sequence shown.

The present invention refers to sequences that are "substantially homologous". Typically, "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

"Conservative modifications" are defined as:

a) conservative substitutions of amino acids as hereafter defined, and b) single or multiple insertions or deletions of amino acids at the termini, at interdomain boundaries, in loops or in other segments of relatively high mobility (as indicated, for example, by high temperature factors or lack of resolution in X-ray diffraction, neutron diffraction, or NMR). Preferably, except at the termini, no more than about five amino acids are inserted or deleted at a particular locus, and the modifications are outside regions known to contain binding sites important to activity.

"Conservative substitutions" are herein defined as exchanges within on of the following five groups:
I. Small aliphatic, nonpolar or slightly polar residues: [Ala, Ser, Thr, (Pro, Gly)],
II. Acidic amino acids and their amides: [Asp, Glu, Asn, Gln],
III. Polar, positively charged residues: [His, Lys, Arg],
IV. Large, aliphatic nonpolar residues: [Met, Leu, Ile, Val, (Cys)], and
V. Large, aromatic residues: [Phe, Tyr, Trp]

Residues Pro, Gly, and Cys are parenthesized because they have special conformational roles. Cys often participates in disulfide bonds; when not so doing, it is highly hydrophobic. Gly imparts flexibility to the chain; it is often described as a "helix breaker" although many α helices contain Gly. Pro imparts rigidity to the chain and is also described as a "helix breaker". Although Pro is most often found in turns, Pro is also found in helices and sheets. These residues may be essential at certain positions and substitutable elsewhere.

"Semi-conservative substitutions" are defined to be exchanges between two of groups (I)–(V) above which are limited either to the supergroup consisting of (I), (II), and (III) or to the supergroup consisting of (IV) and (V).

A protein sequence can be called an "aprotinin-like Kunitz domain" if it can be aligned, with four or fewer mismatches, to the pattern:

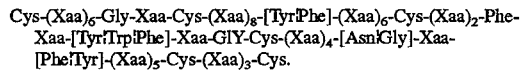

Cys-(Xaa)$_6$-Gly-Xaa-Cys-(Xaa)$_8$-[Tyr!Phe]-(Xaa)$_6$-Cys-(Xaa)$_2$-Phe-Xaa-[Tyr!Trp!Phe]-Xaa-Gly-Cys-(Xaa)$_4$-[Asn!Gly]-Xaa-[Phe!Tyr]-(Xaa)$_5$-Cys-(Xaa)$_3$-Cys.

(The sequence having the most prevalent amino acid at each ambiguous position has SEQ ID NO. 234). For the above test, an insertion or deletion is counted as a single mismatch. By convention, the first Cys is numbered 5 and the last Cys is numbered 51. The probability that a random sequence will pass this test is about $4.7 \times 10^{-11}$.

A protein that is a Kunitz domain would be substantially homologous to one of the proteins here disclosed if:
1) there is a Phe at position 18,
2) there is either Ile or Val at position 15, and
3) in the regions 10–21 and 30–42, there are six or fewer mismatches.

A protein would also be viewed as substantially homologous to the proteins of the present invention if it contains at least 50 amino acids and if a part of the sequence can be made to align with the specification in Table 790 with no more than about five mismatches. In making this alignment, insertions and deletions are counted as mismatches.

Contents

| Item | | page |
|---|---|---|
| SUMMARY OF THE INVENTION | | 6 |
| BRIEF DESCRIPTION OF THE DRAWINGS | | 6 |
| Example 1: | Expression and display of BPTI, ITI-D1, and other Kunitz Domains | 14 |
| Example 2: | Fractination of MA-ITI-D1 phage bound to agarose-immobilized protease beads. | 15 |
| Example 3: | Alteration of the P1 region of ITI-D1. | 16 |
| Example 4: | Fractionation of MA-ITI-D1E7 phage | 17 |
| Example 5: | Preparation of BITI-E7 Phage | 18 |
| Table 10: | Recovery of Display phage | 20 |
| Example 6: | Production and properties of MA-BITI-E7-1222 and MA-BITI-E7-141 | 21 |
| Example 7: | Mutagenesis of BITI-E7-141 | 22 |
| Example 8: | hNE-binding properties of mutagenized MA-BITI-E7-141 display phage | 24 |
| Example 9: | Amino-acid sequences of EPI-HNE-3 and EPI-HNE-4 | 27 |
| Example 10: | *Pichia pastoris* production system | 28 |
| Example 11: | Protein Production | 30 |
| Example 12: | Purification of EPI-HNE-2 | 31 |
| Example 13: | Purification of EPI-HNE-3 | 32 |
| Example 14: | Tricine-PAGE Analysis of EPI-HNE-2 and EPI-HNE-3 | 35 |
| Example 15: | Measured $K_D$s of EPI-HNE proteins for hNE | 36 |
| Example 16: | Specificity of EPI-HNE proteins | 37 |
| Example 17: | Resistance to Oxidative Inactivation | 38 |
| Example 18: | pH Stability | 38 |
| Table 14: | Buffers used in stability studies | 39 |
| Example 19: | Temperature Stability | 39 |
| Example 20: | Relationship of various hNE-inhibiting Kunitz Domains | 40 |
| Example 21: | Substitution of Segments in Kunitz Domains | 40 |
| Example 22: | Point substitutions in Kunitz Domains | 41 |
| Example 23: | Libraries of Kunitz Domains | 43 |
| Table 28: | Sequences of EPI-HNE-7 and ITI-D1 in the active site | 45 |
| Table 30: | IIIs::bpti::mautreIII fusion gene | 46 |
| Table 35: | IIIsp::itiD1::matureIII fusion gene | 50 |
| Table 40: | Local sequences of Kunitz domains derived from BPTI or ITI-D1 | 53 |
| Table 55: | Affinity Classes of ITI-D1-derived hNE inhibitors | 54 |
| Table 100: | hNE-inhibiting Kunitz domains and their parental domains | 55 |
| TABLE 208: | SEQUENCES OF THE EpiNE CLONES IN THE P1 REGION | 56 |
| Table 209: | BPTI analogues selected for binding to Cathepsin G | 57 |
| Table 210: | Derivatives of EpiNE7 Obtained by Variegation at positions 34, 36, 39, 40 and 41 | 58 |
| TABLE 211: | Effects of antisera on phage infectivity | 60 |
| TABLE 212: | Fractionation of EpiNE-7 and MA-ITI-D1 phage on hNE beads | 61 |
| TABLE 213: | Fractionation of EpiC-10 and MA-ITI-D1 phage on Cat-G beads | 62 |
| TABLE 214: | Abbreviated fractionation of display phage on hNE beads | 63 |
| TABLE 215: | Fractionation of EpiNE-7 and MA-ITI-D1E7 phage on hNE beads | 64 |
| TABLE 216: | Fractionation of MA-EpiNE-7, MA-BITI and MA-BITI-E7 on hNE beads | 65 |
| TABLE 217: | Fractionation of MA-BITI-E7 and MA-BITI-E7-1222 on hNE beads | 66 |
| TABLE 218: | Fractionation of MA-EpiNE7 and MA-BITI-E7-141 on hNE beads | 67 |
| TABLE 219: | pH Elution Analysis of hNE Binding by BITI-E7-141 Varient Display Phage | 68 |
| TABLE 220: | ITI-D1-derived hNE Inhibitors | |
| Table 221: | Same sequences as in Table 220 showing only changes | 70 |
| Table 250: | Plasmid pHIL-D2 | 71 |
| Table 251: | pHIL-D2(MFαPrePro::EPI-HNE-3) | 75 |
| Table 252: | BstBI-AatII-EcoRI cassette for expression of EPI-HNE-4 | 81 |
| Table 253: | pD2pick(MFαPrePro::EPI-HNE-3) | 82 |

-continued

Contents

| Item | | page |
|---|---|---|
| Table 254: | restriction map of pD2pick(MFαPrePro::EPI-HNE-3) | 87 |
| Table 399: | Number of amino-acid differences between some Kunitz domains | 89 |
| Table 400: | Amino-acid Sequence of ITI light chain | 90 |
| Table 401: | Kunitz-domain hNE inhibitors producible in *Pichia pastoris* | 91 |
| TABLE 601: | Sequences of purified hNE inhibitors derived from Kunitz domains | 92 |
| TABLE 602: | Physical properties of hNE inhibitors derived from Kunitz domains | 93 |
| TABLE 603: | SUMMARY OF PURIFICATION OF EPI-HNE-2 | 94 |
| TABLE 604: | SUMMARY OF PURIFICATION OF EPI-HNE-3 | 95 |
| TABLE 605: | $K_i$ VALUES OF EPI-HNE PROTEINS FOR VARIOUS HUMAN SERUM SERINE PROTEASES | 96 |
| Table 607: | PEY-33 which produces EPI-HNE-2 | 97 |
| Table 608: | PEY-43 Which produces EPI-HNE-3 | 98 |
| Table 610: | Inhibitory properties of EPI-HNE-2 | 99 |
| Table 611: | hNE inhibitory properties of EPI-HNE-3 | 100 |
| Table 612: | pH stability of Kunitz-domain hNE inhibitors | 101 |
| Table 620: | Stability of hNE inhibitory proteins to oxidation by Chloramine-T | 102 |
| Table 630: | Temperature stability of EPI-HNE proteins | 104 |
| Table 700: | Kunitz domains in segments | 105 |
| Table 701: | Substitutions for Segment 1 (amino terminus to residue 4) that are likely to give Kunitz Domains that could have very-high affinity for hNE | 109 |
| Table 702: | Substitutions for Segment 3 (residues 10–13) that are likely to give Knuitz Domains that could have very-high affinity for hNE | 109 |
| Table 703: | Substitutions for Segment 5 (residues 15–21) that are likely to give Kunitz Domains that could have very-high affinity for hNE | 110 |
| Table 704: | Substitutions for Segment 7 (residues 31–35) that are likely to give Kunitz Domains that could have very-high affinity for hNE | 111 |
| Table 705: | Substitutions for Segment 9 (residues 39–41) that are likely to give Kunitz Domains that could have very-high affinity for hNE | 112 |
| Table 706: | Sample Candidate hNE inhibitor proteins | 113 |
| Table 710: | Cumulative collection of allowed amino acids | 114 |
| Table 711: | Mutations that are likely to improve the affinity of a Kunitz domain for hNE | 117 |
| Table 720: | M13_III_signal::Human_LACI-D2::mature_M13_III | 118 |
| Table 725: | Synthetic laci-d1 with sites for cloning into display vector | 119 |
| Table 730: | LACI-D1 hNE Library | 120 |
| Table 735: | LACI-D2 hNE Library | 121 |
| Table 750: | M13_III_signal::Human_LACI-D3::mature_M13_III | 122 |
| Table 760: | Variegation of LACI-D3 | 123 |
| Table 790: | Amino acids allowed in hNE-inhibiting Kunitz domains | 124 |
| Table 800: | Amino-acid sequences of Kunitz domains | 126 |
| Table 810: | Frequency of amino-acid types at the positions in BPTI-homologous Kunitz domains and identification of residues in five surface groups | 133 |
| CITATIONS | | 135 |
| CLAIMS | | 157 |

EXAMPLE 1

Expression and display of BPTI, ITI-D1, and other Kunitz Domains.

Table 30 shows a display gene that comprises codons that encode: 1) the M13 III signal peptide, 2) BPTI, and 3) mature M13 III protein. Phage have been made in which this gene is the only iii-like gene so that all copies of III expressed are expected to be modified at the amino terminus of the mature protein. Substitutions in the BPTI domain can be made in the cassettes delimited by the AccIII, XhoI, PflMI, ApaI, BssHII, StuI, XcaI, EspI, SphI, or NarI sites.

Tables 208 and 209 give sequences that may be substituted into BPTI to give hNE-binding or CatG-binding Kunitz domains. Table 100, Table 208, and Table 210 give amino-acid sequences of a number of hNE-binding Kunitz domains. Each of the sequences shown in Table 100, Table 208, and Table 210 can be expressed as an intact hNE-binding protein or can be incorporated into a larger protein as a domain. Proteins that comprise part of one of the sequences found in Table 100, Table 208, and Table 210 are expected to exhibit hNE-inhibitory activity. This is particularly true if the sequence beginning with the first cysteine and continuing through the last cysteine is retained.

Table 209 gives amino-acid sequences of Cathepsin-G-binding Kunitz domains. The sequences in Table 209 may be expressed as intact proteins or they may be incorporated into a larger protein as a Cathepsin-G-inhibitory domain. Proteins that comprise part of one of the sequences found in Table 209 are expected to exhibit Cathepsin-G-inhibitory activity. This is particularly true if the sequence beginning with the first cysteine and continuing through the last cysteine is retained.

ITI domain 1 is a Kunitz domain as discussed below. The ability of display phage to be retained on matrices that display hNE is related to the affinity of the particular Kunitz domain (or other protein) displayed on the phage. Expression of the ITI domain 1::iii fusion gene and display of the fusion protein on the surface of phage were demonstrated by Western analysis and phage titer neutralization experiments, data for which is given in Table 211.

Table 35 gives the sequence of a fusion gene comprising: a) the signal sequence of M13 III, b) ITI-D1, and c) mature III of M13. The displayed ITI-D1 domain can be altered by standard methods including: i) oligonucleotide-directed mutagenesis of single-stranded phage DNA, and ii) cassette mutagenesis of RF DNA using the restriction sites (BglI, EagI, NcoI, StyI, PstI, and KasI (two sites)) designed into the gene.

EXAMPLE 2

Fractionation of MA-ITI-D1 phage bound to agarose-immobilized protease beads.

To test if phage displaying the ITI-D1::III fusion protein interact strongly with the proteases human neutrophil elastase (hNE) or cathepsin-G, aliquots of display phage were incubated with agarose-immobilized hNE or cathepsin-G beads (hNE beads or Cat-G beads, respectively). The beads were washed and bound phage eluted by pH fractionation as described in U.S. Pat. No. 5,223,409. The pHs used in the step gradient were 7.0, 6.0, 5.5, 5.0, 4.5, 4.0, 3.5, 3.0, 2.5, and 2.0. Following elution and neutralization, the various input, wash, and pH elution fractions were titered. Phage displaying ITI-D1 were compared to phage that display either EpiNE-7 or EpiC-10.

The results of several fractionations are summarized in Table 212 (EpiNE-7 or MA-ITI-D1 phage bound to hNE beads) and Table 213 (EpiC-10 or MA-ITI-D1 phage bound to Cat-G beads). For the two types of beads (hNE or Cat-G), the pH elution profiles obtained using the control display phage (EpiNE-7 or EpiC-10, respectively) were similar to those seen previously (U.S. Pat. No. 5,223,409). About 0.3% of the EpiNE-7 display phage applied to the hNE beads were eluted during the fractionation procedure and the elution profile had a maximum for elution at about pH 4.0. A smaller fraction, 0.02%, of the EpiC-10 phage applied to the Cat-G beads were eluted and the elution profile displayed a maximum near pH 5.5.

The MA-ITI-D1 phage show no evidence of great affinity for either hNE or cathepsin-G immobilized on agarose beads. The pH elution pro fries for MA-ITI-D1 phage bound to hNE or Cat-G beads show essentially monotonic decreases in phage recovered with decreasing pH. Further, the total fractions of the phage applied to the beads that were recovered during the fractionation procedures were quite low: 0.002% from hNE beads and 0.003% from Cat-G beads.

Published values of $K_i$ for inhibition neutrophil elastase by the intact, large ($M_r$=240,000) ITI protein range between 60 and 150 nM and values between 20 and 6,000 nM have been reported for the inhibition of Cathepsin G by ITI (SWAI88, ODOM90). Our own measurements of pH fraction of display phage bound to hNE beads show that phage displaying proteins with low affinity (>1 μM) for hNE are not bound by the beads while phage displaying proteins with greater affinity (nM) bind to the beads and are eluted at about pH 5. If the first Kunitz-type domain of the ITI light chain is entirely responsible for the inhibitory activity of ITI against hNE, and if this domain is correctly displayed on the MA-ITI-D1 phage, then it appears that the minimum affinity of an inhibitor for hNE that allows binding and fractionation of display phage on hNE beads is between 50 and 100 nM.

EXAMPLE 3

Alteration of the P1 region of ITI-D1.

We assume that ITI-D1 and EpiNE-7 have the same 3D configuration in solution as BPTI. The amino acid sequences of these proteins in the primary and secondary binding loops are shown in Table 28. (Table 810 (derived from Table 34 of U.S. Pat. No. 5,223,409) identifies several interaction surfaces of Kunitz domains. Table 810 also shows the frequency of each amino-acid type at each position in BPTI-homologous Kunitz domains.) Although EpiNE-7 and ITI-D1 are identical at positions 13, 17, 20, 32, and 39, they differ greatly in their affinities for hNE. To improve the affinity of ITI-D1 for hNE, the EpiNE-7 sequence $Val_{15}$-$Ala_{16}$-$Met_{17}$-$Phe_{18}$-$Pro_{19}$-$Arg_{20}$ (bold, underscored amino acids are alterations) was incorporated into the ITI-D1 sequence by cassette mutagenesis between the EagI and StyI/NcoI sites shown in Table 35. Phage isolates containing the ITI-D1::III fusion gene with the EpiNE-7 changes around the P1 position are called MA-ITI-D1E7.

EXAMPLE 4

Fractionation of MA-ITI-D1E7 phage.

To test if the changes at positions 15, 16, 18, and 19 of the ITI-D1::III fusion protein (named ITI-D1E7) influence binding of display phage to hNE beads, abbreviated pH elution profiles were measured. Aliquots of EpiNE-7, MA-ITI-D1, and MA-ITI-D1E7 display phage were incubated with hNE beads for three hours at room temperature. The beads were washed and phage were eluted as described in U.S. Pat. No. 5,223,409, except that only three pH elutions were performed: pH 7.0, 3.5, and 2.0. The results of these elutions are shown in Table 214.

Binding and elution of the EpiNE-7 and MA-ITI-D1 display phage were found to be as previously described. The total fraction of input phages was high (0.4%) for EpiNE-7 phage and low (0.001%) for MA-ITI-D1 phage. Further, the EpiNE-7 phage showed maximum phage elution in the pH 3.5 fraction while the MA-ITI-D1 phage showed only a monotonic decrease in phage yields with decreasing pH, as seen above. Thus, ITI-D1 has very little if any affinity for hNE.

The two strains of MA-ITI-D1E7 phage show increased levels of binding to hNE beads relative to MA-ITI-D1 phage. The total fraction of the input phage eluted from the beads is 10-fold greater for both MA-ITI-D1E7 phage strains than for MA-ITI-D1 phage (although still 40-fold lower that EpiNE-7 phage). Further, the pH elution profiles of the MA-ITI-D1E7 phage strains show maximum elutions in the pH 3.5 fractions, similar to EpiNE-7 phage.

To further define the binding properties of MA-ITI-D1E7 phage, the extended pH fractionation procedure described previously was performed using phage bound to hNE beads. These data are summarized in Table 215. The pH elution profile of EpiNE-7 display phage is as previously described. In this more resolved, pH elution profile, MA-ITI-D1E7 phage show a broad elution maximum centered around pH 5. Once again, the total fraction of MA-ITI-D1E7 phage obtained on pH elution from hNE beads was about 40-fold less than that obtained using EpiNE-7 display phage.

The pH elution behavior of MA-ITI-D1E7 phage bound to hNE beads is qualitatively similar to that seen using BPTI[K15L]-III-MA phage. BPTI with the K15L mutation has an affinity for hNE of ≈3 nM. Assuming all else remains the same, the pH elution profile for MA-ITI-D1E7 suggests that the affinity of the free ITI-D1E7 domain for hNE might be in the nM range. If this is the case, the substitution of the EpiNE-7 sequence in place of the ITI-D1 sequence around the P1 region has produced a 20- to 50-fold increase in affinity for hNE (assuming $K_i$=60 to 150 nM for the unaltered ITI-D1).

If EpiNE-7 and ITI-D1E7 have the same solution structure, these proteins present the identical amino acid sequences to hNE over the interaction surface. Despite this similarity, EpiNE-7 exhibits a roughly 1000-fold greater affinity for hNE than does ITI-D1E7. Again assuming similar structure, this observation highlights the importance of non-contacting secondary residues in modulating interaction strengths.

Native ITI light chain is glycosylated at two positions, $Ser_{10}$ and $Asn_{45}$ (GEBH86). Removal of the glycosaminoglycan chains has been shown to decrease the affinity of the inhibitor for hNE about 5-fold (SELL87). Another potentially important difference between EpiNE-7 and ITI-D1E7 is that of net charge. The changes in BPTI that produce EpiNE-7 reduce the total charge on the molecule from +6 to +1. Sequence differences between EpiNE-7 and ITI-D1E7 further reduce the charge on the latter to −1. Furthermore, the change in net charge between these two molecules arises from sequence differences occurring in the central portions of the molecules. Position 26 is Lys in EpiNE-7 and is Thr in ITI-D1E7, while at position 31 these residues are Gln and Glu, respectively. These changes in sequence not only alter the net charge on the molecules but also position a negatively charged residue close to the interaction surface in ITI-D1E7. It may be that the occurrence of a negative charge at position 31 (which is not found in any other of the hNE inhibitors described here) destabilized the inhibitor-protease interaction.

EXAMPLE 5

Preparation of BITI-E7 Phage

Possible reasons for MA-ITI-D1E7 phage having lower affinity for hNE than do MA-EpiNE7 phage include: a) incorrect cleavage of the IIIsignal::ITI-D1E7::matureIII fusion protein, b) inappropriate negative charge on the ITI-D1E7 domain, c) conformational or dynamic changes in the Kunitz backbone caused by substitutions such as $Phe_4$ to $Ser_4$, and d) non-optimal amino acids in the ITI-D1E7:hNE interface, such as $Q_{34}$ or $A_{11}$.

To investigate the first three possibilities, we substituted the first four amino acids of EpiNE7 for the first four amino acids of ITI-D1E7. This substitution should provide a peptide that can be cleaved by signal peptidase-I in the same manner as is the IIIsignal::EpiNE7::matureIII fusion. Furthermore, $Phe_4$ of BPTI is part of the hydrophobic core of the protein; replacement with serine may alter the stability or dynamic character of ITI-D1E7 unfavorably. ITI-D1E7 has a negatively charged Glu at position 2 while EpiNE7 has Pro.

We introduced the three changes at the amino terminus of the ITI-D1E7 protein (K1R, E2P, and S4F) by oligonucleotide-directed mutagenesis. We used ssDNA purified from MA-ITI-D1E7 display phage as the template for mutagenesis and performed the mutagenesis using the Amersham Oligonucleotide-directed in vitro Mutagenesis System (Version 2) according to the manufacturer's specifications.

We extracted RF DNA from Ap$^r$ transformants and screened the RF DNA for the presence of an unique AccIII site introduced as a portion of the desired DNA sequence. We confirmed the entire DNA sequence encoding the altered ITI-D1E7 protein by DNA sequencing. Phage isolates containing the ITI-D1E7-III fusion gene incorporating the changes in the putative amino terminus of the displayed protein are called MA-BITI-E7.

We used the same mutagenic oligonucleotide to introduce the identical changes at the putative amino terminus of the ITI-III fusion protein displayed by the phage MA-ITI-D1. These phage isolates are called MA-BITI.

We compared the properties of the ITI-III fusion proteins displayed by phage MA-ITI-D1 and MA-BITI using Western analysis as described previously and found no significant differences in apparent size or relative abundance of the fusion proteins produced by either display phage strain. Thus, there are no large differences in the processed forms of either fusion protein displayed on the phage. By extension, there are also no large differences in the processed forms of the gene III fusion proteins displayed by MA-ITI-D1E7 and MA-EpiNE7. Large changes in protein conformation due to greatly altered processing are therefore not likely to be responsible for the great differences in binding to hNE-beads shown by MA-ITI-D1E7 and MA-EpiNE7 display phage.

We characterized the binding properties to hNE-beads of MA-BITI and MA-BITI-E7 display phage using the extended pH fractionation procedure described in U.S. Pat. No. 5,223,409. The results are summarized in Table 216. The pH elution profile of MA-EpiNE7 display phage bound to hNE-beads is similar to that previously described. In contrast, the pH elution profiles for MA-BITI and MA-BITI-E7 show significant differences from the profiles exhibited by MA-ITI-D1 and MA-ITI-D1E7 (cf. Tables 212 and 215). In both cases, the alterations at the putative amino terminus of the displayed fusion protein produce a several-fold increase in the fraction of the input display phage eluted from the hNE-beads.

The binding capacity of hNE-beads for display phage varies among preparations of beads and with age for each individual preparation of beads. Thus, it is difficult to directly compare absolute yields of phage from elutions performed at different times. For example, the fraction of MA-EpiNE7 display phage recovered from hNE-beads varies two-fold among the experiments shown in Tables 212, 215, and 216. However, the shapes of the pH elution profiles are similar. It is possible to correct somewhat for variations in binding capacity of hNE-beads by normalizing display phage yields to the total yield of MA-EpiNE7 phage recovered from the beads in a concurrent elution. When the data shown in Tables 212, 215, and 216 are so normalized, the recoveries of display phage, relative to recovered MA-EpiNE7, are:

TABLE 10

Recovery of Display phage

| Display Phage strain | Normalized fraction of input |
|---|---|
| MA-ITI-D1 | 0.0067 |
| MA-BITI | 0.018 |
| MA-ITI-D1E7 | 0.027 |
| MA-BITI-E7 | 0.13 |

Thus, the alterations in the amino terminal sequence of the displayed fusion protein produce a three- to five-fold increase in the fraction of display phage eluted from hNE-beads.

In addition to increased binding, the sequence changes introduced into MA-BITI-E7 produce display phage that elute from hNE-beads at a lower pH than do the parental MA-ITI-D1E7 phage. While the parental display phage elute with a broad pH maximum centered around pH 5.0, the pH elution profile for MA-BITI-E7 display phage has a pH maximum at around pH 4.75 to pH 4.5.

The pH elution maximum of the MA-BITI-E7 display phage is located between the maxima exhibited by the BPTI(K15L) and BPTI(K15V, R17L) display phage (pH 4.75 and pH 4.5 to pH 4.0, respectively) described in U.S. Pat. No. 5,223,409. From the pH maximum exhibited by the display phage we predict that the BITI-E7 protein free in solution may have an affinity for hNE in the 100 pM range. This would represent an approximately ten-fold increase in affinity for hNE over that estimated above for ITI-D1E7.

As was described above, Western analysis of phage proteins show that there are no large changes in gene III fusion proteins upon alteration of the amino terminal sequence. Thus, it is unlikely that the changes in affinity of display phage for hNE-beads can be attributed to large-scale alterations in protein folding resulting from altered ("correct") processing of the fusion protein in the amino terminal mutants. The improvements in binding may in part be due to: 1) the decrease in the net negative charge (−1 to 0) on the protein arising from the Glu to Pro change at position 2, or 2) increased protein stability resulting from the Ser to Phe substitution at residue 4 in the hydrophobic core of the protein, or 3) the combined effects of both substitutions.

EXAMPLE 6

Production and properties of MA-BITI-E7-1222 and MA-BITI-E7-141

Within the presumed Kunitz:hNE interface, BITI-E7 and EpiNE7 differ at only two positions: 11 and 34. In EpiNE7 these residues are Thr and Val, respectively. In BITI-E7 they are Ala and Gln. In addition BITI-E7 has Glu at 31 while EpiNE7 has Gln. The presence of this negative charge may influence binding although the residue is not directly in the interface: We used oligonucleotide-directed mutagenesis to investigate the effects of substitutions at positions 11, 31 and 34 on the protease:inhibitor interaction.

We used two mutagenic bottom-strand oligonucleotides in separate mutageneses to alter the sequence of the BITI-E7 polypeptide at residues 11 or at residues 31 and 34. In the first oligonucleotide, the codon for Ala$_{11}$ was altered to encode Thr. The second mutagenic oligonucleotide was used to produce a E31Q, Q34V double mutation. Mutagenesis was performed as described above except that MA-BITI-E7 ssDNA was used as the template.

RF DNA isolated from Ap$^r$ transformants was assayed for correct structure by restriction enzyme analysis. We confirmed the entire DNA sequence encoding the altered BITI-E7 polypeptides by DNA sequencing. A phage strain containing the biti-e7::iii fusion gene incorporating the A11T change is called MA-BITI-E7-1222. Likewise, a phage strain containing the Biti-e7::iii fusion gene incorporating the E31Q, Q34V double mutation is called MA-BITI-E7-141.

We determined the binding properties to hNE-beads of MA-BITI-E7-1222 and MA-BITI-E7-141 display phage using the extended pH fractionation protocol described previously. The results are summarized in Tables 217 (for MA-BITI-E7 and MA-BITI-E7-1222) and 218 (for MA-EpiNE7 and MA-BITI-E7-141).

The pH elution profiles for the MA-BITI-E7 and MA-BITI-E7-1222 phage are almost identical (Table 217). Both phage strains exhibit pH elution profiles with identical maxima (between pH 5.0 and pH 4.5) as well as the same total fraction of input phage eluted from the hNE-beads (0.03%). Thus, the T11A substitution in the displayed ITI-D1 derivatives has no appreciable effect on the binding of display phage to hNE-beads.

In contrast, the changes at positions 31 and 34 profoundly affect the hNE-binding properties of the display phage (Table 218). The elution profile pH maximum of MA-BITI-E7-141 phage is shifted to lower pH relative to the parental MA-BITI-E7 phage. Further, the position of the maximum (between pH 4.5 and pH 4.0) is identical to that exhibited by MA-EpiNE7 phage in this experiment. Finally, the MA-BITI-E7-141 phage show a ten-fold increase, relative to the parental MA-BITI-E7, in the total fraction of input phage eluted from hNE-beads (0.3% vs 0.03%). Indeed, the total fraction of MA-BITI-E7-141 phage eluted from the hNE-beads is nearly twice that of MA-EpiNE7 phage.

The results discussed above show that binding by MA-BITI-E7-141 display phage to hNE-beads is comparable to that of MA-EpiNE7 phage. If the two proteins (EpiNE7 and BITI-E7-141) free in solution also have similar affinities for hNE, then the affinity of the BITI-E7-141 protein for hNE is on the order of 1 pM. Such an affinity is approximately 100-fold greater than that estimated above for the parental protein (BITI-E7) and is $10^5$ to $10^6$ times as great as the affinity for hNE reported for the intact ITI protein.

EXAMPLE 7

Mutagenesis of BITI-E7-141

BITI-E7-141 differs from ITI-D1 at nine positions (1, 2, 4, 15, 16, 18, 19, 31, and 34). To obtain the protein having the fewest changes from ITI-D1 while retaining high specific affinity for hNE, we have investigated the effects of reversing the changes at positions 1, 2, 4, 16, 19, 31, and 34. The changes we have introduced into the BITI-E7-141 protein are given in Table 40.

ITI-D1 residues in Table 40 are shown in bold type and residues found in neither ITI-D1 nor in BITI-E7-141 are shown underlined. The changes shown in Table 40 were accomplished via oligonucleotide directed mutagenesis.

Two mutagenic oligonucleotides introduced changes in the primary inhibitory loop of BITI-E7-141. MUT1619 restores the ITI-D1 residues $Ala_{16}$ and $Ser_{19}$. The sequence designated "MUTP1" asserts the amino acids $I_{15}$, $G_{16}$, $S_{19}$ in the context of BITI-E7-141. It is likely that $M_{17}$ and $F_{18}$ are optimal for high affinity hNE binding. $G_{16}$ and $S_{19}$ occurred frequently in the high affinity hNE-binding BPTI-variants obtained from fractionation of a library of BPTI-variants against hNE (ROBE92). Thus, it seems likely that the ITI-D1 sequence at these positions can be restored while maintaining high specific affinity for hNE.

Three changes at the putative amino terminus of the displayed ITI-D1 domain were introduced to produce the MA-BITI series of display phage. AMINO1 carries the sequence $K_1$-$E_2$ while AMINO2 carries $K_1$-$S_4$. Other amino acids in the amino-terminal region of these sequences are as in ITI-D1.

Two changes had been introduced into the sequence for BITI-E7 to produce BITI-E7-141: E31Q and Q34V. The MUTQE mutagenic oligonucleotide reverses the change at position 31 by asserting $Glu_{31}$.

Finally, the mutagenic oligonueleotide MUTT26A is intended to remove a potential site of N-linked glycosylation. The BITI-E7-141 protein sequence $N_{24}$-$G_{25}$-$T_{26}$ matches the general recognition sequence Asn-X-Thr/Ser for N-linked glycosylation in eukaryotic organisms. In the intact ITI molecule isolated from human serum, the light chain polypeptide is glycosylated at this site ($N_{45}$, ODOM90). It is likely that $N_{24}$ will be glycosylated if the BITI-E7-141 protein is produced via eukaryotic expression. Such glycosylation may render the protein immunogenic when used for long-term treatment. The MUTT26A oligonucleotide asserts the mutation T26A and removes the potential glycosylation site with minimal changes in the overall chemical properties of the residue at that position (Ser, Pro, or Cys, were considered undesirable). In addition, an Ala residue is frequently found in other BPTI homologues at position 26.

Mutagenesis of ssDNA isolated from MA-BITI-E7-141 display phage was performed as previously described. The DNA sequence of the entire BITI-E7-141-derived insert in the mutagenized phage was confirmed by DNA sequencing. Individual populations of phage displaying mutagenized BITI-E7-141 proteins fused to gene III protein were prepared from large-scale cultures of bacteria infected with phage isolated from single plaques.

EXAMPLE 8 hNE-binding properties of mutagenized MA-BITI-E7-141 display phage

The binding properties of the individual phage populations to hNE-beads were determined using the abbreviated and extended pH elution protocols described previously. The results of these studies are presented, in a common format, in Table 219.

Table 219 shows pH elution data for the various display phage eluted from hNE-beads. Total pfu applied to the beads are shown in the second column. The fractions of this input pfu recovered in each pH fraction of the abbreviated pH elution protocol (pH 7.0, pH 3.5, and pH 2.0) are listed in the next three columns. For data obtained using the extended pH elution protocol, the pH 3.5 listing represents the sum of the fractions of input recovered in the pH 6.0, pH 5.5, pH 5.0, pH 4.5, pH 4.0, and pH 3.5 elution samples. Likewise, the pH 2.0 listing is the sum of the fractions of input obtained from the pH 3.0, pH 2.5, and pH 2.0 elution samples. The total fraction of the input pfu obtained throughout the pH elution protocol is recorded in the sixth column of Table 219. The final column of the table lists the total fraction of input pfu recovered normalized to the value obtained for MA-BITI-E7-141 display phage.

Two factors must be considered when making comparisons among the data shown in Table 219. The first is that due to the kinetic nature of phage release from hNE-beads and the longer time involved in the extended pH elution protocol, the fraction of input pfu recovered in the pH 3.5 fraction will be enriched at the expense of the pH 2.0 fraction in the extended protocol relative to those values obtained in the abbreviated protocol. The magnitude of this effect can be seen by comparing the results obtained when MA-BITI-E7-141 display phage were eluted from hNE-beads using the two protocols. The second factor is that, for the range of input pfu listed in Table 219, the input pfu influences recovery. The greater the input pfu, the greater the total fraction of the input recovered in the elution. This effect is apparent when input pfu differ by more than a factor of about 3 to 4. The effect can lead to an overestimate of affinity of display phage for hNE-beads when data from phage applied at higher titers is compared with that from phage applied at lower titers.

With these caveats in mind, we can interpret the data in Table 219. The effects of the mutations introduced into MA-BITI-E7-141 display phage ("parental") on binding of display phage to hNE-beads can be grouped into three categories: those changes that have little or no measurable effects, those that have moderate (2- to 3-fold) effects, and those that have large (>5-fold) effects.

The MUTF26A and MUTQE changes appear to have little effect on the binding of display phage to hNE-beads. In terms of total pfu recovered, the display phage containing these alterations bind as well as the parental to hNE-beads. Indeed, the pH elution profiles obtained for the parental and the MUTT26A display phage from the extended pH elution protocol are indistinguishable. The binding of the MUTTQE display phage appears to be slightly reduced relative to the parental and, in light of the applied pfu, it is likely that this binding is somewhat overestimated.

The sequence alterations introduced via the MUTP1 and MUT1619 oligonucleotides appear to reduce display phage binding to hNE-beads about 2- to 3-fold. In light of the input titers and the distributions of pfu recovered among the various elution fractions, it is likely that 1) both of these display phage have lower affinities for hNE-beads than do MA-EpiNE7 display phage, and 2) the MUT1619 display phage have a greater affinity for hNE-beads than do the MUTP1 display phage.

The sequence alterations at the amino terminus of BITI-E7-14 appear to reduce binding by the display phage to hNE-beads at least ten fold. The AMINO2 changes are likely to reduce display phage binding to a substantially greater extent than do the AMINO1 changes.

On the basis of the above interpretations of the data in Table 219, we can conclude that:

1.) The substitution of ALA for THR at position 26 in ITI-D1 and its derivatives has no effect on the interaction of the inhibitor with hNE. Thus, the possibility of glycosylation at $Asn_{24}$ of an inhibitor protein produced in eukaryotic cell culture can be avoided with no reduction in affinity for hNE.
2.) The increase in affinity of display phage for hNE-beads produced by the changes Glu to Gln at position 31 and Gln to Val at 34 results primarily from the Val substitution at 34.
3.) All three changes introduced at the amino terminal region of ITI-D1 (positions 1,2, and 4) influence display phage binding to hNE-beads to varying extents. The change at position 4 (Ser to Phe) appears to have about the same effect as does the change at position 2 (Glu to Pro). The change at position 1 appears to have only a small effect.
4.) The changes in the region around the P1 residue in BITI-E7-141 (position 15) influence display phage binding to hNE. The changes Ala to Gly at 16 and Pro to Ser at 19 appear to reduce the affinity of the inhibitor somewhat (perhaps 3-fold). The substitution of Ile for Val at position 15 further reduces binding.

BITI-E7-141 differs from ITI-D1 at nine positions. On the basis of the discussion above it appears likely that a high affinity hNE-inhibitor based on ITI-D1 could be constructed that would differ from the ITI-D1 sequence at only five or six positions. These differences would be: Pro at position 2, Phe at position 4, Val at position 15, Phe at position 18, Val at position 34, and Ala at position 26. If glycosylation of $Asn_{24}$ is not a concern Thr could be retained at 26.
Summary: estimated affinities of isolated ITI-D1 derivatives for hNE On the basis of display phage binding to and elution from hNE beads, it is possible to estimate affinities for hNE that various derivatives of ITI-D1 may display free in solution. These estimates are summarized in Table 55. Table 220 and Table 221 give the amino-acid sequences of the ITI-D1-derived proteins grouped by affinity for hNE. Each of these sequences may be used as the sequence of an entire protein having hNE-inhibitory activity. One may also incorporate any of the sequences of Table 220 into a larger protein where each is expected to confer hNE-inhibition on the fusion protein.

hNE Inhibitors Derived from ITI Domain 2

In addition to hNE inhibitors derived from ITI-D1, the present invention comprises hNE inhibitors derived from ITI-D2. These inhibitors have been produced in the yeast *Pichia pastoris* in good yield. Tests on these inhibitors show that EPI-HNE-4 inhibits human neutrophil elastase with a $K_D \approx 5$ pM.

PURIFICATION AND PROPERTIES OF EPI-HNE PROTEINS

I. EPI-HNE Proteins.

EXAMPLE 9

Amino-acid sequences of EPI-HNE-3 and EPI-HNE-4

Table 601 provides the amino acid sequences of four human-neutrophil-elastase (hNE) inhibitor proteins: EPI-HNE-1, EPI-HNE-2, EPI-HNE-3, and EPI-HNE4. These proteins have been derived from the parental Kunitz-type domains shown. Each of the proteins is shown aligned to the parental domain using the six cysteine residues (shaded) characteristic of the Kunitz-type domain. Residue position numbers are based on BPTI so that the first cysteine in each protein is assigned position 5. Residues within the inhibitor proteins that differ from those in the parental protein are highlighted in bold text. Entire proteins having the sequence shown in Table 601 have been produced. Larger proteins that comprise one of the sequences in Table 601 are expected to have potent hNE-inhibitory activity. It is expected that proteins that comprise part of one of the sequences found in Table 601, particularly if the sequence starting at the first cysteine and continuing through the last cysteine is retained, will exhibit potent hNE-inhibitory activity.

The hNE-inhibitors EPI-HNE-1 and EPI-HNE-2 are derived from the bovine protein BPTI (aprotinin). Within the Kunitz-type domain, these two inhibitors both differ from the parental protein sequence at the same eight positions: K15I, R17F, I18F, I19P, R39M, A40G, K41N, and R42G. In addition, EPI-HNE-2 differs from both BPTI and EPI-HNE-1 in the presence of four additional residues (EAEA) present at the amino terminus of the molecule. These residues were added to facilitate secretion of the protein in *Pichia pastoris*.

EPI-HNE-3 is derived from the second Kunitz-type domain of the light chain of the human inter-α inhibitor protein (ITI-D2). The amino acid sequence of EH-HNE-3 differs from that of ITI-D2 at only four positions: R15I, I18F, Q19P and L20R. EPI-HNE-4 differs from EPI-HNE-3 by the substitution A3E (the amino-terminal residue) which both facilitates secretion of the protein in *P. pastoris* and improves the $K_D$ for hNE.

Table 602 presents some physical properties of the hNE inhibitor proteins. All four proteins are small, high-affinity ($K_i$=2 to 6 pM), fast-acting ($k_{on}$=4 to $11 \times 10^6 M^{-1}s^{-1}$) inhibitors of hNE.

II. Production of the hNE-inhibitors EPI-HNE-2, EPI-HNE-3, and EPI-HNE-4.

EXAMPLE 10

*Pichia pastoris* production system.

Transformed strains of *Pichia pastoris* were used to express the various EPI-HNE proteins derived from BPTI and ITI-D2. Protein expression cassettes are cloned into the plasmid pHIL-D2 using the BstBI and EcoRI sites shown in FIG. 1. The DNA sequence of pHIL-D2 is given in Table 250. The cloned gene is under transcriptional control of *P. pastoris* upstream (labeled "aox1 5'") aox1 gene promoter and regulatory sequences (dark shaded region) and downstream polyadenylation and transcription termination sequences (second cross-hatched region, labeled "aox1 3'"). *P. pastoris* GS115 is a mutant strain containing a non-functional histidinol dehydrogenase (his4) gene. The his4 gene contained on plasmid pHIL-D2 and its derivatives can be used to complement the histidine deficiency in the host strain. Linearization of plasmid pHIL-D2 at the indicated sacI site directs plasmid incorporation into the host genome at the aox1 locus by homologous recombination during transformation. Strains of *P. pastoris* containing integrated copies of the expression plasmid will express protein genes under control of the aox1 promoter when the promoter is activated by growth in the presence of methanol as the sole carbon source.

We have used this high density *Pichia pastoris* production system to produce proteins by secretion into the cell culture medium. Expression plasmids were constructed by ligating synthetic DNA sequences encoding the *S. cerevisiae* mating factor α prepro peptide fused directly to the amino terminus of the desired hNE inhibitor into the plasmid pHIL-D2 using the BstBI and the EcoRI sites shown. Table 251 gives the DNA sequence of pHIL-D2(MFα-PrePro::EPI-HNE-3). In these constructions, the fusion protein is placed under control of the upstream inducible *P. pastoris* aox1 gene promoter and the downstream aox1 gene transcription termination and polyadenylation sequences. Expression plasmids were linearized by SacI digestion and the linear DNA was incorporated by homologous recombination into the genome of the *P. pastoris* strain GS115 by spheroplast transformation. Regenerated spheroplasts were selected for growth in the absence of added histidine, replated, and individual isolates were screened for methanol utilization phenotype (mut$^+$), secretion levels, and gene dose (estimated via Southern hybridization experiments). High level secretion stains were selected for production of hNE inhibitors: PEY-33 for production of EPI-HNE-2 and PEY43 for production of EPI-HNE-3. In both of these strains, we estimate that four copies of the expression plasmid are integrated as a tandem array into the aox1 gene locus.

To facilitate alteration of the Kunitz-domain encoding segment of pHIL-D2 derived plasmids, we removed two restriction sites shown in FIG. 1: the BstBI at about 7 o'clock and the AatII site at about 8 o'clock. Thus, the Kunitz-domain encoding segment is bounded by unique AatII and EcoRI sites. The new plasmids are called pD2pick ("insert") where "insert" defines the domain encoded under control of the aox1 promoter. Table 253 gives the DNA sequence of pD2pick(MFα::EPI-HNE-3). Table 254 gives a list of restriction sites in pD2pick(MFα::EPI-HNE-3).

EPI-HNE-4 is encoded by pD2pick(MFαPrePro::EPI-HNE-4) which differs from pHIL-D2 in that: 1) the AatII/EcoRI segment of the sequence given in Table 251 is replaced by the segment shown in Table 252 and 2) the changes in the restriction sites discussed above have been made. Strain PEY-53 is *P. pastoris* GS115 transformed with pD2pick(MFα::EPI-HNE-4).

EXAMPLE 11

Protein Production

To produce the proteins, *P. pastoris* strains were grown in mixed-feed fermentations similar to the procedure described by Digan et al. (DIGA89). Although others have reported production of Kunitz domains in *P. pastoris*, it is well known that many secretion systems involve proteases. Thus, it is not automatic that an altered Kunitz domain having a high potency in inhibiting hNE could be secreted from *P. pastoris* because the new inhibitor might inhibit some key enzyme in the secretion pathway. Nevertheless, we have found that *P. pastoris* can secrete hNE inhibitors in high yield.

Briefly, cultures were first grown in batch mode with glycerol as the carbon source. Following exhaustion of glycerol, the culture was grown for about four hours in glycerol-limited feed mode to further increase cell mass and to derepress the aox1 promoter. In the final production phase, the culture was grown in methanol-limited feed mode. During this phase, the aox1 promoter is fully active and protein is secreted into the culture medium.

Table 607 and Table 608 give the kinetics of cell growth (estimated as $A_{600}$) and protein secretion (mg/l) for cultures of PEY-33 and PEY-43 during the methanol-limited feed portions of the relevant fermentations. Concentrations of inhibitor proteins in the fermentation cultures were determined from in vitro assays of hNE inhibition by diluted aliquots of cell-free culture media obtained at the times indicated. Despite similarities in gene dose, fermentation conditions, cell densities, and secretion kinetics, the final concentrations of inhibitor proteins secreted by the two strains differ by nearly an order of magnitude. The final concentration of EPI-HNE-2 in the PEY-33 fermentation culture medium was 720 mg/l. The final concentration of EPI-HNE-3 in the PEY-43 fermentation culture medium was 85 mg/l. The differences in final secreted protein concentrations may result from idiosyncratic differences in the efficiencies with which the yeast synthesis and processing systems interact with the different protein sequences.

Strain PEY-33 secreted EPI-HNE-2 protein into the culture medium as a single molecular species which amino acid composition and N-terminal sequencing reveled to be the correctly-processed Kunitz domain with the sequence shown in Table 601. The major molecular species produced by PEY-43 cultures was the properly-processed EPI-HNE-3 protein. However, this strain also secreted a small amount (about 15% to 20% of the total EPI-HNE-3) of incorrectly-processed material. This material proved to be a mixture of proteins with amino terminal extensions (primarily nine or seven residues in length) arising from incorrect cleavage of the MF α PrePro leader peptide from the mature Kunitz domain. The correctly processed protein was purified substantially free of these contaminants as described below.

III. Purification of the hNE-inhibitors EPI-HNE-2 and EPI-HNE-3.

The proteins can be readily purified from fermenter culture medium by standard biochemical techniques. The specific purification procedure varies with the specific properties of each protein as described below.

EXAMPLE 12

Purification of EPI-HNE-2.

Table 603 gives particulars of the purification of EPI-HNE-2, lot 1. The PEY-33 fermenter culture was harvested by centrifugation at 8000×g for 15 min and the cell pellet was discarded. The 3.3 liter supernatant fraction was microfiltered used a Minitan Ultrafiltration System (Millipore Corporation, Bedford, Mass.) equipped with four 0.2μ filter packets.

The filtrate obtained from the microfiltration step was used in two subsequent ultrafiltration steps. First, two 30K ultrafiltrations were performed on the 0.2μ microfiltrate using the Minitan apparatus equipped with eight 30,000 NMWL polysulfone filter plates (#PLTK0MP04, Millipore Corporation, Bedford, Mass.). The retentate solution from the first 30K ultrafiltration was diluted with 10 mM NaCitrate, pH=3.5, and subjected to a second 30K ultrafiltration. The two 30K ultrafiltrates were combined to give a final volume of 5 liters containing about 1.4 gram of EPI-HNE-2 protein (estimated from hNE-inhibition measurements).

The 30K ultrafiltrate was concentrated with change of buffer in the second ultrafiltration step using the Minitan apparatus equipped with eight 5,000 NMWL filter plates (#PLCC0MP04, Millipore Corporation, Bedford, Mass.). At two times during the 5K ultrafiltration, the retentate solution was diluted from about 300 ml to 1.5 liters with 10 mM NaCitrate, pH=3.5. The final 5K ultrafiltration retentate (Ca. 200 ml) was diluted to a final volume of 1000 ml with 10 mM NaCitrate, pH-3.5.

EPI-HNE-2 protein was obtained from the 5K ultrafiltration retentate solution by ammonium sulfate precipitation at room temperature. 100 ml of 0.25M ammonium acetate, pH=3.2, (1/10 volume) was added to the 5K ultrafiltration retentate, followed by one final volume (1.1 liter) of 3M ammonium sulfate. Following a 30 minute incubation at room temperature, precipitated material was pelleted by centrifugation at 10,000×g for 45 minutes. The supernatant solution was removed, the pellet was dissolved in water in a final volume of 400 ml, and the ammonium sulfate precipitation was repeated using the ratios described above. The pellet from the second ammonium sulfate precipitation was dissolved in 50 mM sodium acetate, pH=3.5 at a final volume of 300 ml.

Residual ammonium sulfate was removed from the EPI-HNE-2 preparation by ion exchange chromatography. The solution from the ammonium sulfate precipitation step was applied to a strong cation-exchange column (50 ml bed volume Macroprep 50S) (Bio-Rad Laboratories, Inc, Hercules, Calif.) previously equilibrated with 10 mM NaCitrate, pH=3.5. After loading, the column was washed with 300 ml of 10 mM NaCitrate, pH=3.5. EPI-HNE-2 was then batch-eluted from the column with 300 ml of 50 mM $NH_4OAc$, pH=6.2. Fractions containing EPI-HNE-2 activity were pooled and the resulting solution was lyophilized. The dried protein powder was dissolved in 50 ml $dH_2O$ and the solution was passed through a 0.2μ filter (#4192, Gelman Sciences, Ann Arbor, Mich.). The concentration of the active inhibitor in the final stock solution was determined to be 2 mM (13.5 mg/ml). This stock solution (EPI-HNE-2, Lot 1) has been stored as 1 ml aliquots at both 4° C. and −70° C. for more than eleven months with no loss in activity.

Table 603 summarizes the yields and relative purity of EPI-HNE-2 at various steps in the purification procedure. The overall yield of the purification procedure was about 30%. The major source of loss was retention of material in the retentate fractions of the 0.2μ microfiltration and 30k ultrafiltration steps.

EXAMPLE 13

Purification of EPI-HNE-3.

Purification of EPI-HNE-3, lot 1, is set out in Table 604. The PEY-43 fermenter culture was harvested by centrifugation at 8,000×g for 15 min and the cell pellet was discarded. The superantant solution (3100 ml) was microfiltered through 0.2μ Minitan packets (4 packets). After the concentration, a diafiltration of the retentate was performed so that the final filtrate volume from the 0.2μ filtration was 3300 ml.

A 30K ultrafiltration was performed on the filtrate from the 0.2μ microfiltration step. When the retentate volume had been reduced to 250 ml, a diafiltration of the retentate was performed at a constant retentate volume (250 ml) for 30 min at a rate of 10 ml/min. The resulting final volume of filtrate was 3260 ml.

EPI-HNE-3 protein and other medium components were found to precipitate from solution when the fermenter culture medium was concentrated. For this reason, the 5k ultrafiltration step was not performed.

Properly processed EPI-HNE-3 was purified substantially free of mis-processed forms and other fermenter culture components by ion exchange chromatography. A 30 ml bed volume strong cation ion exchange column (Macroprep 50S) was equilibrated with 10 mM NaCitrate pH=3.5. The 30K ultrafiltration filtrate was applied to the column and binding of EPI-HNE-3 to the column was confirmed by demonstrating the complete loss of inhibitor activity in the column flow through. The column was then washed with 300 ml of 10 mM NaCitrate, pH=3.5.

EPI-HNE-3 was removed from the column over the course of a series of step elutions. The column was sequentially eluted with 300 ml volumes of the following solutions:

100 mM ammonium acetate, pH=3.5
50 mM ammonium acetate, pH=4.8
50 mM ammonium acetate, pH=6.0
50 mM ammonium acetate, pH=6.0, 0.1M NaCl
50 mM ammonium acetate, pH=6.0, 0.2M NaCl
50 mM ammonium acetate, pH=6.0, 0.3M NaCl
50 mM ammonium acetate, pH=6.0, 0.4M NaCl
50 mN Tris/Cl pH=8.0, 1.0 NaCl The majority of the EPI-HNE-3 eluted in two 50 mM ammonium acetate, pH=6.0 fractions. The 0.1M NaCl fraction contained about 19% of the input EPI-HNE-3 activity (28 mg of 159 mg input) and essentially all of the mis-processed forms of EPI-HNE-3. The 0.2M NaCl fraction contained about 72% (114 mg) of the input EPI-HNE-3 and was almost completely free of the higher molecular weight mis-processed forms and other UV-absorbing contaminants. The fractions from the 50 mM ammonium acetate, pt=6.0, 0.2M NaCl elution having the highest concentrations of EPI-HNE-3 were combined (95 mg).

An ammonium sulfate precipitation was performed on the 0.2M NaCl, pH=6.0 ion exchange column eluate. 800 ml of 3M ammonium sulfate was added to 160 ml of eluate solution (final ammonium sulfate concentration=2.5M) and the mixture was incubated at room temperature for 18 hours. The precipitated material was then pelleted by centrifugation at 10,000×g for 45 minutes. The supernatant fluid was discarded and the pelleted material was dissolved in 100 ml of water.

Residual ammonium sulfate was removed from the EPI-HNE-3 preparation by batch ion exchange chromatography. The pH of the protein solution was adjusted to 3.0 with diluted (1/10) HOAc and the solution was then applied to a 10 ml bed volume Macroprep 50S column that had been equilibrated with 10 mM NaCitrate, pH=3.5. Following sample loading, the column was washed with 100 ml of 10 mM NaCitrate, pH=3.5 followed by 100 ml of $dH_2O$. EPI-HNE-3 was eluted from the column with 100 ml of 50 mM $NH_4CO_3$, pH-9.0. pH9 fractions having the highest concentrations of EPI-HNE-3 were combined (60 mg) and stored at 4° C. for 7 days before lyophilization.

The lyophilized protein powder was dissolved in 26 ml $dH_2O$ and the solution was passed through a 0.2μ filter (#4912, Gelman Sciences, Ann Arbor, Mich.). The concentration of active inhibitor in the final stock solution was found to be 250 μM (1.5 mg/ml). This stock solution (EPI-HNE-3, Lot 1) has been stored as 1 ml aliquots at −70° C. for more than six months with no loss of activity. EPI-HNE-3 stored in water solution (without any buffering) deteriorated when kept at 4° C. After five months, about 70% of the material was active with a $K_i$ of about 12 pM.

Table 604 summarizes the yield and relative purity of EPI-HNE-3 at various steps in the purification procedure. A major purification step occurred at the first ion exchange chromatography procedure. The ammonium sulfate precipitation step provided only a small degree of further purification. Some loss of inhibitor activity occurred on incubation at pt=9 (See pH stability data).

Production and purification of EPI-HNE-1 and EPI-HNE-4 were analogous to the production and purification of EPI-HNE-2 and EPI-HNE-3.

EXAMPLE 14

Tricine-PAGE Analysis of EPI-HNE-2 and EPI-HNE-3.

The high resolution tricine gel system of Schagger and von Jagow (SCHA87) was used to analyze the purified proteins produced as described above. For good resolution of the low molecular weight EPI-HNE proteins we used a 16.5% resolving layer in conjunction with 10% separating and 4% stacking layers. Following silver staining, we inspected a gel having:

Lane 1: EPI-HNE-2 25 ng,

Lane 2: EPI-HNE-2 50 ng,

Lane 3: EPI-HNE-2 100 ng,

Lane 4: EPI-HNE-2 200 ng,

Lane 5: EPI-HNE-3 25 ng,

Lane 6: EPI-HNE-3 50 ng,

Lane 7: EPI-HNE-3 100 ng,

Lane 8: EPI-HNE-3 200 ng, and

Lane 9: Molecular-weight standards: RPN 755, (Amersham Corporation, Arlington Heights, Ill.).

Stained proteins visible on the gel and their molecular weights in Daltons are: ovalbin (46,000), carbonic anhydrase (30,000), trypsin inhibitor (21,500), lysozyme (14,300), and aprotinin (6,500). The amount of protein loaded was determined from measurements of hNE-inhibition. We found the following features. EPI-HNE-2, Lot 1 shows a single staining band of the anticipated size (ca. 6,700 D) at all loadings. Similarly, EPI-HNE-3, Lot 1 protein shows a single staining band of the anticipated size (ca. 6,200 D). At the highest loading, traces of the higher molecular weight (ca. 7,100 D) incorrectly processed form can be detected. On the basis of silver-stained high-resolution PAGE analysis, the purity of both protein preparations is assessed to be significantly greater than 95%.

IV. Properties of EPI-HNE-2 and EPI-HNE-3.

A. Inhibition of hNE.

EXAMPLE 15

Measured $K_D$s of EPI-HNE proteins for hNE

Inhibition constants for the proteins reacting with hNE ($K_i$) were determined using room temperature measurements of hydrolysis of a fluorogenic substrate (N-methoxysuccinyl-Ala-Ala-Pro-Val-7-amino-4-methylcoumarin, Sigma M-9771) by hNE. For these measurements, aliquots of the appropriately diluted inhibitor stocks were added to 2 ml solutions of 0.847 nM hNE in reaction buffer (50 mM Tris-Cl, pH=8.0, 150 mM NaCl, 1 mM $CaCl_2$, 0.25% Triton-X-100) in plastic fluorescence cuvettes. The reactions were incubated at room temperature for 30 minutes. At the end of the incubation period, the fluorogenic substrate was added at a concentration of 25 µM and the time course for increase in fluorescence at 470 nm (excitation at 380 nm) due to enzymatic substrate cleavage was recorded using a spectrofluorimeter (Perkin-Elmer 650-15) and strip chart recorder. We did not correct for competition between substrate and inhibitor because ($S_0/K_m$) is 0.07 (where $S_0$ is the substrate concentration and $K_m$ is the binding constant of the substrate for hNE). $K_i$ is related to $K_{apparent}$ by $$K_i = K_{apparent} \times \left( \frac{1}{1 + \left( \frac{S_0}{K_m} \right)} \right).$$

The correction is small compared to the possible errors in determining $K_{apparent}$. Rates of enzymatic substrate cleavage were determined from the linear slopes of the recorded increases in fluorescence. The percent residual activity of hNE in the presence of the inhibitor was calculated as the percentage of the rate of fluorescence increase observed in the presence of the inhibitor to that observed when no added inhibitor was present.

We recorded data used to determine $K_i$ for EPI-HNE-2 and EPI-HNE-3 reacting with hNE. Data obtained as described above are recorded as percent residual activity plotted as a function of added inhibitor. Values for $K_i$ and for active inhibitor concentration in the stock are obtained from a least-squares fit program. From the data, $K_i$ values for EPI-HNE-2 and for EPI-HNE-3 reacting with hNE at room temperature were calculated to be 4.8 pM and 6.2 pM, respectively. Determinations of $K_i$ for EPI-HNE-2 and EPI-HNE-3 reacting with hNE are given in Table 610 and Table 611.

The kinetic on-rates for the inhibitors reacting with hNE ($k_{on}$) were determined from measurements of progressive inhibition of substrate hydrolytic activity by hNE following addition of inhibitor. For these experiments, a known concentration of inhibitor was added to a solution of hNE (0.847 nM) and substrate (25 µM) in 2 ml of reaction buffer in a plastic fluorescence cuvette. The change in fluorescence was recorded continuously following addition of the inhibitor. In these experiments, sample fluorescence did not increase linearly with time. Instead, the rate of fluorescence steadily decreased reflecting increasing inhibition of hNE by the added inhibitor. The enzymatic rate at selected times following addition of the inhibitor was determined from the slope of the tangent to the fluorescence time course at that time.

The kinetic constant $k_{on}$ for EPI-HNE-2 reacting with hNE was determined as follows. EPI-HNE-2 at 1.3 nM was added to buffer containing 0.867 nM hNE (I:E=1.5:1) at time 0. Measured percent residual activity was recorded as a function of time after addition of inhibitor. A least-squares fit program was used to obtain the value of $k_{on}=4.0\times10^6 M^{-1}s^{-1}$.

The kinetic off rate, $k_{off}$, is calculated from the measured values of $K_i$ and $k_{on}$ as:

$$k_{off} = K_D \times k_{on}$$

The values from such measurements are included in Table 602. The EPI-HNE proteins are small, high affinity, fast acting inhibitors of hNE.

B. Specificity.

EXAMPLE 16

Specificity of EPI-HNE proteins

We attempted to determine inhibition constants for EPI-HNE proteins reacting with several serine proteases. The results are summarized in Table 605. In all cases except chymotrypsin, we were unable to observe any inhibition even when 10 to 100 µM inhibitor was added to enzyme at concentrations in the nM range. In Table 605, our calculated values for $K_i$ (for the enzymes other than chymotrypsin) are based on the conservative assumption of less than 10% inhibition at the highest concentrations of inhibitor tested. For chymotrypsin, the $K_i$ is about 10 µM and is probably not specific.

C. In Vitro Stability.

EXAMPLE 17

Resistance to Oxidative Inactivation.

Table 620 shows measurements of the susceptibility of EPI-HNE proteins to oxidative inactivation as compared with that of two other natural protein hNE inhibitors: α 1 Protease Inhibitor (API) and Secretory Leucocyte Protease Inhibitor (SLPI). API (10 µM), SLPI (8.5 µM), EPI-HNE-1 (5 µM), EPI-HNE-2 (10 µM), EPI-HNE-3 (10 µM), and EPI-HNE-4 (10 µM) were exposed to the potent oxidizing agent, Chloramine-T, at the indicated oxidant:inhibitor ratios in 50 mM phosphate buffer, pH=7.0 for 20 minutes at room temperature. At the end of the incubation period, the oxidation reactions were quenched by adding methionine to a final concentration of 4 mM. After a further 10 minute incubation, the quenched reactions were diluted and assayed for residual inhibitor activity in our standard hNE-inhibition assay.

Both API and SLPI are inactivated by low molar ratios of oxidant to inhibitor. The Chloramine-T:protein molar ratios required for 50% inhibition of API and SLPI are about 1:1 and 2:1, respectively. These ratios correspond well with the reported presence of two and four readily oxidized methionine residues in API and SLPI, respectively. In contrast, all four EPI-HNE proteins retain essentially complete hNE-inhibition activity following exposure to Chloramine-T at all molar ratios tested (up to 50:1, in the cases of EPI-HNE-3 and EPI-HNE-4). Neither EPI-HNE-3 nor EPI-HNE-4 contain any methionine residues. In contrast, EPI-HNE-1 and EPI-HNE-2 each contains two methionine residues (see Tables 401 and 601). The resistance of these proteins to oxidative inactivation indicates that the methionine residues are either inaccessible to the oxidant or are located in a region of the protein that does not interact with hNE.

EXAMPLE 18 pH Stability.

Table 612 shows the results of measurements of the pH stability of EPI-HNE proteins. The stability of the proteins to exposure to pH conditions in the range of pH 1 to pH 10 was assessed by maintaining the inhibitors in buffers of defined pH at 37° C. for 18 hours and determining the residual hNE inhibitory activity in the standard hNE-inhibition assay. Proteins were incubated at a concentration of 1 µM. The following buffers were formulated as described (STOL90) and used in the pH ranges indicated:

TABLE 14

| Buffers used in stability studies | | |
|---|---|---|
| Buffer | Lowest pH | Highest pH |
| Glycine-HCl | 1 | 2.99 |
| Citrate-Phosphate | 3 | 7 |
| Phosphate | 7 | 8 |
| Glycine-NaOH | 8.5 | 10 |

Both BPTI-derived inhibitors, EPI-HNE-1 and EPI-HNE-2, are stable at all pH values tested. EPI-HNE-3 and EPI-HNE-4, the inhibitors derived from the human protein Kunitz-type domain, were stable when incubated at low pH, but showed some loss of activity at high pH. When incubated at 37° C. for 18 hours at pH=7.5, the EPI-HNE-3 preparation lost 10 to 15% of its hNE-inhibition activity. EPI-HNE-4 retains almost full activity to pH 8.5. Activity of the ITI-D2-derived inhibitor declined sharply at higher pH levels so that at pH 10 only 30% of the original activity remained. The sensitivity of EPI-HNE-3 to incubation at high pH probably explains the loss of activity of the protein in the final purification step noted previously.

EXAMPLE 19

Temperature Stability.

The stability of EPI-HNE proteins to exposure to temperatures in the range 0° C. to 95° C. was assessed by incubating the inhibitors for thirty minutes at various temperatures and determining residual inhibitory activity for hNE. In these experiments, protein concentrations were 1 µM in phosphate buffer at pH=7. As is shown in Table 630, the four inhibitors are quite temperature stable.

EPI-HNE-1 and EPI-HNE-2 maintain full activity at all temperatures below about 90° C. EPI-HNE-3 and EPI-HNE-4 maintain full inhibitory activity when incubated at temperatures below 65° C. The activity of the protein declines somewhat at higher temperatures. However, all three proteins retain more than ≈50% activity even when incubated at 95° C. for 30 minutes.

EXAMPLE 20

Relationship of various hNE-inhibiting Kunitz Domains:

Table 399 shows the number of amino-acid differences between 1) the consensus Kunitz domain, 2) BPTI, and 3) several hNE-inhibitory Kunitz domains. Of all the actual proteins listed, EPI-HNE-1 and EPI-HNE-2 are most like the consensus. Although EPI-HNE-3 and EPI-HNE-4 differ substantially from EPI-HNE-1 and EPI-HNE-2, all four proteins have remarkably similar abilities to inhibit HNE.

ROUTES to OTHER hNE-INHIBITORY SEQUENCES:

The present invention demonstrates that very high-affinity hNE inhibitors can be devised from Kunitz domains of human origin with very few amino-acid substitutions. It is believed that almost any Kunitz domain can be made into a potent and specific hNE inhibitor with eight or fewer substitutions. In particular, any one of the known human Kunitz domains could be remodeled to provide a highly stable, highly potent, and highly selective hNE inhibitor. There are at least three routes to hNE inhibitory Kunitz domains: 1) replacement of segments known to be involved in specifying hNE binding, 2) replacement of single residues thought to be important for hNE binding, and 3) use of libraries of Kunitz domains to select hNE inhibitors.

EXAMPLE 21

Substitution of Segments in Kunitz Domains

Table 700 shows the amino-acid sequences of 12 Kunitz domains. One of these is a consensus of seventy naturally-occurring Kunitz domains, one is bovine pancreatic trypsin inhibitor, and the rest are of human origin. The sequences have been broken into ten segments. Segments 1, 3, 5, 7, and 9 contain residues that show strong influence on the binding properties of Kunitz domains. Segment 1 is at the amino terminus and influences the binding by affecting the stability and dynamics of the protein. Segments 3, 5, 7, and 9 contain residues that contact serine proteases when a Kunitz domain binds in the active site. Other than segment 1, all the segments are the same length except for TFPI-2 Domain 2 which carries an extra residue in segment 2 and two extra residues in segment 10.

High-affinity hNE inhibition requires a molecule that is highly complementary to hNE. The sequences in segments 1, 3, 5, 7, and 9 must work together in the context supplied by the each other and the other segments. Nevertheless, we have demonstrated that very many sequences are capable of high-affinity hNE inhibition. It may be desirable to have an hNE inhibitor that is highly similar to a human protein to reduce the chance of immunogenicity. Candidate high-affinity hNE inhibitor protein sequences may be obtained by taking Segments 2, 4, 6, 8, and 10 for one protein in Table 700. The sequences for Segments 1, 3, 5, 7, and 9 are taken from Tables 701, 702, 703, 704, and 705 or may be taken from Table 700 for the parental protein. Segments of any other Kunitz domain could also be used.

EXAMPLE 22
Point substitutions in Kunitz Domains

Table 710 shows a collection of very potent hNB inhibitory Kunitz domains. At the bottom of Table 710 we have collected the amino-acid types at each residue that are compatible with high-affinity hNE binding. It is not believed that all the amino-acid positions are equally important. The two most important positions are 18 and 15. Any Kunitz domain is likely to become a very good hNE inhibitor if Val or Ile is at 15 and Phe is at 18. If a Kunitz domain has Phe at 18 and either Ile or Val at 15 and is not a good hNE inhibitor, there must be one or more residues in the interface preventing proper binding. Imposing the mutations X18F and either X15V or X15I on a Kunitz domain is the first step in making an hNE inhibitor.

The Kunitz domains having high affinity for hNE here disclosed have no charged groups at residues 10, 13, 16, 17, 21, and 32. At positions 11 and 19, only neutral and positively charged groups have been observed in high affinity hNE inhibitors. At position 31, only neutral and negatively charged groups have been observed in high-affinity hNE inhibitors. If a parental Kunitz domain has a charged group at any of those positions where only neutral groups are allowed, then each of the charged groups should be changed to an uncharged group picked from the possibilities in Table 790 as the next step in improving binding to hNE. Similarly, negatively charged groups at 11 and 19 and positively charged groups at 31 should be replaced by groups picked from Table 790.

Most Kunitz domains (82%) have either Gly or Ala at 16 and this may be quite important. If residue 16 is not Gly or Ala, change 16 to either Gly or Ala.

Position 17 in potent hNE inhibitors has one of Met, Phe, Ile, or Leu. preferred. Met should be used only if resistance to oxidation is not important.

It has been shown that high-affinity hNE inhibitors may have one of Pro, Ser, Gln, or Lys at position 19.

All of the high-affinity hNE inhibitors produced so far have $Pro_{13}$, but it has not been shown that this is required. Many (62.5%) Kunitz domains have $Pro_{13}$. If 13 is not Pro, then changing to Pro may improve the hNE affinity. Val may also be acceptable here.

It appears that many amino acid types may be placed at position 34 while retaining high affinity for hNE; large hydrophobic residues (Phe, Trp, Tyr) are unfavorable. Val, Gln, and Pro are most preferred at 34.

Position 39 seems to tolerate a variety of types. Met and Gln are known to work in very high-affinity inhibitors.

Position 32 may be outside the Kunitz-hNE interface, but unsuitable residues here could substantially reduce binding. Thr and Leu are known to work at 32.

Position 31 may be outside the Kunitz-hNE interface, but unsuitable residues here could substantially reduce binding. Gln, Glu, and Val are known to work here.

Position 12 is always Gly. At position 11, Thr, Ala, and Arg are known to be compatible with high-affinity hNE inhibition. At position 10, Tyr, Ser, and Val are known to be compatible with high-affinity hNE inhibition.

Either Ala or Gly are acceptable at position 40.

Finally, positions that are highly conserved in Kunitz domains may be converted to the conserved type if needed. For example, the mutations X36G, X37G, and X12G may be desirable in those cases that do not already have these amino acids at these positions.

The above mutations are summarized in Table 711. Table 711 contains, for example, mutations of the form X15I which means change the residue at position 15 (whatever it is) to Ile or leave it alone if it is already Ile. A Kunitz domain that contains the mutation X18F and either X15V or X15I will have strong affinity for hNE. As from one up to about eight of the mutations found in Table 711 are asserted, the affinity of the protein for hNE will increase so that the $K_i$ approaches the range 1–5 pM.

Table 706 shows some candidate hNE inhibitors. The sequence of CEPINE001 was constructed from the sequence of human LACI-D2 by the mutations R15V and I18F. The rest of the sequence of LACI-D2 appears to be compatible with hNE binding. CEPINE002 carries two further mutations that make it more like the hNE inhibitors here disclosed: Y17F and K34V. CEPINE003 has the additional mutation N25A that will prevent glycosylation when the protein is produced in a eukaryotic cell. Other substitutions that would prevent glycosylation include: N25K, T27A, T27E, N25S, and N25S. CEPINE004 moves further toward the ITI-D1, ITI-D2, and BPTI derivatives that are known to have affinity for hNE in the 1–5 pM range through the mutations I13P, R15V, Y17F, I18F, T19Q, N25A, K34V, and L39Q. In CEPINE005, the T19Q and N25A mutations have been reverted. Thus the protein would be glycosylated in yeast or other eukaryotic cells at $N_{25}$.

CEPINE010 is derived from human LACI domain 3 by the mutations R15V and E18F. CEPINE011 carries the mutations R15V, N17F, E18F, and T46K. The T46K mutation should prevent glycosylation at $N_{44}$. CEPINE012 carries more mutations so that it is much more similar to the known high-affinity hNE inhibitors. The mutations are D10V, L13P, R15V, N17F, E18F, K34V, 836G, and T46K.

EXAMPLE 23
Libraries of Kunitz Domains

Other Kunitz domains that can potently inhibit hNE may be derived from human Kunitz domains either by substituting hNE-inhibiting sequences into human domains or by using the methods of U.S. Pat. No. 5,223,409 and related patents. Table 720 shows a gene that will cause display of human LACI-D2 on M13 gIIIp; essentially the same gene could be used to achieve display on M13 gVIIIp or other anchor proteins (such as bacterial outer-surface proteins (OSPs)). Table 725 shows a gene to cause display of human LACI D1 while Table 750 shows a gene to cause display of LACI-D3.

Table 730, Table 735, and Table 760 give variegations of LACI-D1, LACI-D2, and LACI-D3 respectively. Each of these is divided into variegation of residues 10–21 in one segment and residues 31–42 in another. In each case, the appropriate vgDNA is introduced into a vector that displays the parental protein and the library of display phage are fractionated for binding to immobilized hNE.

Table 800 gives the sequences of naturally-occurring Kunitz domains. Table 810 gives the cumulative composition of each position over the sequences on Table 800 and shows which residues are found in five interaction surfaces defined in U.S. Pat. No. 5,223,409.

TABLE 28

Sequences of EPI-HNE-7 and ITI-D1 in the active site.

| Protein | Primary loop | | | | | | | | | Secondary loop | | | |
|---|---|---|---|---|---|---|---|---|---|---|---|---|---|
| | 10 | 11 | 13 | 15 | 16 | 17 | 18 | 19 | 20 | 31 | 32 | 34 | 39 |
| EpiNE-7 (Seq ID No. 001) | Y | T | P | V | A | M | F | P | R | Q | T | V | M |
| ITI-D1 (Seq ID No. 002) | S | A | P | M | G | M | T | S | R | E | T | Q | M |
| ITI-D2 (Seq ID No. 003) | V | R | P | R | A | F | I | Q | L | V | L | P | Q |

TABLE 30 sp::bpti::mautreIII fusion gene. The DNA sequence
has SEQ ID NO. 004; Amino-acid sequence has SEQ ID NO. 005
The DNA is linear. The amino-acid sequence is processed in vivo
and disulfide bonds form.

```
              m   k   k   l   l   f   a   I   p   l
              1   2   3   4   5   6   7   8   9   10
        5'-gt g aaa aaa tta tta ttc gca att cct tta
           |<---- gene III signal peptide ----------------
                                              ⌈ cleavage site
                                              ↓
          v   v   p   f   y   s   G   A
          11  12  13  14  15  16  17  18
          gtt gtt cct ttc tat tct GGc Gc c
          ---------------------------->|

| R | P | D | F | C | L | E |
          | 19| 20| 21| 22| 23| 24| 25|
          |CGT|CCC|GAT|TTC|TGT|CTC|GAG|-
        ↑  | AccIII |         | AvaI  |
  M13/BPTI Jnct                | XhoI  |

| P | P | Y | T | G | P | C | K | A | R |
| 26| 27| 28| 29| 30| 31| 32| 33| 34| 35|
|CCA|CCA|TAC|ACT|GGG|CCC|TGC|AAA|GCG|CGC|-
     | PflMI |                   | BssHII |
            | ApaI |
            | DraII |
            | PssI  |

| I | I | R | Y | F | Y | N | A | K | A |
| 36| 37| 38| 39| 40| 41| 42| 43| 44| 45|
|ATC|ATC|CGC|TAT|TTC|TAC|AAT|GCT|AAA|GC |-

| G | L | C | Q | T | F | V | Y | Q | G |
  | 46| 47| 48| 49| 50| 51| 52| 53| 54| 55|
 A|GGC|CTG|TGC|CAG|ACC|TTT|GTA|TAC|GGT|GGT|-
  | StuI |                 | AccI  |
                           | XcaI  |

| C | R | A | K | R | N | N | F | K |
| 56| 57| 58| 59| 60| 61| 62| 63| 64|
|TGC|CGT|GCT|AAG|CGT|AAC|AAC|TTT|AAA|-
     | EspI  |

| S | A | E | D | C | M | R | T | C | G |
| 65| 66| 67| 68| 69| 70| 71| 72| 73| 74|
|TCG|GCC|GAA|GAT|TGC|ATG|CGT|ACC|TGC|GGT|-
  | XmaIII |      | SphI  |

BPTI/M13 boundary
  ↓
```

TABLE 30-continued

```
!!  G  |  A  |  A    E       (Residue numbers of mature III have had
!!  75 |  76 | 119  120      118 added to the usual residue numbers.)
   | GGC | GCC | gct  gaa  -
!!     BbeI     |
!!     NarI     |
!
! 121 122 123 124 125 126 127 128 129 130 131 132 133 134 135
!  T   V   E   S   C   L   A   K   P   H   T   E   N   S   F
   act gtt gaa agt tgt tta gca aaa ccc cat aca gaa aat tca ttt
!
! 136 137 138 139 140 141 142 143 144 145 146 147 148 149 150
!  T   N   V   W   K   D   D   K   T   L   D   R   Y   A   N
   act aac gtc tgg aaa gac gac aaa act tta gat cgt tac gct aac
!
! 151 152 153 154 155 156 157 158 159 160 161 162 163 164 165
!  Y   E   G   C   L   W   N   A   T   G   V   V   V   C   T
   tat gag ggt tgt ctg tgg aat gct aca ggc gtt gta gtt tgt act
!
! 166 167 168 169 170 171 172 173 174 175 176 177 178 179 180
!  G   D   E   T   Q   C   Y   G   T   W   V   P   I   G   L
   ggt gac gaa act cag tgt tac ggt aca tgg gtt cct att ggg ctt
!
! 181 182 183 184 185 186 187 188 189 190 191 192 193 194 195
!  A   I   P   E   N   E   G   G   G   S   E   G   G   G   S
   gct atc cct gaa aat gag ggt ggt ggc tct gag ggt ggc ggt tct
!
! 196 197 198 199 200 201 202 203 204 205 206 207 208 209 210
!  E   G   G   G   S   E   G   G   G   T   K   P   P   E   Y
   gag ggt ggc ggt tct gag ggt ggc ggt act aaa cct cct gag tac
!
! 211 212 213 214 215 216 217 218 219 220 221 222 223 224 225
!  G   D   T   P   I   P   G   Y   T   Y   I   N   P   L   D
   ggt gat aca cct att ccg ggc tat act tat atc aac cct ctc gac
!
! 226 227 228 229 230 231 232 233 234 235 236 237 238 239 240
!  G   T   Y   P   P   G   T   E   Q   N   P   A   N   P   N
   ggc act tat ccg cct ggt act gag caa aac ccc gct aat cct aat
!
! 241 242 243 244 245 246 247 248 249 250 251 252 253 254 255
!  P   S   L   E   E   S   Q   P   L   N   T   F   M   F   Q
   cct tct ctt gag gag tct cag cct ctt aat act ttc atg ttt cag
!
! 256 257 258 259 260 261 262 263 264 265 266 267 268 269 270
!  N   N   R   F   R   N   R   Q   G   A   L   T   V   Y   T
   aat aat agg ttc cga aat agg cag ggg gca tta act gtt tat acg
!
! 271 272 273 274 275 276 277 278 279 280 281 282 283 284 285
!  G   T   V   T   Q   G   T   D   P   V   K   T   Y   Y   Q
   ggc act gtt act caa ggc act gac ccc gtt aaa act tat tac cag
!
! 286 287 288 289 290 291 292 293 294 295 296 297 298 299 300
!  Y   T   P   V   S   S   K   A   M   Y   D   A   Y   W   N
   tac act cct gta tca tca aaa gcc atg tat gac gct tac tgg aac
!
! 301 302 303 304 305 306 307 308 309 310 311 312 313 314 315
!  G   K   F   R   D   C   A   F   H   S   G   F   N   E   D
   ggt aaa ttc aga gac tgc gct ttc cat tct ggc ttt aat gag gat
```

TABLE 30-continued

| 316 | 317 | 318 | 319 | 320 | 321 | 322 | 323 | 324 | 325 | 326 | 327 | 328 | 329 | 330 |
|---|---|---|---|---|---|---|---|---|---|---|---|---|---|---|
| P | F | V | C | E | Y | Q | G | Q | S | S | D | L | P | Q |
| cca | ttc | gtt | tgt | gaa | tat | caa | ggc | caa | tcg | tct | gac | ctg | cct | caa |

| 331 | 332 | 333 | 334 | 335 | 336 | 337 | 338 | 339 | 340 | 341 | 342 | 343 | 344 | 345 |
|---|---|---|---|---|---|---|---|---|---|---|---|---|---|---|
| P | P | V | N | A | G | G | S | G | G | G | S | G | G | |
| cct | cct | gtc | aat | gct | ggc | ggc | ggc | tct | ggt | ggt | ggt | tct | ggt | ggc |

| 346 | 347 | 348 | 349 | 350 | 351 | 352 | 353 | 354 | 355 | 356 | 357 | 358 | 359 | 360 |
|---|---|---|---|---|---|---|---|---|---|---|---|---|---|---|
| G | S | E | G | G | S | E | G | G | S | E | G | G | | |
| ggc | tct | gag | ggt | ggt | ggc | tct | gag | ggt | ggc | ggt | tct | gag | ggt | ggc |

| 361 | 362 | 363 | 364 | 365 | 366 | 367 | 368 | 369 | 370 | 371 | 372 | 373 | 374 | 375 |
|---|---|---|---|---|---|---|---|---|---|---|---|---|---|---|
| G | S | E | G | G | S | G | G | S | G | S | G | D | | |
| ggc | tct | gag | gga | ggc | ggt | tcc | ggt | ggt | ggc | tct | ggt | tcc | ggt | gat |

| 376 | 377 | 378 | 379 | 380 | 381 | 382 | 383 | 384 | 385 | 386 | 387 | 388 | 389 | 390 |
|---|---|---|---|---|---|---|---|---|---|---|---|---|---|---|
| F | D | Y | E | K | M | A | N | A | N | K | G | A | M | T |
| ttt | gat | tat | gaa | aag | atg | gca | aac | gct | aat | aag | ggg | gct | atg | acc |

| 391 | 392 | 393 | 394 | 395 | 396 | 397 | 398 | 399 | 400 | 401 | 402 | 403 | 404 | 405 |
|---|---|---|---|---|---|---|---|---|---|---|---|---|---|---|
| E | N | A | D | E | N | A | L | Q | S | D | A | K | G | K |
| gaa | aat | gcc | gat | gaa | aac | gcg | cta | cag | tct | gac | gct | aaa | ggc | aaa |

| 406 | 407 | 408 | 409 | 410 | 411 | 412 | 413 | 414 | 415 | 416 | 417 | 418 | 419 | 420 |
|---|---|---|---|---|---|---|---|---|---|---|---|---|---|---|
| L | D | S | V | A | T | D | Y | G | A | A | I | D | G | F |
| ctt | gat | tct | gtc | gct | act | gat | tac | ggt | gct | gct | atc | gat | ggt | ttc |

| 421 | 422 | 423 | 424 | 425 | 426 | 427 | 428 | 429 | 430 | 431 | 432 | 433 | 434 | 435 |
|---|---|---|---|---|---|---|---|---|---|---|---|---|---|---|
| I | G | D | V | S | G | L | A | N | G | N | G | A | T | G |
| att | ggt | gac | gtt | tcc | ggc | ctt | gct | aat | ggt | aat | ggt | gct | act | ggt |

| 436 | 437 | 438 | 439 | 440 | 441 | 442 | 443 | 444 | 445 | 446 | 447 | 448 | 449 | 450 |
|---|---|---|---|---|---|---|---|---|---|---|---|---|---|---|
| D | F | A | G | S | N | S | Q | M | A | Q | V | G | D | G |
| gat | ttt | gct | ggc | tct | aat | tcc | caa | atg | gct | caa | gtc | ggt | gac | ggt |

| 451 | 452 | 453 | 454 | 455 | 456 | 457 | 458 | 459 | 460 | 461 | 462 | 463 | 464 | 465 |
|---|---|---|---|---|---|---|---|---|---|---|---|---|---|---|
| D | N | S | P | L | M | N | N | F | R | Q | Y | L | P | S |
| gat | aat | tca | cct | tta | atg | aat | aat | ttc | cgt | caa | tat | tta | cct | tcc |

| 466 | 467 | 468 | 469 | 470 | 471 | 472 | 473 | 474 | 475 | 476 | 477 | 478 | 479 | 480 |
|---|---|---|---|---|---|---|---|---|---|---|---|---|---|---|
| L | P | Q | S | V | E | C | R | P | F | V | F | S | A | G |
| ctc | cct | caa | tcg | gtt | gaa | tgt | cgc | cct | ttt | gtc | ttt | agc | gct | ggt |

| 481 | 482 | 483 | 484 | 485 | 486 | 487 | 488 | 489 | 490 | 491 | 492 | 493 | 494 | 495 |
|---|---|---|---|---|---|---|---|---|---|---|---|---|---|---|
| K | P | Y | E | F | S | I | D | C | D | K | I | N | L | F |
| aaa | cca | tat | gaa | ttt | tct | att | gat | tgt | gac | aaa | ata | aac | tta | ttc |

| 496 | 497 | 498 | 499 | 500 | 501 | 502 | 503 | 504 | 505 | 506 | 507 | 508 | 509 | 510 |
|---|---|---|---|---|---|---|---|---|---|---|---|---|---|---|
| R | G | V | F | A | F | L | L | Y | V | A | T | F | M | Y |
| cgt | ggt | gtc | ttt | gcg | ttt | ctt | tta | tat | gtt | gcc | acc | ttt | atg | tat |

| 511 | 512 | 513 | 514 | 515 | 516 | 517 | 518 | 519 | 520 | 521 | 522 | 523 | 524 | 525 |
|---|---|---|---|---|---|---|---|---|---|---|---|---|---|---|

TABLE 30-continued

| ! | V | F | S | T | F | A | N | I | L | R | N | K | E | S | . |
|---|---|---|---|---|---|---|---|---|---|---|---|---|---|---|---|
|   | gta | ttt | tct | acg | ttt | gct | aac | ata | ctg | cgt | aat | aag | gag | tct | taa |

!

TABLE 35

IIIsp::itiD1::matureIII fusion gene.
DNA has SEQ ID NO. 006; amino-acid sequence has SEQ ID NO. 007. The DNA is a linear segment and the amino-acid sequence is a protein that is processed in vivo and which contains disulfides.

| | m | k | k | l | l | f | a | I | p | l | v | v | p | f | y |
|---|---|---|---|---|---|---|---|---|---|---|---|---|---|---|---|
| | -18 | -17 | -16 | -15 | -14 | -13 | -12 | -11 | -10 | -9 | -8 | -7 | -6 | -5 | -4 |
| 5'- | gtg | aaa | aaa | tta | tta | ttc | gca | att | cct | tta | gtt | gtt | cct | ttc | tat |

| <---- gene III signal peptide ---------------------------------------·

┌─ cleavage site

| | s | G | A | K | E | D | S | C | Q | L | G | Y | S | A | G |
|---|---|---|---|---|---|---|---|---|---|---|---|---|---|---|---|
| | -3 | -2 | -1 | 1 | 2 | 3 | 4 | 5 | 6 | 7 | 8 | 9 | 10 | 11 | 12 |
| | tct | GGc | Gcc | aaa | gaa | gaC | tcT | tGC | CAG | CTG | GGC | tac | tCG | GCC | Ggt |
| | | | | | | | | └─ BglII ─┘ | | | └─ EagI ─┘ | |

········>|
└ KasI ┘

| 13 | 14 | 15 | 16 | 17 | 18 | 19 | 20 | 21 | 22 | 23 | 24 | 25 | 26 |
|---|---|---|---|---|---|---|---|---|---|---|---|---|---|
| P | C | M | G | M | T | S | R | Y | F | Y | N | G | T |
| ccc | tgc | atg | gga | atg | acc | agc | agg | tat | ttc | tat | aat | ggt | aca |

| 27 | 28 | 29 | 30 | 31 | 32 | 33 | 34 | 35 | 36 | 37 | 38 | 39 | 40 | 41 |
|---|---|---|---|---|---|---|---|---|---|---|---|---|---|---|
| S | M | A | C | E | T | F | Q | Y | G | G | C | M | G | N |
| tCC | ATG | Gcc | tgt | gag | act | ttc | cag | tac | ggc | ggc | tgc | atg | ggc | aac |
| └ NcoI ┘ | | | | | | | | | | | | | | |
| └ StyI ┘ | | | | | | | | | | | | | | |

| 42 | 43 | 44 | 45 | 46 | 47 | 48 | 49 | 50 | 51 | 52 | 53 | 54 | 55 | 56 |
|---|---|---|---|---|---|---|---|---|---|---|---|---|---|---|
| G | N | N | F | V | T | E | K | E | C | L | Q | T | C | R |
| ggt | aac | aac | ttc | gtc | aca | gaa | aag | gag | tgt | CTG | CAG | acc | tgc | cga |
| | | | | | | | | | | └─ PstI ─┘ | | | | |

| 57 | 58 | 101 | 102 | 119 | 120 |
|---|---|---|---|---|---|
| T | V | g | g | A | E |
| act | gtg | ggc | gcc | gct | gaa |
| | | └ BbeI ┘ | | | |
| | | └ NarI ┘ | | | |
| | | └ KasI ┘ | | | |

(Residue numbers of mature III have had 118 added to the usual residue numbers.)

| 121 | 122 | 123 | 124 | 125 | 126 | 127 | 128 | 129 | 130 | 131 | 132 | 133 | 134 | 135 |
|---|---|---|---|---|---|---|---|---|---|---|---|---|---|---|
| T | V | E | S | C | L | A | K | P | H | T | E | N | S | F |
| act | gtt | gaa | agt | tgt | tta | gca | aaa | ccc | cat | aca | gaa | aat | tca | ttt |

| 136 | 137 | 138 | 139 | 140 | 141 | 142 | 143 | 144 | 145 | 146 | 147 | 148 | 149 | 150 |
|---|---|---|---|---|---|---|---|---|---|---|---|---|---|---|
| T | N | V | W | K | D | D | K | T | L | D | R | Y | A | N |
| act | aac | gtc | tgg | aaa | gac | gac | aaa | act | tta | gat | cgt | tac | gct | aac |

| 151 | 152 | 153 | 154 | 155 | 156 | 157 | 158 | 159 | 160 | 161 | 162 | 163 | 164 | 165 |
|---|---|---|---|---|---|---|---|---|---|---|---|---|---|---|
| Y | E | G | C | L | W | N | A | T | G | V | V | V | C | T |
| tat | gag | ggt | tgt | ctg | tgg | aat | gct | aca | ggc | gtt | gta | gtt | tgt | act |

| 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|
| G | D | E | T | Q | C | Y | G | T | W | V | P | I | G | L |
| ggt | gac | gaa | act | cag | tgt | tac | ggt | aca | tgg | gtt | cct | att | ggg | ctt |

| 181 | 182 | 183 | 184 | 185 | 186 | 187 | 188 | 189 | 190 | 191 | 192 | 193 | 194 | 195 |
|---|---|---|---|---|---|---|---|---|---|---|---|---|---|---|
| A | I | P | E | N | E | G | G | S | E | G | G | G | G | S |
| gct | atc | cct | gaa | aat | gag | ggt | ggc | tct | gag | ggt | ggc | ggt | tct |

| 196 | 197 | 198 | 199 | 200 | 201 | 202 | 203 | 204 | 205 | 206 | 207 | 208 | 209 | 210 |
|---|---|---|---|---|---|---|---|---|---|---|---|---|---|---|
| E | G | G | G | S | E | G | G | G | T | K | P | P | E | Y |
| gag | ggt | ggc | ggt | tct | gag | ggt | ggc | ggt | act | aaa | cct | cct | gag | tac |

| 211 | 212 | 213 | 214 | 215 | 216 | 217 | 218 | 219 | 220 | 221 | 222 | 223 | 224 | 225 |
|---|---|---|---|---|---|---|---|---|---|---|---|---|---|---|
| G | D | T | P | I | P | G | Y | T | Y | I | N | P | L | D |
| ggt | gat | aca | cct | att | ccg | ggc | tat | act | tat | atc | aac | cct | ctc | gac |

TABLE 35-continued

IIIsp::itiD1::matureIII fusion gene.
DNA has SEQ ID NO. 006; amino-acid sequence has SEQ ID NO. 007. The DNA is a linear segment and the amino-acid sequence is a protein that is processed in vivo and which contains disulfides.

| 226 | 227 | 228 | 229 | 230 | 231 | 232 | 233 | 234 | 235 | 236 | 237 | 238 | 239 | 240 |
|---|---|---|---|---|---|---|---|---|---|---|---|---|---|---|
| G | T | Y | P | P | G | T | E | Q | N | P | A | N | P | N |
| ggc | act | tat | ccg | cct | ggt | act | gag | caa | aac | ccc | gct | aat | cct | aat |

| 241 | 242 | 243 | 244 | 245 | 246 | 247 | 248 | 249 | 250 | 251 | 252 | 253 | 254 | 255 |
|---|---|---|---|---|---|---|---|---|---|---|---|---|---|---|
| P | S | L | E | E | S | Q | P | L | N | T | F | M | F | Q |
| cct | tct | ctt | gag | gag | tct | cag | cct | ctt | aat | act | ttc | atg | ttt | cag |

| 256 | 257 | 258 | 259 | 260 | 261 | 262 | 263 | 264 | 265 | 266 | 267 | 268 | 269 | 270 |
|---|---|---|---|---|---|---|---|---|---|---|---|---|---|---|
| N | N | R | F | R | N | R | Q | G | A | L | T | V | Y | T |
| aat | aat | agg | ttc | cga | aat | agg | cag | ggg | gca | tta | act | gtt | tat | acg |

| 271 | 272 | 273 | 274 | 275 | 276 | 277 | 278 | 279 | 280 | 281 | 282 | 283 | 284 | 285 |
|---|---|---|---|---|---|---|---|---|---|---|---|---|---|---|
| G | T | V | T | Q | G | T | D | P | V | K | T | Y | Y | Q |
| ggc | act | gtt | act | caa | ggc | act | gac | ccc | gtt | aaa | act | tat | tac | cag |

| 286 | 287 | 288 | 289 | 290 | 291 | 292 | 293 | 294 | 295 | 296 | 297 | 298 | 299 | 300 |
|---|---|---|---|---|---|---|---|---|---|---|---|---|---|---|
| Y | T | P | V | S | S | K | A | M | Y | D | A | Y | W | N |
| tac | act | cct | gta | tca | tca | aaa | gcc | atg | tat | gac | gct | tac | tgg | aac |

| 301 | 302 | 303 | 304 | 305 | 306 | 307 | 308 | 309 | 310 | 311 | 312 | 313 | 314 | 315 |
|---|---|---|---|---|---|---|---|---|---|---|---|---|---|---|
| G | K | F | R | D | C | A | F | H | S | G | F | N | E | D |
| ggt | aaa | ttc | aga | gac | tgc | gct | ttc | cat | tct | ggc | ttt | aat | gaG | GAT |

⌞ BamHI

| 316 | 317 | 318 | 319 | 320 | 321 | 322 | 323 | 324 | 325 | 326 | 327 | 328 | 329 | 330 |
|---|---|---|---|---|---|---|---|---|---|---|---|---|---|---|
| P | F | V | C | E | Y | Q | G | Q | S | S | D | L | P | Q |
| CCa | ttc | gtt | tgt | gaa | tat | caa | ggc | caa | tcg | tct | gac | ctg | cct | caa |

⌝ BamHI

| 331 | 332 | 333 | 334 | 335 | 336 | 337 | 338 | 339 | 340 | 341 | 342 | 343 | 344 | 345 |
|---|---|---|---|---|---|---|---|---|---|---|---|---|---|---|
| P | P | V | N | A | G | G | S | G | G | G | S | G | G |
| cct | cct | gtc | aat | gct | ggc | ggc | ggc | tct | ggt | ggt | ggt | tct | ggt | ggc |

| 346 | 347 | 348 | 349 | 350 | 351 | 352 | 353 | 354 | 355 | 356 | 357 | 358 | 359 | 360 |
|---|---|---|---|---|---|---|---|---|---|---|---|---|---|---|
| G | S | E | G | G | S | E | G | G | S | E | G | G |
| ggc | tct | gag | ggt | ggt | ggc | tct | gag | ggt | ggc | ggt | tct | gag | ggt | ggc |

| 361 | 362 | 363 | 364 | 365 | 366 | 367 | 368 | 369 | 370 | 371 | 372 | 373 | 374 | 375 |
|---|---|---|---|---|---|---|---|---|---|---|---|---|---|---|
| G | S | E | G | G | S | G | G | S | G | S | G | D |
| ggc | tct | gag | gga | ggc | ggt | tcc | ggt | ggt | ggc | tct | ggt | tcc | ggt | gat |

| 376 | 377 | 378 | 379 | 380 | 381 | 382 | 383 | 384 | 385 | 386 | 387 | 388 | 389 | 390 |
|---|---|---|---|---|---|---|---|---|---|---|---|---|---|---|
| F | D | Y | E | K | M | A | N | A | N | K | G | A | M | T |
| ttt | gat | tat | gaa | aag | atg | gca | aac | gct | aat | aag | ggg | gct | atg | acc |

| 391 | 392 | 393 | 394 | 395 | 396 | 397 | 398 | 399 | 400 | 401 | 402 | 403 | 404 | 405 |
|---|---|---|---|---|---|---|---|---|---|---|---|---|---|---|
| E | N | A | D | E | N | A | L | Q | S | D | A | K | G | K |
| gaa | aat | gcc | gat | gaa | aac | gcg | cta | cag | tct | gac | gct | aaa | ggc | aaa |

| 406 | 407 | 408 | 409 | 410 | 411 | 412 | 413 | 414 | 415 | 416 | 417 | 418 | 419 | 420 |
|---|---|---|---|---|---|---|---|---|---|---|---|---|---|---|
| L | D | S | V | A | T | D | Y | G | A | A | I | D | G | F |
| ctt | gat | tct | gtc | gct | act | gat | tac | ggt | gct | gct | atc | gat | ggt | ttc |

| 421 | 422 | 423 | 424 | 425 | 426 | 427 | 428 | 429 | 430 | 431 | 432 | 433 | 434 | 435 |
|---|---|---|---|---|---|---|---|---|---|---|---|---|---|---|
| I | G | D | V | S | G | L | A | N | G | N | G | A | T | G |
| att | ggt | gac | gtt | tcc | ggc | ctt | gct | aat | ggt | aat | ggt | gct | act | ggt |

| 436 | 437 | 438 | 439 | 440 | 441 | 442 | 443 | 444 | 445 | 446 | 447 | 448 | 449 | 450 |
|---|---|---|---|---|---|---|---|---|---|---|---|---|---|---|
| D | F | A | G | S | N | S | Q | M | A | Q | V | G | D | G |
| gat | ttt | gct | ggc | tct | aat | tcc | caa | atg | gct | caa | gtc | ggt | gac | ggt |

| 451 | 452 | 453 | 454 | 455 | 456 | 457 | 458 | 459 | 460 | 461 | 462 | 463 | 464 | 465 |
|---|---|---|---|---|---|---|---|---|---|---|---|---|---|---|
| D | N | S | P | L | M | N | N | F | R | Q | Y | L | P | S |
| gat | aat | tca | cct | tta | atg | aat | aat | ttc | cgt | caa | tat | tta | cct | tcc |

| 466 | 467 | 468 | 469 | 470 | 471 | 472 | 473 | 474 | 475 | 476 | 477 | 478 | 479 | 480 |
|---|---|---|---|---|---|---|---|---|---|---|---|---|---|---|
| L | P | Q | S | V | E | C | R | P | F | V | F | S | A | G |
| ctc | cct | caa | tcg | gtt | gaa | tgt | cgc | cct | ttt | gtc | ttt | agc | gct | ggt |

| 481 | 482 | 483 | 484 | 485 | 486 | 487 | 488 | 489 | 490 | 491 | 492 | 493 | 494 | 495 |
|---|---|---|---|---|---|---|---|---|---|---|---|---|---|---|
| K | P | Y | E | F | S | I | D | C | D | K | I | N | L | F |
| aaa | cca | tat | gaa | ttt | tct | att | gat | tgt | gac | aaa | ata | aac | tta | ttc |

TABLE 35-continued

IIIsp::itiD1::matureIII fusion gene.
DNA has SEQ ID NO. 006; amino-acid sequence has SEQ ID NO. 007. The DNA is a linear segment and the amino-acid sequence is a protein that is processed in vivo and which contains disulfides.

| 496 | 497 | 498 | 499 | 500 | 501 | 502 | 503 | 504 | 505 | 506 | 507 | 508 | 509 | 510 |
|---|---|---|---|---|---|---|---|---|---|---|---|---|---|---|
| R | G | V | F | A | F | L | L | Y | V | A | T | F | M | Y |
| cgt | ggt | gtc | ttt | gcg | ttt | ctt | tta | tat | gtt | gcc | acc | ttt | atg | tat |

| 511 | 512 | 513 | 514 | 515 | 516 | 517 | 518 | 519 | 520 | 521 | 522 | 523 | 524 | 525 |
|---|---|---|---|---|---|---|---|---|---|---|---|---|---|---|
| V | F | S | T | F | A | N | I | L | R | N | K | E | S | . |
| gta | ttt | tct | acg | ttt | gct | aac | ata | ctg | cgt | aat | aag | gag | tct | taa |

TABLE 40

Local sequences of Kunitz domains derived from BPTI or ITI-D1.

| Protein | 1 | 2 | 3 | 4 | 11 | 15 | 16 | 17 | 18 | 19 | 26 | 31 | 34 |
|---|---|---|---|---|---|---|---|---|---|---|---|---|---|
| EpiNE-7 SEQ ID NO. 001 | R | P | D | F | T | V | A | M | F | P | K | Q | V |
| ITI-D1 SEQ ID NO. 008 | K | E | D | S | A | M | G | M | T | S | T | E | Q |
| ITI-D1E7 SEQ ID NO. 009 | K | E | D | S | A | V | A | M | F | P | T | E | Q |
| BITI-E7 SEQ ID NO. 010 | R | P | D | F | A | V | A | M | F | P | T | E | Q |
| BITI-E7-141 SEQ ID NO. 011 | R | P | D | F | A | V | A | M | F | P | T | E | Q |
| BITI-E7-1222 SEQ ID NO. 012 | R | P | D | F | T | V | A | M | F | P | T | E | Q |
| MUT1619 SEQ ID NO. 013 | R | P | D | F | A | V | G | M | F | S | T | Q | V |
| MUTP1 SEQ ID NO. 014 | R | P | D | F | A | I | G | M | F | S | T | Q | V |
| AMINO1 SEQ ID NO. 015 | K | E | D | F | A | V | A | M | F | P | T | Q | V |
| AMINO2 SEQ ID NO. 016 | K | P | D | S | A | V | A | M | F | P | T | Q | V |
| MUTQE SEQ ID NO. 017 | R | P | D | F | A | V | A | M | F | P | T | E | V |
| MUTT26A SEQ ID NO. 018 | R | P | D | F | A | V | A | M | F | P | A | Q | V |

TABLE 55

Affinity Classes of ITI-D1-derived hNE inhibitors

| Affinity Class | Estimated $K_D$ | Fraction of Input bound | pH Elution Maximum | Protein |
|---|---|---|---|---|
| WEAK | $K_D$ > 10 nM | <0.005% | >6.0 | ITI-D1 |
| MODERATE | 1 to 10 nM | 0.01% to 0.03% | 5.5 to 5.0 | BITI<br>ITI-D1E7 |
| STRONG | 10 to 1000 pM | 0.03% to 0.06% | 5.0 to 4.5 | BITI-E7<br>BITI-E7-1222<br>AMINO1<br>AMINO2<br>MUTP1 |
| VERY STRONG | <10 pM | >0.1% | ≦4.0 | BITI-E7-141<br>MUTT26A<br>MUTQE<br>MUT1619 |

TABLE 100 hNE-inhibiting Kunitz domains and their parental domains

| Sequence | Name | Parental Domain | SEQ ID NO. |
|---|---|---|---|
| RPDFCLEPPYTGPCKARIIRYFYNAKAGLCQTFVYGGCRAKRNNFKSAEDCMRTCGGA | BPTI | BPTI | 021 |
| RPDFCLEPPYTGPCvAmfpRYFYNAKAGLCQTFVYGGCmgngNNFKSAEDCMRTCGGA | EpiNE7 (5) | BPTI | 001 |
| RPDFCLEPPYTGPCvpftsRYFYNAKAGLCQTFVYGGCmgngNNFKSAEDCMRTCGGA | EpiNE3 (6) | BPTI | 022 |
| RPDFCLEPPYTGPCvgftqRYFYNAKAGLCQTFVYGGCmgngNNFKSAEDCMRTCGGA | EpiNE6 | BPTI | 023 |
| RPDFCLEPPYTGPCvAifpRYFYNAKAGLCQTFVYGGCmgngNNFKSAEDCMRTCGGA | EpiNE4 | BPTI | 024 |
| RPDFCLEPPYTGPCvAffpRYFYNAKAGLCQTFVYGGCmgngNNFKSAEDCMRTCGGA | EpiNE8 | BPTI | 025 |
| RPDFCLEPPYTGPCiAffpRYFYNAKAGLCQTFVYGGCmgngNNFKSAEDCMRTCGGA | EpiNE1 (4) | BPTI | 026 |
| RPDFCLEPPYTGPCiAffqRYFYNAKAGLCQTFVYGGCmgngNNFKSAEDCMRTCGGA | EPI-HNE-2 | BPTI | 027 |
| RPDFCLEPPYTGPCiAftqRYFYNAKAGLCQTFVYGGCmgngNNFKSAEDCMRTCGGA | EpiNE5 | BPTI | 028 |
| RPDFCLEPPYTGPClAlfkRYFYNAKAGLCQTFVYGGCmgngNNFKSAEDCMRTCGGA | EpiNE2 | BPTI | 029 |
| KEDSCQLGYSAGPCMGMTSRYFYNGTSMACETFQYGGCMGNGNNFVTEKDCLQTCRGA | ITI-D1 | ITI-D1 | 008 |
| KEDSCQLGYSAGPCvaMEpRYFYNGTSMACETFQYGGCMGNGNNFVTEKDCLQTCRGA | ITI-D1E7 | ITI-D1 | 009 |
| pDfCQLGYSAGPCMGMTSRYFYNGTSMACETFQYGGCMGNGNNFVTEKDCLQTCRGA | BITI | ITI-D1 | 030 |
| pDfCQLGYSAGPCvaMEpRYFYNGTSMACETFQYGGCMGNGNNFVTEKDCLQTCRGA | BITI-E7 | ITI-D1 | 010 |
| pDfCQLGYSAGPCfGpCyaMEpRYFYNGTSMACETFQYGGCMGNGNNFVTEKDCLQTCRGA | BITI-E7-1222 | ITI-D1 | 012 |
| KEDSCQLGYSAGPCvaMEpRYFYNGTSMACETFQYGGCMGNGNNFVTEKDCLQTCRGA | AMINO1 | ITI-D1 | 015 |
| KpDSCQLGYSAGPCiGMfSRYFYNGTSMAcETFQYGGCMGNGNNFVTEKDCLQTCRGA | AMINO2 | ITI-D1 | 016 |
| pDfCQLGYSAGPCvaMfpRYFYNGTSMACETFQYGGCMGNGNNFVTEKDCLQTCRGA | MUTP1 | ITI-D1 | 014 |
| pDfCQLGYSAGPCvaMfpRYFYNGaSMACiTFtYGGCMGNGNNFVTEKDCLQTCRGA | BITI-E7-141 | ITI-D1 | 011 |
| pDfCQLGYSAGPCvaMfpRYFYNGTSMACiTFtYGGCMGNGNNFVTEKDCLQTCRGA | MUTT26A | ITI-D1 | 018 |
| pDfCQLGYSAGPCvaMfpRYFYNGTSMACqTFtYGGCMGNGNNFVTEKDCLQTCRGA | MUTQE | ITI-D1 | 017 |
| pDfCQLGYSAGPCvGMfSRYFYNGTSMACqTFtYGGCMGNGNNFVTEKDCLQTCRGA | MUT1619 | ITI-D1 | 013 |
| TVAACNLPIVRGPCRAFIQLWAFDAVKGKCVLFPYGGCQGNGNKFYSEKECREYCGVP | ITI-D2 | ITI-D2 | 003 |
| AACNLPIVRGPCiAFfpfWAFDAVKGKCVLFPYGGCQGNGNKFYSEKECREYCGVP | EPI-hNE-3 | ITI-D2 | 019 |
| tACNLPIVRGPCiAFfpfWAFDAVKGKCVLFPYGGCQGNGNKFYSEKECREYCGVP | EPI-hNE-4 | ITI-D2 | 020 |

The lines show disulfides. The numbers in parentheses after Epine3, Epine7, and Epine1 show how many times these sequences were isolated.

TABLE 208

SEQUENCES OF THE EpiNE CLONES IN THE P1 REGION
Proteins have the sequence of BPTI at other residues except that all carry the changes
R39M, A40G, K41N, and R42G.

| Protein | _____ Residue _____ | | | | | | | | |
|---|---|---|---|---|---|---|---|---|---|
| | 13 | 14 | 15 P1 | 16 | 17 | 18 | 19 | 20 | 21 |
| EpiNE3 | P | C | V | G | F | F | S | R | Y |
| SEQ ID NO. 022 | CCT | TGC | GTC | GGT | TTC | TTC | TCA | CGC | TAT |
| EpiNE6 | P | C | V | G | F | F | Q | R | Y |
| SEQ ID NO. 023 | CCT | TGC | GTC | GGT | TTC | TTC | CAA | CGC | TAT |
| EpiNE7 | P | C | V | A | M | F | P | R | Y |
| SEQ ID NO. 001 | CCT | TGC | GTC | GCT | ATG | TTC | CCA | CGC | TAT |
| EpiNE4 | P | C | V | A | I | F | P | R | Y |
| SEQ ID NO. 024 | CCT | TGC | GTC | GCT | ATC | TTC | CCA | CGC | TAT |
| EpiNE8 | P | C | V | A | I | F | K | R | S |
| SEQ ID NO. 025 | CCT | TGC | GTC | GCT | ATC | TTC | AAA | CGC | TCT |
| EpiNE1 | P | C | I | A | F | F | P | R | Y |
| SEQ ID NO. 026 | CCT | TGC | ATC | GCT | TTC | TTC | CCA | CGC | TAT |
| EpiNE5 | P | C | I | A | F | F | Q | R | Y |
| SEQ ID NO. 028 | CCT | TGC | ATC | GCT | TTC | TTC | CAA | CGC | TAT |
| EpiNE2 | P | C | I | A | L | F | K | R | Y |
| SEQ ID NO. 029 | CCT | TGC | ATC | GCT | TTG | TTC | AAA | CGC | TAT |

TABLE 209

BPTI analogues selected for binding to Cathepsin G
DNA sequences and predicted amino acid sequences around the P1 region of BPTI
analogues selected for binding to Cathepsin G. Proteins have the sequence of BPTI at
other residues except that all carry the changes R39M, A40G, K41N, and R42G.

| Protein | _____ Residue _____ | | | | | | | | | |
|---|---|---|---|---|---|---|---|---|---|---|
| | 10 | 11 | 12 | 13 | 14 | 15 P1 | 16 | 17 | 18 | 19 |
| BPTI | Y | T | G | P | C | K | A | R | I | I |
| SEQ ID NO. 021 | TAC | ACT | GGG | CCC | TGC | AAA | GCG | CGC | ATC | ATC |
| EpiC 1 | Y | T | G | P | C | M | G | F | S | K |
| SEQ ID NO. 031 | TAC | ACT | GGG | CCC | TGC | ATG | GGT | TTC | TCC | AAA |
| EpiC 7 | Y | T | G | P | C | M | A | L | F | K |
| SEQ ID NO. 032 | TAC | ACT | GGG | CCC | TGC | ATG | GCT | TTG | TTC | AAA |
| EpiC 8 | N | T | G | P | C | F | A | I | T | P |
| SEQ ID NO. 033 | AAC | ACT | GGG | CCC | TGC | TTC | GCT | ATC | ACC | CCA |
| EpiC 10 | Y | T | G | P | C | M | A | L | F | Q |
| SEQ ID NO. 034 | TAC | ACT | GGG | CCC | TGC | ATG | GCT | TTG | TTC | CAA |
| EpiC 20 | Y | T | G | P | C | M | A | I | S | P |
| SEQ ID NO. 035 | TAC | ACT | GGG | CCC | TGC | ATG | GCT | ATC | TCC | CCA |

TABLE 210

Derivatives of EpiNE7 Obtained by Variegation at positions 34, 36, 39, 40 and 41

```
           1          2          3          4          5
1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8   Protein              SEQ ID No.
RPDFCLEPPYTGPCvAmfpRYFYNAKAGLCQTFVYGGCmgngNNFKSAEDCMRTCGGA                                         EpiNE7               001
RPDFCLEPPYTGPCvAmfpRYFYNAKAGLCQTFl Yg GCk gkGNNFKSAEDCMRTCGGA                                      EpiNE7.6             036

RPDFCLEPPYTGPCvAmfpRYFYNAKAGLCQTFe Yg GCwakGNNFKSAEDCMRTCGGA                                       EpiNE7.8, 7.9, & 7.31 037

RPDFCLEPPYTGPCvAmfpRYFYNAKAGLCQTFg Ya GCr akGNNFKSAEDCMRTCGGA                                      EpiNE7.11            038

RPDFCLEPPYTGPCvAmfpRYFYNAKAGLCQTFe Yg GCh aeGNNFKSAEDCMRTCGGA                                      EpiNE7.7             039

RPDFCLEPPYTGPCvAmfpRYFYNAKAGLCQTFl Yg GCwaqGNNFKSAEDCMRTCGGA                                       EpiNE7.4 & 7.14      040

RPDFCLEPPYTGPCvAmfpRYFYNAKAGLCQTFr Yg GCl aeGNNFKSAEDCMRTCGGA                                      EpiNE7.5             041

RPDFCLEPPYTGPCvAmfpRYFYNAKAGLCQTFd Yg GCh adGNNFKSAEDCMRTCGGA                                      EpiNE7.10 & 7.20     042

RPDFCLEPPYTGPCvAmfpRYFYNAKAGLCQTFk Yg GCl ahGNNFKSAEDCMRTCGGA                                      EpiNE7.1             043

RPDFCLEPPYTGPCvAmfpRYFYNAKAGLCQTFt Yg GCwanGNNFKSAEDCMRTCGGA                                       EpiNE7.16            044

RPDFCLEPPYTGPCvAmfpRYFYNAKAGLCQTFn Yg GCe gkGNNFKSAEDCMRTCGGA                                      EpiNE7.19            045

RPDFCLEPPYTGPCvAmfpRYFYNAKAGLCQTFq Yg GCe gyGNNFKSAEDCMRTCGGA                                      EpiNE7.12            046

RPDFCLEPPYTGPCvAmfpRYFYNAKAGLCQTFq Yg GCl geGNNFKSAEDCMRTCGGA                                      EpiNE7.17            047

RPDFCLEPPYTGPCvAmfpRYFYNAKAGLCQTFh Yg GCwgqGNNFKSAEDCMRTCGGA                                       EpiNE7.21            048

RPDFCLEPPYTGPCvAmfpRYFYNAKAGLCQTFh Yg GCwgeGNNFKSAEDCMRTCGGA                                       EpiNE7.22            049

RPDFCLEPPYTGPCvAmfpRYFYNAKAGLCQTFk Yg GCwgkGNNFKSAEDCMRTCGGA                                       EpiNE7.23            050

RPDFCLEPPYTGPCvAmfpRYFYNAKAGLCQTFk Yg GCh gnGNNFKSAEDCMRTCGGA                                      EpiNE7.24            051

RPDFCLEPPYTGPCvAmfpRYFYNAKAGLCQTFp Yg GCwakGNNFKl AEDCMRTCGGA                                      EpiNE7.25            052

RPDFCLEPPYTGPCvAmfpRYFYNAKAGLCQTFk Yg GCwghGNNFKSAEDCMRTCGGA                                       EpiNE7.26            053

RPDFCLEPPYTGPCvAmfpRYFYNAKAGLCQTFn Yg GCwgkGNNFKSAEDCMRTCGGA                                       EpiNE7.27            054

RPDFCLEPPYTGPCvAmfpRYFYNAKAGLCQTFt Yg GCl ghGNNFKSAEDCMRTCGGA                                      EpiNE7.28            055

RPDFCLEPPYTGPCvAmfpRYFYNAKAGLCQTFt Yg GCl gyGNNFKSAEDCMRTCGGA                                      EpiNE7.29            056

RPDFCLEPPYTGPCvAmfpRYFYNAKAGLCQTFk Yg GCwaeGNNFKSAEDCMRTCGGA                                       EpiNE7.30, .34, & .35 057

RPDFCLEPPYTGPCvAmfpRYFYNAKAGLCQTFg Yg GCwgeGNNFKSAEDCMRTCGGA                                       EpiNE7.32            058

RPDFCLEPPYTGPCvAmfpRYFYNAKAGLCQTFe Yg GCwanGNNFKSAEDCMRTCGGA                                       EpiNE7.33            059

RPDFCLEPPYTGPCvAmfpRYFYNAKAGLCQTFv Yg GCh gdGNNFKSAEDCMRTCGGA                                      EpiNE7.36            060

RPDFCLEPPYTGPCvAmfpRYFYNAKAGLCQTFmYg GCq gkGNNFKSAEDCMRTCGGA                                       EpiNE7.37            061

RPDFCLEPPYTGPCvAmfpRYFYNAKAGLCQTFy Yg GCwakGNNFKSAEDCMRTCGGA                                       EpiNE7.38            062

RPDFCLEPPYTGPCvAmfpRYFYNAKAGLCQTFmYg GCwgdGNNFKSAEDCMRTCGGA                                        EpiNE7.39            063

RPDFCLEPPYTGPCvAmfpRYFYNAKAGLCQTFt Yg GCh gnGNNFKSAEDCMRTCGGA                                      EpiNE7.40            064
```

Notes to Table 210:
a) Lower case letters in EpiNE7.6 to 7.38 indicate changes from BPTI that were selected in the first round (residues 15–19) or positions where the PBD was variegated in the second round (residues 34, 36, 39, 40, and 41).
b) All EpiNE7 derivatives have $G_{42}$.

TABLE 211

Effects of antisera on phage infectivity

| Strain (dilution of stock) | Incubation Conditions | pfu/ml | Relative Titer |
|---|---|---|---|
| MA-ITI-D1 (0.10) | PBS | $1.2 \cdot 10^{11}$ | 1.00 |
|  | NRS | $6.8 \cdot 10^{10}$ | 0.57 |
|  | anti-ITI | $1.1 \cdot 10^{10}$ | 0.09 |
| MA-ITI-D1 | PBS | $7.7 \cdot 10^{8}$ | 1.00 |
| (0.001) | NRS | $6.7 \cdot 10^{8}$ | 0.87 |
|  | anti-ITI | $8.0 \cdot 10^{6}$ | 0.01 |
| MA (0.10) | PBS | $1.3 \cdot 10^{12}$ | 1.00 |
|  | NRS | $1.4 \cdot 10^{12}$ | 1.10 |

TABLE 211-continued

Effects of antisera on phage infectivity

| Strain (dilution of stock) | Incubation Conditions | pfu/ml | Relative Titer |
|---|---|---|---|
| | anti-ITI | $1.6 \cdot 10^{12}$ | 1.20 |
| MA | PBS | $1.3 \cdot 10^{10}$ | 1.00 |
| (0.001) | NRS | $1.2 \cdot 10^{10}$ | 0.92 |
| | anti-ITI | $1.5 \cdot 10^{10}$ | 1.20 |

PBS is phosphate buffered saline
NRS is Normal Rabbit serum
anti-ITI is serum from rabbits immunized to human ITI.

TABLE 212

Fractionation of EpiNE-7 and MA-ITI-D1 phage on hNE beads

| | EpiNE-7 | | MA-ITI-D1 | |
|---|---|---|---|---|
| | pfu | pfu/INPUT | pfu | pfu/INPUT |
| INPUT | $3.3 \cdot 10^9$ | 1.00 | $3.4 \cdot 10^{11}$ | 1.00 |
| Final TBS-TWEEN Wash | $3.8 \cdot 10^5$ | $1.2 \cdot 10^{-4}$ | $1.8 \cdot 10^6$ | $5.3 \cdot 10^{-6}$ |
| pH | | | | |
| 7.0 | $6.2 \cdot 10^5$ | $1.8 \cdot 10^{-4}$ | 1.66 | $4.7 \cdot 10^{-6}$ |
| 6.0 | $1.4 \cdot 10^6$ | $4.1 \cdot 10^{-4}$ | $1.0 \cdot 10^6$ | $2.9 \cdot 10^{-6}$ |
| 5.5 | $9.4 \cdot 10^5$ | $2.8 \cdot 10^{-4}$ | $1.6 \cdot 10^6$ | $4.7 \cdot 10^{-6}$ |
| 5.0 | $9.5 \cdot 10^5$ | $2.9 \cdot 10^{-4}$ | $3.1 \cdot 10^5$ | $9.1 \cdot 10^{-7}$ |
| 4.5 | $1.2 \cdot 10^6$ | $3.5 \cdot 10^{-4}$ | $1.2 \cdot 10^5$ | $3.5 \cdot 10^{-7}$ |
| 4.0 | $1.6 \cdot 10^6$ | $4.8 \cdot 10^{-4}$ | $7.2 \cdot 10^4$ | $2.1 \cdot 10^{-7}$ |
| 3.5 | $9.5 \cdot 10^5$ | $2.9 \cdot 10^{-4}$ | $4.9 \cdot 10^4$ | $1.4 \cdot 10^{-7}$ |
| 3.0 | $6.6 \cdot 10^5$ | $2.0 \cdot 10^{-4}$ | $2.9 \cdot 10^4$ | $8.5 \cdot 10^{-8}$ |
| 2.5 | $1.6 \cdot 10^5$ | $4.8 \cdot 10^{-5}$ | $1.4 \cdot 10^4$ | $4.1 \cdot 10^{-8}$ |
| 2.0 | $3.0 \cdot 10^5$ | $9.1 \cdot 10^{-5}$ | $1.7 \cdot 10^4$ | $5.0 \cdot 10^{-8}$ |
| SUM | $6.4 \cdot 10^6$ | $3 \cdot 10^{-3}$ | $5.7 \cdot 10^6$ | $2 \cdot 10^{-5}$ |

*SUM is the total pfu (or fraction of input) obtained from all pH elution fractions

TABLE 213

Fractionation of EpiC-10 and MA-ITI-D1 phage on Cat-G beads

| | EpiC-10 | | MA-ITI-D1 | |
|---|---|---|---|---|
| | pfu | pfu/INPUT | pfu | pfu/INPUT |
| INPUT | $5.0 \cdot 10^{11}$ | 1.00 | $4.6 \cdot 10^{11}$ | 1.00 |
| Final TBS-TWEEN Wash | $1.8 \cdot 10^7$ | $3.6 \cdot 10^{-5}$ | $7.1 \cdot 10^6$ | $1.5 \cdot 10^{-5}$ |
| pH | | | | |
| 7.0 | $1.5 \cdot 10^7$ | $3.0 \cdot 10^{-5}$ | $6.1 \cdot 10^6$ | $1.3 \cdot 10^{-5}$ |
| 6.0 | $2.3 \cdot 10^7$ | $4.6 \cdot 10^{-5}$ | $2.3 \cdot 10^6$ | $5.0 \cdot 10^{-6}$ |
| 5.5 | $2.5 \cdot 10^7$ | $5.0 \cdot 10^{-5}$ | $1.2 \cdot 10^6$ | $2.6 \cdot 10^{-6}$ |
| 5.0 | $2.1 \cdot 10^7$ | $4.2 \cdot 10^{-5}$ | $1.1 \cdot 10^6$ | $2.4 \cdot 10^{-6}$ |
| 4.5 | $1.1 \cdot 10^7$ | $2.2 \cdot 10^{-5}$ | $6.7 \cdot 10^5$ | $1.5 \cdot 10^{-6}$ |
| 4.0 | $1.9 \cdot 10^6$ | $3.8 \cdot 10^{-6}$ | $4.4 \cdot 10^5$ | $9.6 \cdot 10^{-7}$ |
| 3.5 | $1.1 \cdot 10^6$ | $2.2 \cdot 10^{-6}$ | $4.4 \cdot 10^5$ | $9.6 \cdot 10^{-7}$ |
| 3.0 | $4.8 \cdot 10^5$ | $9.6 \cdot 10^{-7}$ | $3.6 \cdot 10^5$ | $7.8 \cdot 10^{-7}$ |
| 2.5 | $2.0 \cdot 10^5$ | $4.0 \cdot 10^{-7}$ | $2.7 \cdot 10^5$ | $5.9 \cdot 10^{-7}$ |
| 2.0 | $2.4 \cdot 10^5$ | $4.8 \cdot 10^{-7}$ | $3.2 \cdot 10^5$ | $7.0 \cdot 10^{-7}$ |
| SUM | $9.9 \cdot 10^7$ | $2 \cdot 10^{-4}$ | $1.4 \cdot 10^7$ | $3 \cdot 10^{-5}$ |

SUM is the total pfu (or fraction of input) obtained from all pH elution fractions

TABLE 214

Abbreviated fractionation of display phage on hNE beads

| | Display phage | | | |
|---|---|---|---|---|
| | EpiNE-7 | MA-ITI-D1 2 | MA-ITI-D1E7 1 | MA-ITI-D1E7 2 |
| INPUT (pfu) | 1.00 ($1.8 \times 10^9$) | 1.00 ($1.2 \times 10^{10}$) | 1.00 ($3.3 \times 10^9$) | 1.00 ($1.1 \times 10^9$) |
| Wash | $6 \cdot 10^{-5}$ | $1 \cdot 10^{-5}$ | $2 \cdot 10^{-5}$ | $2 \cdot 10^{-5}$ |
| pH 7.0 | $3 \cdot 10^{-4}$ | $1 \cdot 10^{-5}$ | $2 \cdot 10^{-5}$ | $4 \cdot 10^{-5}$ |
| pH 3.5 | $3 \cdot 10^{-3}$ | $3 \cdot 10^{-6}$ | $8 \cdot 10^{-5}$ | $8 \cdot 10^{-5}$ |
| pH 2.0 | $1 \cdot 10^{-3}$ | $1 \cdot 10^{-6}$ | $6 \cdot 10^{-6}$ | $2 \cdot 10^{-5}$ |
| SUM | $4.3 \cdot 10^{-3}$ | $1.4 \cdot 10^{-5}$ | $1.1 \cdot 10^{-4}$ | $1.4 \cdot 10^{-4}$ |

Each entry is the fraction of input obtained in that component.
SUM is the total fraction of input pfu obtained from all pH elution fractions

TABLE 215

Fractionation of EpiNE-7 and MA-ITI-D1E7 phage on hNE beads

| | EpiNE-7 | | MA-ITI-D1E7 | |
|---|---|---|---|---|
| | Total pfu | Fraction of Input | Total pfu | Fraction of Input |
| INPUT | $1.8 \cdot 10^9$ | 1.00 | $3.0 \cdot 10^9$ | 1.00 |
| pH 7.0 | $5.2 \cdot 10^5$ | $2.9 \cdot 10^{-4}$ | $6.4 \cdot 10^4$ | $2.1 \cdot 10^{-5}$ |
| pH 6.0 | $6.4 \cdot 10^5$ | $3.6 \cdot 10^{-4}$ | $4.5 \cdot 10^4$ | $1.5 \cdot 10^{-5}$ |
| pH 5.5 | $7.8 \cdot 10^5$ | $4.3 \cdot 10^{-4}$ | $5.0 \cdot 10^4$ | $1.7 \cdot 10^{-5}$ |
| pH 5.0 | $8.4 \cdot 10^5$ | $4.7 \cdot 10^{-4}$ | $5.2 \cdot 10^4$ | $1.7 \cdot 10^{-5}$ |
| pH 4.5 | $1.1 \cdot 10^6$ | $6.1 \cdot 10^{-4}$ | $4.4 \cdot 10^4$ | $1.5 \cdot 10^{-5}$ |
| pH 4.0 | $1.7 \cdot 10^6$ | $9.4 \cdot 10^{-4}$ | $2.6 \cdot 10^4$ | $8.7 \cdot 10^{-6}$ |
| pH 3.5 | $1.1 \cdot 10^6$ | $6.1 \cdot 10^{-4}$ | $1.3 \cdot 10^4$ | $4.3 \cdot 10^{-6}$ |
| pH 3.0 | $3.8 \cdot 10^5$ | $2.1 \cdot 10^{-4}$ | $5.6 \cdot 10^3$ | $1.9 \cdot 10^{-6}$ |
| pH 2.5 | $2.8 \cdot 10^5$ | $1.6 \cdot 10^{-4}$ | $4.9 \cdot 10^3$ | $1.6 \cdot 10^{-6}$ |
| pH 2.0 | $2.9 \cdot 10^5$ | $1.6 \cdot 10^{-4}$ | $2.2 \cdot 10^3$ | $7.3 \cdot 10^{-7}$ |
| SUM | $7.6 \cdot 10^6$ | $4.1 \cdot 10^{-3}$ | $3.1 \cdot 10^5$ | $1.1 \cdot 10^{-4}$ |

SUM is the total pfu (or fraction of input) obtained from all pH elution fractions

TABLE 216

Fractionation of MA-EpiNE-7, MA-BITI and MA-BITI-E7 on hNE beads

| | MA-BITI | | MA-BITI-E7 | | MA-EpiNE7 | |
|---|---|---|---|---|---|---|
| | pfu | pfu/Input | pfu | pfu/Input | pfu | pfu/Input |
| INPUT | $2.0 \cdot 10^{10}$ | $1.2 \cdot 10^{-5}$ | $6.0 \cdot 10^9$ | 1.00 | $1.5 \cdot 10^9$ | 1.00 |
| pH | | | | | | |
| 7.0 | $2.4 \cdot 10^5$ | $1.2 \cdot 10^{-5}$ | $2.8 \cdot 10^5$ | $4.7 \cdot 10^{-5}$ | $2.9 \cdot 10^5$ | $1.9 \cdot 10^{-4}$ |
| 6.0 | $2.5 \cdot 10^5$ | $1.2 \cdot 10^{-5}$ | $2.8 \cdot 10^5$ | $4.7 \cdot 10^{-5}$ | $3.7 \cdot 10^5$ | $2.5 \cdot 10^{-4}$ |
| 5.0 | $9.6 \cdot 10^4$ | $4.8 \cdot 10^{-6}$ | $3.7 \cdot 10^5$ | $6.2 \cdot 10^{-5}$ | $4.9 \cdot 10^5$ | $3.3 \cdot 10^{-4}$ |
| 4.5 | $4.4 \cdot 10^4$ | $2.2 \cdot 10^{-6}$ | $3.8 \cdot 10^5$ | $6.3 \cdot 10^{-5}$ | $6.0 \cdot 10^5$ | $4.0 \cdot 10^{-4}$ |
| 4.0 | $3.1 \cdot 10^4$ | $1.6 \cdot 10^{-6}$ | $2.4 \cdot 10^5$ | $4.0 \cdot 10^{-5}$ | $6.4 \cdot 10^5$ | $4.3 \cdot 10^{-4}$ |
| 3.5 | $8.6 \cdot 10^4$ | $4.3 \cdot 10^{-6}$ | $9.0 \cdot 10^4$ | $1.5 \cdot 10^{-5}$ | $5.0 \cdot 10^5$ | $3.3 \cdot 10^{-4}$ |
| 3.0 | $2.2 \cdot 10^4$ | $1.1 \cdot 10^{-6}$ | $8.9 \cdot 10^4$ | $1.5 \cdot 10^{-5}$ | $1.9 \cdot 10^5$ | $1.3 \cdot 10^{-4}$ |
| 2.5 | $2.2 \cdot 10^4$ | $1.1 \cdot 10^{-6}$ | $2.3 \cdot 10^4$ | $3.8 \cdot 10^{-6}$ | $7.7 \cdot 10^4$ | $5.1 \cdot 10^{-5}$ |
| 2.0 | $7.7 \cdot 10^3$ | $3.8 \cdot 10^{-7}$ | $8.7 \cdot 10^3$ | $1.4 \cdot 10^{-6}$ | $9.7 \cdot 10^4$ | $6.5 \cdot 10^{-5}$ |
| SUM | $8.0 \cdot 10^5$ | $3.9 \cdot 10^{-5}$ | $1.8 \cdot 10^6$ | $2.9 \cdot 10^{-4}$ | $3.3 \cdot 10^6$ | $2.2 \cdot 10^{-3}$ |

*SUM is the total pfu (or fraction of input) obtained from all pH elution fractions

TABLE 217

Fractionation of MA-BITI-E7 and MA-BITI-E7-1222 on hNE beads

| | MA-BITI-E7 | | MA-BITI-E7-1222 | |
|---|---|---|---|---|
| | pfu | pfu/INPUT | pfu | pfu/INPUT |
| INPUT | $1.3 \cdot 10^9$ | 1.00 | $1.2 \cdot 10^9$ | 1.00 |
| pH | | | | |
| 7.0 | $4.7 \cdot 10^4$ | $3.6 \cdot 10^{-5}$ | $4.0 \cdot 10^4$ | $3.3 \cdot 10^{-5}$ |
| 6.0 | $5.3 \cdot 10^4$ | $4.1 \cdot 10^{-5}$ | $5.5 \cdot 10^4$ | $4.6 \cdot 10^{-5}$ |
| 5.5 | $7.1 \cdot 10^4$ | $5.5 \cdot 10^{-5}$ | $5.4 \cdot 10^4$ | $4.5 \cdot 10^{-5}$ |
| 5.0 | $9.0 \cdot 10^4$ | $6.9 \cdot 10^{-5}$ | $6.7 \cdot 10^4$ | $5.6 \cdot 10^{-5}$ |
| 4.5 | $6.2 \cdot 10^4$ | $4.8 \cdot 10^{-5}$ | $6.7 \cdot 10^4$ | $5.6 \cdot 10^{-5}$ |
| 4.0 | $3.4 \cdot 10^4$ | $2.6 \cdot 10^{-5}$ | $2.7 \cdot 10^4$ | $2.2 \cdot 10^{-5}$ |
| 3.5 | $1.8 \cdot 10^4$ | $1.4 \cdot 10^{-5}$ | $2.3 \cdot 10^4$ | $1.9 \cdot 10^{-5}$ |
| 3.0 | $2.5 \cdot 10^3$ | $1.9 \cdot 10^{-6}$ | $6.3 \cdot 10^3$ | $5.2 \cdot 10^{-6}$ |
| 2.5 | $<1.3 \cdot 10^3$ | $<1.0 \cdot 10^{-6}$ | $<1.3 \cdot 10^3$ | $<1.0 \cdot 10^{-6}$ |
| 2.0 | $1.3 \cdot 10^3$ | $1.0 \cdot 10^{-6}$ | $1.3 \cdot 10^3$ | $1.0 \cdot 10^{-6}$ |
| SUM | $3.8 \cdot 10^5$ | $2.9 \cdot 10^{-4}$ | $3.4 \cdot 10^5$ | $2.8 \cdot 10^{-4}$ |

SUM is the total pfu (or fraction of input) obtained from all pH elution fractions

TABLE 218

Fractionation of MA-EpiNE7 and MA-BITI-E7-141 on hNE beads

| | MA-EpiNE7 | | MA-BITI-E7-141 | |
|---|---|---|---|---|
| | pfu | pfu/INPUT | pfu | pfu/INPUT |
| INPUT | $6.1 \cdot 10^8$ | 1.00 | $2.0 \cdot 10^9$ | 1.00 |
| pH | | | | |
| 7.0 | $5.3 \cdot 10^4$ | $8.7 \cdot 10^{-5}$ | $4.5 \cdot 10^5$ | $2.2 \cdot 10^{-4}$ |
| 6.0 | $9.7 \cdot 10^4$ | $1.6 \cdot 10^{-4}$ | $4.4 \cdot 10^5$ | $2.2 \cdot 10^{-4}$ |
| 5.5 | $1.1 \cdot 10^5$ | $1.8 \cdot 10^{-4}$ | $4.4 \cdot 10^5$ | $2.2 \cdot 10^{-4}$ |
| 5.0 | $1.4 \cdot 10^5$ | $2.3 \cdot 10^{-4}$ | $7.2 \cdot 10^5$ | $3.6 \cdot 10^{-4}$ |
| 4.5 | $1.0 \cdot 10^5$ | $1.6 \cdot 10^{-4}$ | $1.3 \cdot 10^6$ | $6.5 \cdot 10^{-4}$ |
| 4.0 | $2.0 \cdot 10^5$ | $3.3 \cdot 10^{-4}$ | $1.1 \cdot 10^6$ | $5.5 \cdot 10^{-4}$ |
| 3.5 | $9.7 \cdot 10^4$ | $1.6 \cdot 10^{-4}$ | $5.9 \cdot 10^5$ | $3.0 \cdot 10^{-4}$ |
| 3.0 | $3.8 \cdot 10^4$ | $6.2 \cdot 10^{-5}$ | $2.3 \cdot 10^5$ | $1.2 \cdot 10^{-4}$ |
| 2.5 | $1.3 \cdot 10^4$ | $2.1 \cdot 10^{-5}$ | $1.2 \cdot 10^5$ | $6.0 \cdot 10^{-5}$ |
| 2.0 | $1.6 \cdot 10^4$ | $2.6 \cdot 10^{-5}$ | $1.0 \cdot 10^5$ | $5.0 \cdot 10^{-5}$ |
| SUM | $8.6 \cdot 10^5$ | $1.4 \cdot 10^{-3}$ | $5.5 \cdot 10^6$ | $2.8 \cdot 10^{-3}$ |

SUM is the total pfu (or fraction of input) obtained from all pH elution fractions.

TABLE 219 pH Elution Analysis of hNE Binding by BITI-E7-141 Varient Display Phage

| | Input | Fraction of Input recovered at pH | | | Recovery | |
|---|---|---|---|---|---|---|
| Displayed protein | PFU ($\times 10^9$) | pH7.0 | pH3.5 $\times 10^{-4}$ | pH2.0 $\times 10^{-4}$ | Total $\times 10^{-4}$ | Relative |
| AMINO1 (EE) | 0.96 | 0.24 | 2.3 | 0.35 | 2.9 | 0.11 |
| AMINO2 (AE) | 6.1 | 0.57 | 2.1 | 0.45 | 3.1 | 0.12 |
| BITI-E7-1222 (EE) | 1.2 | 0.72 | 4.0 | 0.64 | 5.4 | 0.21 |
| EpiNE7 (EE) | 0.72 | 0.44 | 6.4 | 2.2 | 9.0 | 0.35 |
| MUTP1 (AE) | 3.9 | 1.8 | 9.2 | 1.2 | 12.0 | 0.46 |
| MUT1619 (EE) | 0.78 | 0.82 | 9.9 | 0.84 | 12.0 | 0.46 |
| MUTQE (AE) | 4.7 | 1.2 | 16. | 5.3 | 22.0 | 0.85 |
| MUTT26A (EE) | 0.51 | 2.5 | 19.0 | 3.3 | 25.0 | 0.96 |

TABLE 219-continued pH Elution Analysis of hNE Binding by BITI-E7-141 Varient Display Phage

| Displayed protein | Input PFU (× 10^9) | pH7.0 | Fraction of Input recovered at pH pH3.5 × 10^-4 | pH2.0 × 10^-4 | Recovery Total × 10^-4 | Relative |
|---|---|---|---|---|---|---|
| BITI-E7-141 (AE) | 1.7 | 2.2 | 18.0 | 5.4 | 26.0 | 1.00 |
| BITI-E7-141 (EE) | 0.75 | 2.1 | 21. | 3.2 | 26.0 | 1.00 |

Notes:
EE  Extended pH elution protocol
Ae  Abbreviated pH elution protocol
Total  Total fraction of input = Sum of fractions collected at pH 7.0, pH 3.5, and pH 2.0.
Relative  Total fraction of input recovered divided by total fraction of input recovered for BITI-E7-141

TABLE 220

ITI-D1-derived hNE Inhibitors

WEAK ($K_D > 10^{-8}$ M)
```
          1    1    2    2    3    3    4    4    5    5
    1....5....0....5....0....5....0....5....0....5....0....5...
```
1. KEDSCQLGYSAGPCMGMTSRYFYNGTSMACETFQYGGCMGNGNNFVTEKDCLQTCRGA

MODERATE ($10^{-8} >$ RD 22 $10^{-9}$)
2. KEDSCQLGYSAGPCVAMFPRYFYNGTSMACETFQYGGCMGNGNNFVTEKDCLQTCRGA
3. RPDFCQLGYSAGPCMGMTSRYFYNGTSMACETFQYGGCMGNGNNFVTEKDCLQTCRGA

STRONG ($10^{-9} >$ KD $> 10^{-11}$D)
4. RPDFCQLGYSAGPCVAMFPRYFYNGTSMACETFQYGGCMGNGNNFVTEKDCLQTCRGA
5. RPDFCQLGYSTGPCVAMFPRYFYNGTSMACETFQYGGCMGNGNNFVTEKDCLQTCRGA
6. KEDFCQLGYSAGPCVAMFPRYFYNGTSMACETFQYGGCMGNGNNFVTEKDCLQTCRGA
7. KPDSCQLGYSAGPCVAMFPRYFYNGTSMACETFQYGGCMGNGNNFVTEKDCLQTCRGA
8. RPDFCQLGYSAGPCIGMFSRYFYNGTSMACETFQYGGCMGNGNNFVTEKDCLQTCRGA

VERY STRONG ($K_D < 10^{-11}$ M)
9. RPDFCQLGYSAGPCVAMFPRYFYNGTSMACQTFVYGGCMGNGNNFVTEKDCLQTCRGA
10. RPDFCQLGYSAGPCVAMFPRYFYNGASMACQTFVYGGCMGNGNNFVTEKDCLQTCRGA
11. RPDFCQLGYSAGPCVAMFPRYFYNGTSMACETFVYGGCMGNGNNFVTEKDCLQTCRGA
12. RPDFCQLGYSAGPCVGMFSRYFYNGTSMACQTFVYGGCMGNGNNFVTEKDCLQTCRGA

Residues shown underlined and bold are changed from those presen in ITI-D1.
Sequences Key:

| | | |
|---|---|---|
| 1. | ITI-D1 | SEQ ID NO. 008 |
| 2. | ITI-DIE7 | SEQ ID NO. 009 |
| 3. | BITI | SEQ ID NO. 030 |
| 4. | BITI-E7 | SEQ ID NO. 010 |
| 5. | BITI-E7-1222 | SEQ ID NO. 012 |
| 6. | AMINO1 | SEQ ID NO. 015 |
| 7. | AMINO2 | SEQ ID NO. 016 |
| 8. | MUTP1 | SEQ ID NO. 014 |
| 9. | BITI-E7-141 | SEQ ID NO. 011 |
| 10. | MUTT26A | SEQ ID NO. 018 |
| 11. | MUTQE | SEQ ID NO. 017 |
| 12. | MUT1619 | SEQ ID NO. 013 |

TABLE 221

Same sequences as in Table 220 showing only changes (and Cysteines for alignment).

WEAK ($K_D > 10^{-8}$ M)
```
          1    1    2    2    3    3    4    4    5    5
    1....5....0....5....0....5....0....5....0....5....0....5...
```
1. KEDSCQLGYSAGPCMGMTSRYFYNGTSMACETFQYGGCMGNGNNFVTEKDCLQTCRGA

MODERATE ($10^{-8} >$ RD 22 $10^{-9}$)
2. - - - - C- - - - - - - - CVA- FP- - - - - - - - - - C- - - - - - - C- - - - - - - - - - - - C- - - C- - -
3. RP- - C- - - - - - - - C- - - - - - - - - - - - - - - - - C- - - - - - - C- - - - - - - - - - - - C- - - C- - -

TABLE 221-continued

Same sequences as in Table 220 showing only changes (and Cysteines for alignment).

STRONG ($10^{-9}$ > KD > $10^{-11}$D)
4.  RP- - C- - - - - - - - - CVA- FP- - - - - - - - - - - C- - - - - - - C- - - - - - - - - - - - C- - - C- - -
5.  RP- - C- - - - - T- - CVA- FP- - - - - - - - - - - C- - - - - - - C- - - - - - - - - - - - C- - - C- - -
6.  - - - FC- - - - - - - - CVA- FP- - - - - - - - - - - C- - - - - - - C- - - - - - - - - - - - C- - - C- - -
7.  - P- - C- - - - - - - - CVA- FP- - - - - - - - - - - C- - - - - - - C- - - - - - - - - - - - C- - - C- - -
8.  RP- FC- - - - - - - - CI- - FP- - - - - - - - - - - C- - - - - - - C- - - - - - - - - - - - C- - - C- - -

VERY STRONG ($K_D < 10^{-11}$ M)
9.  RP- FC- - - - - - - - CVA- FP- - - - - - - - - - CQ- - V- - - C- - - - - - - - - - - - C- - - C- - -
10. RP- FC- - - - - - - - CVA- FP- - - - - - A- - - CQ- - V- - - C- - - - - - - - - - - - C- - - C- - -
11. RP- FC- - - - - - - - CVA- FP- - - - - - - - - - - C- - - V- - - C- - - - - - - - - - - - C- - - C- - -
12. RP- FC- - - - - - - - CV- - F- - - - - - - - - - - CQ- - V- - - C- - - - - - - - - - - - C- - - C- - -

Residues shown underlined and bold are changed from those present in III-D1.

TABLE 250

Plasmid pHIL-D2 SEQ ID NO. 065
8157 base pairs. Only one strand is shown, but the DNA exists as
double-stranded circular DNA in vivo.

|  | 1<br>1234567890 | 2<br>1234567890 | 3<br>1234567890 | 4<br>1234567890 | 5<br>1234567890 |
|---|---|---|---|---|---|
| 1 | AgATCgCggC | CgCgATCTAA | CATCCAAAgA | CgAAAggTTg | AATgAAACCT |
| 51 | TTTTgCCATC | CgACATCCAC | AggTCCATTC | TCACACATAA | gTgCCAAACg |
| 101 | CAACAggAgg | ggATACACTA | gCAgCAgACC | gTTgCAAACg | CAggACCTCC |
| 151 | ACTCCTCTTC | TCCTCAACAC | CCACTTTTgC | CATCgAAAAA | CCAgCCCAgT |
| 201 | TATTgggCTT | gATTggAgCT | CgCTCATTCC | AATTCCTTCT | ATTAggCTAC |
| 251 | TAACACCATg | ACTTTATTAg | CCTgTCTATC | CTggCCCCCC | TggCgAggTC |
| 301 | ATgTTTgTTT | ATTTCCgAAT | gCAACAAgCT | CCgCATTACA | CCCgAACATC |
| 351 | ACTCCAgATg | AgggCTTTCT | gAgTgTgggg | TCAAATAgTT | TCATgTTCCC |
| 401 | AAATggCCCA | AAACTgACAg | TTTAAACgCT | gTCTTggAAC | CTAATATgAC |
| 451 | AAAAgCgTgA | TCTCATCCAA | gATgAACTAA | gTTTggTTCg | TTgAAATgCT |
| 501 | AACggCCAgT | TgggTCAAAAA | gAAAACTTCCA | AAAgTCgCCA | TACCgTTTgT |
| 551 | CTTgTTTggT | ATTgATTgAC | gAATgCTCAA | AAATAATCTC | ATTAATgCTT |
| 601 | AgCgCAgTCT | CTCTATCgCT | TCTgAACCCg | gTggCACCTg | TgCCgAAACg |
| 651 | CAAATggggA | AACAACCCgC | TTTTTggATg | ATTATgCATT | gTCCTCCACA |
| 701 | TTgTATgCTT | CCAAgATTCT | ggTgggAATA | CTgCTgATAg | CCTAACgTTC |
| 751 | ATgATCAAAA | TTTAACTgTT | CTAACCCCTA | CTTgACAggC | AATATATAAA |
| 801 | CAgAAggAAg | CTgCCCTgTC | TTAAACCTTT | TTTTTTATCA | TCATTATTAg |
| 851 | CTTACTTTCA | TAATTgCgAC | TggTTCCAAT | TgACAAgCTT | TTgATTTTAA |
| 901 | CgACTTTTAA | CgACAACTTg | AgAAgATCAA | AAAACAACTA | ATTATTCgAA |
|  |  |  |  |  | BstBI |
| 951 | ACgAggAATT | CgCCTTAgAC | ATgACTgTTC | CTCAgTTCAA | gTTgggCATT |
|  | EcoRI |  |  |  |  |
| 1001 | ACgAgAAgAC | CggTCTTgCT | AgATTCTAAT | CAAgAggATg | TCAgAATgCC |
| 1051 | ATTTgCCTgA | gAgATgCAgg | CTTCATTTTT | gATACTTTTT | TATTTgTAAC |
| 1101 | CTATATAgTA | TAggATTTTT | TTTgTCATTT | TgTTTCTTCT | CgTACgAgCT |
| 1151 | TgCTCCTgAT | CAgCCTATCT | CgCAgCTgAT | gAATATCTTg | TggTAggggT |
| 1201 | TTgggAAAAT | CATTCgAgTT | TgATgTTTTT | CTTggTATTT | CCCACTCCTC |
| 1251 | TTCAgAgTAC | AgAAgATTAA | gTgAgAAgTT | CgTTTgTgCA | AgCTTATCgA |
| 1301 | TAAgCTTTAA | TgCggTAgTT | TATCACAgTT | AAATTgCTAA | CgCAgTCAgg |
| 1351 | CACCgTgTAT | gAAAATCTAAC | AATgCgCTCA | TCgTCATCCT | CggCACCgTC |
| 1401 | ACCCTggATg | CTgTAggCAT | AggCTTggTT | ATgCCggTAC | TgCCgggCCT |
| 1451 | CTTgCgggAT | ATCgTCCATT | CCgACAgCAT | CgCCAgTCAC | TATggCgTgC |
| 1501 | TgCTAgCgCT | ATATgCgTTg | ATgCAATTTC | TATgCgCACC | CgTTCTCggA |
| 1551 | gCACTgTCCg | ACCgCTTTgg | CCgCCgCCCA | gTCCTgCTCg | CTTCgCTACT |
| 1601 | TggAgCCACT | ATCgACTACg | CgATCATggC | gACCCACACC | gTCCTgTggA |
| 1651 | TCTATCgAAT | CTAAATgTAA | gTTAAAATCT | CTAAATAATT | AAATAAgTCC |
| 1701 | CAgTTTCTCC | ATACgAACCT | TAACAgCATT | gCggTgAgCA | TCTAgACCTT |
| 1751 | CAACAgCAgC | CAgATCCATC | ACTgCTTggC | CAATATgTTT | CAgTCCCTCA |
| 1801 | ggAgTTACgT | CTTgTgAAgT | gATgAACTTC | TggAAggTTg | CAgTgTTAAC |
| 1851 | TCCgCTgTAT | TgACgggCAT | ATCCgTACgT | TggCAAAgTg | TggTTggTAC |
| 1901 | CggAggAgTA | ATCTCCACAA | CTCTCTggAg | AgTAggCACC | AACAAACACA |
| 1951 | gATCCAgCgT | gTTgTACTTg | ATCAACATAA | gAAgAAgCAT | TCTCgATTTg |
| 2001 | CAggATCAAg | TgTTCAggAg | CgTACTgATT | ggACATTTCC | AAAgCCTgCT |
| 2051 | CgTAggTTgC | AACCgATAgg | gTTgTAgAgT | gTgCAATACA | CTTgCgTACA |
| 2101 | ATTTCAACCC | TTggCAACTg | CACAgCTTgg | TTgTgAACAg | CATCTTCAAT |
| 2151 | TCTggCAAgC | TCCTTgTCTg | TCATATCgAC | AgCCAACAgA | ATCACCTggg |
| 2201 | AATCAATACC | ATgTTCAgCT | TgAgCAgAAg | gTCTgAggCA | ACgAAATCTg |
| 2251 | gATCAgCgTA | TTTATCAgCA | ATAACTAgAA | CTTCAgAAgg | CCCAgCAggC |
| 2301 | ATgTCAATAC | TACACAgggC | TgATgTgTCA | TTTTgAACCA | TCATCTTggC |
| 2351 | AgCAgTAACg | AACTggTTTC | CTggACCAAA | TATTTTgTCA | CACTTAggAA |

TABLE 250-continued

Plasmid pHIL-D2 SEQ ID NO. 065
8157 base pairs. Only one strand is shown, but the DNA exists as
double-stranded circular DNA in vivo.

| | | | | | |
|---|---|---|---|---|---|
| 2401 | CAgTTTCTgT | TCCgTAAgCC | ATAgCAgCTA | CTgCCTgggC | gCCTCCTgCT |
| 2451 | AgCACgATAC | ACTTAgCACC | AACCTTgTgg | gCAACgTAgA | TgACTTCTgg |
| 2501 | ggTAAgggTA | CCATCCTTCT | TAggTggAgA | TgCAAAAACA | ATTTCTTTgC |
| 2551 | AACCAgCAAC | TTTggCAggA | ACACCCAgCA | TCAgggAAgT | ggAAggCAgA |
| 2601 | ATTgCggTTC | CACCAggAAT | ATAgAggCCA | ACTTTCTCAA | TAggTCTTgC |
| 2651 | AAAACgAgAg | CAgACTACAC | CAgggCAAgT | CTCAACTTgC | AACgTCTCCg |
| 2701 | TTAgTTgAgC | TTCATggAAT | TTCCTgACgT | TATCTATAgA | gAgATCAATg |
| 2751 | gCTCTCTTAA | CgTTATCTgg | CAATTgCATA | AgTTCCTCTg | ggAAAggAgC |
| 2801 | TTCTAACACA | ggTgTCTTCA | AAgCgACTCC | ATCAAACTTg | gCAgTTAgTT |
| 2851 | CTAAAAgggC | TTTgTCACCA | TTTTgACgAA | CATTgTCgAC | AATTggTTTg |
| 2901 | ACTAATTCCA | TAATCTgTTC | CgTTTTCTgg | ATAggACgAC | gAAgggCATC |
| 2951 | TTCAATTTCT | TgTgAggAgg | CCTTAgAAAC | gTCAATTTTg | CACAATTCAA |
| 3001 | TACgACCTTC | AgAAgggACT | TCTTTAggTT | TggATTCTTC | TTTAggTTgT |
| 3051 | TCCTTggTgT | ATCCTggCTT | ggCATCTCCT | TTCCTTCTAg | TgACCTTTAg |
| 3101 | ggACTTCATA | TCCAgTTTC | TCTCCACCTC | gTCCAACgTC | ACACCgTACT |
| 3151 | TggCACATCT | AACTAATgCA | AAATAAAATA | AgTCAgCACA | TTCCCAggCT |
| 3201 | ATATCTTCCT | TggATTTAgC | TTCTgCAAgT | TCATCAgCTT | CCTCCCTAAT |
| 3251 | TTTAgCgTTC | AACAAAACTT | CgTCgTCAAA | TAACCgTTTg | gTATAAgAAC |
| 3301 | CTTCTggAgC | ATTgCTCTTA | CgATCCCACA | AggTgCTTCC | ATggCTCTAA |
| 3351 | gACCCTTTgA | TTggCCAAAA | CAggAAgTgC | gTTCCAAgTg | ACAgAAACCA |
| 3401 | ACACCTgTTT | gTTCAACCAC | AAATTTCAAg | CAgTCTCCAT | CACAATCCAA |
| 3451 | TTCgATACCC | AgCAACTTTT | gAgTTCgTCC | AgATgTAgCA | CCTTTATACC |
| 3501 | ACAAACCgTg | ACgACgAgAT | TggTAgACTC | CAgTTTgTgT | CCTTATAgCC |
| 3551 | TCCggAATAg | ACTTTTTggA | CgAgTACACC | AggCCCAACg | AgTAATTAgA |
| 3601 | AgAgTCAgCC | ACCAAAgTAg | TgAATAgACC | ATCggggCgg | TCAgTAgTCA |
| 3651 | AAgACgCCAA | CAAAATTTCA | CTgACAgggA | ACTTTTTgAC | ATCTTCAgAA |
| 3701 | AgTTCgTATT | CAgTAgTCAA | TTgCCgAgCA | TCAATAATgg | ggATTATACC |
| 3751 | AgAAgCAACA | gTggAAgTCA | CATCTACCAA | CTTTgCggTC | TCAgAAAAAg |
| 3801 | CATAAACAgT | TCTACTACCg | CCATTAgTgA | AACTTTTCAA | ATCgCCCAgT |
| 3851 | ggAgAAgAAA | AAgg CACAgC | gATACTAgCA | TTAgCgggCA | AggATgCAAC |
| 3901 | TTTATCAACC | AgggTCCTAT | AgATAACCCT | AgCgCCTggg | ATCATCCTTT |
| 3951 | ggACAACTCT | TTCTgCCAAA | TCTAggTCCA | AAATCACTTC | ATTgATACCA |
| 4001 | TTATACggAT | gACTCAACTT | gCACATTAAC | TTgAAgCTCA | gTCgATTgAg |
| 4051 | TgAACTTgAT | CAggTTgTgC | AgCTggTCAg | CAgCATAggg | AAACACggCT |
| 4101 | TTTCCTACCA | AACTCAAggA | ATTATCAAAC | TCTgCAACAC | TTgCgTATgC |
| 4151 | AggTAgCAAg | ggAAATgTCA | TACTTgAAgT | CggACAgTgA | gTgTAgTCTT |
| 4201 | gAgAAATTCT | gAAgCCgTAT | TTTTATTATC | AgTgAgTCAg | TCATCAggAg |
| 4251 | ATCCTCTACg | CCggACgCAT | CgTggCCggC | ATCACCggCg | CCACAggTgC |
| 4301 | ggTTgCTggC | gCCTATATCg | CCgACATCAC | CgATggggAA | gATCgggCTC |
| 4351 | gCCACTTCgg | gCTCATgAgC | gCTTgTTTCg | gCgTgggTAT | ggTggCAggC |
| 4401 | CCCgTggCCg | ggggACTgTT | gggCgCCATC | TCCTTgCATg | CACCATTCCT |
| 4451 | TgCggCggCg | gTgCTCAACg | gCCTCAACCT | ACTACTgggC | TgCTTCCTAA |
| 4501 | TgCAggAgTC | gCATAAgggA | gAgCgTCgAg | TATCTATgAT | TggAAgTATg |
| 4551 | ggAATggTgA | TACCCgCATT | CTTCAgTgTC | TTgAggTCTC | CTATCAgATT |
| 4601 | ATgCCCAACT | AAAgCAACCg | gAggAggAgA | TTTCATggTA | AATTTCTCTg |
| 4651 | ACTTTTggTC | ATCAgTAgAC | TCgAACTgTg | AgACTATCTC | ggTTATgACA |
| 4701 | gCAgAAATgT | CCTTCTTggA | gACAgTAAAT | gAAgTCCCAC | CAATAAAgAA |
| 4751 | ATCCTTgTTA | TCAggAACAA | ACTTCTTgTT | TCgAACTTTT | TCggTgCCTT |
| 4801 | gAACTATAAA | ATgTAgAgTg | gATATgTCgg | gTAggAATgg | AgCgggCAAA |
| 4851 | TgCTTACCTT | CTggACCTTC | AAgAggTATg | TAgggTTTgT | AgATACTgAT |
| 4901 | gCCAACTTCA | gTgACAACgT | TgCTATTTCg | TTCAAACCAT | TCCgAATCCA |
| 4951 | gAgAAATCAA | AgTTgTTTgT | CTACTATTgA | TCCAAgCCAg | TgCggTCTTg |
| 5001 | AAACTgACAA | TAgTgTgCTC | gTgTTTTgAg | gTCATCTTTg | TATgAATAAA |
| 5051 | TCTAgTCTTT | gATCTAAATA | ATCTTgACgA | gCCAAggCgA | TAAATACCCA |
| 5101 | AATCTAAAAC | TCTTTTAAAA | CgTTAAAAgg | ACAAgTATgT | CTgCCgTAT |
| 5151 | TAAACCCCAA | ATCAgCTCgT | AgTCTgATCC | TCATCAACTT | gAggggCACT |
| 5201 | ATCTTgTTTT | AgAgAAATTT | gCggAgATgC | gATATCgAgA | AAAAgTACg |
| 5251 | CTgATTTTAA | ACgTgAAATT | TATCTCAAgA | TCgCggCCgC | gATCTCgAAT |
| 5301 | AATAACTgTT | ATTTTTCAgT | gTTCCCgATC | TgCgTCTATT | TCACAATACC |
| 5351 | AACATgAgTC | AgCTTATCgA | TgATAAgCTg | TCAAACATgA | gAATTAATTC |
| 5401 | gATgATAAgC | TgTCAAACAT | gAgAAATCTT | gAAgACgAAA | gggCCTCgTg |
| 5451 | ATACgCCTAT | TTTTATAggT | TAATgTCATg | ATAATAATgg | TTTCTTAgAC |
| 5501 | gTCAggTggC | ACTTTTCggg | gAAATgTgCg | CggAACCCCT | ATTTgTTTAT |
| 5551 | TTTTCTAAAT | ACATTCAAAT | ATgTATCCgC | TCATgAgACA | ATAACCCTgA |
| 5601 | TAAATgCTTC | AATAATATTg | AAAAAggAAg | AgTATgAgTA | TTCAACATTT |
| 5651 | CCgTgTCgCC | CTTATTCCCT | TTTTTgCggC | ATTTTgCCTT | CCTgTTTTTg |
| 5701 | CTCACCCAgA | AACgCTggTg | AAAgTAAAAg | ATgCTgAAgA | TCAgTTgggT |
| 5751 | gCACgAgTgg | gTTACATCgA | ACTggATCTC | AACAgCggTA | AgATCCTTgA |
| 5801 | gAgTTTTCgC | CCCgAAgAAC | gTTTTCCAAT | gATgAgCACT | TTTAAAgTTC |
| 5851 | TgCTATgTgg | CgCggTATTA | TCCCgTgTTg | ACgCCgggCA | AgAgCAACTC |
| 5901 | ggTCgCCgCA | TACACTATTC | TCAgAATgAC | TTggTTgAgT | ACTCACCAgT |
| 5951 | CACAgAAAAg | CATCTTACgg | ATggCATgAC | AgTAAgAgAA | TTATgCAgTg |
| 6001 | CTgCCATAAC | CATgAgTgAT | AACACTgCgg | CCAACTTACT | TCTgACAACg |
| 6051 | ATCggAggAC | CgAAggAgCT | AACCgCTTTT | TTgCACAACA | TgggggATCA |
| 6101 | TgTAACTCgC | CTTgATCgTT | gggAACCggA | gCTgAATgAA | gCCATACCAA |

TABLE 250-continued

Plasmid pHIL-D2 SEQ ID NO. 065
8157 base pairs. Only one strand is shown, but the DNA exists as
double-stranded circular DNA in vivo.

| | | | | |
|---|---|---|---|---|
| 6151 ACg ACg Ag Cg | Tg ACACCACg | ATg CCTg CAg | CAATg g CAAC | AACg TTg Cg C |
| 6201 AAACTATTAA | CTg g Cg AACT | ACTTACTCTA | g CTTCCCg g C | AACAATTAAT |
| 6251 Ag ACTg g ATg | g Ag g Cg g ATA | AAg TTg CAg g | ACCACTTCTg | Cg CTCg g CCC |
| 6301 TTCCg g CTg g | CTg g TTTATT | g CTg ATAAAT | CTg g Ag CCg g | Tg Ag Cg Tg g g |
| 6351 TCTCg Cg g TA | TCATTg CAg C | ACTg g g g CCA | g ATg g TAAg C | CCTCCCg TAT |
| 6401 Cg TAg TTATC | TACACg ACg g | g g Ag TCAg g C | AACTATg g AT | g AACg AAATA |
| 6451 g ACAg ATCg C | Tg Ag ATAg g T | g CCTCACTg A | TTAAg CATTg | g TAACTg TCA |
| 6501 g ACCAAg TTT | ACTCATATAT | ACTTTAg ATT | g ATTTAAATT | g TAAACg TTA |
| 6551 ATATTTg TT | AAAATTCg Cg | TTAAATTTTT | g TTAAATCAg | CTCATTTTTT |
| 6601 AACCAATAg g | CCg AAATCg g | CAAAATCCCT | TATAAATCAA | AAg AATAg AC |
| 6651 Cg Ag ATAg g g | TTg Ag Tg TTg | TTCCAg TTTg | g AACAAg Ag T | CCACTATTAA |
| 6701 Ag AACg Tg g A | CTCCAACg TC | AAAg g g Cg AA | AAACCg TCTA | TCAg g g Cg AT |
| 6751 g g CCCACTAC | g Tg AACCATC | ACCCTAATCA | Ag TTTTTTg g | g g TCg Ag g Tg |
| 6801 CCg TAAAg CA | CTAAATCg g A | ACCCTAAAg g | g Ag CCCCCg A | TTTAg Ag CTT |
| 6851 g ACg g g g AAA | g CCg g Cg AAC | g Tg g Cg Ag AA | Ag g AAg g g AA | g AAAg Cg AAA |
| 6901 g g Ag Cg g g Cg | CTAg g g Cg CT | g g CAAg Tg TA | g Cg g TCACg C | Tg Cg Cg TAAC |
| 6951 CACCACACCC | g CCg Cg CTTA | ATg Cg CCg CT | ACAg g g Cg Cg | TAAAAg g ATC |
| 7001 TAg g Tg AAg A | TCCTTTTg A | TAATCTCATg | ACCAAAATCC | CTTAACg Tg A |
| 7051 g TTTTCg TTC | CACTg Ag Cg T | CAg ACCCCg T | Ag AAAAg ATC | AAAg g ATCTT |
| 7101 CTTg Ag ATCC | TTTTTTTCTg | Cg Cg TAATCT | g CTg CTTg CA | AACAAAAAAA |
| 7151 CCACCg CTAC | CAg Cg g Tg g T | TTg TTTg CCg | g ATCAAg Ag C | TACCAACTCT |
| 7201 TTTTCCg AAg | g TAACTg g CT | TCAg CAg Ag C | g CAg ATACCA | AATACTg TCC |
| 7251 TTCTAg Tg TA | g CCg TAg TTA | g g CCACCACT | TCAAg AACTC | Tg TAg CACCg |
| 7301 CCTACATACC | TCg CTCTg CT | AATCCTg TTA | CCAg Tg g CTg | CTg CCAg Tg g |
| 7351 Cg ATAAg TCg | Tg TCTTACCg | g g TTg g ACTC | AAg ACg ATAg | TTACCg g ATA |
| 7401 Ag g Cg CAg Cg | g TCg g g CTg A | ACg g g g g g TT | Cg Tg CACACA | g CCCAg CTTg |
| 7451 g Ag Cg AACg A | CCTACACCg A | ACTg Ag ATAC | CTACAg Cg Tg | Ag CATTg Ag A |
| 7501 AAg Cg CCACg | CTTCCCg AAg | g g Ag AAAg g C | g g ACAg g TAT | CCg g TAAg Cg |
| 7551 g CAg g g TCg g | AACAg g Ag Ag | Cg CACg Ag g g | Ag CTTCCAg g | g g g AAACg CC |
| 7601 Tg g TATCTTT | ATAg TCCTg T | Cg g g TTTCg C | CACCTCTg AC | TTg Ag Cg TCg |
| 7651 ATTTTTg Tg A | Tg CTCg TCAg | g g g g g Cg g Ag | CCTATg g AAA | AACg CCAg CA |
| 7701 ACg Cg g CCTT | TTTACg g TTC | CTg g CCTTTT | g CTg g CCTTT | Tg CTCACATg |
| 7751 TTCTTTCCTg | Cg TTATCCCC | Tg ATTCTg Tg | g ATAACCg TA | TTACCg CCTT |
| 7801 Tg Ag Tg Ag CT | g ATACCg CTC | g CCg CAg CCg | AACg ACCg Ag | Cg CAg Cg Ag T |
| 7851 CAg Tg Ag Cg A | g g AAg Cg g AA | g Ag Cg CCTg A | Tg Cg g TATTT | TCTCCTTACg |
| 7901 CATCTg Tg Cg | g TATTTCACA | CCg CATATg g | Tg CACTCTCA | g TACAATCTg |
| 7951 CTCTg ATg CC | g CATAg TTAA | g CCAg TATAC | ACTCCg CTAT | Cg CTACg Tg A |
| 8001 CTg g g TCATg | g CTg Cg CCCC | g ACACCCg CC | AACACCCg CT | g ACg Cg CCCT |
| 8051 g ACg g g CTTg | TCTg CTCCCg | g CATCCg CTT | ACAg ACAAg C | Tg Tg ACCg TC |
| 8101 TCCg g g Ag CT | g CATg Tg TCA | g Ag g TTTTCA | CCg TCATCAC | Cg AAACg Cg C |
| 8151 g Ag g CAg | | | | |

TABLE 251 pHIL-D2 (MFαPrePro::EPI-HNE-3) 8584 b.p.
DNA has SEQ ID NO. 066; Encoded polypeptide has SEQ ID NO. 067
DNA is circular and double stranded, only one strand is shown.
Translation of the protein to be expressed is shown.

| | 1<br>1234567890 | 2<br>1234567890 | 3<br>1234567890 | 4<br>1234567890 | 5<br>1234567890 |
|---|---|---|---|---|---|
| 1 | AgATCgCggC | CgCgATCTAA | CATCCAAAgA | CgAAAggTTg | AATgAAACCT |
| 51 | TTTTgCCATC | CgACATCCAC | AggTCCATTC | TCACACATAA | gTgCCAAACg |
| 101 | CAACAggAgg | ggATACACTA | gCAgCAgACC | gTTgCAAACg | CAggACCTCC |
| 151 | ACTCCTCTTC | TCCTCAACAC | CCACTTTTgC | CATCgAAAAA | CCAgCCCAgT |
| 201 | TATTgggCTT | gATTggAgCT | CgCTCATTCC | AATTCCTTCT | ATTAggCTAC |
| 251 | TAACACCATg | ACTTTATTAg | CCTgTCTATC | CTggCCCCCCC | TggCgAggTC |
| 301 | ATgTTTgTTT | ATTTCCgAAT | gCAACAAgCT | CCgCATTACA | CCCgAACATC |
| 351 | ACTCCAgATg | AgggCTTTCT | gAgTgTgggg | TCAAATAgTT | TCATgTTCCC |
| 401 | AAATggCCCA | AAACTgACAg | TTTAAACgCT | gTCTTggAAC | CTAATATgAC |
| 451 | AAAAgCgTgA | TCTCATCCAA | gATgAACTAA | gTTTggTTCg | TTgAAATgCT |
| 501 | AACggCCAgT | TggTCAAAAA | gAAACTTCCA | AAAgTCgCCA | TACCgTTTgT |

TABLE 251-continued pHIL-D2 (MFαPrePro::EPI-HNE-3) 8584 b.p.
DNA has SEQ ID NO. 066; Encoded polypeptide has SEQ ID NO. 067
DNA is circular and double stranded, only one strand is shown.
Translation of the protein to be expressed is shown.

| | | | | | |
|---|---|---|---|---|---|
| 551 | CTTgTTTggT | ATTgATTgAC | gAATgCTCAA | AAATAATCTC | ATTAATgCTT |
| 601 | AgCgCAgTCT | CTCTATCgCT | TCTgAACCCg | gTggCACCTg | TgCCgAAACg |
| 651 | CAAATggggA | AACAACCCgC | TTTTTggATg | ATTATgCATT | gTCCTCCACA |
| 701 | TTgTATgCTT | CCAAgATTCT | ggTgggAATA | CTgCTgATAg | CCTAACgTTC |
| 751 | ATgATCAAAA | TTTAACTgTT | CTAACCCCTA | CTTgACAggC | AATATATAAA |
| 801 | CAgAAggAAg | CTgCCCTgTC | TTAAACCTTT | TTTTTTATCA | TCATTATTAg |
| 851 | CTTACTTTCA | TAATTgCgAC | TggTTCCAAT | TgACAAgCTT | TTgATTTTAA |
| 901 | CgACTTTTAA | CgACAACTTg | AgAAgATCAA | AAAACAACTA | ATTATTCgAA |

```
                                                                    BstBI
     ACg
          M   R   F   P   S   I   F   T   A   V   L   F   A      13
          ATg AgA TTC CCA TCT ATC TTC ACT gCT gTT TTg TTC gCT
              |   BsaBI   |

A   S   S   A   L   A   A   P   V   N   T   T   T   E  27
          gCT TCC TCT gCT TTg gCT gCT CCA gTT AAC ACC ACT ACT gAA
                                          BpmI  HpaI                BbsI

D   E   T   A   Q   I   P   A   E   A   V   I   G   Y  41
          gAC gAg ACT gCT CAA ATT CCT gCT gAg gCT gTC ATC ggT TAC
     BbsI

S   D   L   E   G   D   F   D   V   A   V   L   P   F  55
          TCT gAC TTg gAA ggT gAC TTC gAC gTC gCT gTT TTg CCA TTC
                                          AatII

S   N   S   T   N   N   G   L   L   F   I   N   T   T  69
          TCT AAC TCT ACT AAC AAC ggT TTg TTg TTC ATC AAC ACT ACC

I   A   S   I   A   A   K   E   E   G   V   S   L   D  83
          ATC gCT TCT ATC gCT gCT AAg gAg gAA ggT gTT TCC TTg gAC

K   R       A   A   C   N   L   P                       91
          AAg AgA     gCT gCT TgT AAC TTg CCA
                      └──────── Site of cleavage!

I   V   R   G   P   C   I   A   F   F   P   R   W   A  105
          ATC gTC AgA ggT CCA TgC ATT gCT TTC TTC CCA AgA Tgg gCT
                              NsiI

F   D   A   V   K   G   K   C   V   L   F   P   Y   G  119
          TTC gAC gCT gTT AAg ggT AAg TgC gTC TTg TTC CCA TAC ggT
                                                      |   PflMI

G   C   Q   G   N   G   N   K   F   Y   S   E   K   E  133
          ggT TgT CAA ggT AAC ggT AAC AAg TTC TAC TCT gAg AAg gAg
     pflMI C   R   E   Y   C   G   V   P   .   .                   141
          TgT AgA gAg TAC TgT ggT gTT CCA TAg TAA gAATTCgCCT
                                                  EcoRI
                                                      TAgACATg
```

| | | | | | |
|---|---|---|---|---|---|
| 1401 | ACTgTTCCTC | AgTTCAAgTT | gggCATTACg | AgAAgACCgg | TCTTgCTAgA |
| 1451 | TTCTAATCAA | gAggATgTCA | gAATgCCATT | TgCCTgAgAg | ATgCAggCTT |
| 1501 | CATTTTTgAT | ACTTTTTTAT | TTgTAACCTA | TATAgTATAg | gATTTTTTTT |
| 1551 | gTCATTTTgT | TTCTTCTCgT | ACgAgCTTgC | TCCTgATCAg | CCTATCTCgC |
| 1601 | AgCTgATgAA | TATCTTgTgg | TAggggTTTg | ggAAAATCAT | TCgAgTTTgA |
| 1651 | TgTTTTTCTT | ggTATTTCCC | ACTCCTCTTC | AgAgTACAgA | AgATTAAgTg |
| 1701 | AgAAgTTCgT | TTgTgCAAgC | TTATCgATAA | gCTTTAATgC | ggTAgTTTAT |
| 1751 | CACAgTTAAA | TTgCTAACgC | AgTCAggCAC | CgTgTATgAA | ATCTAACAAT |
| 1801 | gCgCTCATCg | TCATCCTCgg | CACCgTCACC | CTggATgCTg | TAggCATAgg |
| 1851 | CTTggTTATg | CCggTACTgC | CgggCCTCTT | gCgggATATC | gTCCATTCCg |

TABLE 251-continued pHIL-D2 (MFαPrePro::EPI-HNE-3) 8584 b.p.
DNA has SEQ ID NO. 066; Encoded polypeptide has SEQ ID NO. 067
DNA is circular and double stranded, only one strand is shown.
Translation of the protein to be expressed is shown.

| | | | | |
|---|---|---|---|---|
| 1901 ACAgCATCgC | CAgTCACTAT | ggCgTgCTgC | TAgCgCTATA | TgCgTTgATg |
| 1951 CAATTTCTAT | gCgCACCCgT | TCTCggAgCA | CTgTCCgACC | gCTTTggCCg |
| 2001 CCgCCCAgTC | CTgCTCgCTT | CgCTACTTgg | AgCCACTATC | gACTACgCgA |
| 2051 TCATggCgAC | CACACCCgTC | CTgTggATCT | ATCgAATCTA | AATgTAAgTT |
| 2101 AAAATCTCTA | AATAATTAAA | TAAgTCCCAg | TTTCTCCATA | CgAACCTTAA |
| 2151 CAgCATTgCg | gTgAgCATCT | AgACCTTCAA | CAgCAgCCAg | ATCCATCACT |
| 2201 gCTTggCCAA | TATgTTTCAg | TCCCTCAggA | gTTACgTCTT | gTgAAgTgAT |
| 2251 gAACTTCTgg | AAggTTgCAg | TgTTAACTCC | gCTgTATTgA | CgggCATATC |
| 2301 CgTACgTTgg | CAAAgTgTgg | TTggTACCgg | AggAgTAATC | TCCACAACTC |
| 2351 TCTggAgAgT | AggCACCAAC | AAACACAgAT | CCAgCgTgTT | gTACTTgATC |
| 2401 AACATAAgAA | gAAgCATTCT | CgATTTgCAg | gATCAAgTgT | TCAggAgCgT |
| 2451 ACTgATTggA | CATTTCCAAA | gCCTgCTCgT | AggTTgCAAC | CgATAgggTT |
| 2501 gTAgAgTgTg | CAATACACTT | gCgTACAATT | TCAACCCTTg | gCAACTgCAC |
| 2551 AgCTTggTTg | TgAACAgCAT | CTTCAATTCT | ggCAAgCTCC | TTgTCTgTCA |
| 2601 TATCgACAgC | CAACAgAATC | ACCTgggAAT | CAATACCATg | TTCAgCTTgA |
| 2651 gCAgAAggTC | TgAggCAACg | AAATCTggAT | CAgCgTATTT | ATCAgCAATA |
| 2701 ACTAgAACTT | CAgAAggCCC | AgCAggCATg | TCAATACTAC | ACAgggCTgA |
| 2751 TgTgTCATTT | TgAACCATCA | TCTTggCAgC | AgTAACgAAC | TggTTTCCTg |
| 2801 gACCAAATAT | TTTgTCACAC | TTAggAACAg | TTTCTgTTCC | gTAAgCCATA |
| 2851 gCAgCTACTg | CCTgggCgCC | TCCTgCTAgC | ACgATACACT | TAgCACCAAC |
| 2901 CTTgTgggCA | ACgTAgATgA | CTTCTggggT | AAgggTACCA | TCCTTCTTAg |
| 2951 gTggAgATgC | AAAAACAATT | TCTTTgCAAC | CAgCAACTTT | ggCAggAACA |
| 3001 CCCAgCATCA | gggAAgTggA | AggCAgAATT | gCggTTCCAC | CAggAATATA |
| 3051 gAggCCAACT | TTCTCAATAg | gTCTTgCAAA | ACgAgAgCAg | ACTACACCAg |
| 3101 ggCAAgTCTC | AACTTgCAAC | gTCTCCgTTA | gTTgAgCTTC | ATggAATTTC |
| 3151 CTgACgTTAT | CTATAgAgAg | ATCAATggCT | CTCTTAACgT | TATCTggCAA |
| 3201 TTgCATAAgT | TCCTCTgggA | AAggAgCTTC | TAACACAggT | gTCTTCAAAg |
| 3251 CgACTCCATC | AAACTTggCA | gTTAgTTCTA | AAAgggCTTT | gTCACCATTT |
| 3301 TgACgAACAT | TgTCgACAAT | TggTTTgACT | AATTCCATAA | TCTgTTCCgT |
| 3351 TTTCTggATA | ggACgACgAA | gggCATCTTC | AATTTCTTgT | gAggAggCCT |
| 3401 TAgAAACgTC | AATTTTgCAC | AATTCAATAC | gACCTTCAgA | AgggACTTCT |
| 3451 TTAggTTTgg | ATTCTTCTTT | AggTTgTTCC | TTggTgTATC | CTggCTTggC |
| 3501 ATCTCCTTTC | CTTCTAgTgA | CCTTTAgggA | CTTCATATCC | AggTTTCTCT |
| 3551 CCACCTCgTC | CAACgTCACA | CCgTACTTgg | CACATCTAAC | TAATgCAAAA |
| 3601 TAAAATAAgT | CAgCACATTC | CCAggCTATA | TCTTCCTTgg | ATTTAgCTTC |
| 3651 TgCAAgTTCA | TCAgCTTCCT | CCCTAATTTT | AgCgTTCAAC | AAAACTTCgT |
| 3701 CgTCAAATAA | CCgTTTggTA | TAAgAACCTT | CTggAgCATT | gCTCTTACgA |
| 3751 TCCCACAAgg | TgCTTCCATg | gCTCTAAgAC | CCTTTgATTg | gCCAAAAACAg |
| 3801 gAAgTgCgTT | CCAAgTgACA | gAAACCAACA | CCTgTTTgTT | CAACCACAAA |
| 3851 TTTCAAgCAg | TCTCCATCAC | AATCCAATTC | gATACCCAgC | AACTTTTgAg |

TABLE 251-continued pHIL-D2 (MFαPrePro::EPI-HNE-3) 8584 b.p.
DNA has SEQ ID NO. 066; Encoded polypeptide has SEQ ID NO. 067
DNA is circular and double stranded, only one strand is shown.
Translation of the protein to be expressed is shown.

| | | | | | |
|---|---|---|---|---|---|
| 3901 | TTCgTCCAgA | TgTAgCACCT | TTATACCACA | AACCgTgACg | ACgAgATTgg |
| 3951 | TAgACTCCAg | TTTgTgTCCT | TATAgCCTCC | ggAATAgACT | TTTTggACgA |
| 4001 | gTACACCAgg | CCCAACgAgT | AATTAgAAgA | gTCAgCCACC | AAAgTAgTgA |
| 4051 | ATAgACCATC | ggggCggTCA | gTAgTCAAAg | ACgCCAACAA | AATTTCACTg |
| 4101 | ACAgggAACT | TTTTgACATC | TTCAgAAAgT | TCgTATTCAg | TAgTCAATTg |
| 4151 | CCgAgCATCA | ATAATggggA | TTATACCAgA | AgCAACAgTg | gAAgTCACAT |
| 4201 | CTACCAACTT | TgCggTCTCA | gAAAAAgCAT | AAACAgTTCT | ACTACCgCCA |
| 4251 | TTAgTgAAAC | TTTTCAAATC | gCCCAgTggA | gAAgAAAAAg | gCACAgCgAT |
| 4301 | ACTAgCATTA | gCgggCAAgg | ATgCAACTTT | ATCAACCAgg | gTCCTATAgA |
| 4351 | TAACCCTAgC | gCCTgggATC | ATCCTTTggA | CAACTCTTTC | TgCCAAATCT |
| 4401 | AggTCCAAAA | TCACTTCATT | gATACCATTA | TACggATgAC | TCAACTTgCA |
| 4451 | CATTAACTTg | AAgCTCAgTC | gATTgAgTgA | ACTTgATCAg | gTTgTgCAgC |
| 4501 | TggTCAgCAg | CATAgggAAA | CACggCTTTT | CCTACCAAAC | TCAAggAATT |
| 4551 | ATCAAACTCT | gCAACACTTg | CgTATgCAgg | TAgCAAgggA | AATgTCATAC |
| 4601 | TTgAAgTCgg | ACAgTgAgTg | TAgTCTTgAg | AAATTCTgAA | gCCgTATTTT |
| 4651 | TATTATCAgT | gAgTCAgTCA | TCAggAgATC | CTCTACgCCg | gACgCATCgT |
| 4701 | ggCCggCATC | ACCggCgCCA | CAggTgCggT | TgCTggCgCC | TATATCgCCg |
| 4751 | ACATCACCgA | TggggAAgAT | CgggCTCgCC | ACTTCgggCT | CATgAgCgCT |
| 4801 | TgTTTCggCg | TgggTATggT | ggCAggCCCC | gTggCCgggg | gACTgTTggg |
| 4851 | CgCCATCTCC | TTgCATgCAC | CATTCCTTgC | ggCggCggTg | CTCAACggCC |
| 4901 | TCAACCTACT | ACTgggCTgC | TTCCTAATgC | AggAgTCgCA | TAAgggAgAg |
| 4951 | CgTCgAgTAT | CTATgATTgg | AAgTATgggA | ATggTgATAC | CCgCATTCTT |
| 5001 | CAgTgTCTTg | AggTCTCCTA | TCAgATTATg | CCCAACTAAA | gCAACCggAg |
| 5051 | gAggAgATTT | CATggTAAAT | TTCTCTgACT | TTTggTCATC | AgTAgACTCg |
| 5101 | AACTgTgAgA | CTATCTCggT | TATgACAgCA | gAAATgTCCT | TCTTggAgAC |
| 5151 | AgTAAATgAA | gTCCCACCAA | TAAAgAAATC | CTTgTTATCA | ggAACAAACT |
| 5201 | TCTTgTTTCg | AACTTTTTCg | gTgCCTTgAA | CTATAAAATg | TAgAgTggAT |
| | BstBI | | | | |
| 5251 | ATgTCgggTA | ggAATggAgC | gggCAAATgC | TTACCTTCTg | gACCTTCAAg |
| 5301 | AggTATgTAg | ggTTTgTAgA | TACTgATgCC | AACTTCAgTg | ACAACgTTgC |
| 5351 | TATTTCgTTC | AAACCATTCC | gAATCCAgAg | AAATCAAAgT | TgTTTgTCTA |
| 5401 | CTATTgATCC | AAgCCAgTgC | ggTCTTgAAA | CTgACAATAg | TgTgCTCgTg |
| 5451 | TTTTgAggTC | ATCTTTgTAT | gAATAAATCT | AgTCTTTgAT | CTAAATAATC |
| 5501 | TTgACgAgCC | AAggCgATAA | ATACCCAAAT | CTAAAACTCT | TTTAAAACgT |
| 5551 | TAAAAggACA | AgTATgTCTg | CCTgTATTAA | ACCCCAAATC | AgCTCgTAgT |
| 5601 | CTgATCCTCA | TCAACTTgAg | gggCACTATC | TTgTTTTAgA | gAAATTTgCg |
| 5651 | gAgATgCgAT | ATCgAgAAAA | AggTACgCTg | ATTTTAAACg | TgAAATTTAT |
| 5701 | CTCAAgATCg | CggCCgCgAT | CTCgAATAAT | AACTgTTATT | TTTCAgTgTT |
| 5751 | CCCgATCTgC | gTCTATTTCA | CAATACCAAC | ATgAgTCAgC | TTATCgATgA |
| 5801 | TAAgCTgTCA | AACATgAgAA | TTAATTCgAT | gATAAgCTgT | CAAACATgAg |
| 5851 | AAATCTTgAA | gACgAAAggg | CCTCgTgATA | CgCCTATTTT | TATAggTTAA |

TABLE 251-continued pHIL-D2 (MFαPrePro::EPI-HNE-3) 8584 b.p.
DNA has SEQ ID NO. 066; Encoded polypeptide has SEQ ID NO. 067
DNA is circular and double stranded, only one strand is shown.
Translation of the protein to be expressed is shown.

| | | | | | |
|---|---|---|---|---|---|
| 5901 | TgTCATgATA | ATAATggTTT | CTTAgACgTC <br> AatII | AggTggCACT | TTTCggggAA |
| 5951 | ATgTgCgCgg | AACCCCTATT | TgTTTATTTT | TCTAAATACA | TTCAAATATg |
| 6001 | TATCCgCTCA | TgAgACAATA | ACCCTgATAA | ATgCTTCAAT | AATATTgAAA |
| 6051 | AAggAAgAgT | ATgAgTATTC | AACATTTCCg | TgTCgCCCTT | ATTCCCTTTT |
| 6101 | TTgCggCATT | TTgCCTTCCT | gTTTTTgCTC | ACCCAgAAAC | gCTggTgAAA |
| 6151 | gTAAAAgATg | CTgAAgATCA | gTTgggTgCA | CgAgTgggTT | ACATCgAACT |
| 6201 | ggATCTCAAC | AgCggTAAgA | TCCTTgAgAg | TTTTCgCCCC | gAAgAACgTT |
| 6251 | TTCCAATgAT | gAgCACTTTT | AAAgTTCTgC | TATgTggCgC | ggTATTATCC |
| 6301 | CgTgTTgACg | CCgggCAAgA | gCAACTCggT | CgCCgCATAC | ACTATTCTCA |
| 6351 | gAATgACTTg | gTTgAgTACT | CACCAgTCAC | AgAAAAgCAT | CTTACggATg |
| 6401 | gCATgACAgT | AAgAgAATTA | TgCAgTgCTg | CCATAACCAT | gAgTgATAAC |
| 6451 | ACTgCggCCA | ACTTACTTCT | gACAACgATC | ggAggACCgA | AggAgCTAAC |
| 6501 | CgCTTTTTTg | CACAACATgg | gggATCATgT | AACTCgCCTT | gATCgTTggg |
| 6551 | AACCggAgCT | gAATgAAgCC | ATACCAAACg | ACgAgCgTgA | CACCACgATg |
| 6601 | CCTgCAgCAA | TggCAACAAC | gTTgCgCAAA | CTATTAACTg | gCgAACTACT |
| 6651 | TACTCTAgCT | TCCCggCAAC | AATTAATAgA | CTggATggAg | gCggATAAAg |
| 6701 | TTgCAggACC | ACTTCTgCgC | TCggCCCTTC | CggCTggCTg | gTTTATTgCT |
| 6751 | gATAAATCTg | gAgCCggTgA | gCgTgggTCT | CgCggTATCA | TTgCAgCACT |
| 6801 | ggggCCAgAT | ggTAAgCCCT | CCCgTATCgT | AgTTATCTAC | ACgACggggA |
| 6851 | gTCAggCAAC | TATggATgAA | CgAAATAgAC | AgATCgCTgA | gATAggTgCC |
| 6901 | TCACTgATTA | AgCATTggTA | ACTgTCAgAC | CAAgTTTACT | CATATATACT |
| 6951 | TTAgATTgAT | TTAAATTgTA | AACgTTAATA | TTTTgTTAAA | ATTCgCgTTA |
| 7001 | AATTTTTgTT | AAATCAgCTC | ATTTTTTAAC | CAATAggCCg | AAATCggCAA |
| 7051 | AATCCCTTAT | AAATCAAAAg | AATAgACCgA | gATAgggTTg | AgTgTTgTTC |
| 7101 | CAgTTTggAA | CAAgAgTCCA | CTATTAAAgA | ACgTggACTC | CAACgTCAAA |
| 7151 | gggCgAAAAA | CCgTCTATCA | gggCgATggC | CCACTACgTg | AACCATCACC |
| 7201 | CTAATCAAgT | TTTTTggggT | CgAggTgCCg | TAAAgCACTA | AATCggAACC |
| 7251 | CTAAAgggAg | CCCCCgATTT | AgAgCTTgAC | ggggAAAgCC | ggCgAACgTg |
| 7301 | gCgAgAAAgg | AAgggAAgAA | AgCgAAAggA | gCgggCgCTA | gggCgCTggC |
| 7351 | AAgTgTAgCg | gTCACgCTgC | gCgTAACCAC | CACACCCgCC | gCgCTTAATg |
| 7401 | CgCCgCTACA | gggCgCgTAA | AAggATCTAg | gTgAAgATCC | TTTTTgATAA |
| 7451 | TCTCATgACC | AAAATCCCTT | AACgTgAgTT | TTCgTTCCAC | TgAgCgTCAg |
| 7501 | ACCCCgTAgA | AAAgATCAAA | ggATCTTCTT | gAgATCCTTT | TTTTCTgCgC |
| 7551 | gTAATCTgCT | gCTTgCAAAC | AAAAAAACCA | CCgCTACCAg | CggTggTTTg |
| 7601 | TTTgCCggAT | CAAgAgCTAC | CAACTCTTTT | TCCgAAggTA | ACTggCTTCA |
| 7651 | gCAgAgCgCA | gATACCAAAT | ACTgTCCTTC | TAgTgTAgCC | gTAgTTAggC |
| 7701 | CACCACTTCA | AgAACTCTgT | AgCACCgCCT | ACATACCTCg | CTCTgCTAAT |
| 7751 | CCTgTTACCA | gTggCTgCTg | CCAgTggCgA | TAAgTCgTgT | CTTACCgggT |
| 7801 | TggACTCAAg | ACgATAgTTA | CCggATAAgg | CgCAgCggTC | gggCTgAACg |
| 7851 | ggggggTTCgT | gCACACAgCC | CAgCTTggAg | CgAACgACCT | ACACCgAACT |

TABLE 251-continued pHIL-D2 (MFαPrePro::EPI-HNE-3) 8584 b.p.
DNA has SEQ ID NO. 066; Encoded polypeptide has SEQ ID NO. 067
DNA is circular and double stranded, only one strand is shown.
Translation of the protein to be expressed is shown.

| | | | | | |
|---|---|---|---|---|---|
| 7901 | gAgATACCTA | CAgCgTgAgC | ATTgAgAAAg | CgCCACgCTT | CCCgAAgggA |
| 7951 | gAAAggCggA | CAggTATCCg | gTAAgCggCA | gggTCggAAC | AggAgAgCgC |
| 8001 | ACgAgggAgC | TTCCAggggg | AAACgCCTgg | TATCTTTATA | gTCCTgTCgg |
| 8051 | gTTTCgCCAC | CTCTgACTTg | AgCgTCgATT | TTTgTgATgC | TCgTCAgggg |
| 8101 | ggCggAgCCT | ATggAAAAAC | gCCAgCAACg | CggCCTTTTT | ACggTTCCTg |
| 8151 | gCCTTTTgCT | ggCCTTTTgC | TCACATgTTC | TTTCCTgCgT | TATCCCCTgA |
| 8201 | TTCTgTggAT | AACCgTATTA | CCgCCTTTgA | gTgAgCTgAT | ACCgCTCgCC |
| 8251 | gCAgCCgAAC | gACCgAgCgC | AgCgAgTCAg | TgAgCgAggA | AgCggAAgAg |
| 8301 | CgCCTgATgC | ggTATTTTCT | CCTTACgCAT | CTgTgCggTA | TTTCACACCg |
| 8351 | CATATggTgC | ACTCTCAgTA | CAATCTgCTC | TgATgCCgCA | TAgTTAAgCC |
| 8401 | AgTATACACT | CCgCTATCgC | TACgTgACTg | ggTCATggCT | gCgCCCCgAC |
| 8451 | ACCCgCCAAC | ACCCgCTgAC | gCgCCCTgAC | gggCTTgTCT | gCTCCCggCA |
| 8501 | TCCgCTTACA | gACAAgCTgT | gACCgTCTCC | gggAgCTgCA | TgTgTCAgAg |
| 8551 | gTTTTCACCg | TCATCACCgA | AACgCgCgAg | gCAg | |

Restriction map of pHIL-D2 (MFαPrePro::EPI-HNE-3)

Non-cutters

| | | | | |
|---|---|---|---|---|
| AflIII | ApaI | AscI | AvaI | AvrII |
| BamHI | BglII | BssHII | BstEII | MluI |
| NruI | PacI | PmlI | RsrII | SacII |
| SfiI | SnaBI | SpeI | XhoI | XmaI |

Cutters, 5 or fewer sites

| | | | | | | |
|---|---|---|---|---|---|---|
| AatII | 2 | 1098 | 5925 | | | |
| AccI | 5 | 3312 | 3950 | 5092 | 5396 | 8402 |
| AflIII | 1 | 8173 | | | | |
| AgeI | 1 | 1436 | | | | |
| AlwNI | 3 | 2828 | 2852 | 7759 | | |
| ApaLI | 3 | 6176 | 7859 | 8357 | | |
| AseI | 3 | 591 | 5820 | 6672 | | |
| BanII | 4 | 216 | 4772 | 4786 | 7258 | |
| BbsI | 4 | 1032 | 1432 | 3241 | 5858 | |
| BclI | 4 | 752 | 1584 | 2396 | 4484 | |
| BglI | 3 | 284 | 2717 | 6724 | | |
| BsaAI | 2 | 7185 | 8421 | | | |
| BsaBI | 4 | 958 | 1449 | 1605 | 5603 | |
| BsgI | 2 | 2545 | 4494 | | | |
| BsiWI | 2 | 1568 | 2301 | | | |
| BsmI | 5 | 317 | 571 | 1471 | 2414 | 4993 |
| BspDI | 2 | 1723 | 5793 | | | |

TABLE 251-continued pHIL-D2 (MFαPrePro::EPI-HNE-3) 8584 b.p.
DNA has SEQ ID NO. 066; Encoded polypeptide has SEQ ID NO. 067
DNA is circular and double stranded, only one strand is shown.
Translation of the protein to be expressed is shown.

| Enzyme | Count | Positions |
|---|---|---|
| BspEI | 1 | 3978 |
| BspHI | 5 | 749 4790 5903 6008 7453 |
| BspMI | 1 | 4576 |
| Bst1107I | 1 | 8402 |
| BstBI (AsuII) | 2 | 945 5207 |
| BstXI | 3 | 711 2765 2896 |
| Bsu36I | 1 | 2223 |
| DraI (AhaIII) | 5 | 421 5541 5683 6268 6960 |
| DraIII | 2 | 3754 7182 |
| DrdI | 5 | 1092 5557 7136 8065 8478 |
| EagI | 3 | 7 5711 8591 |
| Eam1105I | 2 | 5077 6843 |
| EarI | 5 | 155 1675 4026 6054 8295 |
| Ecl136I | 1 | 216 |
| Eco47III | 2 | 1932 4795 |
| EcoNI | 3 | 3433 4923 5293 |
| EcoRI | 1 | 1383 |
| EcoRV | 2 | 1885 5658 |
| Esp3I (BsaI) | 2 | 3120 8524 |
| EspI (Bpu1102I) | 1 | 597 |
| FspI | 2 | 1960 6623 |
| HincII | 4 | 1017 2272 3312 6304 |
| HindIII | 3 | 885 1717 1729 |
| HpaI | 2 | 1017 2272 |
| KasI | 4 | 2865 4714 4735 4849 |
| KpnI | 2 | 2323 2934 |
| MscI | 2 | 2204 3789 |
| MunI | 4 | 877 3198 3317 4145 |
| NcoI | 1 | 3766 |
| NdeI | 1 | 8351 |
| NgoMI | 2 | 4702 7288 |
| NheI | 2 | 1929 2875 |
| NotI | 3 | 6 5710 8590 |
| NsiI | 2 | 684 1241 |
| PflMI | 2 | 196 1302 |
| PmeI | 1 | 420 |
| PpuMI | 2 | 142 4339 |
| PstI | 1 | 6602 |
| PvuI | 1 | 6476 |
| PvuII | 2 | 1600 4497 |

TABLE 251-continued pHIL-D2 (MFαPrePro::EPI-HNE-3) 8584 b.p.
DNA has SEQ ID NO. 066; Encoded polypeptide has SEQ ID NO. 067
DNA is circular and double stranded, only one strand is shown.
Translation of the protein to be expressed is shown.

| | | |
|---|---|---|
| SacI | 1 | 216 |
| SalI | 1 | 3312 |
| ScaI | 2 | 1360 6365 |
| SphI | 1 | 4863 |
| SspI | 3 | 2806 6041 6977 |
| StuI | 1 | 3395 |
| Tth111I | 1 | 8426 |
| XbaI | 1 | 2168 |
| XcmI | 1 | 711 |
| XmnI | 5 | 2825 4256 5210 5818 6244 |

TABLE 252

BstBI-AatII-EcoRI cas8ette for expression of EPI-HNE-4 DNA has SEQ ID NO. 068;
amino-acid sequence has SEQ ID NO. 069

```
                                              5'-TTCgAA      ACg
                                                 BstBI

M    R    F    P    S    I    F    T    A    V    L    F    A       13
  ATg  AgA  TTC  CCA  TCT  ATC  TTC  ACT  gCT  gTT  TTg  TTC  gCT
        |   BsaBi    |

A    S    S    A    L    A    A    P    V    N    T    T    T    E  27
  gCT  TCC  TCT  gCT  TTg  gCT  gCT  CCA  gTT  AAC  ACC  ACT  ACT  gAA
                                       BpmI     HpaI                BbsI

D    E    T    A    Q    I    P    A    E    A    V    I    G    Y  41
  gAC  gAg  ACT  gCT  CAA  ATT  CCT  gCT  gAg  gCT  gTC  ATC  ggT  TAC
  BbsI

S    D    L    E    G    D    F    D    V    A    V    L    P    F  55
  TCT  gAC  TTg  gAA  ggT  gAC  TTC  gAC  gTC  gCT  gTT  TTg  CCA  TTC
                                             AatII

S    N    S    T    N    N    G    L    L    F    I    N    T    T  69
  TCT  AAC  TCT  ACT  AAC  AAC  ggT  TTg  TTg  TTC  ATC  AAC  ACT  ACC

I    A    S    I    A    A    K    E    E    G    V    S    L    D  83
  ATC  gCT  TCT  ATC  gCT  gCT  AAg  gAg  gAA  ggT  gTT  TCC  TTg  gAC

K    R    E    A    C    N    L    P                                 91
  AAg  AgA  gAg  gCT  TgT  AAC  TTg  CCA

I    V    R    G    P    C    I    A    F    F    P    R    W    A  105
  ATC  gTC  AgA  ggT  CCA  TgC  ATT  gCT  TTC  TTC  CCA  AgA  Tgg  gCT
                                NsiI

F    D    A    V    K    G    K    C    V    L    F    P    Y    G  119
  TTC  gAC  gCT  gTT  AAg  ggT  AAg  TgC  gTC  TTg  TTC  CCA  TAC  ggT
                                                            |  PflMI

G    C    Q    G    N    G    N    K    F    Y    S    E    K    E  133
```

TABLE 252-continued

BstBI-AatII-EcoRI cas8ette for expression of EPI-HNE-4 DNA has SEQ ID NO. 068;
amino-acid sequence has SEQ ID NO. 069

```
  ggT  TgT  CAA  ggT  AAC  ggT  AAC  AAg  TTC  TAC  TCT  gAg  AAg  gAg
! PflMI
!
!   C    R    E    Y    C    G    V    P    .    .
  TgT  AgA  gAg  TAC  TgT  ggT  gTT  CCA  TAg  TAA  gAATTCgCCT                    141
!                                                       EcoRI
```

The DNA is a linear fragment that is double stranded in vivo, only one strand is shown. The amino acid sequence is that of a disulfide-containing protein that is processed in vivo.

TABLE 253 pD2pick(MFαPrePro::EPI-HNE-3), 8590 bp, CIRCULAR
dsDNA, one strand shown. pD2pick(MFαPrePro::EPI-HNE-3) DNA has
SEQ ID NO. 070 Encoded protein has SEQ ID NO. 069

```
            1            2            3            4            5
     1234567890   1234567890   1234567890   1234567890   1234567890
   1 AgATCgCggC   CgCgATCTAA   CATCCAAAgA   CgAAAggTTg   AATgAAACCT

51 TTTTgCCATC   CgACATCCAC   AggTCCATTC   TCACACATAA   gTgCCAAACg

101 CAACAggAgg   ggATACACTA   gCAgCAgACC   gTTgCAAACg   CAggACCTCC

151 ACTCCTCTTC   TCCTCAACAC   CCACTTTTgC   CATCgAAAAA   CCAgCCCAgT

201 TATTgggCTT   gATTggAgCT   CgCTCATTCC   AATTCCTTCT   ATTAggCTAC
                    SacI
 251 TAACACCATg   ACTTTATTAg   CCTgTCTATC   CTggCCCCCC   TggCgAggTC 301 ATgTTTgTTT   ATTTCCgAAT   gCAACAAgCT   CCgCATTACA   CCCgAACATC 351 ACTCCAgATg   AgggCTTTCT   gAgTgTgggg   TCAAATAgTT   TCATgTTCCC 401 AAATggCCCA   AAACTgACAg   TTTAAACgCT   gTCTTggAAC   CTAATATgAC
                                PmeI
 451 AAAAgCgTgA   TCTCATCCAA   gATgAACTAA   gTTTggTTCg   TTgAAATgCT 501 AACggCCAgT   TggTCAAAAA   gAAACTTCCA   AAAgTCgCCA   TACCgTTTgT 551 CTTgTTTggT   ATTgATTgAC   gAATgCTCAA   AAATAATCTC   ATTAATgCTTAgC
                                                                EspI
 604      gCAgTCT   CTCTATCgCT   TCTgAACCCg   gTggCACCTg   TgCCgAAACg 651 CAAATggggA   AACAACCCgC   TTTTTggATg   ATTATgCATT   gTCCTCCACA 701 TTgTATgCTT   CCAAgATTCT   ggTgggAATA   CTgCTgATAg   CCTAACgTTC
                    XcmI
 751 ATgATCAAAA   TTTAACTgTT   CTAACCCCTA   CTTgACAggC   AATATATAAA 801 CAgAAggAAg   CTgCCCTgTC   TTAAACCTTT   TTTTTTATCA   TCATTATTAg 851 CTTACTTTCA   TAATTgCgAC   TggTTCCAAT   TgACAAgCTT   TTgATTTTAA 901 CgACTTTTAA   CgACAACTTg   AgAAgATCAA   AAAACAACTA   ATTATTCaAA
                                                              BstBI
! 951 ACg
!
!      M    R    F    P    S    I    F    T    A    V    L    F    A
  954 ATg  AgA  TTC  CCA  TCT  ATC  TTC  ACT  gCT  gTT  TTg  TTC  gCT
!
!      A    S    S    A    L    A    A    P    V    N    T    T    T
  993 gCT  TCC  TCT  gCT  TTg  gCT  gCT  CCA  gTT  AAC  ACC  ACT  ACT
!
!      E    D    E    T    A    Q    I    P    A    E    A    V    I
 1032 gAA  gAC  gAg  ACT  gCT  CAA  ATT  CCT  gCT  gAg  gCT  gTC  ATC
!
!      G    Y    S    D    L    E    G    D    F    D    V    A    V
 1071 ggT  TAC  TCT  gAC  TTg  gAA  ggT  gAC  TTC  gAC  gTC  gCT  gTT
                                                     AatII
!
!      L    P    F    S    N    S    T    N    N    G    L    L    F
 1110 TTg  CCA  TTC  TCT  AAC  TCT  ACT  AAC  AAC  ggT  TTg  TTg  TTC
!
!      I    N    T    T    I    A    S    I    A    A    K    E    E
 1149 ATC  AAC  ACT  ACC  ATC  gCT  TCT  ATC  gCT  gCT  AAg  gAg  gAA
```

TABLE 253-continued pD2pick(MFαPrePro::EPI-HNE-3), 8590 bp, CIRCULAR dsDNA, one strand shown. pD2pick(MFαPrePro::EPI-HNE-3) DNA has SEQ ID NO. 070 Encoded protein has SEQ ID NO. 069

```
!       G    V    S    L    D    K    R    A    A    C    N    L    P
 1188  ggT  gTT  TCC  TTg  gAC  AAg  AgA  gCT  gCT  TgT  AAC  TTg  CCA
!
!       I    V    R    G    P    C    I    A    F    F    P    R    W
 1227  ATC  gTC  AgA  ggT  CCA  TgC  ATT  gCT  TTC  TTC  CCA  AgA  Tgg
!
!       A    F    D    A    V    K    G    K    C    V    L    F    P
 1266  gCT  TTC  gAC  gCT  gTT  AAg  ggT  AAg  TgC  gTC  TTg  TTC  CCA
!
!       Y    G    G    C    Q    G    N    G    N    K    F    Y    S
 1305  TAC  ggT  ggT  TgT  CAA  ggT  AAC  ggT  AAC  AAg  TTC  TAC  TCT
!
!       E    K    E    C    R    E    Y    C    G    V    P    .    .
 1344  gAg  AAg  gAg  TgT  AgA  gAg  TAC  TgT  ggT  gTT  CCA  TAg  TAA
!
 1383  gAATTC                                         gC   CTTAgACATg
!      EcoRI
 1401  ACTgTTCCTC   AgTTCAAgTT   gggCATTACg   AgAAgACCgg   TCTTgCTAgA
                                                  AegI
 1451  TTCTAATCAA   gAggATgTCA   gAATgCCATT   TgCCTgAgAg   ATgCAggCTT
 1501  CATTTTTgAT   ACTTTTTTAT   TTgTAACCTA   TATAgTATAg   gATTTTTTTT
 1551  gTCATTTTgT   TTCTTCTCgT   ACgAgCTTgC   TCCTgATCAg   CCTATCTCgC
 1601  AgCTgATgAA   TATCTTgTgg   TAggggTTTg   ggAAAATCAT   TCgAgTTTgA
 1651  TgTTTTTCTT   ggTATTTCCC   ACTCCTCTTC   AgAgTACAgA   AgATTAAgTg
 1701  AgAAgTTCgT   TTgTgCAAgC   TTATCgATAA   gCTTTAATgC   ggTAgTTTAT
 1751  CACAgTTAAA   TTgCTAACgC   AgTCAggCAC   CgTgTATgAA   ATCTAACAAT
 1801  gCgCTCATCg   TCATCCTCgg   CACCgTCACC   CTggATgCTg   TAggCATAgg
 1851  CTTggTTATg   CCggTACTgC   CgggCCTCTT   gCgggATATC   gTCCATTCCg
 1901  ACAgCATCgC   CAgTCACTAT   ggCgTgCTgC   TAgCgCTATA   TgCgTTgATg
 1951  CAATTTCTAT   gCgCACCCgT   TCTCggAgCA   CTgTCCgACC   gCTTTggCCg
 2001  CCgCCCAgTC   CTgCTCgCTT   CgCTACTTgg   AgCCACTATC   gACTACgCgA
 2051  TCATggCgAC   CACACCCgTC   CTgTggATCT   ATCgAATCTA   AATgTAAgTT
 2101  AAAATCTCTA   AATAATTAAA   TAAgTCCCAg   TTTCTCCATA   CgAACCTTAA
 2151  CAgCATTgCg   gTgAgCATCT   AgACCTTCAA   CAgCAgCCAg   ATCCATCACT
                             XbaI
 2201  gCTTggCCAA   TATgTTTCAg   TCCCTCAggA   gTTACgTCTT   gTgAAgTgAT
                                      Bsu36I
 2251  gAACTTCTgg   AAggTTgCAg   TgTTAACTCC   gCTgTATTgA   CgggCATATC
 2301  CgTACgTTgg   CAAAgTgTgg   TTggTACCgg   AggAgTAATC   TCCACAACTC
 2351  TCTggAgAgT   AggCACCAAC   AAACACAgAT   CCAgCgTgTT   gTACTTgATC
 2401  AACATAAgAA   gAAgCATTCT   CgATTTgCAg   gATCAAgTgT   TCAggAgCgT
 2451  ACTgATTggA   CATTTCCAAA   gCCTgCTCgT   AggTTgCAAC   CgATAgggTT
 2501  gTAgAgTgTg   CAATACACTT   gCgTACAATT   TCAACCCTTg   gCAACTgCAC
 2551  AgCTTggTTg   TgAACAgCAT   CTTCAATTCT   ggCAAgCTCC   TTgTCTgTCA
 2601  TATCgACAgC   CAACAgAATC   ACCTgggAAT   CAATACCATg   TTCAgCTTgA
 2651  gCAgAAggTC   TgAggCAACg   AAATCTggAT   CAgCgTATTT   ATCAgCAATA
 2701  ACTAgAACTT   CAgAAggCCC   AgCAggCATg   TCAATACTAC   ACAgggCTgA
 2751  TgTgTCATTT   TgAACCATCA   TCTTggCAgC   AgTAACgAAC   TggTTTCCTg
 2801  gACCAAATAT   TTTgTCACAC   TTAggAACAg   TTTCTgTTCC   gTAAgCCATA
 2851  gCAgCTACTg   CCTgggCgCC   TCCTgCTAgC   ACgATACACT   TAgCACCAAC
 2901  CTTgTgggCA   ACgTAgATgA   CTTCTggggT   AAgggTACCA   TCCTTCTTAg
```

TABLE 253-continued pD2pick(MFαPrePro::EPI-HNE-3), 8590 bp, CIRCULAR
dsDNA, one strand shown. pD2pick(MFαPrePro::EPI-HNE-3) DNA has
SEQ ID NO. 070 Encoded protein has SEQ ID NO. 069

| | | | | |
|---|---|---|---|---|
| 2951 gTggAgATgC | AAAAACAATT | TCTTTgCAAC | CAgCAACTTT | ggCAggAACA |
| 3001 CCCAgCATCA | gggAAgTggA | AggCAgAATT | gCggTTCCAC | CAggAATATA |
| 3051 gAggCCAACT | TTCTCAATAg | gTCTTgCAAA | ACgAgAgCAg | ACTACACCAg |
| 3101 ggCAAgTCTC | AACTTgCAAC | gTCTCCgTTA | gTTgAgCTTC | ATggAATTTC |
| 3151 CTgACgTTAT | CTATAgAgAg | ATCAATggCT | CTCTTAACgT | TATCTggCAA |
| 3201 TTgCATAAgT | TCCTCTgggA | AAggAgCTTC | TAACACAggT | gTCTTCAAAg |
| 3251 CgACTCCATC | AAACTTggCA | gTTAgTTCTA | AAAgggCTTT | gTCACCATTT |
| 3301 TgACgAACAT | TgTCgACAAT | TggTTTgACT | AATTCCATAA | TCTgTTCCgT |
| 3351 TTTCTggATA | ggACgACgAA | gggCATCTTC | AATTTCTTgT | gAgg<u>AggCCT</u> |
| | | | | StuI |
| 3401 TAgAAACgTC | AATTTTgCAC | AATTCAATAC | gACCTTCAgA | AgggACTTCT |
| 3451 TTAggTTTgg | ATTCTTCTTT | AggTTgTTCC | TTggTgTATC | CTggCTTggC |
| 3501 ATCTCCTTTC | CTTCTAgTgA | CCTTTAgggA | CTTCATATCC | AggTTTCTCT |
| 3551 CCACCTCgTC | CAACgTCACA | CCgTACTTgg | CACATCTAAC | TAATgCAAAA |
| 3601 TAAAATAAgT | CAgCACATTC | CCAggCTATA | TCTTCCTTgg | ATTTAgCTTC |
| 3651 TgCAAgTTCA | TCAgCTTCCT | CCCTAATTTT | AgCgTTCAAC | AAAACTTCgT |
| 3701 CgTCAAATAA | CCgTTTggTA | TAAgAACCTT | CTggAgCATT | gCTCTTACgA |
| 3751 TCCCACAAgg | TgCTT<u>CCATg</u> | gCTCTAAgAC | CCTTTgATTg | gCCAAAACAg |
| | NcoI | | | |
| 3801 gAAgTgCgTT | CCAAgTgACA | gAAACCAACA | CCTgTTTgTT | CAACCACAAA |
| 3851 TTTCAAgCAg | TCTCCATCAC | AATCCAATTC | gATACCCAgC | AACTTTTgAg |
| 3901 TTCgTCCAgA | TgTAgCACCT | TTATACCACA | AACCgTgACg | ACgAgATTgg |
| 3951 TAgACTCCAg | TTTgTgTCCT | TATAg<u>CCTCC</u> | ggAATAgACT | TTTTggACgA |
| | | BspEI | | |
| 4001 gTACACCAgg | CCCAACgAgT | AATTAgAAgA | gTCAgCCACC | AAAgTAgTgA |
| 4051 ATAgACCATC | ggggCggTCA | gTAgTCAAAg | ACgCCAACAA | AATTTCACTg |
| 4101 ACAgggAACT | TTTTgACATC | TTCAgAAAgT | TCgTATTCAg | TAgTCAATTg |
| 4151 CCgAgCATCA | ATAATggggA | TTATACCAgA | AgCAACAgTg | gAAgTCACAT |
| 4201 CTACCAACTT | TgCggTCTCA | gAAAAAgCAT | AAACAgTTCT | ACTACCgCCA |
| 4251 TTAgTgAAAC | TTTTCAAATC | gCCCAgTggA | gAAgAAAAAg | gCACAgCgAT |
| 4301 ACTAgCATTA | gCgggCAAgg | ATgCAACTTT | ATCAACCAgg | gTCCTATAgA |
| 4351 TAACCCTAgC | gCCTgggATC | ATCCTTTggA | CAACTCTTTC | TgCCAAATCT |
| 4401 AggTCCAAAA | TCACTTCATT | gATACCATTA | TACggATgAC | TCAACTTgCA |
| 4451 CATTAACTTg | AAgCTCAgTC | gATTgAgTgA | ACTTgATCAg | gTTgTgCAgC |
| 4501 TggTCAgCAg | CATAgggAAA | CACggCTTTT | CCTACCAAAC | TCAAggAATT |
| 4551 ATCAAACTCT | gCAACACTTg | CgTATgCAgg | TAgCAAgggA | AATgTCATAC |
| 4601 TTgAAgTCgg | ACAgTgAgTg | TAgTCTTgAg | AAAATTCTgAA | gCCgTATTTT |
| 4651 TATTATCAgT | gAgTCAgTCA | TCAggAgATC | CTCTACgCCg | gACgCATCgT |
| 4701 ggCCggCATC | ACCggCgCCA | CAggTgCggT | TgCTggCgCC | TATATCgCCg |
| 4751 ACATCACCgA | TggggAAgAT | CgggCTCgCC | ACTTCgggCT | CATgAgCgCT |
| 4801 TgTTTCggCg | TgggTATggT | ggCAggCCCC | gTggCCgggg | gACTgTTggg |
| 4851 CgCCATCTCC | TTgCATgCAC | CATTCCTTgC | ggCggCggTg | CTCAACggCC |

TABLE 253-continued pD2pick(MFαPrePro::EPI-HNE-3), 8590 bp, CIRCULAR
dsDNA, one strand shown. pD2pick(MFαPrePro::EPI-HNE-3) DNA has
SEQ ID NO. 070 Encoded protein has SEQ ID NO. 069

| | | | | |
|---|---|---|---|---|
| 4901 TCAACCTACT | ACTgggCTgC | TTCCTAATgC | AggAgTCgCA | TAAgggAgAg |
| 4951 CgTCgAgTAT | CTATgATTgg | AAgTATgggA | ATggTgATAC | CCgCATTCTT |
| 5001 CAgTgTCTTg | AggTCTCCTA | TCAgATTATg | CCCAACTAAA | gCAACCggAg |
| 5051 gAggAgATTT | CATggTAAAT | TTCTCTgACT | TTTggTCATC | AgTAgACTCg |
| 5101 AACTgTgAgA | CTATCTCggT | TATgACAgCA | gAAATgTCCT | TCTTggAgAC |

```
                    1                   2                   3                   4                   5
           1234567890          1234567890          1234567890          1234567890          1234567890
```

| | | | | |
|---|---|---|---|---|
| 5151 AgTAAATgAA | gTCCCACCAA | TAAAgAAATC | CTTgTTATCA | ggAACAAACT |
| 5201 TCTTgTTTCg | CgAACTTTTT | CggTgCCTTg | AACTATAAAA | TgTAgAgTgg |
| 5251 ATATgTCggg | TAggAATggA | gCgggCAAAT | gCTTACCTTC | TggACCTTCA |
| 5301 AgAggTATgT | AgggTTTgTA | gATACTgATg | CCAACTTCAg | TgACAACgTT |
| 5351 gCTATTTCgT | TCAAACCATT | CCgAATCCAg | AgAAATCAAA | gTTgTTTgTC |
| 5401 TACTATTgAT | CCAAgCCAgT | gCggTCTTgA | AACTgACAAT | AgTgTgCTCg |
| 5451 TgTTTTgAgg | TCATCTTTgT | ATgAATAAAT | CTAgTCTTTg | ATCTAAATAA |
| 5501 TCTTgACgAg | CCAAggCgAT | AAATACCCAA | ATCTAAAACT | CTTTTAAAAC |
| 5551 gTTAAAAggA | CAAgTATgTC | TgCCTgTATT | AAACCCCAAA | TCAgCTCgTA |
| 5601 gTCTgATCCT | CATCAACTTg | AggggCACTA | TCTTgTTTTA | gAgAAATTTg |
| 5651 CggAgATgCg | ATATCgAgAA | AAAggTACgC | TgATTTTAAA | CgTgAAATTT |
| 5701 ATCTCAAgAT | CgCggCCgCg | ATCTCgAATA | ATAACTgTTA | TTTTTCAgTg |
| 5751 TTCCCgATCT | gCgTCTATTT | CACAATACCA | ACATgAgTCA | gCTTATCgAT |
| 5801 gATAAgCTgT | CAAACATgAg | AATTAATTCg | ATgATAAgCT | gTCAAACATg |
| 5851 AgAAAATCTTg | AAgACgAAAg | ggCCTCgTgA | TACgCCTATT | TTTATAggTT |
| 5901 AATgTCATgA | TAATAATggT | TTCTTAgACg | TACgTCAggT | ggCACTTTTC |
| 5951 ggggAAATgT | gCgCggAACC | CCTATTTgTT | TATTTTTCTA | AATACATTCA |
| 6001 AATATgTATC | CgCTCATgAg | ACAATAACCC | TgATAAATgC | TTCAATAATA |
| 6051 TTgAAAAAgg | AAgAgTATgA | gTATTCAACA | TTTCCgTgTC | gCCCTTATTC |
| 6101 CCTTTTTTgC | ggCATTTTgC | CTTCCTgTTT | TTgCTCACCC | AgAAACgCTg |
| 6151 gTgAAAgTAA | AAgATgCTgA | AgATCAgTTg | ggTgCACgAg | TgggTTACAT |
| 6201 CgAACTggAT | CTCAACAgCg | gTAAgATCCT | TgAgAgTTTT | CgCCCCgAAg |
| 6251 AACgTTTTCC | AATgATgAgC | ACTTTTAAAg | TTCTgCTATg | TggCgCggTA |
| 6301 TTATCCCgTg | TTgACgCCgg | gCAAgAgCAA | CTCggTCgCC | gCATACACTA |
| 6351 TTCTCAgAAT | gACTTggTTg | AgTACTCACC | AgTCACAgAA | AAgCATCTTA |
| 6401 CggATggCAT | gACAgTAAgA | gAATTATgCA | gTgCTgCCAT | AACCATgAgT |
| 6451 gATAACACTg | CggCCAACTT | ACTTCTgACA | ACgATCggAg | gACCgAAggA |
| 6501 gCTAACCgCT | TTTTTgCACA | ACATggggA | TCATgTAACT | CgCCTTgATC |
| 6551 gTTgggAACC | ggAgCTgAAT | gAAgCCATAC | CAAACgACgA | gCgTgACACC |
| 6601 ACgATgCCTg | CAgCAATggC | AACAACgTTg | CgCAAACTAT | TAACTggCgA |
| 6651 ACTACTTACT | CTAgCTTCCC | ggCAACAATT | AATAgACTgg | ATggAggCgg |
| 6701 ATAAAgTTgC | AggACCACTT | CTgCgCTCgg | CCCTTCCggC | TggCTggTTT |
| 6751 ATTgCTgATA | AATCTggAgC | CggTgAgCgT | gggTCTCgCg | gTATCATTgC |
| 6801 AgCACTgggg | CCAgATggTA | AgCCCTCCCg | TATCgTAgTT | ATCTACACgA |

TABLE 253-continued pD2pick(MFαPrePro::EPI-HNE-3), 8590 bp, CIRCULAR
dsDNA, one strand shown. pD2pick(MFαPrePro::EPI-HNE-3) DNA has
SEQ ID NO. 070 Encoded protein has SEQ ID NO. 069

| | | | | |
|---|---|---|---|---|
| 6851 CggggAgTCA | ggCAACTATg | gATgAACgAA | ATAgACAgAT | CgCTgAgATA |
| 6901 ggTgCCTCAC | TgATTAAgCA | TTggTAACTg | TCAgACCAAg | TTTACTCATA |
| 6951 TATACTTTAg | ATTgATTTAA | ATTgTAAACg | TTAATATTTT | gTTAAAATTC |
| 7001 gCgTTAAATT | TTTgTTAAAT | CAgCTCATTT | TTTAACCAAT | AggCCgAAAT |
| 7051 CggCAAAATC | CCTTATAAAT | CAAAAgAATA | gACCgAgATA | gggTTgAgTg |
| 7101 TTgTTCCAgT | TTggAACAAg | AgTCCACTAT | TAAAgAACgT | ggACTCCAAC |
| 7151 gTCAAAgggC | gAAAAACCgT | CTATCAgggC | gATggCCCAC | TACgTgAACC |
| 7201 ATCACCCTAA | TCAAgTTTTT | TggggTCgAg | gTgCCgTAAA | gCACTAAATC |
| 7251 ggAACCCTAA | AgggAgCCCC | CgATTTAgAg | CTTgACgggg | AAAgCCggCg |
| 7301 AACgTggCgA | gAAAggAAgg | gAAgAAACg | AAAggAgCgg | gCgCTAgggC |
| 7351 gCTggCAAgT | gTAgCggTCA | CgCTgCgCgT | AACCACCACA | CCCgCCgCgC |
| 7401 TTAATgCgCC | gCTACAgggC | gCgTAAAAgg | ATCTAggTgA | AgATCCTTTT |
| 7451 TgATAATCTC | ATgACCAAAA | TCCCTTAACg | TgAgTTTTCg | TTCCACTgAg |

|  | 1<br>1234567890 | 2<br>1234567890 | 3<br>1234567890 | 4<br>1234567890 | 5<br>1234567890 |
|---|---|---|---|---|---|
| 7501 | CgTCAgACCC | CgTAgAAAAg | ATCAAAggAT | CTTCTTgAgA | TCCTTTTTTT |
| 7551 | CTgCgCgTAA | TCTgCTgCTT | gCAAACAAAA | AAACCACCgC | TACCAgCggT |
| 7601 | ggTTTgTTTg | CCggATCAAg | AgCTACCAAC | TCTTTTTCCg | AAggTAACTg |
| 7651 | gCTTCAgCAg | AgCgCAgATA | CCAAATACTg | TCCTTCTAgT | gTAgCCgTAg |
| 7701 | TTAggCCACC | ACTTCAAgAA | CTCTgTAgCA | CCgCCTACAT | TCgTgTCTTA |
| 7751 | gCTAATCCTg | TTACCAgTgg | CTgCTgCCAg | TggCgATAAg | TCgTgTCTTA |
| 7801 | CCgggTTggA | CTCAAgACgA | TAgTTACCgg | ATAAgCgCA | gCggTCgggC |
| 7851 | TgAACggggg | gTTCgTgCAC | ACAgCCCAgC | TTggAgCgAA | CgAACTACAC |
| 7901 | CgAACTgAgA | TACCTACAgC | gTgAgCATTg | AgAAAgCgCC | ACgCTTCCCg |
| 7951 | AAgggAgAAA | ggCggACAgg | TATCCggTAA | gCggCAgggT | CggAACAggA |
| 8001 | gAgCgCACgA | gggAgCTTCC | AggggggAAAC | gCCTggTATC | TTTATAgTCC |
| 8051 | TgTCgggTTT | CgCCACCTCT | gACTTgAgCg | TCgATTTTTg | TgATgCTCgT |
| 8101 | CAggggggCg | gAgCCTATgg | AAAAACgCCA | gCAACgCggC | CTTTTTACgg |
| 8151 | TTCCTggCCT | TTTgCTggCC | TTTTgCTCAC | ATgTTCTTTC | CTgCgTTATC |
| 8201 | CCCTgATTCT | gTggATAACC | gTATTACCgC | CTTTgAgTgA | gCTgATACCg |
| 8251 | CTCgCCgCAg | CCgAACgACC | gAgCgCAgCg | AgTCAgTgAg | CgAggAggCg |
| 8301 | gAAgAgCgCC | TgATgCggTA | TTTTCTCCTT | ACgCATCTgT | gCggTATTTC |
| 8351 | ACACCgCATA | TggTgCACTC | TCAgTACAAT | CTgCTCTgAT | gCCgCATAgT |
| 8401 | TAAgCCAgTA | TACACTCCgC | TATCgCTACg | TgACTgggTC | ATggCTgCgC |
| 8451 | CCCgACACCC | gCCAACACCC | gCTgACgCgC | CCTgACgggC | TTgTCTgCTC |
| 8501 | CCggCATCCg | CTTACAgACA | AgCTgTgACC | gTCTCCgggA | gCTgCATgTg |
| 8551 | TCAgAggTTT | TCACCgTCAT | CACCgAAACg | CgCgAggCAg |  |

TABLE 254 restriction map of pD2pick (MFαPrePro::EPI-HNE-3)

Non-cutters

| | | | | |
|---|---|---|---|---|
| AflII | ApaI | AscI | AvaI | AvrII |
| BamHI | BglII | BssHII | BstEII | MluI |
| PacI | PmlI | RsrII | SacII | SfiI |
| SnaBI | SpeI | XhoI | XmaI | |

Cutters, 5 or fewer sites

| Enzyme | Count | | | | | |
|---|---|---|---|---|---|---|
| AatII | 1 | 1098 | | | | |
| AccI | 5 | 3312 | 3950 | 5092 | 5398 | 8408 |
| AflIII | 1 | 8179 | | | | |
| AgeI | 1 | 1436 | | | | |
| AlwNI | 3 | 2828 | 2852 | 7765 | | |
| ApaLI | 3 | 6182 | 7865 | 8363 | | |
| AseI | 3 | 591 | 5822 | 6678 | | |
| BanII | 4 | 216 | 4772 | 4786 | 7264 | |
| BbsI | 4 | 1032 | 1432 | 3241 | 5860 | |
| BclI | 4 | 752 | 1584 | 2396 | 4484 | |
| BglI | 3 | 284 | 2717 | 6730 | | |
| BsaAI | 2 | 7191 | 8427 | | | |
| BsaBI | 4 | 958 | 1449 | 1605 | 5605 | |
| BsgI | 2 | 2545 | 4494 | | | |
| BsiWI | 3 | 1568 | 2301 | 5929 | | |
| BsmI | 5 | 317 | 571 | 1471 | 2414 | 4993 |
| BspDI | 2 | 1723 | 5795 | | | |
| BspEI | 1 | 3978 | | | | |
| BspHI | 5 | 749 | 4790 | 5905 | 6014 | 7459 |
| BspMI | 1 | 4576 | | | | |
| Bst1107I | 1 | 8408 | | | | |
| BstBI (AsuII) | 1 | 945 | | | | |
| BstXI | 3 | 711 | 2765 | 2896 | | |
| Bsu36I | 1 | 2223 | | | | |
| DraI (AhaIII) | 5 | 421 | 5543 | 5685 | 6274 | 6966 |
| DraIII | 2 | 3754 | 7188 | | | |
| DrdI | 5 | 1092 | 5559 | 7142 | 8071 | 8484 |
| EagI | 3 | 7 | 5713 | 8597 | | |
| Eam1105I | 2 | 5077 | 6849 | | | |
| EarI | 5 | 155 | 1675 | 4026 | 6060 | 8301 |
| Ecl136I | 1 | 216 | | | | |
| Eco47III | 2 | 1932 | 4795 | | | |
| EcoNI | 3 | 3433 | 4923 | 5295 | | |
| EcoRI | 1 | 1383 | | | | |
| EcoRV | 2 | 1885 | 5660 | | | |
| Esp3I (BsaI) | 2 | 3120 | 8530 | | | |
| EspI (Bpu1102I) | 1 | 597 | | | | |
| FspI | 2 | 1960 | 6629 | | | |
| HincII | 4 | 1017 | 2272 | 3312 | 6310 | |
| HindIII | 3 | 885 | 1717 | 1729 | | |
| HpaI | 2 | 1017 | 2272 | | | |
| KasI | 4 | 2865 | 4714 | 4735 | 4849 | |
| KpnI | 2 | 2323 | 2934 | | | |
| MscI | 2 | 2204 | 3789 | | | |
| MunI | 4 | 877 | 3198 | 3317 | 4145 | |
| NcoI | 1 | 3766 | | | | |
| NdeI | 1 | 8357 | | | | |
| NgoMI | 2 | 4702 | 7294 | | | |
| NheI | 2 | 1929 | 2875 | | | |
| NotI | 3 | 6 | 5712 | 8596 | | |
| NruI | 1 | 5208 | | | | |
| NsiI | 2 | 684 | 1241 | | | |
| PflMI | 2 | 196 | 1302 | | | |
| PmeI | 1 | 420 | | | | |
| PpuMI | 2 | 142 | 4339 | | | |
| PstI | 1 | 6608 | | | | |
| PvuI | 1 | 6482 | | | | |
| PvuII | 2 | 1600 | 4497 | | | |
| SacI | 1 | 216 | | | | |
| SalI | 1 | 3312 | | | | |
| ScaI | 2 | 1360 | 6371 | | | |
| SphI | 1 | 4863 | | | | |
| SspI | 3 | 2806 | 6047 | 6983 | | |
| StuI | 1 | 3395 | | | | |
| Tth111I | 1 | 8432 | | | | |
| XbaI | 1 | 2168 | | | | |
| XcmI | 1 | 711 | | | | |
| XmnI | 5 | 2825 | 4256 | 5212 | 5820 | 6250 |

TABLE 399

Number of amino-acid differences between some Kunitz domains
Differences counted for resideues 3 through 57 where residue 5 is the first cysteine of each domain.

| | Consensus | BPTI | ITI-D1 | ITI-D2 | EPI-HNE-1 | EPI-HNE-2 | EPI-HNE-3 | EPI-HNE-4 |
|---|---|---|---|---|---|---|---|---|
| Consensus | — | 21 | 26 | 27 | 19 | 19 | 27 | 27 |
| BPTI | 21 | — | 32 | 34 | 8 | 8 | 34 | 34 |
| ITI-D1 | 26 | 32 | — | 34 | 28 | 28 | 33 | 33 |
| ITI-D2 | 27 | 34 | 34 | — | 31 | 31 | 4 | 5 |
| EPI-HNE-1 | 19 | 8 | 28 | 31 | — | — | 27 | 27 |
| EPI-HNE-2 | 19 | 8 | 28 | 31 | — | — | 27 | 27 |
| EPI-HNE-3 | 27 | 34 | 33 | 4 | 27 | 27 | — | 1 |
| EPI-HNE-4 | 27 | 34 | 33 | 5 | 27 | 27 | 1 | — |

TABLE 400

Amino-acid Sequence of ITI light chain (SEQ ID NO. 072)

```
          111111 111122
12345 6789012345 678901
avlpq eeegsgggql vtevtk
```

```
2 2 2 2 2 2 2 2 3 3 3 3 3 3 3 3 3 3 4 4 4 4 4 4 4 4 4 4 5 5 5 5 5 5 5 5 5 5 6 6 6 6 6 6 6 6 6 6 7 7 7 7 7 7 7
2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6
K E D S C Q L G Y S A G P C MG MT S R YF YN GT S MA C E T F Q Y GG C MG N G N N F V T E K E C L Q T C
```

```
77788
78901
rtvaa
```

```
                        1 1 1 1 1 1 1 1 1 1 1 1 1 1 1 1 1 1 1 1 1 1 1 1 1 1 1 1 1 1 1 1 1 1
8 8 8 8 8 8 8 8 9 9 9 9 9 9 9 9 9 9 0 0 0 0 0 0 0 0 0 0 1 1 1 1 1 1 1 1 1 1 2 2 2 2 2 2 2 2 2 2 3 3 3 3 3 3
2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5
C N L P I V R G P C R A F I Q L WA F D A V K G K C V L F P Y G G C Q G N G N K F Y S E K E C R E Y C G V P
```

```
              111111111111
              333344444444
              678901234567
              gdgdeelrfsn
```

ITI-D1 comprises residues 22-76 and optionally one of residue 77, residues 77 and 78, or residues 77-79.
ITI-D2 comprises residues 80-135 and optionally one of residue 79 or residues 78-79.

The lines under the sequences represent disulfides.

TABLE 401

Kunitz-domain hNE inhibitors producible in *Pichia pastoris*

| Protein name | Residue number<br>          1 1 1 1 1 1 1 1 1 1 2 2 2 2 2 2 2 2 2 2 3 3 3 3 3 3 3 3 3 3 4 4 4 4 4 4 4 4 4 4 5 5 5 5 5 5 5 5<br>1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 |
|---|---|
| BPTI<br>SEQ ID NO. 021 | R P D F C L E P P Y T G P C K A R I I R Y F Y N A K A G L C Q T F V Y G G C R A K R N N F K S A E D C M R T C G G A |
| EPI-HNE-1<br>SEQ ID NO. 026 | R P D F C L E P P Y T G P C E A F F R Y F Y N A K A G L C Q T F V Y G G C M G N N N F K S A E D C M R T C G G A |
| EPI-HNE-2<br>SEQ ID NO. 027 | E A E A R P D F C L E P P Y T G P C E A F F R Y F Y N A K A G L C Q T F V Y G G C M G N N N F K S A E D C M R T C G G A |
| ITI-D2<br>SEQ ID NO. 003 | T V A A C N L P I V R G P C R A F I Q L W A F D A V K G K C V L F P Y G G C Q G N G N K F Y S E K E C R E Y C G V P |
| EPI-HNE-3<br>SEQ ID NO. 019 | A A C N L P I V R G P C E A F F R W A F D A V K G K C V L F P Y G G C Q G N G N K F Y S E K E C R E Y C G V P |
| EPI-HNE-4<br>SEQ ID NO. 020 | E A C N L P I V R G P C E A F F R W A F D A V K G K C V L F P Y G G C Q G N G N K F Y S E K E C R E Y C G V P |

The lines represent disulfides.

Each of the proteins has the same disulfide-bonding pattern shown for EPI-HNE-4.

TABLE 601

Sequences of purified hNE inhibitors derived from Kunitz domains

| Protein Name | Sequence (positions 1–58) | SEQ ID NO. |
|---|---|---|
| BPTI | RPDFCLEPPYTGPCKARIIRYFYNAKAGLCQTFVYGGCRAKRNNFKSAEDCMRTCGGA | SEQ ID NO. 021 |
| EPI-HNE-1 | RPDFCLEPPYTGPCIAFFPRYFYNAKAGLCQTFVYGGCMGNGNNFKSAEDCMRTCGGA | SEQ ID NO. 026 |
| EPI-HNE-2 | EAEARPDFCLEPPYTGPCIAFFPRYFYNAKAGLCQTFVYGGCMGNGNNFKSAEDCMRTCGGA | SEQ ID NO. 027 |
| BPTI | RPDFCLEPPYTGPCKARIIRYFYNAKAGLCQTFVYGGCRAKRNNFKSAEDCMRTCGGA | SEQ ID NO. 021 |
| EPI-HNE-1 | ------------I-FFP--------------------MGNM---- | SEQ ID NO. 026 |
| EPI-HNE-2 | EAEA--------I-FFP--------------------MGNM---- | SEQ ID NO. 027 |
| ITI-D2 | TVAACNLPIVRGPCRAFIQLWAFDAVKGKCVLFPYGGCQGNGNKFYSEKECREYCGVP | SEQ ID NO. 003 |
| EPI-HNE-3 | AACNLPIVRGPCIAFFPRWAFDAVKGKCVLFPYGGCQGNGNKFYSEKECREYCGVP | SEQ ID NO. 019 |
| EPI-HNE-4 | EACNLPIVRGPCIAFFPRWAFDAVKGKCVLFPYGGCQGNGNKFYSEKECREYCGVP | SEQ ID NO. 020 |
| ITI-D2 | TVAACNLPIVRGPCRAFIQLWAFDAVKGKCVLFPYGGCQGNGNKFYSEKECREYCGVP | SEQ ID NO. 003 |
| EPI-HNE-3 | ------------I-FPR---- | SEQ ID NO. 019 |
| EPI-HNE-4 | E-----------I-FPR---- | SEQ ID NO. 020 |

-- means that the named protein has the same amino acid as the parental domain.

TABLE 602

Physical properties of hNE inhibitors derived from Kunitz domains

| Protein | Parent | # Residues | Mol Wt | Pre-dicted pI | $K_D$ (pM) | $k_{on}$ ($10^6$/M/s) | $k_{off}$ ($10^{-6}$/s) |
|---|---|---|---|---|---|---|---|
| EPI-HNE-1 | BPTI | 58 | 6359 | 9.10 | 2.0 | 3.7 | 7.4 |
| EPI-HNE-2 | BPTI | 62 | 6759 | 4.89 | 4.9 | 4.0 | 20. |
| EPI-HNE-3 | ITI-D2 | 56 | 6179 | 10.04 | 6.2 | 8.0 | 50. |
| EPI-HNE-4 | ITI-D2 | 56 | 6237 | 9.73 | 4.6 | 10.6 | 49. |

The constants $K_D$ and $k_{on}$ above were measured with [hNE] = $8.47 \times 10^{-10}$ molar; $k_{off}$ was calculated from $k_{off} = K_D \times k_{on}$.

TABLE 603

SUMMARY OF PURIFICATION OF EPI-HNE-2

| STAGE | Volume (ml) | Concentration (mg/ml) | Total (mg) | Activity (mg/$A_{280}$) |
|---|---|---|---|---|
| HARVEST | 3,300 | 0.70 | 2.31 | <0.01 |
| 30K ULTRA-FILTRATION FILTRATE | 5,000 | 0.27 | 1.40 | <0.01 |
| 5K ULTRA-FILTRATION FILTRATE | 1,000 | 1.20 | 1.20 | 0.63 |
| AMMONIUM SULFATE PRECIPITATE | 300 | 2.42 | 0.73 | 1.05 |
| IEX pH6.2 ELUATE | 98 | 6.88 | 0.67 | 1.03 |
| EPI-HNE-3, LOT 1 | 50 | 13.5 | 0.68 | 1.04 |

TABLE 604

SUMMARY OF PURIFICATION OF EPI-HNE-3

| STAGE | VOLUME (ml) | CONCENTRATION (mg/ml) | TOTAL (mg) | ACTIVITY (mg/$A_{280}$) |
|---|---|---|---|---|
| HARVEST | 3,100 | 0.085 | 263 | ND |
| 30K ULTRA-FILTRATION FILTRATE | 3,260 | 0.055 | 179 | 0.007 |
| FIRST IEX: pH6.2 ELUATE | 180 | 0.52 | 94 | 0.59 |
| AMMONIUM SULFATE PRECIPITATE | 100 | 0.75 | 75 | 0.59 |
| IEX pH9 ELUATE | 60 | 1.01 | 60 | 0.59 |
| EPI-HNE-3, LOT 1 | 26 | 1.54 | 40 | 0.45 |

TABLE 605

$K_I$ VALUES OF EPI-HNE PROTEINS FOR VARIOUS HUMAN SERUM SERINE PROTEASES

| Enzyme | EPI-HNE-1 | EPI-HNE-2 | EPI-HNE-3 | EPI-HNE-4 |
|---|---|---|---|---|
| Human Neutrophil Elastase | 2 pM | 5 pM | 6 pM | 5 pM |
| Human Serum Plasmin | >6 μM | >100 μM | >100 μM | >90 μM |
| Human Serum Kallikrein | >10 μM | >100 μM | >100 μM | >90 μM |
| Human Serum Thrombin | >90 μM | >100 μM | >100 μM | >90 μM |
| Human Urine Urokinase | >90 μM | >100 μM | >100 μM | >90 μM |
| Human Plasma Factor $X_a$ | >90 μM | >100 μM | >100 μM | >90 μM |
| Human Pancreatic Chymotrypsin | ~10 μM | ~10 μM | ~30 μM | ~10 μM |

TABLE 607

PEY-33 which Produces EPI-HNE-2

| Elapse Fermenter Time Hours:minutes | Cell Density ($A_{600}$) | Activity in supernatent (mg/l) |
|---|---|---|
| 41:09 | 89 | 28 |
| 43:08 | 89 | 57 |
| 51:54 | 95 | 92 |
| 57:05 | 120 | 140 |
| 62:43 | 140 | 245 |
| 74:45 | 160 | 360 |
| 87:56 | 170 | 473 |
| 98:13 | 190 | 656 |
| 102:25 | 200 | 678 |
| 109:58 | 230 | 710 |

Fermenter culture growth and EPI-HNE protein secretion by *P. pastoris* strains PEY-33. Time course is shown for fermenter cultures following initiation of methanol-limited feed growth phase. Increase in cell mass is estimated by $A_{600}$. Concentration of inhibitor protein in the fermenter culture medium was determined from measurements of hNE inhibition by diluted aliquots of cell-free culture medium obtained at the times indicated and stored at −20° C. until assay.

TABLE 608

PEY-43 Which produces EPI-HNE-3

| Elapse Fermenter Time Hours:minutes | Cell Density ($A_{600}$) | Activity in supernatent (mg/l) |
|---|---|---|
| 44:30 | 107 | 0.63 |
| 50:24 | 70 | 9.4 |
| 52:00 | 117 | 14. |
| 62:00 | 131 | 28. |
| 76:00 | 147 | 39. |
| 86:34 | 200 | 56. |
| 100:27 | 185 | 70. |
| 113:06 | 207 | 85. |

Fermenter culture growth and EPI-HNE protein secretion by *P. pastoris* strains PEY-43. Time course is shown for fermenter cultures following initiation of methanol-limited feed growth phase. Increase in cell mass is estimated by $A_{600}$. Concentration of inhibitor protein in the fermenter culture medium was determined from measurements of hNE inhibition by diluted aliquots of cell-free culture medium obtained at the times indicated and stored at −20° C. until assay.

TABLE 610

Inhibitory properties of EPI-BNE-2

| μl of EPI-HNE-2 solution added | Percent residual hNE activity |
|---|---|
| 0. | 101.1 |
| 0. | 100.0 |
| 0. | 100.0 |
| 0. | 100.0 |
| 0. | 100.0 |
| 0. | 98.9 |
| 10. | 82.9 |
| 20. | 71.8 |
| 30. | 59.5 |
| 40. | 46.2 |
| 50. | 39.2 |
| 55. | 32.2 |
| 60. | 22.5 |
| 65. | 23.5 |
| 70. | 15.0 |
| 75. | 10.4 |
| 80. | 8.6 |
| 85. | 4.8 |
| 90. | 1.4 |
| 95. | 2.0 |
| 100. | 2.5 |
| 120. | 0.2 |
| 150. | 0.2 |
| 200. | 0.04 |

TABLE 611 hNE inhibitory properties of EPI-BNE-3

| μl of EPI-HNE-3 solution added | Percent residual hNE activity |
|---|---|
| 0. | 101.2 |
| 0. | 100.0 |
| 0. | 100.0 |
| 0. | 100.0 |
| 0. | 100.0 |
| 0. | 98.8 |
| 10. | 81.6 |
| 20. | 66.9 |
| 30. | 53.4 |
| 40. | 38.0 |
| 50. | 27.6 |
| 55. | 21.5 |
| 60. | 13.0 |
| 65. | 11.0 |
| 70. | 7.9 |
| 75. | 3.8 |
| 80. | 3.3 |
| 85. | 2.1 |
| 90. | 1.8 |
| 100. | 1.6 |
| 110. | 0.8 |
| 120. | 0.7 |
| 160. | 0.6 |
| 200. | 0.2 |

TABLE 612 pH stability of Kunitz-domain hNE inhibitors

| | Percent Residual hNE Inhibitory Activity | | | |
|---|---|---|---|---|
| Incubation pH | EPI-HNE-1 | EPI-HNE-2 | EPI-HNE-3 | EPI-HNE-4 |
| 1.0 | 102 | 98 | 97 | 98 |
| 2.0 | 100 | 97 | 97 | 100 |
| 2.6 | 101 | | | |
| 3.0 | 100 | 101 | 100 | 96 |
| 4.0 | 98 | 101 | 102 | 94 |
| 5.0 | 100 | | | |
| 5.5 | | 99 | 99 | 109 |
| 6.0 | 100 | | 103 | 99 |
| 6.5 | | | 99 | 100 |
| 7.0 | 93 | 103 | 103 | 93 |
| 7.5 | | | 87 | 109 |
| 8.0 | 96 | | 84 | 83 |
| 8.5 | | 104 | 68 | 86 |
| 9.4 | 100 | | 44 | 40 |
| 10.0 | 98 | 102 | 27 | 34 |

Proteins were incubated at 37° C. for 18 hours in buffers of defined pH (see text). In all cases protein concentrations were 1 μM. At the end of the incubation period, aliquots of the reactions were diluted and residual hNE-inhibition activity determined.

TABLE 620

Stability of hNE inhibitory proteins to oxidation by Chloramine-T

| Molar Ratio CHL-T: Inhibitor | Percent Residual hNE-Inhibitory Activity | | | | | |
|---|---|---|---|---|---|---|
| | EPI-HNE-1 | EPI-HNE-2 | EPI-HNE-3 | EPI-HNE-4 | α1 anti trypsin | SLPI |
| 0 | 100 | 100 | 100 | 100 | 100 | 100 |
| 0.25 | | 94 | | | | |
| 0.29 | | | | | | 93 |
| 0.30 | | | | | 97 | |
| .48 | 102 | | | | | |
| .50 | | 102 | 97 | 100 | 85 | |
| .59 | | | | | | 82 |
| .88 | | | | | | 73 |
| .95 | 100 | | | | | |
| 1.0 | | 102 | 97 | 100 | 41 | |
| 1.2 | | | | | | 65 |
| 1.4 | 98 | | | | | |
| 1.5 | | 95 | | | | |
| 1.9 | 102 | | | | | |
| 2.0 | | 102 | | | | |
| 2.1 | | | | | 7 | |
| 2.4 | | | | | | 48 |
| 3.0 | | | 97 | 100 | | |
| 3.8 | 94 | | | | | |
| 4.0 | | 95 | | | | |
| 5.0 | | | 94 | 100 | | |
| 5.2 | | | | | 7 | |
| 5.9 | | | | | | 18 |
| 9.5 | 95 | | | | | |
| 10. | | 98 | 97 | 104 | | |
| 10.4 | | | | | >5 | |
| 12. | | | | | | 15 |
| 19. | 92 | | | | | |
| 30. | | | 100 | 100 | | |
| 50. | | | 94 | 100 | | |

Inhibitors were incubated in the presence of Chloramine-T at the molar ratios indicated for 20 minutes at room temperature. Oxidation reactions were quenched by adding methionine to a final concentration of 4 mM. Residual hNE-inhibition activity remaining in the quenched reactions is shown as a percentage of the activity observed with no added oxidant. Proteins and concentrations in the oxidation reactions are: EPI-HNE-1, (5 μM); EPI-HNE-2, (10 μM); EPI-HNE-3, (10 μM); EPI-HNE-4, (10 μM); API, (10 μM); and SLPI, (8.5 μM).

TABLE 630

Temperature stability of EPI-HNE proteins

| Temperature (°C.) | Residual hNE Inhibitory Activity | | | |
|---|---|---|---|---|
| | EPI-HNE-1 | EPI-HNE-2 | EPI-HNE-3 | EPI-HNE-4 |
| 0 | 97 | 101 | 96 | 100 |
| 23 | 100 | 103 | 105 | 103 |
| 37 | 100 | 97 | 99 | 98 |
| 45 | 103 | | | |
| 52 | | 101 | 100 | |
| 55 | 99 | | | 98 |
| 65 | 94 | 95 | 87 | |
| 69 | | | | 82 |
| 75 | 100 | | | |
| 80 | | 101 | 79 | |
| 85 | 106 | | | 63 |
| 93 | | 88 | 57 | |
| 95 | 64 | | | 48 |

Proteins were incubated at the stated temperature for 18 hours in buffer at pH 7.0. In all cases protein concentrations were 1 μM. At the end of the incubation period, aliquots of the reactions were diluted and residual hNE-inhibition activity determined.

TABLE 700

Kunitz domains in segments.

| | Segment # | | | | | | | | | |
|---|---|---|---|---|---|---|---|---|---|---|
| | 1<br>N-4 | 2<br>5-9 | 3<br>10-13 | 4<br>14 | 5<br>15-21 | 6<br>22-30 | 7<br>31-35 | 8<br>36-38 | 9<br>39-42 | 10<br>43-58 |
| Consensus Kunitz domain SEQ ID NO. 071 | RPDF | CLLPA | ETGP | C | RAMIPRF | YYNAKSGKC | EPFIY | GGC | GGNA | NNFKTEEECRRTCGGA |
| HUMAN PROTEASE NEXIN-II P05067 SEQ ID NO. 073 | VREV | CSEQA | ETGP | C | RAMISRW | YFDVTEGKC | APFFY | GGC | GGNR | NNFDTEEYCMAVCGSA |
| Human Alzheimer's β protease inhibitor SEQ ID NO. 074 | RNREV | CSEQA | ETGP | C | RAMISRW | YFDVTEGKC | APFFY | GGC | GGNR | NNFDTEEYCMAVCGSA |
| BPTI SEQ ID NO. 021 | RPDF | CLEPP | YTGP | C | KARIIRY | FYNAKAGLC | QTFVY | GGC | RAKR | NNFKSAEDCMRTCGGA |
| Human LACI-D3 p10646 SEQ ID NO. 075 | GPSW | CLTPA | DRGL | C | RANENRF | YYNSVIGKC | RPFKY | SGC | GGNE | NNFTSKQECLRACKKG |
| Human ITI-D1 P02760 (HI-8e) SEQ ID NO. 002 | KEDS | CQLGY | SAGP | C | MGMTSRY | FYNGTSMAC | ETFQY | GGC | MGNG | NNFVTEKECLQTCRTV |
| Human ITI-D2 P02760 (HI-8t) SEQ ID NO. 003 | TVAA | CNLPI | VRGP | C | RAFIQLW | AFDAVKGKC | VLFPY | GGC | QGNG | NKFYSEKECREYCGVP |
| Human LACI-D2 P10646 SEQ ID NO 076 | KPDF | CFLEE | DPGI | C | RGYITRY | FYNNQTKQC | ERFKY | GGC | LGNM | NNFETLEECKNICEDG |
| Human LACI-D1 P10646 SEQ ID NO. 077 | MHSF | CAFKA | DDGP | C | KAIMKRF | FFNIFTRQC | EEFIY | GGC | EGNQ | NRFESLEECKKMCTRD |
| Human HKI B9 Domain SEQ ID NO. 078 | LPNV | CAFPM | EKGP | C | QTYMTRW | FFNFETGEC | ELFAY | GGC | GGNS | NNFLRKEKCEKFCKFT |
| Human collagen α3 domain SEQ ID NO. 079 | ETDI | CKLPK | DEGT | C | RDFILKW | YYDPNTKSC | ARFWY | GGC | GGNE | NKFGSQKECEKVCAPV |
| TFPI-2 D1 PNAS 91:3353-3357 ('94) SEQ ID NO. 080 | NAEI | CLLPL | DYGP | C | RALLLRY | YYDRYTQSC | RQFLY | GGC | EGNA | NNFYTWEACDDACWRI |
| TFPI-2 D2 PNAS 91:3353-3357 ('94) SEQ ID NO. 081 | VPKV | CRLQVS | VDDQ | C | EGSTEKY | FFNLSSMTC | EKFFS | GGC | HRNR | IENRFPDEATCMGFCAPK |
| TFPI-2 D3 PNAS 91:3353-3357 ('94) SEQ ID NO. 082 | IPSF | CYSPK | DEGL | C | SANVTRY | YFNPRYRTC | DAFTY | TGC | GGND | NNFVSREDCKRACAKA |

TABLE 701

Substitutions for Segment 1 (amino terminus to residue 4) that are likely to give Kunitz Domains that could have very-high affinity for hNE.

| Sequence:<br>NH$_3$-Residue 4 | Source and reason | SEQ ID NO. |
|---|---|---|
| RPDF | BPTI, consensus KuDom, EpiNE1-8, | 163 |
| EAEARPDF | EPI-HNE-2 | 164 |
| KEDS | ITI-D1, ITI-D1E7 | 165 |
| KEDf | AMINO1 | 166 |
| KPDS | AMINO2 | 167 |
| TVAA | ITI-D2 | 168 |
| AA | EPI-HNE-3 | 169 |
| EA | EPI-HNE-4 | 170 |
| DF | Truncation of EpiNE1 | 171 |

TABLE 702

Substitutions for Segment 3 (residues 10-13) that are likely to give Kunitz Domains that could have very-high affinity for hNE.

| Sequence: 10-13 | Source and reason | SEQ ID NO. |
|---|---|---|
| YTGP | BPTI, EpiNE1-EpiNE8, EPI-HNE-2 | 172 |
| SAGP | ITI-D1 and derivatives | 173 |
| STGP | BITI-E7-1222 | 174 |
| VRGP | ITI-D2, EPI-HNE-3, EPI-HNE-4 | 175 |

TABLE 703

Substitutions for Segment 5 (residues 15-21) that are likely to give Kunitz Domains that could have very-high affinity for hNE.

| Sequence: 15-21 | Source and reason | SEQ ID NO. |
|---|---|---|
| vAmfpRY | EpiNE7, ITI-D1E7 | 176 |
| vgffsRY | EpiNE3 | 177 |
| vgffqRY | EpiNE6 | 178 |
| vAifpRY | EpiNE4 | 179 |
| vAffkRS | EpiNE8 | 180 |
| iAffpRY | EpiNE1, EPI-HNE-2 | 181 |
| iAffqRY | EpiNE5 | 182 |
| iAlfkRY | EpiNE2 | 183 |
| iGMfSRY | MUTP1 | 184 |
| iAFfprW | EPI-HNE-3, EPI-HNE-4 | 185 |
| VAFFPRW | Analogy to EPI-HNE-3 with P1=Val | 186 |
| VAIFPRW | Combine EPI-HNE-3 and EpiNE4 | 187 |
| VAFFPRW | Combine EPI-HNE-3 and EpiNE1 | 188 |
| vgffsRW | Combine EPI-HNE-3 and EpiNE3 | 189 |
| vAmfpRW | Combine EPI-HNE-3 and EpiNE7 | 190 |
| VAFFPRF | SEQ 188 with F21 | 191 |
| vgffsRF | SEQ 189 with F21 | 192 |
| vAmfpRF | SEQ 190 with F21 | 193 |

TABLE 704

Substitutions for Segment 7 (residues 31-35) that are likely to give Kunitz Domains that could have very-high affinity for hNE.

| Sequence: Residues 31-35 | Source and reason | SEQ ID NO. |
|---|---|---|
| QTFVY | BPTI, EpiNE1-8, EpiNE7.36 | 194 |
| VLFPY | EPI-HNE-3, EPI-HNE-4 | 195 |
| ETFQY | ITI-DL and derivatives | 196 |
| qTFvY | BITI-E7-141, MUTT26A, MUT1619 | 197 |
| ETFvY | MUTQE | 198 |
| VLFPY | ITI-D2 and Derivatives | 199 |
| QTFIY | EpiNE7.6, 7.4 & 7.14 | 200 |
| QTFeY | EpiNE7.8, 7.7, 7.33 | 201 |
| QTFgY | EpiNE7.11, 7.32 | 202 |
| QTFrY | EpiNE7.5 | 203 |
| QTFdy | EpiNE7.10 & 7.20 | 204 |
| QTFkY | EpiNE7.1, 7.23, 7.24, 7.26, 7.30, .34, & .35 | 205 |
| QTFtY | EpiNE7.16, 7.28, 7.29 | 206 |
| QTFnY | EpiNE7.19, 7.27 | 207 |
| QTFqY | EpiNE7.12, 7.17 | 208 |
| QTFHY | EpiNE7.21, 7.22 | 209 |
| QTFpY | EpiNE7.25 | 210 |

TABLE 705

Substitutions for Segment 9 (residues 39-42) that are likely to give Kunitz Domains that could have very-high affinity for hNE.

| Sequence: Residues 39-42 | Source and reason | SEQ ID NO. |
|---|---|---|
| mgng | EpiNE1-8, ITI-D1 and derivatives | 211 |
| QGNG | ITI-D2 and derivatives | 212 |
| kgkG | EpiNE7.6 | 213 |
| wakg | EpiNE7.8, 7.9, 7.31, 7.25 | 214 |
| rakG | EpiNE7.13, | 215 |
| haeG | EpiNE7.7 | 216 |
| waqG | EpiNE7.4 & 7.14 | 217 |
| laeG | EpiNE7.5 | 218 |
| hadg | EpiNE7.10 & 7.20 | 219 |
| lahG | EpiNE7.1 | 220 |
| wanG | EpiNE7.16, 7.33 | 221 |
| egkG | EpiNE7.19 | 222 |
| egyG | EpiNE7.12 | 223 |
| lgeg | EpiNE7.17 | 224 |
| wgqG | EpiNE7.21 | 225 |
| wgeG | EpiNE7.22, 7.32 | 226 |
| wgkG | EpiNE7.23, 7.27 | 227 |
| hgnG | EpiNE7.24 | 228 |
| wghg | EpiNE7.26 | 229 |
| lghG | EpiNE7.28 | 230 |
| lgyG | EpiNE7.29 | 231 |
| waeG | EpiNE7.30, .34, & .35 | 232 |
| hgdG | EpiNE7.36 | 233 |

TABLE 706

Sample Candidate hNE inhibitor proteins

| | 5 | 10 | 15 | 20 | 25 | 30 | 35 | 40 | 45 | 50 | 55 | 58 | SEQ ID NO. |
|---|---|---|---|---|---|---|---|---|---|---|---|---|---|
| hLACI-D2 | KP DF CFLEEDP GI CRGYI TRYF YNNQTKQCERF KYGGCL GNMNNFETLEECKNI CEDG | | | | | | | | | | | | 076 |
| CEPINE001 | KP DF CFLEEDP GI Cv GYf TRYF YNNQTKQCERF KYGGCL GNMNNFETLEECKNI CEDG | | | | | | | | | | | | 083 |
| | -------------- V- - F---------------------------------------- | | | | | | | | | | | | |
| CEPINE002 | KP DF CFLEEDP GI Cv Gf f TRYF YNNQTKQCERF v YGGCL GNMNNFETLEECKNI CEDG | | | | | | | | | | | | 084 |
| | -------------- V- FF------------------- V---------------------- | | | | | | | | | | | | |
| CEPINE003 | KP DF CFLEEDP GI Cv Gf f TRYF YNaQTKQCERF v YGGCL GNMNNFETLEECKNI CEDG | | | | | | | | | | | | 085 |
| | -------------- V- FF-------- A-------- V---------------------- | | | | | | | | | | | | |
| CEPINE004 | KP DF CFLEEDP Gp Cv Gf f q RYF YNaQTKQCERF v YGGCq GNMNNFETLEECKNI CEDG | | | | | | | | | | | | 086 |

TABLE 706-continued

Sample Candidate hNE inhibitor proteins

```
              - - - - - - - - - - - - P- V- FFQ - - - - - - A- - - - - - - V- - - - Q - - - - - - - - - - - - - - - - - - - -
CEPINE005     DF CF LEE DP Gp Cv Gf f TR YF YNNQ TKQ CERF v YGGCq GNMNNF ETLEECKNI CEDG        087
              - - - - - - - - - - - - - P- V- FF- - - - - - - - - - - - - - - - V- - - - Q - - - - - - - - - - - - - - - - - - - - hLACI-D3      GP S WCLTP ADRGL CRANENRF YYNS VI GKCRPFKYS GCGGNE NNFTS KQECL RACKKG            075
CEPINE010     GP S WCL TP ADRGL Cv ANf NRF YYNS VI GKCRPF KYS GCGGNE NNFTS KQECL RACKKG         088
              - - - - - - - - - - - - - - V- - F- - - - - - - - - - - - - - - - - - - - - - - - - - - - - - - - - -
CEPINE011     GP S WCL TP ADRGL Cv Af f NRF YYNS VI GKCRPF KYS GCGGNE NNFk SKQECL RACKKG        089
              - - - - - - - - - - - - - - V- FF - - - - - - - - - - - - - - - - - - - - - - - - - - K - - - - - - - - - - - -
CEPINE012     GP S WCL TP Av RGp Cv Af f NRF YYNS VI GKCRPF v Yg GCGGNE NNFk SKQECL RACKKG      090
              - - - - - - - - - V- - P- V- FF - - - - - - - - - - - - - - - - V- G- - - - - - - - - K - - - - - - - - - - - -
```

TABLE 710

Cumulative collection of allowed amino acids.

| Sequence | Name | SEQ ID |
|---|---|---|
| RPDFCLEPPYTGPCvAmfpRYFYNAKAGLCQTFVYGGCmgngNNFKSAEDCMRTCGGA | EpiNE7 | (SEQ ID NO: 1) |
| RPDFCLEPPYTGPCvgffsRYFYNAKAGLCQTFVYGGCmgngNNFKSAEDCMRTCGGA | EpiNE3 | (SEQ ID NO: 22) |
| RPDFCLEPPYTGPCvgffqRYFYNAKAGLCQTFVYGGCmgngNNFKSAEDCMRTCGGA | EpiNE6 | (SEQ ID NO: 23) |
| RPDFCLEPPYTGPCvAifpRYFYNAKAGLCQTFVYGGCmgngNNFKSAEDCMRTCGGA | EpiNE4 | (SEQ ID NO: 24) |
| RPDFCLEPPYTGPCvAffkRsFYNAKAGLCQTFVYGGCmgngNNFKSAEDCMRTCGGA | EpiNE8 | (SEQ ID NO: 25) |
| RPDFCLEPPYTGPCiAffpRYFYNAKAGLCQTFVYGGCmgngNNFKSAEDCMRTCGGA | EpiNE1 | (SEQ ID NO: 26) |
| RPDFCLEPPYTGPCiAffqRYFYNAKAGLCQTFVYGGCmgngNNFKSAEDCMRTCGGA | EpiNE5 | (SEQ ID NO: 28) |
| RPDFCLEPPYTGPCiAlfkRYFYNAKAGLCQTFVYGGCmgngNNFKSAEDCMRTCGGA | EpiNE2 | (SEQ ID NO: 29) |
| rpDfCQLGYSAGPCvaMfpRYFYNGTSMACETFQYGGCMGNGNNFVTEKDCLQTCRGA | BITI-E7 | (SEQ ID NO: 10) |
| rpDfCQLGYStGPCvaMfpRYFYNGTSMACETFQYGGCMGNGNNFVTEKDCLQTCRGA | BITI-E7-1222 | (SEQ ID NO: 12) |
| KEDfCQLGYSAGPCvaMfpRYFYNGTSMACETFQYGGCMGNGNNFVTEKDCLQTCRGA | AMINO1 | (SEQ ID NO: 15) |
| KpDSCQLGYSAGPCvaMfpRYFYNGTSMACETFQYGGCMGNGNNFVTEKDCLQTCRGA | AMINO2 | (SEQ ID NO: 16) |
| AACNLPIVRGPCiAFfprWAFDAVKGKCVLFPYGGCQGNGNKFYSEKECREYCGVP | EPI-hNE-3 | (SEQ ID NO: 19) |
| EACNLPIVRGPCiAFfprWAFDAVKGKCVLFPYGGCQGNGNKFYSEKECREYCGVP | EPI-hNE-4 | (SEQ ID NO: 20) |
| RPDFCLEPPYTGPCvAmfpRYFYNAKAGLCQTFIYgGCkgkGNNFKSAEDCMRTCGGA | EpiNE7.6 | (SEQ ID NO: 36) |
| RPDFCLEPPYTGPCvAmfpRYFYNAKAGLCQTFeYgGCwakGNNFKSAEDCMRTCGGA | EpiNE7.8 | (SEQ ID NO: 37) |
| RPDFCLEPPYTGPCvAmfpRYFYNAKAGLCQTFgYaGCrakGNNFKSAEDCMRTCGGA | EpiNE7.11 | (SEQ ID NO: 38) |
| RPDFCLEPPYTGPCvAmfpRYFYNAKAGLCQTFeYgGChaeGNNFKSAEDCMRTCGGA | EpiNE7.7 | (SEQ ID NO: 39) |
| RPDFCLEPPYTGPCvAmfpRYFYNAKAGLCQTFlYgGCwaqGNNFKSAEDCMRTCGGA | EpiNE7.4 | (SEQ ID NO: 40) |
| RPDFCLEPPYTGPCvAmfpRYFYNAKAGLCQTFrYgGClaeGNNFKSAEDCMRTCGGA | EpiNE7.5 | (SEQ ID NO: 41) |
| RPDFCLEPPYTGPCvAmfpRYFYNAKAGLCQTFdYgGChadGNNFKSAEDCMRTCGGA | EpiNE7.10 | (SEQ ID NO: 42) |
| RPDFCLEPPYTGPCvAmfpRYFYNAKAGLCQTFkYgGClahGNNFKSAEDCMRTCGGA | EpiNE7.1 | (SEQ ID NO: 43) |
| RPDFCLEPPYTGPCvAmfpRYFYNAKAGLCQTFtYgGCwanGNNFKSAEDCMRTCGGA | EpiNE7.16 | (SEQ ID NO: 44) |
| RPDFCLEPPYTGPCvAmfpRYFYNAKAGLCQTFnYgGCegkGNNFKSAEDCMRTCGGA | EpiNE7.19 | (SEQ ID NO: 45) |
| RPDFCLEPPYTGPCvAmfpRYFYNAKAGLCQTFqYgGCegyGNNFKSAEDCMRTCGGA | EpiNE7.12 | (SEQ ID NO: 46) |
| RPDFCLEPPYTGPCvAmfpRYFYNAKAGLCQTFhYgGCwgqGNNFKSAEDCMRTCGGA | EpiNE7.21 | (SEQ ID NO: 48) |
| RPDFCLEPPYTGPCvAmfpRYFYNAKAGLCQTFhYgGCwgeGNNFKSAEDCMRTCGGA | EpiNE7.22 | (SEQ ID NO: 49) |
| RPDFCLEPPYTGPCvAmfpRYFYNAKAGLCQTFkYgGCwgkGNNFKSAEDCMRTCGGA | EpiNE7.23 | (SEQ ID NO: 50) |
| RPDFCLEPPYTGPCvAmfpRYFYNAKAGLCQTFkYgGChgnGNNFKSAEDCMRTCGGA | EpiNE7.24 | (SEQ ID NO: 51) |
| RPDFCLEPPYTGPCvAmfpRYFYNAKAGLCQTFpYgGCwakGNNFKlAEDCMRTCGGA | EpiNE7.25 | (SEQ ID NO: 52) |
| RPDFCLEPPYTGPCvAmfpRYFYNAKAGLCQTFkYgGCwghGNNFKSAEDCMRTCGGA | EpiNE7.26 | (SEQ ID NO: 53) |
| RPDFCLEPPYTGPCvAmfpRYFYNAKAGLCQTFnYgGCwgkGNNFKSAEDCMRTCGGA | EpiNE7.27 | (SEQ ID NO: 54) |
| RPDFCLEPPYTGPCvAmfpRYFYNAKAGLCQTFtYgGClghGNNFKSAEDCMRTCGGA | EpiNE7.28 | (SEQ ID NO: 55) |
| RPDFCLEPPYTGPCvAmfpRYFYNAKAGLCQTFtYgGClgyGNNFKSAEDCMRTCGGA | EpiNE7.29 | (SEQ ID NO: 56) |
| RPDFCLEPPYTGPCvAmfpRYFYNAKAGLCQTFkYgGCwaeGNNFKSAEDCMRTCGGA | EpiNE7.30 | (SEQ ID NO: 57) |
| RPDFCLEPPYTGPCvAmfpRYFYNAKAGLCQTFgYgGCwgeGNNFKSAEDCMRTCGGA | EpiNE7.32 | (SEQ ID NO: 58) |
| RPDFCLEPPYTGPCvAmfpRYFYNAKAGLCQTFeYgGCwanGNNFKSAEDCMRTCGGA | EpiNE7.33 | (SEQ ID NO: 59) |
| RPDFCLEPPYTGPCvAmfpRYFYNAKAGLCQTFvYgGChgdGNNFKSAEDCMRTCGGA | EpiNE7.36 | (SEQ ID NO: 60) |
| RPDFCLEPPYTGPCvAmfpRYFYNAKAGLCQTFmYgGCqgkGNNFKSAEDCMRTCGGA | EpiNE7.37 | (SEQ ID NO: 61) |
| RPDFCLEPPYTGPCvAmfpRYFYNAKAGLCQTFyYgGCwakGNNFKSAEDCMRTCGGA | EpiNE7 38 | (SEQ ID NO: 62) |
| RPDFCLEPPYTGPCvAmfpRYFYNAKAGLCQTFmYgGCwgdGNNFKSAEDCMRTCGGA | EpiNE7.39 | (SEQ ID NO: 63) |
| RPDFCLEPPYTGPCvAmfpRYFYNAKAGLCQTF t YgGChgnGNNFKSAEDCMRTCGGA | EpiNE7.40 | (SEQ ID NO: 64) |

TABLE 710-continued

Cumulative collection of allowed amino acids.

```
         1 11 11 11 1 1 1 2 2 2 2 2 2 2 2 2 2 3 3 3 3 3 3 3 3 3 3 4 4 4 4 4 4 4 4 4 4 5 5 5 5 5 5 5 5
1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8
R P D F C L E P P Y T G P C v A mf p R Y F Y N A K A G L C Q T F V Y G G C mg ng N N F K S A E D C M R T C G G A
k e a s   Q L G Y S A     i g f   s   w a f d G T S M A E1   Q         q A k     k   V T E K e   L Q y   R v p
    a n       v r         i   q           v k   k v         p         k E       y           r e
    e                     1   k                              L         W Q
                                                             E         R D
                                                             G         H H
                                                             R         L Y
                                                             D         E
                                                             K
                                                             T
                                                             N
                                                             H
                                                             M
                                                             Y
```

Cumulative (SEQ ID NO. 134)

x x x x C x x x x x x x GPC xx Ik R x x x x x x x x x C x x F x YGGC xxx g N x F x x x x x C x x x C x x x    (SEQ ID NO. 134)

TABLE 711

Mutations that are likely to improve the affinity of a Kunitz domain for hNE

| | |
|---|---|
| X18F; | Required |
| [X15V, X15I]; | |
| [X16A, X16G]; | Important |
| [X17F, X17L, X17I, X17L]; | |
| [X19P, X19O, X19K, X19S]; | |
| X13P; | Desirable and perhaps important |
| [X34V, X34P, X34Q]; | |
| [X39Q, X39M]; | |
| [X32T, X32L]; | |
| [X31Q, X31E, X31V]; | |
| [X11T, X11A, X11R]; | |
| [X10Y, X10S, X10V]; | |
| [X40G, X40A]; | |
| X36G; | |
| X37G; | |
| X12G. | |

TABLE 720

M13_III_signal::Human_LACI-D2::mature_M13_III
DNA has SEQ ID NO. 135, amino-acid sequence has SEQ ID NO. 136
DNA is linear and in vivo it is double stranded.
Amino-acid sequence is of a protein that is processed in vivo by cleavage after Ala_-1; the entire gene encodes an amino-acid sequence that continues to give a functional M13 III protein.

```
M   K     K L       L F
-18 -17  -16 -15   -14 -13
atg aaG | aaGktt  | ctc lttc |
        HindIII
```

```
A     I     P     L     V     V     P     F     Y     S     G     A
-12  -11  -10   -9   -8   -7   -6   -5   -4   -3   -2   -1
gcc latt | cct | ctg | gtg | gta | cct | ttc | ttat | ttcc | ggc lgcc |
  BstXI  | KpnI |                              |        KasI
      XcmI
```

```
K   P   D   F   C   F       L E       E D       P  G
1   2   3   4   5   6        7 8       9 10     11 12
laaglcctlgaclttcltgclttc |  ctclgag | gaglgat | ccclggg |
                             XhoI              XmaI
```

TABLE 720-continued

M13_III_signal::Human_LACI-D2::mature_M13_III
DNA has SEQ ID NO. 135, amino-acid sequence has SEQ ID NO. 136
DNA is linear and in vivo it is double stranded.
Amino-acid sequence is of a protein that is processed in vivo by cleavage after Ala_-1; the entire gene encodes an amino-acid sequence that continues to give a functional M13 III protein.

```
I    C    R    G    Y    I         T    R         Y   F
13  14   15   16   17   18        19   20        21  22
latt ltgclcgclggt ltat latt |   acglcgt |  tat lttc |
         SacII                    MluI
```

```
Y    N    N    Q    T    K    Q    C         E   R
23  24   25   26   27   28  29   30         31  32
ltat laat laac lcaglact laaglcaaltgt |  gaglcgg |
         BsrDI                         BsrI
```

```
F    K    Y    G    G    C    L    G    N    M
33  34   35   36   37   38   39   40   41   42
lttc laagltat lggt lggt ltgclcta lggt laat latg |
                AvrII
```

```
N    N    F    E    T    L    E    E    C    K
43  44   45   46   47   48   49   50   51  52
laac laac lttc lgaglact lcta lgaalgagltgt laagl
                XbaI
```

```
N    I    C    E    D    G    G    A    E    T    V    E    S
53  54   55   56   57   58  100  101  102  103  104  105  106
laac lata ltgt lgaglgat lggt lggt lgct lgaglact lgtt lgagltct |
     NdeI                                              DrdI
```

Ala_101 is the first residue of mature M13 III.

TABLE 725

Synthetic laci-d1 with sites for cloning into display vector
DNA has SEQ ID NO. 137, amino-acid sequence has SEQ ID NO. 138

```
A    A   E       M   H      S   F   C    A   F   K   A   D
                 1   2      3   4   5    6   7   8   9  10
5'-gcglgcclgag | atglcat | tcclttcltgclgctlttclaaalgctlgatl
      EagI        NsiI
```

TABLE 725-continued

Synthetic laci-d1 with sites for cloning into display vector
DNA has SEQ ID NO. 137, amino-acid sequence has SEQ ID NO. 138

```
    D   G   P   C   K   A   I   M   K   R
    11  12  13  14  15  16  17  18  19  20
   |gaC|ggT|ccG|tgt|aaa|gct|atc|atg|aaa|cgt|
        RsrII          BspHI F   F   F   N   I   F       T   R       Q   C
    21  22  23  24  25  26      27  28      29  30
   |ttc|ttc|ttc|aac|att|ttc|   |acG|cgt|   |cag|tgc|
                                  MluI E   E   F   I   Y   G   G   C   E   G   N   Q
    31  32  33  34  35  36  37  38  39  40  41  42
   |gag| gaA|ttC| att|tac|ggt|ggt|tgt|gaa| ggt|aac|cag|
              EcoRI                        BstEII N   R       F   E       S   L   E   E
          43  44      45  46      47  48  49  50
         |aac|cgG|   |ttc|gaa|   |tct|ctA|gag|gaa|
              AgeI      BstBI         XbaI C   K   K   M   C   T   R   D       G   A
    51  52  53  54  55  56  57  58      59  101
   |tgt|aag|aag|atg|tgc|act|cgt|gac|   |ggc|gcc|
                                          KasI
```

Ala₁₀₁ is the first residue of mature M13 III.

TABLE 730

LACI-D1 hNE Library
DNA has SEQ ID NO. 139, amino-acid sequence has SEQ ID NO. 140

```
         A   A   E   M   H   S   F   C   A   F   K   A
                         1   2   3   4   5   6   7   8   9
     5'-gcg|gcc|gag|atg|cat|tcc|ttc|tgc|gct|ttc|aaa|gct|
            EagI         NsiI
```

```
                                              S
    T|N                                       T|N
   C|R K|R                                    I|M
   S|G S|A                                    Q|H
   Y|H E|G       H|R              F|L         L|P
   D|N D|    G   P|L   C   V|I A|G I|V F|K    R   R
   10    11  12  13  14  15  16  17  18 19   20
   |NRt|RVS|ggT|cNt|tgt| Rtt | gSt | Ntc|ttc|MNS|cgt|
```

```
    C
   Y|W
   F|L F   F   N   I   F       T       R   Q   C
   21    22  23  24  25  26 27         28      29  30
   | tDS |ttc|ttc|aac|att|ttc|acG| cgt |cag|tgc|
                                MluI
```

```
       Q           Q                       Q
      L|P         L|P                     L|P
      T|K         T|K                     T|K
   L|Q V|I     V|E                     V|M          E|G
   E|V E|A  F I|A  Y   G   G   C   E|A  G|A N       Q|R
   31    32  33  34  35  36  37  38  39  40  41    42
   |SWG|VHA|ttC|VHA|tac|ggt|ggt|tgt|VHG| gSt |aac|SRG|
```

```
          N   R       F   E       S   L   E   E
          43  44      45  46      47  48  49  50
         |aac|cgG|   ttc | gaa|   |tct|ctA|gag|gaa|
              AgeI         BstBI         XbaI
```

TABLE 730-continued

LACI-D1 hNE Library
DNA has SEQ ID NO. 139, amino-acid sequence has SEQ ID NO. 140

```
    C   K   K   M   C   T   R   D       G   A
    51  52  53  54  55  56  57  58      59  101
   |tgt|aag|aag|atg|tgc|act|cgt|gac|   |ggc|gcc|
                                          KasI
```

Variegation at 10, 11, 13, 15, 16, 17, 19, and
20 gives rise to 253,400 amino-acid sequences and
589,824 DNA sequences.

Variegation at 31, 32, 34, 39, 40, and
42 gives 23,328 amino-acid and DNA sequences.

There are about $5.9 \times 10^9$ protein sequences and $1.4 \times 10^{10}$
DNA sequences. Ala₁₀₁ would be the first residue of mature M13 III.

TABLE 735

LACI-D2 hNE Library
DNA has SEQ ID NO. 141; amino-acid sequence has SEQ ID NO. 142

```
                                         P|H
                                         T|N
                                    C|R K|R
                                    S|G S|A
                                    Y|H E|G
     G   A   K   P   D   F   C   F   L   E   D|N D|    Q   G
    -2  -1   1   2   3   4   5   6   7   8   9    10    11  12
    |ggc|gcc|aag|cct|gac|ttc|tgc|ttc|ctc | gag|gag|NRt|VVS|ggg|
       KasI                                     XhoI
```

```
                  I|N
   H|R           F|L        Q|M
   P|L           I|V        L|H         C
   N|S           Y|H        K|P         F|L
   I|T   C   V|I G|A N|D F  T  R   R    Y|W F
   13    14  15  16  17 18 19  20  21   22
   |MNt|tgc| Rtt | gSt |NWt|ttt|MNS|cgt|tDS|ttc|
```

```
                                         Q|G
                                         L|P
                                         T|K
                                         V|I
                            L|Q         E|A
    Y   N   N   Q   A   K   Q   C   E|V  R
    23  24  25  26  27  28  29  30  31   32
   |tat|aat|aac|cag|Gct|aag|caa|tgt|SWg|VNA|
                                BsrDI
                                EspI
```

```
    Q|L           Q|P
    P|T           T|K                 R|G
    V|E           V|M                 K|E
    I|A           E|A                 L|Q
    F   K   Y   G   G   C   L   G|A N M|V
    33  34  35  36  37  38  39  40  41  42
   |ttc|VHA|tat|ggt|ggt|tgc|VHG| gSt |aat|VBg|
```

```
    N   N   F   E   T   L   E   E   C   K
    43  44  45  46  47  48  49  50  51  52
   |aac|aac|ttc|gag|act|cta|gaa|gag|tgt|aag|
                                     XbaI
```

```
    N   I   C   E   D   G   G   A   E   T   V   E   S
    53  54  55  56  57  100 101 102 103 104 105 106
   |aac|ata|tgt|gag|gat|ggt|ggt|gct|gag|act|gtt|gag|tct|
         NdeI                                  DrdI
```

$6.37 \times 10^{10}$ amino acid sequences; $1.238 \times 10^{11}$ DNA sequences

TABLE 750

M13_III_signal::Human_LACI-D3::mature_M13_III
DNA has SEQ ID NO. 143; amino-acid sequence has SEQ ID NO. 144.

```
  M    K    K    L    L    F
 -18  -17  -16  -15  -14  -13
|atg |aaG| aaG|ctt | ctc |ttc |
          HindIII
```

```
  A    I    P    L    V    V    P    F    Y    S    G    A
 -12  -11  -10  -9   -8   -7   -6   -5   -4   -3   -2   -1
|gcc |att |cct |ctg |gtg |gta |cct |ttc |tat |tcc |ggt |gct|
     BstXI       KpnI
     Xcm I
```

```
  G    P    S    W    C    L    T    P    A    D    R    G
  1    2    3    4    5    6    7    8    9   10   11   12
|ggg | ccc |tct |tgg |tgc |ctt |acg |ccg |gcn |gac |cgc |ggt|
  ApaI                         NgoMI        SacII
```

```
  L    C    R    A    N    E    N    R    F    Y    Y    N
 13   14   15   16   17   18   19   20   21   22   23   24
|ctc |tgc |aga |gct |aat |gag |aat |cgt |ttc |tac |tac |aaC|
      PstI
```

```
      S    s    I    G    K    C    R    P    F    K    Y    S
     25   26   27   28   29   30   31   32   33   34   35   36
  (C)|tcG |agt |att |ggt |aag |tgc |aga |cct | ttt |aaa |tat |tct|
      XhoI                       BsgI              DraI
```

```
  G    C    G    G    N    E    N    N    F    e    S    K
 37   38   39   40   41   42   43   44   45   46   47   48
|ggt |tgt |ggt |ggc |aat |gag |aat |aat | ttc |gaa |tct |aag|
          BsrDI                           BstBI
```

```
  Q    E    C    L    R    A    C    K    K    G    G    A
 49   50   51   52   53   54   55   56   57   58   59  101
|caa |gag |tgc |ctg |cgc |gca |tgc |aag |aag |ggt | ggc |gcc|
                         SphI                          KasI
     BssHII
```

V26S to allow an XhoI site between the two loops to be varied.
T46E to avoid glycosylation site.

TABLE 760

Variegation of LACI-D3
DNA has SEQ ID NO. 145; amino-acid sequence has SEQ ID NO. 146.

```
                                   D    Q
                                   E    G
                              Y    C    S
                              H    R    T    N
                              N    S    P    H
  G    P    S    W    C    L    T    P    A    D    G    R    K    G
  1    2    3    4    5    6    7    8    9   10   11        12
|ggg | ccc |tct |tgg |tgc |ctt |acg |ccg |gcn |NRt |VVS |ggt|
  ApaI                              NgoMI
```

```
                             T    R
  H   R          F    L      K    P
  P   N          I    V      L    H          C
  S   I          Y    H      Q    M          Y    W
  L   T    C     V  I  A  G  N    D    F     N  I R   F L  Y    N
 13   14   15   16           17   18   19    20        21  22   23   24
|MNt |tgc | Rtt |gSt         |NWt |ttt |MNS |cgt |tDS |tac |tac |aaC|
```

TABLE 760-continued

Variegation of LACI-D3
DNA has SEQ ID NO. 145; amino-acid sequence has SEQ ID NO. 146.

```
                                        Q    G
                                   L    T    Q    L
                                   K    V    P    T
                              E    V    I    E    V    E
                              L    Q    A    R    I    A
      S    s    I    G    K    K    C    R    G    P    F    K    Y    S    G
     25   26   27   28   29   29   30   31   32   33   34   35   36
  (C)|tcG |agt |att |ggt |aag |aag |tgc |SDg |VNa | ttt |VHa |tat |Rgt |
      XhoI
```

```
              Q    P
              T    K
              V    M              M    V
              E    A              L    Q
              L    R              R    K
  G    C    G    G   AN    E     GN    N    F    e    S    K
 37   38   39   40   41   42     43   44   45   46   47   48
|ggt |tgt |VNg |gSt |aat |VBg |aat |aat | ttc |gaa |tct |aag|
                                              BstBI
```

```
  Q    E    C    L    R    A    C    K    K    G    A
 49   50   51   52   53   54   55   56   57   58   59  101
|caa |gag |tgc |ctg |cgc | gca |tgc |aag |aag |ggt | ggc |gcc|
                         SphI                          KasI
     BssHII
```

TABLE 790

Amino acids allowed in
hNE-inhibiting Kunitz domains

| Position | Allowed amino acids |
|---|---|
| 5 | C |
| 10 | YSVN |
| 11 | TARQP |
| 12 | G |
| 13 | PAV |
| 14 | C |
| 15 | IV |
| 16 | AG |
| 17 | FILVM |
| 18 | F |
| 19 | PSQKR |
| 20 | R |
| 21 | YWF |
| 30 | C |
| 31 | QEV |
| 32 | TLP |
| 33 | F |
| 34 | VQP |
|

TABLE 800

| | Amino-acid sequnces of Kunitz domains | |
|---|---|---|
| 1 | rpdfCILPa-etGPCrAmIpRfYYNaksgkCepFiYGGCgGNa--NNFkTeeECrrtCgga<br>Consensus KuDom 93.09.28 (Upper case indicates majority of 72 naturally occurring Kunitz domains have this amino-acid type at this position). | (SEQ ID NO. 071) |
| 2 | ---QDHPKFCYLPA-DPGRCKAHIPRFYYDSASNKCNKFIYGGCPGNA--NNFKTWDECRQTCGASA<br>P00991 *Vipera ammodytes ammodytes* (western sand viper) CTI toxin | (SEQ ID NO. 091) |
| 3 | ---RDRPKFCYLPA-DPGRCLAYMPRFYYNPASNKCEKFIYGGCRGNA--NNFKTWDECRHTCVASGIQPR<br>IVB3_VIPAA, A#P00992 *Vipera ammodytes ammodytes* (western sand viper) | (SEQ ID NO. 092) |
| 4 | -------FCYLPD-DPGVCKAHIPRFYYNPASNKCKNFIYGGCGGNA--NNFETRAECRHTCVASGKGGPR<br>SP:IVBT_ERIMA, A#P24541 *Eristocophis macmahoni* (leaf-nosed viper) | (SEQ ID NO. 093) |
| 5 | -----RPDFCELPA-ETGLCKAYIRSFHYNLAAQQCLQFIYGGCGGNA--NRFKTIDECRRTCVG------<br>SP:IVB2_HEMHA, A#P00985 *Hemachatus haemachatus* HHV II | (SEQ ID NO. 094) |
| 6 | ---HDRPTFCNLPP-ESGRCRGHIRRIYYNLESNKCKVFFYGGCGGNA--NNFETRDECRETCGGK------<br>*Vipera russelli* (Russel's viper) RVV II (TAKA74) | (SEQ ID NO. 095) |
| 7 | ---KNRPTFCNLLP-ETGRCNALIPAFYYNSHLHKCQKFNYGGCGGNA--NNFKTIDECQRTCAAKYGRSS<br>P25660 *Bungarus fasciatus* VIII B toxin (banded krait) | (SEQ ID NO. 096) |
| 8 | -----INGDCELPK- VVGPCRARFPRYYYNSSSKRCEKFIYGGCGGNA--NNFHTLEECEKVCGVRSVGR--<br>P10280 *Anemonia sulcata* (snake-locks sea anemone) 5 II | (SEQ ID NO. 097) |
| 9 | -------EVCSEQA-ETGPCRAMISRWYFDVTEGKCAPFFYGGCGGNR--NNFDTEEYCMAVCGSVMSQSLR<br>P29216 *Macaca mulatta* (rhesus macaque) | (SEQ ID NO. 098) |
| 10 | -----RPRFCELPA-ETGLCKARIRSFHYNRAAQQCLEFIYGGCGGNA--NRFKTIDECHRTCVG------<br>P00986 *Naja nivea* (cape cobra) NNV II | (SEQ ID NO. 099) |
| 11 | SVEEVVREVCSEQA-ETGPCRAMISRWYFDVTEGKCVPFFYGGCGGNR--NNFDTEEYCMAVCGSVSTQSLL<br>P12023 A4 protein homolog precursor | (SEQ ID NO. 100) |
| 12 | ----VVREVCSEQA-ETGPCRAMISRWYFDVTEGKCAPFFYGGCGGNR--NNFDTEEYCMAVCGSVMSQSLR<br>M58726 *Macaca fascicularis* myloid b-protein precursor KuDom | (SEQ ID NO. 101) |
| 13 | SVEEVVREVCSEQA-ETGPCRAMISRWYFDVTEGKCAPFFYGGCGGNR--NNFDTEEYCMAVCGSA---<br>P05067 PROTEASE NEXIN-II (PN-II) (APPI) | (SEQ ID NO. 073) |
| 14 | ----RNREVCSEQA-ETGPCRAMISRWYFDVTEGKCAPFFYGGCGGNR--NNFDTEEYCMAVCGSAI-<br>Schweitz et al. PNAS (1994) 91: 878–882., Shina &al ('90) | (SEQ ID NO. 074) |
| 15 | -----AAKYCKLPL-RIGPCKRKIPSFYYKWKAKQCLPFDYSGCGGNA--NRFKTIEECRRTCVG<br>P00981 *Dendroaspis polylepis polylepis* (black mamba) Kvenom | (SEQ ID NO. 102) |
| 16 | -----AAKYCKLPV-RYGPCKKKFPSFYYNWKAKQCLPFNYSGCGGNA--NRFKTIEECRRTCVG------<br>*Dendroaspis angusticeps* (Eastern green mamba) C13 S1 C3 tox (DUFT85) | (SEQ ID NO. 103) |
| 17 | -----AAKYCKLPV-RYGPCKKKIPSFYYKWKAKQCLPFDYSGCGGNA--NRFKTIEECRRTCVG<br>P00982 *Dendroaspis angusticeps* (eastem green mamba) K toxin | (SEQ ID NO. 104) |
| 18 | -----RPDFCLEPP-YTGPCKARIIRYFYNAKAGLCQPFVYGGCRAKR--NNFKSSEDCMRTCGGA---<br>Isoaprotinin 2 SIEK88 | (SEQ ID NO. 105) |
| 19 | ---LQHRTFCKLPA-EPGPCKASIPAFYYNWAAKKCQLFHYGGCKGNA--NRFSTIEKCRHACVG<br>P00984 *Dendroaspis polylepis polylepis* (black mamba) E toxin | (SEQ ID NO. 106) |
| 20 | SVEEVVREVCSEQA ETGPCRAMISRWYFDVTEGKCAPFFYGGCGGNR--NNFDTEEYCMAVCGSVSSQSLL<br>P08592 Amyloid A4 PROTEIN HOMOLOG PRECURSOR A4_RAT | (SEQ ID NO. 107) |
| 21 | -----RPGFCELPA-AKGLCKAHKPAFYYNKDSHRCQKFIYGGCGGNA--NRFRTIDECNRTCVG------<br>P20229 *Naja naja* (indian cobra) | (SEQ ID NO. 108) |
| 22 | ---HDRPTFCNLAP-ESGRCRGHLRRIYYNLESNKCKVFFYGGCGGNA--NNFETRDECRETCGGK<br>P00990 *Vipera russelli siamensis* (siamese Russell's viper) | (SEQ ID NO. 109) |
| 23 | -----RPDFCLEPP-YTGPCKARMIRYFYNAKAGLCQPFVYGGCRAKR--NNFKSAEDCMRTCGGA------<br>Isoaprotinin G-2: SIEK88. | (SEQ ID NO. 110) |
| 24 | ----ZRPDFCLEPP-YTGPCKARMIRYFYNAKAGLCQPFVYGGCRAKS--NNFKSAEDCMRTCGGA------<br>Isoaprotinin G-1 SIEK88 | (SEQ ID NO. 111) |
| 25 | ---TERPDFCLEPP-YTGPCKAAMIRYFYNAKAGFCETFVYGGCRAKS--NNFKSAEDCMRTCGGA------<br>P00975 bovine serum basic protease inhibitor | (SEQ ID NO. 112) |
| 26 | --QGDKRDICRLPP-EQGPCKGRIPRYFYNPASRMCESFIYGGCKGNK--NNFKTKAECVRACRPPERPGV-<br>P00993 chelonianin, red sea turtle egg white protease inhib. | (SEQ ID NO. 113) |
| 27 | QAKAQRPDFCLEPP-YTGPCKARIIRYFYNAKAGLCQTFVYGGCRAKR--NNFKSAEDCMRTCGGAIGPWEN<br>P00974 BPTI | (SEQ ID NO. 114) |
| 28 | -----RPDFCLEPP-YTGPCKARIIRYFYNAKAGLCQTFVYGGCRAKR--NNFKSAEDCMRTCGGA------<br>BPTI | (SEQ ID NO. 021) |
| 29 | LFEFHGPSWCLTPA-DRGLCRANENRFYYNSVIGKCRPFKYSGCGGNE--NNFTSKQECLRACKKGFIQRIS<br>P10646 Human LACI Domain 3. giml14667: 217..267 | (SEQ ID NO. 075) |
| 30 | QAKAQRPDFCLEPP-YTGPCKAKMIRYFYNAKAGFCETFVYGGCKAKS--NNFRSAEDCMRTCGGAIGPREN<br>P04815 bovine spleen trypsin inhibitors, TI II (FIOR85) | (SEQ ID NO. 115) |
| 31 | ---QGRPSFCNLPA-ETGPCKASFRQYYYNSKSGGCQQFIYGGCRGNQ--NRFDTTQQCQGVCV-----<br>P00994 *Helix pomatia* (roman snail) | (SEQ ID NO. 116) |
| 32 | -----RPYACELIV-AAGPCMFFISAFYYSKGANKCYPFTYSGCRGNA--NRFKTIEECRRTCVV---<br>P00983 *Dendroaspis polylepis polylepis* (black mamba) B toxin | (SEQ ID NO. 117) |
| 33 | ---QPRRKLCILHR-NPGRCYDKIPAFYYNQKKKQCERFDWSGCGGNS--NRFKTIEECRRTCIG------<br>P00980 *Dendroaspis angusticeps* (eastem green mamba) C13 S2 C3 tox | (SEQ ID NO. 118) |
| 34 | ---QPRRKLCILHR-NPGRCYDKIPAFYYNQKKKQCEGFTWSGCGGNS--NRFKTIEECRRTCIG------<br>Green Mamba I venom CREI87. | (SEQ ID NO. 119) |
| 35 | ---EVVREVCSEQA ETGPCRAMISRWYYDVTESKCAQFIYGGCGGNR--NNFESDDYCMAVCGSVIPAT--<br>bbs122117 APP747=b-amyloid prec. prot. APP751 homolog [Xenopus,tadpoles] 281ff | (SEQ ID NO. 120) |
| 36 | ---QPLRKLCILHR-NPGRCYQKIPAFYYNQKKKQCZGFTWSGCGGNS--NRFKTIEECRRTCIRK--<br>P00979 *Dendroaspis polylepis polylepis* (black mamba) venom I | (SEQ ID NO. 121) |
| 37 | ---wqppwyckepv-rigsckkqfssfyfkwtakkclpflfsgcggna--nrfqtigecrkkclgk--<br>Calcicludine from *D. angusticeps* SCHW94. | (SEQ ID NO. 122) |
| 38 | --FQTPPDLCQLPQ-ARGPCKAALLRYFYNSTSNACEPFTYGGCQGNN--NNFETTEMCLRICEPPQQTDKS<br>P00976 bovine colostrum trypsin inhib | (SEQ ID NO. 123) |

TABLE 800-continued

| | Amino-acid sequences of Kunitz domains | |
|---|---|---|
| 39 | TEVTKKEDSCQLGY-SAGPCMGMTSRYFYNGTSMACETFQYGGCMGNG--NNFVTEKECLQTCRTVAA---- <br> SP:HC_HUMAN, A#P02760 ITI-K1 222-286 (HI-8e) | (SEQ ID NO. 002) |
| 40 | TFQKGKPDFCFLEE-DPGICRGYITRYFYNNQSKQCERFKYGGCLGNL--NNFESLEECKNTCENPTSDFQV <br> P19761 Oryctolagus cuniculus (rabbit) LACI Domain 2: 121..171 | (SEQ ID NO. 124) |
| 41 | RWAFHGPSWCLPPA-DRGLCQANEIRFFYNAIIGKCRPFKYSGCGGNE--NNFTSKKACITACKKGFIPKSI <br> P19761 Oryctolagus cuniculus (rabbit) LACI D3: 213..263 | (SEQ ID NO. 125) |
| 42 | ----RTVAACNLPI-VRGPCRAFIQLWAFDAVKGKCVLFPYGGCQGNG--NKFYSEKECREYCGVPGDGDEE <br> SP:HC_HUMAN, A#P02760 ITI-K2 (HI-8t) | (SEQ ID NO. 003) |
| 43 | ----VDKSACLQPK-EVGPCRKSDFVFFYNADTKACEEFLYGGCRGND--NRFNTKEECEKLCL <br> P26228 Sarcophaga bullata (flesh fly) | (SEQ ID NO. 126) |
| 44 | ----RTVQACNLPI-VRGPCRAGIELWAFDAVKGKCVRFTYGGCNGNG--NQFYSQKECKEYCGIPGEADEE <br> SP:IATR_SHEEP, A#P13371 sheep ITI-K2 | (SEQ ID NO. 127) |
| 45 | -----KEDSCQLGY-SQGPCLGMFKRYFYNGTSMACETFYYGGCMGNG--NNFPSEKECLQTCRTVQA---- <br> SP:IATR_SHEEP, A#P13371 sheep ITI-K1 | (SEQ ID NO. 128) |
| 46 | -----KEDSCQLGY-SQGPCLGMIKRYFYNGSSMACETFHYGGCMGNG--NNFVSQKECLQTCRTVSA---- <br> SP:IATR_PIG, A#P04366 Pig ITI-K1 | (SEQ ID NO. 129) |
| 47 | TLQQEKPDFCFLEE-DPGICRGYITRYFYNNQTKQCERFKYGGCLGNM--NNFETLEECKNICEDGPNGFQV <br> SP:LACI_HUMAN, A#P10646 Domain 2. gimll4667: 125..175 | (SEQ ID NO.076) |
| 48 | -----KEDSCELGY-SQGPCLGMIKRYFYNGSSMACETFHYGGCMGNG--NNFVSQKECLQTCR-------- <br> Porcine ITI domain 1, in CREI87 | (SEQ ID NO. 130) |
| 49 | PLQKPTHSFCAMKV-DDGPCRAYIKRFFFNILTHQCEEFIYGGCEGNE--NRFESLEECKEKCARDYPKMTT <br> P19761 Oryctolagus cuniculus (rabbit) LACI Domain 1: 50..100 | (SEQ ID NO. 131) |
| 50 | -----KEDSCQLDH-AQGPCLGMISRYFYNGTSMACETFQYGGCLGNG--NNFASQKECLQTCRTVAA---- <br> P04365 Horse ITI-K1 (CREI87) | (SEQ ID NO. 132) |
| 51 | ----RTVAACNLPI-VQGPCRAFIRLWAFDAAQGKCVLFTYGGCRGNG--NKFYSQKECKEYCGIPGDGDEE <br> P04365 Horse ITI-K2 (CREI87) | (SEQ ID NO. 133) |
| 52 | -----IAACNLPI-VQGPCRAGAELLAFDAAQGKCIQFTYGGCKGNN--NKFYSEPKCKWYCGVPGDGY-- <br> Trypstatin [KITO88] | (SEQ ID NO. 147) |
| 53 | -----IAACNLPI-VQGPCRAFAELLAFDAAQGKCIQFTYGGCKGNN--NKFYSEPKCKWYCGVPGDGY-- <br> P19603 Rattus norvegicus [rat] | (SEQ ID NO. 148) |
| 54 | ----RTVSACSLPI-VQGPCRAFIRLWAFDAAQGKCVLFNYGGCQGNG--NKFYSQKECKEYCGVPGEEDEE <br> SP:IATR PIG, A#P04366 Pig ITI-K2 [CREI87] | (SEQ ID NO. 149) |
| 55 | --TERGFLDCTSPP-VTGPCRAGFKRYNYNTRTKQCEPFKYGGCKGNG--NRYKSEQDCLDACSGF----- <br> P16044 Tachypleus tridentatus [Japanese horseshoe crab, NAKA87] | (SEQ ID NO. 150) |
| 56 | PPLKLMHSFCAFKA-DDGPCKAIMKRFFFNIFTRQCEEFIYGGCEGNQ--NRFESLEECKKMCTRDNANRII <br> SP:LACI_HUMAN, A#P10646 Domain 1. gimll4667: 54..104 | (SEQ ID NO. 077) |
| 57 | ------GSICLEPK- VVGPCTAYFPRFYFDSETGKCTPFIYGGCEGNS--YVDEKLHACRAICRA--- <br> P16344 Radianthus macrodactylus [sea anemone] | (SEQ ID NO. 151) |
| 58 | ----RTVEACNLPI-VQGPCRAFIQLWAFDAVKGKCVRFSYGGCKGNG--NKFYSQKECKEYCGIPGEADER <br> P00978 bovine [BI-8t]ITI-K2 | (SEQ ID NO. 152) |
| 59 | ----KADSCQLDY-SQGPCLGLFKRYFYNGTSMACETFLYGGCMGNL--NNFLSQKECLQTCRTVEA---- <br> P00978 bovine ITI-K1 [BI-8e] | (SEQ ID NO. 153) |
| 60 | -DKPTTKPICEQAFGNSGPCFAYIKLYSYNQKTKKCEEFIYGGCKGND--NRFDTLAECEQKCIK--- <br> P10832 Bombyx mori chymotrypsin inhibitor sci-ii. | (SEQ ID NO. 154) |
| 61 | -DKPTTKPICEQAFGNSGPCFAYIKLYSYNQKTKKCEEFIYGGCQGND--NRFITLAECEQKCIK------ <br> P10831 Bombyx mori (silk moth) | (SEQ ID NO. 155) |
| 62 | -----RPRFCELAP-SAGSCFGFVSSYYYNRYSNTCHSFTYSGCGKNA--NRFRTIDECNRTCVV---- <br> P19859 Naja naja (indian cobra) | (SEQ ID NO. 156) |
| 63 | ---DLLPNVCAFPM-EKGPCQTYMTRWFFNFETGECELFAYGGCGGNS--NNFLRKEKCEKFCKFT-- <br> Novo Nordisk HKI B9 domain | (SEQ ID NO. 078) |
| 64 | EGPENVMDICLLQK-EEGTCRDFVLKWHYDLKTKSCARFWYGGCGGNE--NRFNTQKECEKACSPGNISPGV <br> P15989 Chicken C-term Kunitz domain of Collagen VI | (SEQ ID NO. 157) |
| 65 | -----ETDICKLPK-DEGTCRDFILKWYYDPNTKSCARFWYGGCGGNE--NKFGSQKECEKVCAPV----- <br> Human collagen a3 Kunitz domain | (SEQ ID NO. 079) |
| 66 | ---RQRHRDCDKPP-DKGNC-GPVRAFYYDTRLKTCKAFQYRGCDGDH--GNFKTETLCRCECLVYP----- <br> P00987 Bungarus multicinctus [many-banded krait]bungaro toxin B1 | (SEQ ID NO. 158) |
| 67 | DEPTTDLPICEQAFGDAGLCFGYMKLYSYNQETKNCEEFIYGGCQGND--NRFSTLAECEQKCIN-- <br> P07481 Bombyx mori chymotrypsin inhibitor SCI-III. [SASA84] | (SEQ ID NO. 159) |
| 68 | ---RKRHPDCDKPP-DTKIC-QTVRAFYYKPSAKRCVQFRYGGCDGDH--GNFKSDHLCRCECELYR-- <br> P00989 Bungarus multicinctus [many-banded krait] | (SEQ ID NO. 160) |
| 69 | ---RQRHRDCDKPP-DKGNC-GPVRAFYYDTRLKTCKAFQYRGCDGDH--GNFKSDHLCRCECELY----- <br> P00988 Bungarus multicinctus (many-banded krait) bungaro toxin B2 | (SEQ ID NO. 161) |
| 70 | KNPECGEPHSLDGSPNGISCRGYFPSWSYNPDAQQCVSFVYGGCGGNN--NRFGSQNECEERCI------- <br> Drosophila funebris male accessory gland protease inhib P11424 | (SEQ ID NO. 162) |
| 71 | EPTGNNAEICLLPL-DYGPCRALLLRYYYDRYTQSCRQFLYGGCEGNA--NNFYTWEACDDACWRIEKV-- <br> TFPI-2 DOMAIN 1, Specher et al, PNAS 91:3353-3357 (1994) | (SEQ ID NO. 080) |
| 72 | ---EKVPKVCRLQVSVDDQCEGSTEKYFFNLSSMTCEKFFSGGCHRNRIENRFPDEATCMGFCAPKKI- <br> tfpi-2 DOMAIN 2, Specher et al, PNAS 91:3353-3357 (1994) | (SEQ ID NO. 081) |
| 73 | --PKKIPSFCYSPK-DEGLCSANVTRYYFNPRYRTCDAFTYTGCGGND--NNFVSREDCKRACAKALKKKKK <br> TFPI-2 DOMAIN 3, SPECHER ET AL. PNAS 91:3353-3357 (1994) | (SEQ ID NO. 082) |
| Non-naturally-occurring Kunitz domains: | | |
| | -----RPDFCLEPP-YTGPCIAFFPRYFYNAKAGLCQTFVYGGCMGNG--NNFKSAEDCMRTCGGA <br> EPI-hNE-1 | (SEQ ID NO. 026) |
| | EAEARPDFCLEPP-YTGPCIAFFPRYFYNAKAGLCQTFVYGGCMGNG--NNFKSAEDCMRTCGGA <br> EPI-hNE-2 | (SEQ ID NO. 027) |

TABLE 800-continued

Amino-acid sequnces of Kunitz domains

--AACNLPIVRGPCIAFFPRWAFDAVKGKCVLFPYGGCQGNGNKFYSEKECREYCGVP (SEQ ID NO. 019)
EPI-hNE-3

--EACNLPIVRGPCIAFFPRWAFDAVKGKCVLFPYGGCQGNGNKFYSEKECREYCGVP (SEQ ID NO. 020)
EPI-hNE-4

TABLE 810

Frequency of amino-acid types at the positions in BPTI-homologous Kunitz domains and identification of residues in five surface groups

| Res. Id. | Different AAs | Contents | 1 | 2 | 3 | 4 | 5 |
|---|---|---|---|---|---|---|---|
| 1 | 15 | R23 K9 T8 V7 –5 G4 A3 N2 P2 H2 I2 D2 L2 E M | | | | | 5 |
| 2 | 15 | P28 R11 E6 A5 H5 V5 K3 I2 –2 N G F T L M | | | | s | 5 |
| 3 | 15 | D21 E9 K9 S9 P5 R4 A4 T4 G2 N L Q W Y – | | | | 4 | s |
| 4 | 10 | F25 A9 V9 I8 S6 D5 L4 Y4 W2 H | | | | s | 5 |
| 5 | 2 | C72 S | | | | x | x |
| 6 | 13 | L15 E10 N10 S8 Q6 K6 Y4 D3 A3 I3 F2 R2 T | | | | 4 | |
| 7 | 10 | L42 E16 Q4 K3 F2 S2 P D M T | | | s | 4 | |
| 8 | 10 | P43 Q9 A5 G5 H3 K2 D2 E2 I L | | | 3 | 4 | |
| 9 | 15 | A18 P16 I7 K6 V6 Y5 F3 R3 E2 L2 Q D S M H | | s | 3 | 4 | |
| 9a | 4 | –68 G3 S P | s | s | 3 | 4 | |
| 10 | 8 | E19 D16 V11 Y7 N6 S6 R4 A4 | s | | s | 4 | |
| 11 | 13 | T21 Q11 P9 R5 A4 S4 K4 D3 E3 V3 Y3 I2 G | 1 | s | 3 | 4 | |
| 12 | 4 | G70 D I K | x | | x | x | |
| 13 | 9 | P46 R8 L7 I3 S3 N2 T2 Q V | 1 | | s | 4 | s |
| 14 | 1 | C73 | 1 | | s | s | 5 |
| 15 | 12 | R28 K21 L6 F4 Y3 –3 Q2 M2 S T E N | A | s | 3 | 4 | s |
| 16 | 8 | A43 G17 D4 K4 Q2 F R T | 1 | s | s | s | 5 |
| 17 | 15 | M13 Y11 F9 R8 K7 H5 S4 L3 G3 N3 P2 A2 Q T I | 1 | 2 | 3 | | s |
| 18 | 10 | I39 F9 M8 V6 L3 E2 T2 A2 D K | 1 | s | s | | 5 |
| 19 | 11 | P17 S12 R10 K10 I8 L4 E4 T4 Q2 N F | 1 | 2 | 3 | | s |
| 20 | 7 | R40 L10 A10 S8 K3 Q V | s | s | s | | 5 |
| 21 | 5 | Y27 F26 W16 I2 L2 | | 2 | s | s | s |
| 22 | 6 | Y35 F23 A7 S4 H3 N | | s | 3 | 4 | |
| 23 | 2 | Y53 F20 | | | s | s | |
| 24 | 4 | N47 D21 K4 S | | s | 3 | | |
| 25 | 14 | A17 P7 S7 V7 G6 Q6 L5 W5 R3 T3 I2 N2 K2 F | | | s | s | |
| 26 | 16 | K18 T13 A11 S5 E5 R4 V4 D3 Q2 Y2 G H I F L N | | s | 3 | 4 | |
| 27 | 9 | S20 A17 T13 E7 K6 Q4 L3 I2 Y | | 2 | 3 | 4 | |
| 28 | 8 | G26 K21 N8 M7 Q4 H3 R3 S | | 2 | s | s | |
| 29 | 12 | K29 Q14 A8 L5 T5 S3 R3 F2 E G M N | | 2 | 3 | | |
| 30 | 1 | C73 | | x | x | x | |
| 31 | 14 | E26 Q9 A8 V8 L6 K5 R3 I2 H D T N Y Z | | 2 | 3 | 4 | |
| 32 | 12 | P20 T10 Q7 R7 E7 K6 L5 S3 A3 G2 V2 N | | 2 | 3 | s | |
| 33 | 1 | F73 | x | x | x | x | |
| 34 | 16 | I20 F9 V8 T7 K5 L4 Q4 H3 D3 N3 W2 S P A R Y | 1 | 2 | 3 | x | |
| 35 | 4 | Y68 W3 F S | s | s | s | | 5 |
| 36 | 4 | G59 S11 R2 T | 1 | | | | |
| 37 | 1 | G73 | x | | | | x |
| 38 | 1 | C73 | x | | | x | x |
| 39 | 11 | G31 R11 K8 Q5 M5 E4 L3 D3 P H N | 1 | | | 4 | s |
| 40 | 4 | G64 A7 K R | s | | | s | 5 |
| 41 | 3 | N63 K7 D3 | | | | 4 | s |
| 42 | 12 | A19 R12 G11 S8 E5 D5 N4 H3 L2 Q2 K M | | | | s | 5 |
| 42a | 2 | –72 I | | | | | 5 |
| 42b | 2 | –72 E | | | | | 5 |
| 43 | 3 | N69 G3 Y | | | | | s |
| 44 | 5 | N40 R24 K7 Q V | | | | | s |
| 45 | 3 | F71 D Y | | | | | s |
| 46 | 16 | K24 E10 D8 Y8 V4 R3 P2 G2 S2 T2 L2 N2 I A Q H | | | | | 5 |
| 47 | 5 | T39 S31 R D K | | s | | | 5 |
| 48 | 11 | E15 I14 Q11 L9 A6 K5 R4 D3 W3 T2 S | | 2 | s | | s |
| 49 | 10 | E32 K14 D10 A6 H3 Q3 P2 G N T | | 2 | | | s |
| 50 | 9 | E44 D9 Y7 K4 L3 A3 Q T M | | s | | | 5 |
| 51 | 1 | C73 | | x | | | x |
| 52 | 11 | R21 M15 K11 E9 L9 Q2 N2 D H I V | | 2 | | | s |
| 53 | 12 | R24 Q10 E9 A8 K7 H3 C3 N2 D2 G2 W2 T | | s | | | 5 |
| 54 | 11 | T32 V10 A8 Y7 K5 E3 I3 F2 L M R | | | | | 5 |
| 55 | 1 | C73 | | | | | x |

TABLE 810-continued

Frequency of amino-acid types at the positions in BPTI-homologous Kunitz domains and identification of residues in five surface groups

| Res. Id. | Different AAs | Contents | 1 | 2 | 3 | 4 | 5 |
|---|---|---|---|---|---|---|---|
| 56 | 11 | G26 V12 R8 I7 A5 E5 K3 L3 S2 T W | | | | | |
| 57 | 14 | G21 V8 S7 P5 A5 T5 K5 R4 –4 I3 L2 N2 F D | | | | | |
| 58 | 13 | –20 V1 A10 P10 K6 G4 Y3 S3 D2 T I R F | | | | | | s indicates secondary set
x indicates in or close to surface but buried and/or highly conserved.

CITATIONS

ADEY88: *J Clin Lab Immunol* 27(1)1–4 (1988) Adeyemi, E. O., and H. J. F. Hodgson "Augmented release of human leukocyte lactoferrin (and elastase) during coagulation"

AFFO88: *Biol Chem Hoppe-Seyler* 369:1065–74 (1988) Afford, S. C., D. Burnett, E. J. Campbell, J. D. Cury, and R. A. Stockley, "The Assessment of $\alpha_1$ Proteinase Inhibitor Form and Function in Lung Lavage Fluid from Healthy Subjects"

ALBR83a: Albrecht, G., K. Hochstrasser, and O. L. Schonberger, *Hoppe-Seyler's Z Physiol Chem* (1983), 364:1697–1702. "Kunitz-type proteinase inhibitors derived by limited proteolysis of the inter-α-trypsin inhibitor, IX: isolation and characterization of the inhibitory parts of inter-α-trypsin inhibitors from several mammalian sera"

ALBR83b: Albrecht, G. J., K. Hochstrasser, and J.-P. Salier, *Hoppe-Seyler's Z Physiol Chem* (1983), 364:1703–1708. "Elastase inhibition by the inter-α-trypsin inhibitor and derived inhibitors of man and cattle"

ALTM91: Altman, J. D., D. Henner, B. Nilsson, S. Anderson, and I. D. Kuntz, *Protein Engineering* 4(5) 593–600 (1991) "Intracellular expression of BPTI fusion proteins and single column cleavage/affinity purification by chymotrypsin"

ANGE90: *J Med Chem*, 33:13–16 (1990) Angelastro, M. R., S. Mehdi, J. P. Burkhart, N. P. Peet, and P. Bey, "α-Diketone and α-Keto Ester Derivatives of N-Protected Amino Acids and Peptides as Novel Inhibitors of Cysteine and Serine Proteases"

ANZH88: *FEBS Letts* 234(2)367–73 (1988) An-Zhi, W., I. Mayr, and W. Bode, "The refined 2.3 Å crystal structure of human leukocyte elastase in a complex with a valine chloromethyl ketone inhibitor"

ARSE86: *Agents Actions Suppl* AAS 18(Recent Adv Connect Tissue Res)63–8 (1986) Arsenis, C., E. J. M. A. Thonar, and K. E. Kuettner, "Degradation of cartilage matrix by purified elastase and its control by an endogenous purified specific carthage elastase inhibitor"

ARSE88: *Current Eye Research* (1988) 7(2)95–102. Arsenis, C., K. E. Kuettner, & R. Eisenstein, "Isolation and partial characterization of neutrophil elastase inhibitors from bovine vitreous and aorta."

ASCE90: *Biol Chem Hoppe-Seyler* (1990) 371:389–393. Ascenze, P., et al., "Binding of the Bovine Basic Pancreatic Trypsin Inhibitor (Kunitz Inhibitor) to Human and Bovine Factor Xa: A Thermodynamic Study."

AUER87: Auerswald, E.-A., W. Schroeder, and M. Kotick, *Biol Chem Hoppe-Seyler* (1987), 368:1413–1425. "Synthesis, Cloning and Expression of Recombinant Aprotinin", AUER88: Auerswald, E.-A., D. Hoerlein, G. Reinhardt, W. Schroder, and E. Schnabel, *Bio Chem Hoppe-Seyler* (1988), 369(Supplement):27–35. "Expression, Isolation, and Characterization of Recombinant [Arg$^{15}$,Glu$^{52}$] Aprotinin"

AUER89: Auerswald, E.-A., W. Bruns, D. Hoerlein, G. Reinhardt, E. Schnabel, and W. Schroder, "Variants of bovine pancreatic trypsin inhibitor produced by recombinant DNA technology", UK Patent Application GB 2,208,511 A.

AUER90: Auerswald, E.-A., W. Schroeder, E. Schnabel, W. Burns, G. Reinhard, and M. Kotick, "Homologs of Aprotinin produced from a recombinant host, process ecpression vector and recombinant host therefor and pharmaceutical use thereof", U.S. Pat. No. 4,894,436 (16 Jan. 1990).

AUSU87: Ausubel, F. M., R. Brent, R. E. Kingston, D. D. Moore, J. G. Seidman, J. A. Smith, and K. Struhl, Editors Current Protocols in Molecular Biology, Greene Publishing Associates and Wiley-Interscience, Publishers: John Wiley & Sons, New York, 1987.

BACH90: U.S. Pat. No. 4,935,493 (issued Jun. 19, 1990), Bachovchin, W. W., A. G. Plaut, and C. A. Kettner, "Protease Inhibitors"

BAEK90: *Biochem* 29:4305–11 (1990) Baek, D.-J., P. E. Reed, S. B. Daniels, and J. A. Katzenellenbogen, "Alternate Substrate Inhibitors of an α-Chymotrypsin: Enantioselective Interaction of Aryl-substituted Enol Lactones"

BALD85: Balduyck et al., *Biol Chem Hoppe-Seyler* (1985) 366:9–14.

BAND88a: *J Biol Chem* 263(9)4481–4 (1988) Banda, M. J., A. G. Rice, G. L. Griffin, and R. M. Senior, "$\alpha_1$-Proteinase Inhibitor Is a Neutrophil Chemoattractant after Proteolytic Inactivation by Macrophage Elastase"

BAND88b: *J Exp Med* 167(5)1608–15 (1988) Banda, M. J., A. G. Rice, G. L. Griffin, and R. M. Senior, "The Inhibitory Complex of Human $\alpha_1$-Proteinase Inhibitor and Human Leukocyte Elastase Is a Neutrophil Chemoatractant"

BARB91: Barbas et al., *Proc Natl Acad Sci USA* (1991) 88:7978–82.

BARR86: *Protease Inhibitors*, Editors: Barrett and Salvesen. Elsevier, Amsterdam, 1986.

BASS90 *Proteins* 8:309–14 (1990) Bass, S., R. Greene, and J. A. Wells, "Hormone Phage: An Enrichment Method for Variant Proteins With Altered Binding Properties"

BECK88b: *Eur J Biochem* (1988) 176:675–682. Beckmann et al.

BECK89a: *J Protein Chem* (1989) 8(1)101–113. Beckmann et al.

BERN93: Berndt, K. D., P. Guntert, and K. Wuthrich, *J Mol Biol* (1993) 234 (3) p735–50. "Nuclear magnetic resonance solution structure of dendrotoxin K from the venom of Dendroaspis polylepis polylepis."

BIET86: Bieth, pp. 217–320 in *Regulation of Matrix Accumulation*, Editor: Mecham, Academic Press, Orlando, Fla., 1986.

BLOW72: *J Mol Biol* (1972) 69:137ff, Blow et al.

BODE79: Bode, W. *J Mol Biol.* (1979) 127:357–374. "The Transition of Bovine Trypsinogen to a Trypsin-like State upon Strong Ligand Binding: II. The Binding of the Pancreatic Trypsin Inhibitor and of Isoleucine-valine and of Sequentially Related Peptides to Trypsinogen and to p-Guanidinobenzoate-trypsinogen."

BODE83: Bode, W., Z. Chen, and K. Bartels, J Mol Biol. 1983; 164: 237–282. "Refined 2 A X-ray Crystal Structure of Porcine Pancreatic Kallikrein A, a Specific Trypsin-like Serine Proteinase: Crystallization, Structure Determination, Crystallographic Refinement, Structure and its Comparison with Bovine Trypsin."

BODE84: Bode, W., *Eur J Biochem* (1984) 144:185–190. "The refined 2.2-A (0.22-nm) X-ray crystal structure of the ternary complex formed by bovine trypsinogen, valine-valine and the Arg analogue of bovine pancreatic trypsin inhibitor."

BODE85: Bode, W., et al., *Eur J Biochem* (1985) 147:387–395. "The crystal and molecular structure of the third domain of silver pheasant ovomucoid (OMSVP3)."

BODE86: Bode, W., et al., *EMBO J* (1986) 5(10) 2453–2458. "X-ray crystal structure of the complex of human leukocyte elastase (PMN elastase) and the third domain of the turkey ovomucoid inhibitor."

BODE89: Bode, A. P., and D. T. Miller, *J Lab Clin Med* (1989) 113(6): 753–758. "The use of thrombin inhibitors and aprotinin in the preservation of platelets stored for transfusion."

BONN89 *J Cell Biochem* 39(1)47–53 (1989) Bonney, R. J., B. Ashe, A. Maycock, P. Dellea, K. Hand, D. Osinga, D. Fletcher, R. R. Mumford, P. Davies, D. Frankenfield, T. Nolan, L. Schaeffer, W. Hagmann, P. Finke, S. Shah, C. Dorn, and J. Doherty, "Pharmacological Profile of the Substituted β-Lactam L659,286: A Member of a New Class of Human PMN Elastase Inhibitors"

BORD91: Bordo, D., and P. Argos *J Mol Biol* (1991) 217:721–729. "Suggestions for "Safe" Residue Substitutions in Site-directed Mutagenesis."

BOUD87 *Biol Chem Hoppe-Seyler* 368:981–990 (1987) Boudier, C., A. Pelletier, A. Gast, J.-M. Tournier, G. Pauli, and J. G. Beith, "The Elastase Inhibitory Capacity and the $\alpha_1$-Proteinase Inhibitor and Bronchial Inhibitor Content of Bronchoalveolar Lavage Fluids from Health Subjects"

BOUD89: Boudier, C., and J. G. Bieth, *Biochimica et Biophysica Acta* (1989) 995:36–41. "Mucus proteinase inhibitor: a fast-acting inhibitor of leucocyte elastase."

BRIN90: *Biol Chem Hoppe-Seyler* (1990) 371(Supplement) 43–52. Brinkmann and Tschesche. "Recombinant aprotinin homologue with new inhibitory specificity for cathepsin G."

BRIN91: *Eur J Biochem* (1991) 202(1)95–99. Brinkmann et al.

BUTT91 *Biochem J* 276(2)325–31 (1991) Buttle, D. J.; M. Abrahamson, D. Burnett, J. S. Mort, A. J. Barrett, P. M. Dando, and S. Hill, "Human sputum cathepsin B degrades proteoglycan, is inhibited by $\alpha_2$-macroglobulin and is modulated by neutrophil elastase cleavage of cathepsin B precursor and cystatin C"

CAMP82: *J Clin Invest* 70:845–852 (1982) Campbell, E. J., R. M. Senior, J. A. McDonald, D. L. Cox, J. M. Greco, and J. A. Landis, "Proteolysis by Neutrophils"

CAMP88: *J Cell Biol* 106:667–676 (1988) Campbell, E. J., and M. A. Campbell, "Pericellular Proteolysis by Neutrophils in the Presence of Proteinase Inhibitors: Effects of Substrate Opsonization"

CAMP90: Campanelli, D., et al., *J Exp Med* (1990) 172:1709–1715. "Cloning of cDNA for Proteinase 3: A Serine Protease, Antibiotic, and Autoantigen from Human Neutrophils."

CANT89: Cantor J. O., and G. M. Turino, pp. 159–168 in *Elastin and Elastase*, Vol. II, Editors L. Robert and W. Hornebeck, CRC Press, Boca Raton, Fla., 1989.

CHAZ85: Chazin et al., *Eur J Biochem* (1985) 152:429–437.

CHAZ88.: Chazin, W. J., T. E. Hugli, and P. E. H. Wright, *Biochem* (1988) 27:9139–9148. "NMR Studies of Human C3a Anaphylatoxin in Solution: Sequential Resonance Assignments, Secondary Structure, and Global Fold."

COLL90: Collins, J., et al. *Biol Chem Hoppe-Seyler* (1990) 371(Suppl):29–36. "Human Leukocyte Elastase Inhibitors: Designed Variants of Human Pancreatic Secretory Trypsin Inhibitor (hPSTI)."

COLL91: Collins, J., et al. *Biomed Biochim Acta* (1991) 50(4–6)683–685. "Variants of human seminal acrosin inhibitor (HUSI-II) which inhibit human leukocyte elastase."

COPP87: *Biochem* 26:169–178 (1987). Copp, L. J., A. Krantz, and R. W. Spencer, "Kinetics and Mechanism of Human Leukocyte Elastase Inactivation by Ynenol Lactones"

CREG93: Cregg, J. M., T. S. Vedvick and W. C. Raschke (1993) *Bio/Technology* 11:905ff.

CREI74: Creighton, T. E., *J Mol Biol* (1974) 87:579–602. "Intermediates in the Refolding of Reduced Pancreatic Trypsin Inhibitor"

CREI77a: Creighton, T. E., *J Mol Biol* (1977) 113:275–293. "Conformational Restrictions on the Pathway of Folding and Unfolding of the Pancreatic Trypsin Inhibitor"

CREI77b: Creighton, T. E., *J Mol Biol* (1977) 113:295–312. "Energetics of Folding and Unfolding of Pancreatic Trypsin Inhibitor"

CREI80: Creighton, T. E., "Role of the Environment in the Refolding of Reduced Pancreatic Trypsin Inhibitor", *J Mol Biol* (1980), 144:521–550.

CREI84: Creighton, T. E., pp. 252–264 in *Proteins, Structures and Molecular Properties*. 1984. W. H. Freeman & Co, New York (ISBN 0-7167-1566-X).

CREI87: Creighton, T. E., and I. G. Charles, "Biosynthesis, Processing, and Evolution of Bovine Pancreatic Trypsin Inhibitor", *Cold Spring Harb Syrup Quant Biol* (1987), 52:511–519.

DAVI79: Davis et al., U.S. Pat. No. 4,179,337 (1979).

DAVI91: *Ann NY Acad Sci* 624(Pulmonary Emphysema) 219–29 (1991) Davies, P., B. M. Ashe, R. J. Bonney, C. Dorn, P. Finke, D. Fletcher, W. A. Hanlon, J. L. Humes, A. Maycock, R. A. Mumford, M. A. Navia, E. E. Opas, S. Pacholok, S. Shah, M. Zimmerman, and J. B. Doherty, "The Discovery and Biologic Properties of Cephalosporin-Based Inhibitors of PMN Elastase"

DEAG88: *J Clin Invest* 82(2)700–5 (1988) De Agostini, A., P. A. Patston, V. Marottoli, S. Carrel, P. C. Harpel, and M. Schapira, "A common Neo-epitope is created when the reactive center of C1-inhibitor is cleaved by Plasma Kallikrein, Activated Factor XII fragment, C1 Esterase or neutrophil elastase"

DIAR90: Diarra-Mehrpour, .M, J. Bourguignon, R. Sesboue, J.-P. Salier, T. Leveillard and J.-P. Martin, "Structural analysis of the human inter-α-trypsin inhibitor light-chain gene", *Eur J Biochem* (1990), 191:131–139.

DIGA89: Digan, M. E., S. V. Lair, R. A. Brierly, R. S. Siegel, M. E. Williams, S. B. Ellis, P. A. Kellaris, S. A. Provow, W. S. Chang, G. Velicelebi, M. M. Harpold, and G. P. Thill (1989) *Bio/Technology* 7:160ff.

DOHE90 *Int J Immunopharmacol* 12(7)787–95 (1990) Doherty, N. S., R. J. Dinerstein, and S. Mehdi, "Novel inhibitors of polymorphonuclear neutrophil (PMN)

elastase and cathepsin G: evaluation in vitro of their potential for the treatment of inflammatory connective tissue damage"

DREH89 *Labor-Med* 12(12)671–2 (1989) Dreher, M., G. Gunzer, and H. Lang, "New homogeneous enzyme immunoassay for the routine determination of PMN-elastase/ $\alpha_1$-proteinase inhibitor complex"

DREH89 *Prog Clin Biol Res* 308 (Vienna Shock Forum, 2nd, 1988) p. 707–10 (1989) Dreher, M., G. Gunzer, and H. Lang, "An Automated Homogeneous Enzyme Immunoassay for Human PMN Elastase"

DUFT85: Dufton, M. J., *Eur J Biochem* (1985), 153:647–654. "Proteinase inhibitors and dendrotoxins"

DUFT89: Dufton, M. J., P. Bladon, and A. L. Harvey, *J Mol Evol* (1989) 29:355–366. "Identification of a Locality in Snake Venom alpha-Neurotoxins with a Significant Compositional Similarity to Marine Snail alpha-Conotoxins: Implications for Evolution and Structure/Activity."

EIGE90: Eigenbrot, C., M. Randal, and A. A. Kossiakoff, "Structural effects induced by removal of a disulfidebridge: the X-ray structure of the C30A/C51A mutant of basic pancreatic trypsin inhibitor at 1.6 Å", *Protein Engineering* (1990), 3(7)591–598.

ENGH89: Enghild, J. J., I. B. Thogersen, S. V. Pizzo, and G. Salvesen, "Anallysis of inter-$\alpha$-trypsin inhibitor and a novel inhibitor, pre-$\alpha$-trypsin inhibitor, from human plasma: polypeptide chain stoichiometry and assembly by glycan", *J Biol Chem* (1989), 264:15975–15981.

FALA89 *Thrombosis Research* 54:389–98 (1989). Falanga, A., E. Shaw, M. B. Donati, R. Consonni, T. Barbue, and S. Gordon, "Inhibition of Cancer Procoagulant by Peptidyl Diazomethyl Ketones and Peptidyl Sulfonium Salts"

FERR90: Ferrer-Lopez, P., P. Renesto, M. Schattner, S. Bassot, P. Laurent, and M. Chignard, "Activation of human platelets by C5a-stimulated neutrophils: a role for cathepsin G", *American J Physiology* (1990) 258:C1100–C1107.

FIOR88: Fioretti, E., M. Angeletti, L. Fiorucci, D. Barra, F. Bossa, and F. Ascoli, "Aprotinin-Like Isoinhibitors in Bovine Organs", *Biol Chem Hoppe-Seyler* (1988), 369 (Suppl)37–42.

FIOR89: Fioretti, E., M. Angeletti, D. Passeri, and F. Ascoli, *J Protein Chemistry* (1989) 8(1)51–60. "Interaction Between Leukocytic Elastase and Kunitz-Type Inhibitors from Bovine Spleen."

FOLK79 U.S. Pat. No. 4,164,560 (issued Jul. 14, 1979) Folkman, M. J., and R. J. Langer, Jr, "System for the Controlled Release of Macromolecules"

FOLK83 U.S. Pat. No. 4,391,797 (issued Jul. 5, 1983) Folkman, M. J., and R. S. Langer, Jr, "Systems for the controlled Release of Macromolecules"

FORA93: Foray, M. F., J. M. Lancelin, M. Hollecker, and D. Marion, *Eur J Biochem* (1993) 211(3)813–20. "Sequence-specific 1H-NMR assignment and secondary structure of black mamba dendrotoxin I, a highly selective blocker of voltage-gated potassium channels."

FROM91 *J Biol Chem* 266(23)15356–62 (1991) Frommherz, K. J.; B. Faller, J. G. Bieth, "Heparin Strongly Decreases the Rate of Inhibition of Neutrophil Elastase by $\alpha_1$-Proteinase Inhibitor"

GANU87 *Thrombosis Research* 45:1–6 (1987) Ganu, V. S., and E. Shaw, "Improved Synthetic Inactivators of Plasmin"

GAST88 *Adv Exp Med Biol* 240 (Proteases 2) p. 75–82 (1988) Gast, A., and J. G. Bieth, "Inhibition of human neutrophil elstase by acid-soluble inter-$\alpha$-trypsin inhibitor"

GEBH86: Gebhard, W., and K. Hochstrasser, "Inter-$\alpha$-trypsin inhibitor and its close relatives", pp. 389–401 in Barret and Salvesen (eds.) *Protease Inhibitors* (1986) Elsevier Science Publishers BV (Biomedical Division).

GEBH90: Gebhard, W., K. Hochstrasser, H. Fritz, J. J. Enghild, S. V. Pizzo, and G. Salvesen, *Biol Chem Hoppe-Seyler* (1990), 371, suppl 13–22. "Structure of the inter-$\alpha$-inhibitor (inter-$\alpha$-trypsin inhibitor) and pre-$\alpha$-hibitor: current state and proposition of a new terminology"

GEIG88 *Adv Exp Med Biol* 240(Proteases 2)465–71 (1988) Geiger, R., S. Sokal, G. Trefz, M. Siebeck, and H. Hoffmann, "PMN elastase and leukocyte neutral proteinase inhibitor (LNPI) from granulocytes as inflammation markers in experimental septicemia"

GIRA89: Girard, T. J., L. A. Warren, W. F. Novotny, K. M. Likert, S. G. Brown, J. P. Miletich, and G. J. Broze Jr, "Functional significance of the Kunitz-type inhibitory domains of lipoprotein-associated coagulation inhibitor" *Nature* (1989), 338:518–20.

GIRA90 *Science* 248:1421–4 (1990) Girard, T. J., L. A. MacPhail, K. M. Likert, W. F. Novotny, J. P. Miletich, and G. J. Broze, Jr, "Inhibition of Factor VIIa-Tissue Factor Coagulation Activity by a hybrid Protein"

GLOV89 U.S. Pat. No. 4,829,052 Glover, G. I., C. A. McWherter, and C. S. Schasteen, "Setine Protease Inhibitors"

GOLD83: Goldenberg, D. P., and T. E. Creighton, *J Mol Biol* (1983), 165(2)407–13, "Circular and circularly permuted forms of bovine pancreatic trypsin inhibitor."

GOLD84: Goldenberg, D. P., and T. E. Creighton, *J Mol Biol* (1984), 179:527–45. "Folding Pathway of a circular Form of Bovine Pancreatic Trypsin Inhibitor"

GOLD86 *Am Rev Respir Dis* 134:49–56 (1986) Goldstein, W., and G. Doering, "Lysosomal Enzymes from Polymorphonuclear leukocytes and proteinase inhibitors in patients with cystic fibrosis"

GOLD88: Goldenberg, D. P., *Biochem* (1988), 27:2481–89. "Kinetic Analysis of the Folding and Unfolding of a Mutant Form of Bovine Pancreatic Trypsin Inhibitor Lacking the Cysteine-14 and -38 Thiols"

GOMB91 U.S. Pat. No. 5,019,400 (issued May 28, 1991) Gombotz, W. R., M. S. Healy, and L. R. Brown, "Very low temperature casting of controlled release microspheres"

GOVA90 *Arch Biochem Biophys* 280(1)137–146 (1990) Govardhan, C. P., and R. H. Abeles, "Structure-Activity Studies of Fluoroketone Inhibitors of $\alpha$-Lytic Protease and Human Leukocyte Elastase"

GOVH90: Govhardan and Abeles, *Arch Biochem Biophys* (1990) 280: 137–146.

GREG93: Gregg, J. M., T. S. Vedvick, and W. C. Raschke, *Bio/Technology* (1993) 11:905–910. "Recent Advances in the Expression of Foreign Genes in *Pichia pastoris.*"

GREE91 *Arch Biochem Biophys* 286(1)284–92 (1991) Green, B. G., H. Weston, B. M. Ashe, J. Doherty, P. Finke, W. Hagmann, M. Lark, J. Mao, A. Maycock, V. Moore, R. Mumford, S. Shah, L. Walakovits, and W. B. Knight, "PMN elastases: a comparison of the specificity of human isozymes and enzyme from other species toward substrates and inhibitors"

GROE91: Groeger et al., *J Protein Chem* (1991) 10(2) 245–251.

GUPT90: Gupta, S. K., J. L. Niles, R. T. McCluskey, M. A. Arnaout, *Blood* (Nov. 15, 1990), 76(10)2162. "Identity of Wegener's autoantigen (p29) with proteinase 3 and myeloblastin", HEID86 Heidtmann, H., and J. Travis, pp. 441–446 (Chapter 14) in *Proteinase Inhibitors*, Editors Barrett and Salvesen, Elsevier Science Publishers BV, Amsterdam, 1986. "Human $\alpha_1$-proteinase inhibitor"

HEIN86 *Pulm Emphysema Proteolysis,* 1986, (Conf) EDITOR: Taylor, Joseph C. (Ed). Mittman, Charles (Ed), 297–306 (1987) Heinzel, R., H. Appelhans, H. G. Gassen, U. Seemuller, M. Arnhold, H. Fritz, F. Lottspeich, K. Wiedenmann, and W. Machleidt, "The neutrophil elastase-cathepsin G inhibitor of human mucus tissues and secretions (antileukoprotease, HUSM): complete primary structure as revealed by protein and DNA sequencing"

HIEM91 *Immunobiology* (Stuttgart) 182(2)117–26 (1991) Hiemstra, P. S.; J. A. Kramps, T. M. De Vreede, F. C. Breedveld, and R. Mohamed, "Inhibition of polymorphonuclear leukocyte-mediated endothelial cell detachment by antileukoprotease: a comparison with other proteinase inhibitors"

HOCH84: Hoschstrasser, K., and E. Wachter, "Elastase inhibitors, a process for their preparation and medicaments containing these inhibitors", U.S. Pat. No. 4,485,100 (Nov. 27, 1984).

HOER90 *Arch Surg* (Chicago) 125(5)651–4 (1990) Hoerl, W. H.; R. M. Schaefer, M. Hoerl, and A. Heidland, "Neutrophil activation in acute renal failure and sepsis"

HUBB86: Hubbard, R. C., and R. G. Crystal, *Respiration* (1986), 50(Suppl 1)56–73. "Antiproteases and Antioxidants: Strategies for the Pharmacologic Prevention of Lung Destruction"

HUBB89a: Hubbard, R. C., M. A. Casolaro, M. Mitchell, S. E. Sellers, F. Arabia, M. A. Matthay, and R. G. Crystal, *Proc Natl Acad Sci USA* (1989), 86:680–4. "Fate of aerosolized recombinant DNA-produced $\alpha_1$-antitrypsin: Use of the epithelial surface of the lower respiratory tract to administer proteins of therapeutic importance"

HUBB89b: Hubbard et al., *Annals of Internal Medicine* (1989) 111:206–212.

HUBE74: Huber, R., D. Kukla, W. Bode, P. Schwager, K. Bartels, J. Deisenhofer, and W. Steigemann, *J Mol Biol* (1974), 89:73–101. "Structure of the Complex formed by Bovine Trypsin and Bovine Pancreatic Tryspin Inhibitor", HUBE75: Huber, R., W. Bode, D. Kukla, and U. Kohl, *Biophys Struct Mechan* (1975), 1:189–201. "The Structure of the Complex Formed by Bovine Trypsin and Bovine Pancreatic Trypsin Inhibitor: III. Structure of the Anhydrotrypsin-Inhibitor Complex"

HUBE77: Huber, R., W. Bode, D. Kukla, U. Kohl, C. A. Ryan, *Biophys Struct Mech* (1975), 1(3)189–201. "The structure of the complex formed by bovine trypsin and bovine pancreatic trypsin inhibitor III. Structure of the anhydro-trypsin-inhibitor complex."

HUTC87: Hutchinson, D. C. S., *Eur J Respir Dis* (1987), 71(Suppl. 153)78–85. "The role of proteases and antiproteases in bronchial secretions"

HYNE90: Hynes, T. R., M. Randal, L. A. Kenedy, C. Eigenbrot, and A. A. Kossiakoff, *Biochemistry* (1990), 29:10018–10022. "X-ray crystal structure of the protease inhibitor domain of Alzheimer's amyloid beta-protein precursor"

IMPE86 *Biochemistry* 25:3760–67 (1986), Imperiali, B., and R. H. Abeles, "Inhibition of Serine Proteases by Peptidyl Fluoromethyl Ketones"

IMPE87: Imperiali and Abeles, *Biochem* (1987) 26:4474–4477.

JUNG88 *Biol Chem Hoppe-Seyler* 369(Suppl)63–8 (1988) Junger, W., S. Hallstroem, H. Redl, and G. Schlag, "Preliminary data on isolation of an elastase-like proteinase and its inhibitor from ovine neutrophil granulocytes"

KAOR88: Kao, R. C., N. G. Wehner, K. M. Skubitz, B. H. Gray, and J. R. Hoidal, *J Clin Invest* (1988), 82:1963–73. "Proteinase 3, A Distinct Human Polymorphonuclear Leukocyte Proteinase that Produces Emphysema in Hamsters", KARI89 FASEB, 73rd *Annual Meeting,* Mar. 19–23, 1989 Abstract 3842 Kari, P. H., K. P. Vyas, and M. Hichens, "The Physiological Disposition of L-658-758, A Specific and Potent Inhibitor of PMN Elastase in th Rat, Dog, and Monkey"

KATO88 *J Biochem* 103:820–2 (1988) Kato, Y., H. Kido, N. Fukusen, and N. Katunuma, "Peptide Boronic Acids, Substrate Analogs, Inhibit Chymase, and Histamine Release from Rat Mast Cells"

KAUM86: Kaumerer, J. F., J. O. Polazzi, and M. P. Kotick, *Nucleic Acids Res* (1986), 14:7839–7850. "The mRNA for a proteinase inhibitor related to the HI-30 domain of inter-$\alpha$-trypsin inhibitor also encodes $\alpha_1$-microglobulin (protein HC)"

KAWA91: *Biochem Biophys Res Commun* 177(2)814–20 (1991) Kawabata, K., M. Suzuki, M. Sugitani, K. Imaki, M. Toda, and T. Miyamoto, "ONO-5046, a novel inhibitor of human neutrophil elastase"

KETT88: EP 293,881 (published Dec. 7, 1988) Kettner, C. A., and A. B. Shenvei "Peptide boronic acid inhibitors of trypsin-like proteases"

KETT90: *J Biol Chem* 265(30)18289–97 (1990) Kettner, C., L. Mersinger, and R. Knabb, "The Selective Inhibition of Thrombin by Peptide Boroarginine"

KIDO88: Kido, H., Y. Yokogoshi, and N. Katunuma, *J Biol Chem* (1988), 263:18104–7. "Kunitz-type Protease Inhibitor Found in Rat Mast Cells"

KIDO90: Kido, H., A. Fukutomi, J. Schelling, Y. Wang, B. Cordell, and N. Katunuma, *Biochem & Biophys Res Comm* (16 Mar. 1990), 167(2)716–21. "Protease-Specificity of Kunitz Inhibitor Domain of Alzheimer's Disease Amyloid Protein Precursor"

KITA90: *Biochimica et Biophysica Acta* 1038:105–113 (1990), Kitaguchi, N., Y. Takahashi, K. Oishi, S. Shiojiri, Y. Tokushima, T. Utsunomiya, and H. Ito, "Enzyme specificity of proteinase inhibitor region in amyloid precursor protein of Alzheimer's disease: different properties compared with protease nexin I"

KITO88: Kito &al ('88) *J Biol Chem* 263(34)18104–07.

KOKU90: U.S. Pat. No. 4,980,287 (issued Dec. 25, 1990) Kokubo, M., K. Fujii, J.-i. Oshida, K. Tomimori, and Y. Oejima, "4H-3-1 Benzoxazin-4-one compounds and pharmaceutical compositions thereof for the inhibition of serine proteases"

KRAN87: U.S. Pat. No. 4,657,893 (issued Apr. 14, 1987) Krantz, A., R. Spencer, and T. Tam, "4H-3,1-Benzoxazin-4-ones and related compounds and use as enzyme inhibitors"

KUET88: EP 257,312 (Mar. 2, 1988) Kuettner, K. E.; M. T. DiMuzio, D. Brocks, and D. Tripier, "Cartelin, a new cartilage-derived leukocyte elastase inhibitor"

LASK80: Laskowski, M., Jr, and I. Kato, *Ann Rev Biochem* (1980), 49:593–626. "Protein Inhibitors of Proteases"

LAZU83: Lazure, C., N. G. Seidah, M. Chretien, R. Lallier, and S. St-Pierre, *Canadian J Biochem Cell Biol* (1983), 61:287–92. "Primary structure determination of *Escherichia coli* heat-stable enterotoxin of porcine origin", LEAT91: *Biochem* 30:10717–21 (1991) Leatherbarrow, R. J., and H. J. Salacinski, "Design of a Small Peptide-Based Proteinase Inhibiot by Modeling the Active-Site Region of Barley Chymotrypsin Inhibitor 2"

LOOS91: U.S. Pat. No. 5,006,547 (Apr. 9, 1991) Loose, L. D., "Tendidap as an inhibitor of the release of elastase by neutrophils"

LUCE90 *J Lab Clin Med* 115(2)224–32 (1990) Lucey, E. C., P. J. Stone, D. E. Ciccolella, R. Breuer, T. G. Christensen, R. C. Thompson, and G. L. Snider, "Recombinant human secretory leukocyte-protease inhibitor: in vitro properties, and amelioration of human neutrophil elastase-induced emphysema and secretory cell metaplasia in the hamster"

MAIL90 *Eur J Cell Biol* 52(2)213–18 (1990) Maillard, J. L., C. Favreau, M. Reboud-Ravaux, R. Kobaiter, R. Joyeau, and M. Wakselman, "Biological evaluation of the inhibition of neutrophil elastase by a synthetic β-lactam derivative"

MARQ83: Marquart, M., J. Walter, J. Deisinhoffer, W. Bode, and R. Huber, *Acta Cryst*, B (1983), 39:480ff. "The geometry of the reactive site and of the peptide groups in trypsin, trypsinogen, and its complexes with inhibitors"

MASO88 *Res Monogr Cell Tissue Physiol* 15(Control Tissue Damage)259–67 (1988) Mason, R. W., "The role of cysteine proteinases in elastin degradation"

MCCA91 *Protein Engineering* 4(8)955–961 (1991) McCafferty, J., R. H. Jackson, and D. J. Chiswell, "Phage-enzymes: expression and affinity chromatography of function alkaline phsophatase on the surface of bacteriophage"

MCEL90 *Clinical Research* 38:485A (1990) McElvaney, N., and R. C. Hubbard, "Aerosolization of α1-AntiTrypsin to Establish a Functional AntiNeutrophil Elastase Defense of the Respiratory Epithelium in Cystic Fibrosis"

MCEL91 *The Lancet* 337:392–4 (1991) McElvaney, N. G., R. C. Hubbard, P. Birrer, M. S. Chernick, D. B. Caplan, M. M. Frank, R. G. Crystal, "Aerosol α1-antitrypsin treatment for cystic fibrosis"

MCWH89 *Biochem* 28:5708–5714 (1989) McWherter, C. A., W. F. Walkenhorst, E. J. Campbell, and G. I. Glover, "Novel Inhibitors of Human Leukocyte Elastase and Cathepsin G. Sequence Varients of Squash Seed Protease Inhibitor with altered Protease Selectivity"

MEHD90 *Biochem Biophys Research Comm*, 166(2) 595–600 (1990) Mehdi, S., M. R. Angelastro, J. P. Burkhart, J. R. Koehl, N. P. Peet, and P. Bey, "The Inhibition of Human Neutrophil Elastase and Cathepsin G by Peptidyl 1,2-Dicarbonyl Derivatives"

MIYA88 *J Med Chem* 31(5)1052–61 (1988) Miyano, M., J. R. Deason, A. Nakao, M. A. Stealey, C. I. Villamil, D. D. Sohn, and R. A. Mueller, "(Acyloxy)benzophenones and (acyloxy)-4-pyrones. A new class of inhibitors of human neutrophil elastase"

MIYA91 *Infect Immun* 59(9)3015–20 (1991) Miyasaki, K. T., and A. L. Bodeau, "In vitro killing of *Actinobacillus actinomycetemcomitans* and Capnocytophaga spp. by human neutrophil cathepsin G and elastase"

MOLT89 *Biochem Pharmacol* 38(15)2411–19 (1989) Molteni, A., W. F. Ward, C. H. Ts'ao, and J. M. Hinz, "Monocrotaline-induced cardiopulmonary injury in rats. Modification by the neutrophil elastase inhibitor SC 39026"

NADE87: Nadel, J. A., and B. Borson, *Biorheology* (1987), 24:541–549. "Secretion and ion transport in airways during inflammation"

NADE90: Nadel, J. A., "Neutrophil Proteases and Mucus Secretion", 1990 Cystic Fibrosis Meeting, Arlington, Va., p156.

NAKA87 *Biochem Biophys Res Commun* 147(2)666–74 (1987) Nakao, A., R. A. Partis, G. P. Jung, and R. A. Mueller, "SC-39026, a specific human neutrophil elastase inhibitor"

NAVI89 *Proc Natl Acad Sci U S A* 86(1)7–11 (1989) Navia, M. A., B. M. McKeever, J. P. Springer, T. Y. Lin, H. R. Williams, E. M. Fluder, C. P. Dorn, K. Hoogsteen, "Structure of human neutrophil elastase in complex with a peptide chloromethyl ketone inhibitor at 1.84-Å resolution"

NILE89: Niles, J. L., R. T. McCluskey, M. F. Ahmad, and M. A. Arnaout, *Blood* (1989), 74(6)1888–93. "Wgener's Granulomatosis Autoantigen Is a Novel Neutrophil Serine Proteinase"

NORR83: Norris, G. E., B. F. Anderson, E. N. Baker, *J Mol Biol* (1983) 165:501–521. "Structure of Azurin fronm Alcaligenes denitrificans at 2.5 A Resolution."

NORR89a: Norris, K., and L. C. Petersen, European Patent Application 0 339 942 A2. "Aprotinin analogues and process for the production thereof"

NORR89b: Norris, K., F. Norris, S. BJorn, PCT patent application WO89/01968. "Aprotinin Homologues and Process for the Production of Aprotinin and aprotinin homologues in Yeast"

NORR90: Norris, K., et al., *Biol Chem Hoppe-Seyer* (1990) 371:37–42. "Aprotinin and Aprotinin Analogues Expressed in Yeast."

NORR93a: Norris, F., K. Norris, S. E. Bjorn, L. C. Petersen, and O. H. Olsen, WIPO. Application 93/14120. "A Human Kunitz-Type Protease Inhibitor Variant."

NORR93x: Norris, F., K. Norris, S. E. Bjorn, L. C. Petersen, O. H. Olsen, D. C. Foster, and C. A. Sprecher, "A Novel Human Kunitz-Type Protease Inhibitor and Variants Thereof." WIPO Application 93/14123.

ODOM90: Odom, L., *Int J Biochem* (1990), 22:925–930. "Inter-α-trypsin inhibitor: a plasma proteinase inhibitor with a unique chemical structure"

OHLS86 *Pulm Emphysema Proteolysis*, 1986, (Conf) EDITORS: Taylor, Joseph C. (Ed), Mittman, Charles (Ed), p. 307–22 (1987) Ohlsson, K., M. Rosengren, G. Stefler, M. Brewer, K. K. Hale, and R. C. Thompson, "Structure, genomic organization, and tissue distribution of human secretory leukocyte-protease inhibitor (SLPI): a potent inhibitor of neutrophil elastase"

OKAD88 *FEBS Lett* 229(1)157–60 (1988) Okada, Y., S. Watanabe, I. Nakanishi, J. Kishi, T. Hayakawa, W. Watorek, J. Travis, and H. Nagase, "Inactivation of tissue inhibitor of metalloproteinases by neutrophil elastase and other serine proteinases"

OLEK91 *Biochem* 30:485–493 (1991) Oleksyszyn, J., and J. C. Powers, "Irreversible Inhibition of Serine Proteases by Peptide Derivatives of (α-Amino-alkyl)phosphonate Diphenyl Esters"

OLTE89: Oltersdorf, T., L. C. Fritz, D. B. Schenk, I. Lieberburg, K. L. Johnson-Wood, E. C. Beattie, P. J. Ward, R. W. Blacher, H. F. Dovey, and S. Sinha, *Nature* (1989), 341:144–7. "The Secreted form of the Alzheimer's amyloid precursor protein with the Kunitz domain is protease nexin-II"

PADR89 *Am Rev Respir Dis* 139(3)783–90 (1989) Padrines, M., M. Schneider-Pozzer, and J. G. Bieth, "Inhibition of neutrophil elastase by α-1-proteinase inhibitor oxidized by activated neutrophils"

PARD91 *Am J Respir Cell Mol Biol* 4(2)187–93 (1991) Padrines, M., and J. G. Bieth, "Elastin decreases the efficiency of neutrophil elastase inhibitors"

PEET90 *J Med Chem* 33(1)394–407 (1990) Peet, N. P., J. P. Burkhart, M. R. Angelastro, E. L. Giroux, S. Mehdi, P. Bey, M. Kolb, B. Neises, and D. Schirlin, "Synthesis of peptidyl fluoromethyl ketones and peptidyl α-keto esters as inhibitors of porcine pancreatic elastase, human neutrophil elastase, and rat and human neutrophil cathepsin G"

PERL88 *J Clin Invest* 81(6)1774–80 (1988) Perlmutter, D. H., J. Travis, and P. I. Punsal, "Elastase regulates the synthesis of its inhibitor, $\alpha_1$-proteinase inhibitor, and exaggerates the defect in homozygous PiZZ $\alpha_1$ PI deficiency"

PETE89: Peterson, M. W., *J Lab Clin Med* (1989), 113(3) 297–308. "Neutrophil cathepsin G increases tramendothelial albumin flux"

PONT88: Ponte, P., P. Gonzalez-DeWhitt, J. Schilling, J. Miller, D. Hsu, B. Greenberg, K. Davis, W. Wallace, I. Liederburg, F. Fuller, and B. Cordell, *Nature* (1988), 331:525–7. "A new A4 amyloid mRNA contains a domain homologous to serine proteinase inhibitors"

POTE91 *Biochem J* 274(2)465–71 (1991) Potempa, J., J. K. Wunderlich, and J. Travis, "Comparative properties of three functionally different but structurally related serpin variants from horse plasma"

POWE86 Powers, J. C., and J. W. Harper, "Inhibitors of Serine Proteinases", Chapter 3, pp 55–152 in Proteinase Inhibitors, Editors Barrett and Salvesen, Elsevier Science Publishers BV, Amsterdam, 1986.

POWE89 U.S. Pat. No. 4,845,242 (issued Jul. 4, 1989) Powers, J. C., and C.-M. Kam, "Isocoumarins with basic substituents as serine protease inhibitors, anticoagulants and anti-inflammatory agents"

PRAT87 *Arch Biochem Biophys* 258(2)591–9 (1987) Pratt, C. W., P. A. Roche, and S. V. Pizzo, "The role of inter-$\alpha$-trypsin inhibitor and other proteinase inhibitors in the plasma clearance of neutrophil elastase and plasmin"

REED91 *J Biol Chem* 266(1)13–21 (1991) Reed, P. E., and J. A. Katzenellenbogen, "Proline-Valine Pseudo Peptide Enol Lactones: effective and selective inhibitors of chymotrypsin and human leukocyte elastase"

REMO89 *J Exp Med* 169(3)1071–86 (1989) Remold-O'Donnell, E., J. C. Nixon, & R. M. Rose, "Elastase inhibitor. Characterization of the human elastase inhibitor molecule associated with monocytes, macrophages, and neutrophils."

RITO83: Ritonja, A., B. Meloun, and F. Gubensek, *Biichim Biophys Acta* (1983), 746:138–145. "The Primary Structure of *Vipera ammodytes* venom chymotrypsin inhibitor"

ROBE87 U.S. Pat. No. 4,665,053 (issued May 12, 1987) Robert, L., W. Hornbeck, and E. Moczar, "Peptide Derivatives, the preparation and their use as elastase inhibitors"

ROBE89: *Elastin and Elastases*, Volume II. Editors: Robert and Hornbeck. CRC Press, Boca Raton, Fla., 1989.

ROBE92: Roberts, B. L., W. Markland, A. C. Ley, R. B. Kent, D. W. White, S. K. Guterman, and R. C. Ladner, (1992) "Directed evolution of a protein: selection of potent neutrophil elastase inhibitors displayed on M13 fusion phage."*Proc Natl Acad Sci USA* 89(6)2429–33.

RUEH73: Ruehlmann, A., D. Kukla, P. Schwager, K. Bartels, and R. Huber, *J Mol Biol* (1973), 77:417–436. "Structure of the Complex formed by Bovine Trypsin and Bovine Pancreatic Trypsin Inhibitor: Crystal Structure Determination and Stereochemistry of the Contact Region"

SALI90 *TIBS* 15:435–9 (November 1990) Salier, J.-P., "Inter-$\alpha$-trypsin inhibitor: emergence of a family within the Kunitz-type protease inhibitor superfamily"

SALV87: Salvesen, G., D. S. Farley, J. Shuman, A. Przybyla, C. Reilly, and J. Travis, *Biochemistry* (1987) 26:2289–2293. "Molecular Cloning of Human Cathepsin G: Structural Similarity to Mast Cell and Cytotoxic T Lymphocyte Proteinases."

SAMB89: Sambrook, J., E. F. Fritsch, and T. Maniatis, *Molecular Cloning, A Laboratory Manual*, Second Edition, Cold Spring Harbor Laboratory, 1989.

SCHA87: Schagger, H. and G. von Jagow (1987) *Analytical Biochemistry* 166:368ff.

SCHE67: Schecter and Berger, *Biochem Biophys Res Comm* (1967) 27:157–162.

SCHN86a: Schnabel, E., W. Schroeder, and G. Reinhardt, *Biol Chem Hoppe-Seyler* (1986), 367:1167–76. "[Ala$_2^{14,}$ $_{38}$]Aprotinin: Preparation by Partial Desulphurization of Aprotinin by Means of Raney Nickel and Comparison with other Aprotinin Derivatives"

SCHN86b: Schnebli and Braun, Chapter 21 in BARR86.

SCHN88a: Schnabel, E., G. Reinhardt, W. Schroeder, H. Tschesche, H. R. Wenzel, and A. Mehlich, *Biol Chem Hoppe-Seyler* (1988), 369:461–8. "Enzymatic Resynthesis of the 'Reactive Site' Bond in the Modified Aprotinin Derivatives [Seco-15/16]Aprotinin and [Di-seco-15/16, 39/40]Aprotinin"

SCHW87: Schwarz, H., H. J. Hinz, A. Mehlich, H. Tschesche, and H. R. Wenzel, *Biochemistry* (1987), 26: (12)p3544–51. "Stability studies on derivatives of the bovine pancreatic trypsin inhibitor."

SCHW94: Schweitz et al. *PNAS* (1994) 91:878–882.

SCOT87b: Scott, C. F., H. R. Wenzel, H. R. Tschesche, and R. W. Colman, *Blood* (1987), 69:1431–6. "Kinetics of Inhibition of Human Plasma Kallikrein by a Site-Specific Modified Inhibitor Arg$^{15}$-Aprotinin: Evaluation Using a Microplate System and Comparison With Other Proteases"

SEEM81: Seemuller, U., H. Fritz, and M. Eulitz. *Methods in Enzymology* (1981) 80:804–817. "Eglin: Elastase—Cathepsin G Inhibitor from Leeches."

SEEM86: Chapter 8 in BARR86.

SELL87: Selloum, L., M. Davril, C. Mizon, M. Balduyck, and J. Mizon, *Biol Chem Hoppe-Seyler* (1987), 368:47–55. "The effect of the glycosaminoglycan chain removal on some properties of the human urinary trypsin inhibitor"

SHIN90: Shina et al., 1990. (FIND: in re: Schweitz et al. *PNAS* (1994) 91:878–882.)

SIEK87: Siekmann, J., H. R. Wenzel, W. Schroeder, H. Schutt, E. Truscheit, A. Arens, E. Rauenbusch, W. H. CHazin, K. Wutrieh, and H. Tschesehe, *Biol Chem Hoppe-Seyler* (1987), 368:1589–96. "Pyroglutamul-aprotinin, a new aprotinin homologue from bovine lungs-isolation, properties, sequence analysis and characterization using $^1$H nuclear magnetic resonance in solution"

SIEK88: Siekmann, J., H. R. Wenzel, W. Schroeder, and H. Tschesehe, *Biol Chem Hoppe-Seyler* (1988), 369:157–163. "Characterization and Sequence Determination of Six Aprotinin homologues from bovine lungs"

SIEK89: Siekmann, J., J. Beckmann, A. Mehlich, H. R. Wenzel, H. Tschesche, E. Schnabel, W. Mueller-Esterl, *Biol Chem Hoppe-Seyler* (1989), 370:677–81. "Immunological Characterization of Natural and Semisynthetic Aprotinin Variants"

SINH90: Sinha, S., H. F. Dovey, P. Seubert, P. J. Ward, R. W. Blacher, M. Blaber, R. A. Bradshaw, M. Arici, W. C. Mobley, and I. Lieberburg, *J Biol Chem* (1990), 265(16) 8983–5. "The Protease Inhibitory Properties of the Alzheimer's beta-amyloid Precursor Protein"

SINH91 *J Biol Chem* 266(31)21011–13 (November 1991) Sinha, S., J. Knops, F. Esch, E. D. Moyer, and T. Oltersdorf, "Conversion of the Alzheimer's β-Amyloid Precursor Protein (APP) Kunitz Domain in to a Potent Human Neutrophil Elastase Inhibitor"

SINO89 *Placenta* 10(6)569–78 (1989) Sinosich, M. J., J. Lee, J. P. Wolf, R. F. Williams, and G. D. Hodgen, "RU 486 induced suppression of placental neutrophil elastase inhibitor levels"

SKAR92: Skarzynski, T., *J Mol Biol* (1992) 224(3)671–83. "Crystal structure of alpha-dendrotoxin from the green mamba venom and its comparison with the structure of bovine pancreatic trypsin inhibitor."

SNID91: Snider et al., *Ann New York Acad Sci* (1991) 624:45–59.

SOMM89: Sommerhoff, C. P., G. H. Caughey, W. E. Finkbeiner, S. C. Lazarus, C. B. Basbaum, and J. A. Nadel, *J Immunol* (1989), 142:2450–56. "A Potent Secretagogue for Airway Gland Serous Cells"

SOMM90: Sommerhoff, C. P., J. A. Nadel, C. B. Basbaum, and G. H. Caughey, *J Clin Invest* (March 1990), 85:682–689. "Neutrophil Elastase and Cathepsin G. Stimulate Secretion from Cultured Bovine Airway Gland Serous Cells"

SOMM91 *Eur J Pharmacology*, 193:153–158 (1991) Sommerhoff, C. P., R. D. Krell, J. L. Williams, B. C. Comes, A. M. Strimpler, and J. A. Nadel "Inhibition of human neutrophil elastase by ICI 200,355"

STAT87: States, D. J., T. E. Creighton, C. M. Dobson, and M. Karplus, *J Mol Biol* (1987), 195(3)731–9. "Conformations of intermediates in the folding of the pancreatic trypsin inhibitor."

STOL90: Stoll, V. S. and J. S. Blanchard (1990) *Methods in Enzymology* 182:24ff.

STON88 *Respiration* 54(1)1–15 (1988) Stone, P. J., E. C. Lucey, J. D. Calore, M. P. McMahon, G. L. Snider, and C. Franzblau, "Defenses of the hamster lung against human neutrophil and porcine pancreatic elastase"

STON90 *Eur Respir J* 3(6)673–8 (1990) Stone, P. J., E. C. Lucey, G. D. Virca, T. G. Christensen, R. Breuer, and G. L. Snider, "$\alpha_1$-protease inhibitor moderates human neutrophil elastase-induced emphysema and secretory cell metaplasia in hamsters"

SWAI88: Swaim, M. W., and S. V. Pizzo, *Biochem J* (1988), 254:171–178. "Modification of the tandem reactive centres of human innter-α-trypsin inhibitor with butanedione and cis-dichlorodiammineplatinum(II)"

TAKE89 *J Biol Chem* 264(13)7431–6 (1989) Takeuchi, K. H., and R. T. Swank, "Inhibitors of elastase and cathepsin G in Chediak-Higashi (beige) neutrophils"

TRAB86: Traboni, C., R. Cortese, *Nucleic Acids Res* (1986), 14(15)6340. "Sequence of a full length cDNA coding for human protein HC ($\alpha_1$ microglobulin)"

TRAI87 *Trends Pharmacol Sci* 8(8)303–7 (1987) Trainor, D. A., "Synthetic inhibitors of human neutrophil elastase"

TRAV88 *Am J Med* 84(6A)37–42 (1988) Travis, J., "Structure, function, and control of neutrophil proteinases"

TRAV91 *Ann NY Acad Sci* 624(Pulmonary Emphysema) 81–6 (1991) Travis, J., A. Dubin, J. Potempa, W. Watorek, and A. Kurdowska, "Neutrophil proteinases. Caution signs in designing inhibitors against enzymes with possible multiple functions"

TSCH87: Tschesch, H., J. Beckmann, A. Mehlich, E. Schnabel, E. Truscheit, and H. R. Wenzel, *Biochimica et Biophysica Acta* (1987), 913:97–101. "Semisynthetic engineering of proteinase inhibitor homologues"

TSUD87 *Chem Pharm Bull* 35(9)3576–84 (1987) Tsuda, Y., Y. Okada, Y. Nagamatsu, and U. Okamoto, "Synthesis of Peptide Chloromethyl Ketones and Examination of Their Inhibitory Effects on Human Spleen Fibrinolytic Proteinase (SFP) and Human Leukocyte Elastase (LE)"

TYAG90 *Biochemistry* 29(42)9970–7 (1990) Tyagi, S. C., and S. R. Simon, "Inhibitors directed to binding domains in neutrophil elastase"

TYAG91a *J Biol Chem* 266(8)5279–85 (1991) Tyagi, S. C., "Parinaric acids as probes of binding domains in neutrophil elastase"

TYAG91b *J Biol Chem* 266(23)15185–91 (1991) Tyagi, S. C., and S. R. Simon, "Reversible inhibition of neutrophil elastase by thiol-modified $\alpha_1$-protease inhibitor"

VEDV91: Vedvick, T., R. G. Buckholz, M. Engel, M. Urcan, J. Kinney, S. Provow, R. S. Siegel, and G. P. Thill. *J Ind Microbiol* (1991) 7:197–201. "High-level secretion of biologically active aprotinin from the yeast *Pichia pastoris*."

VINC72: Vincent &al, *Biochem* (1972), 11:2967ff.

VINC74: Vincent &al., *Biochem* (1974), 13:4205.

VOGE90 *J Appl Physiol* 69(5)1843–8 (1990) Vogelmeier, C., R. Buhl, R. F. Hoyt, E. Wilson, G. A. Fells, R. C. Hubbard, H.-P. Schnebli, R. C. Thompson, R. G. Crystal, "Aerosolization of recombinant SLPI to augment antineutrophil elastase protection of pulmonary epithelium"

VOGE91 *J Clin Invest* 87(2)482–8 (1991) Vogelmeier, C., R. C. Hubbard, G. A. Fells, H. P. Schnebli, R. C. Thompson, H. Fritz, R. G. Crystal, "Anti-neutrophil elastase defense of the normal human respiratory epithelial surface provided by the secretory leukoprotease inhibitor"

WACH79: Wachter, E., K. Hochstrasser, G. Bretzel, and S. Heindl, *Hoppe-Seyler Z Physiol Chem* (1979), 360:1297–1303. "Kunitz-Type Proteinase Inhibitors Derived by Limited Proteolysis of the Inter-α-trypsin Inhibitor, II. Characterization of a Second Inhibitory Inactive Domain by Amino Acid Sequence Determination"

WACH80: Wachter, E., K. Deppner, and K. Hochstrasser, *FEBS Letters* (1980), 119:58–62. "A New Kunitz-type Inhibitor from Bovine Serum, Amino Acid Sequence Determination."

WAGN79: Wanger, G., H. Tschesche, and K. Wuthrich, *Eur J Biochem* (1979), 95:239–248. "The Influence of Localized Chemical Modifications of the Basic Pancreatic Trypsin Inhibitor on Static and Dynamic Aspects of the Molecular Conformation in Solution"

WANG87: Wagner, G., D. Bruhwiler, and K. Wuthrich, *J Mol Biol* (1987), 196(1)227–31. "Reinvestigation of the aromatic side-chains in the basic pancreatic trypsin inhibitor by heteronuclear two-dimensional nuclear magnetic resonance."

WAGN92: Wagner, S. L., R. S. Siegel, T. S. Vedvick, W. C. Raschke, and W. E. van Nostrand. Biochem Biophys Res Cornm (1992) 186:1138–1145. "High-level expression, purification and characterization of the Kunitz-type protease inhibitor domain of protease nexin-2/amyloid β-protein precursor."

WAKS90 EP 357,510, published Mar. 7, 1990. Wakselmann, M., J.-P. Mazeleyrat, and M. Reboud, "Derives de cyclopeptides utilisables comme inhibiteurs selectifs, vis-a-vis de proteases a serine active" [Derivates of cyclopeptides useable as selective inhibitors against active serine proteases]

WEIS89 *N Engl J Med* 320:365–76 (1989) Weiss, S. J., "Tissue destruction by Neutrophils"

WELL90: Wells, *Biochem* (1990) 29(37)8509–8517.

WEWE87: Wewers, M. D., M. A. Casolaro, S. E. Sellers, S. C. Swayze, K. M. McPhaul, J. T. Wittes, and R. G. Crystal, *New Engl J Med* (1987), 316(17)1055–62. "Replacement therapy for α-1-antitrypsin deficiency associated with emphysema"

WILL87 *J Biol Chem* 262(35)17178–81 (1987) Williams, H. R., T. Y. Lin, M. A. Navia, J. P. Springer, B. M. McKeever, K. Hoogsteen, C. P. Dorn, Jr, "Crystallization of human neutrophil elastase"

WILL91a: Williams et al., *J Biol Chem* (1991) 266(8) 5182–5190.

WILL91b *Exp Lung Res* 17(4)725–41 (1991) Williams, J. C., R. L. Stein, A. M. Strimpler, B. Reaves, R. D. Krell, "Biochemical and pharmacological characterization of ICI 186,756: a novel, potent, and selective inhibitor of human neutrophil elastase"

WILL91c *Ann NY Acad Sci* 624(Pulmonary Emphysema) 230–43 (1991) Williams, J. C., R. L. Stein, R. E. Giles, and R. D. Krell, "Biochemistry and pharmacology of ICI 200,880, a synthetic peptide inhibitor of human neutrophil elastase"

WLOD84: Wlodawer, A., J. Walter, R. Huber, and L. Sjolin, *J Mol Biol* (1984), 180 (2)301–29. "Structure of bovine pancreatic trypsin inhibitor. Results of joint neutron and X-ray refinement of crystal form II."

WLOD87a: Wlodawer, A., J. Nachman, G. L. Gilliland, W. Gallagher, and C. Woodward, *J Mol Biol* (1987), 198(3) 469–80. "Structure of form III crystals of bovine pancreatic trypsin inhibitor."

WLOD87b: Wlodawer, A., J. Deisenhofer, R. Huber. *J Mol Biol* (1987) 193:145–156. "Comparison of Two Highly Refined Structures of Bovine Pancreatic Trypsin Inhibitor."

WUNT88: Wun, T.-C., K. K. Kretzmer, T. J. Girard, J. P. Miletich, and G. J. Broze, Jr, *J Biol Chem* (1988), 263:6001–4. "Cloning and Characterization of a cDNA Coding for the Lipoprotein-associated Coagulation Inhibitor Shows That It Consists of Three Tandem Kunitz-type Inhibitory Domains"

WUNT90 U.S. Pat. No. 4,966,852, Wun, T.-C., K. K. Kretzmer, and G. J. Broze, Jr, "DNA Clone of Human Time Factor Inhibitor"

YAMA90 *Biochem Biophys Res Commun* 171(2)711–716 (1990) Yamamoto, D., T. Ishida, and M. Inoue, "A Comparison between the Binding Modes of a Substrate and Inhibitor to Papain as Observed in Complex Crystal Structures"

YUAN90 *Clinical Research* 38:485A (1990) Yuan, Z. A., K. Soprano, and F. Kueppers, "Alpha-1 Antitrypsin Production by in vivo Stimulated Blood Monocytes"

---

We claim:

1. A protein that binds and inhibits human neutrophil elastase with a $K_i$ less than about 10 picomolar comprising an amino acid sequence picked from the set of sequences EpiNE1, EpiNE2, EpiNE3, EpiNE4, EpiNE5, EpiNE6, EpiNE7, EpiNE8, EPI-HNE-2, EPI-HNE-3, EPI-HNE-4, BITI-E7, BITI-E7-141, BITI-E7-1222, MUT1619, MUTP1, AMINO1, AMINO2, MUTQE, MUTT26A, EpiNE7.6, EpiNE7.8, EpiNE7.9, EpiNE7.31, EpiNE 7.11, EpiNE7.7, EpiNE7.4, EpiNE7.14, EpiNE7.5, EpiNE7.10, EpiNE7.20, EpiNE7.1, EpiNE7.16, EpiNE7.19, EpiNE7.12, EpiNE7.17, EpiNE7.21, EpiNE7.22, EpiNE7.23, EpiNE7.24, EpiNE7.25, EpiNE7.26, EpiNE7.27, EpiNE7.28, EpiNE7.29, EpiNE7.30, EpiNE7.32, EpiNE7.33, EpiNE7.36, EpiNE7.37, EpiNE7.38, EpiNE7.39, and EpiNE7.40.

2. A protein that binds and inhibits human neutrophil elastase with a $K_i$ less than about 10 picomolar that comprises an amino-acid sequence of at least about 51 amino acids that differs from an amino-acid sequence found in a protein of human origin by no more than about eight amino acids.

3. A protein that binds and inhibits hNE with an $K_i$ less than about 10 picomolar that comprises an amino-acid sequence derived from a parental Kunitz domain, said parental Kunitz domain having a $K_i$ for hNE greater than about 1.0 nanomolar and said derived Kunitz domain carrying at least the mutations X18F and a mutation picked from the set comprising X15V and X15I.

4. A protein as in claim 3 in which the derived Kunitz domain contains at least one mutation from the set comprising: X13P; X36G; X37G; and X12G.

5. A protein as in claim 4 that is secreted from the yeast *Pichia pastoris*.

6. A protein that binds and inhibits human neutrophil elastase with a $K_i$ less than 10 picomolar comprising an amino acid sequence that is substantially homologous to a sequence picked from the set of sequences consisting of EpiNE1, EpiNE2, EpiNE3, EpiNE4, EpiNE5, EpiNE6, EpiNE7, EpiNE8, EPI-HNE-2, EPI-HNE-3, EPI-HNE-4, BITI-E7, BITI-E7-141, BITI-E7-1222, MUT1619, MUTP1, AMINO1, AMINO2, MUTQE, MUTT26A, EpiNE7.6, EpiNE7.8, EpiNE7.9, EpiNE7.31, EpiNE 7.11, EpiNE7.7, EpiNE7.4, EpiNE7.14, EpiNE7.5, EpiNE7.10, EpiNE7.20, EpiNE7.1, EpiNE7.16, EpiNE7.19, EpiNE7.12, EpiNE7.17, EpiNE7.21, EpiNE7.22, EpiNE7.23, EpiNE7.24, EpiNE7.25, EpiNE7.26, EpiNE7.27, EpiNE7.28, EpiNE7.29, EpiNE7.30, EpiNE7.32, EpiNE7.33, EpiNE7.36, EpiNE7.37, EpiNE7.38, EpiNE7.39, and EpiNE7.40.

7. A protein as in claim 1 that is secreted from the yeast *Pichia pastoris*.

8. A protein as in claim 6 wherein the region of homology extends from at least the first cysteine to the last cysteine.

9. A protein as in claim 2 in which the number of differences is four or less.

* * * * *

SEQUENCE LISTING ( 1 ) GENERAL INFORMATION:

( i i i ) NUMBER OF SEQUENCES: 234

( 2 ) INFORMATION FOR SEQ ID NO:1:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Arg Pro Asp Phe Cys Leu Glu Pro Pro Tyr Thr Gly Pro Cys Val Ala
 1               5                  10                  15
Met Phe Pro Arg Tyr Phe Tyr Asn Ala Lys Ala Gly Leu Cys Gln Thr
            20                  25                  30
Phe Val Tyr Gly Gly Cys Met Gly Asn Gly Asn Asn Phe Lys Ser Ala
            35                  40                  45
Glu Asp Cys Met Arg Thr Cys Gly Gly Ala
            50                  55
```

( 2 ) INFORMATION FOR SEQ ID NO:2:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Lys Glu Asp Ser Cys Gln Leu Gly Tyr Ser Ala Gly Pro Cys Met Gly
 1               5                  10                  15
Met Thr Ser Arg Tyr Phe Tyr Asn Gly Thr Ser Met Ala Cys Glu Thr
            20                  25                  30
Phe Gln Tyr Gly Gly Cys Met Gly Asn Gly Asn Asn Phe Val Thr Glu
            35                  40                  45
```

```
Lys Asp Cys Leu Gln Thr Cys Arg Thr Val
 50                  55
```

(2) INFORMATION FOR SEQ ID NO:3:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Thr Val Ala Ala Cys Asn Leu Pro Ile Val Arg Gly Pro Cys Arg Ala
 1               5                  10                  15

Phe Ile Gln Leu Trp Ala Phe Asp Ala Val Lys Gly Lys Cys Val Leu
             20                  25                  30

Phe Pro Tyr Gly Gly Cys Gln Gly Asn Gly Asn Lys Phe Tyr Ser Glu
         35                  40                  45

Lys Glu Cys Arg Glu Tyr Cys Gly Val Pro
 50                  55
```

(2) INFORMATION FOR SEQ ID NO:4:

(i) SEQUENCE CHARACTERISTICS:
        (A) LENGTH:1449 bases
        (B) TYPE: nucleic acid
        (C) STRANDEDNESS: single
        (D) TOPOLOGY: linear (ii) MOLECULE TYPE:other nucleic acid
        (A) DESCRIPTION:synthetic DNA fragment (xi) SEQUENCE DESCRIPTION: SEQ ID NO:4:

```
GTGAAAAAAT TATTATTCGC AATTCCTTTA GTTGTTCCTT TCTATTCTGG      50
CGCCCGTCCG GATTTCTGTC TCGAGCCACC ATACACTGGG CCCTGCAAAG     100
CGCGCATCAT CCGCTATTTC TACAATGCTA AAGCAGGCCT GTGCCAGACC     150
TTTGTATACG GTGGTTGCCG TGCTAAGCGT AACAACTTTA AATCGGCCGA     200
AGATTGCATG CGTACCTGCG GTGGCGCCGC TGAAACTGTT GAAAGTTGTT     250
TAGCAAAACC CCATACAGAA AATTCATTTA CTAACGTCTG GAAAGACGAC     300
AAAACTTTAG ATCGTTACGC TAACTATGAG GGTTGTCTGT GGAATGCTAC     350
AGGCGTTGTA GTTTGTACTG GTGACGAAAC TCAGTGTTAC GGTACATGGG     400
TTCCTATTGG GCTTGCTATC CCTGAAAATG AGGGTGGTGG CTCTGAGGGT     450
GGCGGTTCTG AGGGTGGCGG TTCTGAGGGT GGCGGTACTA AACCTCCTGA     500
GTACGGTGAT ACACCTATTC CGGGCTATAC TTATATCAAC CCTCTCGACG     550
GCACTTATCC GCCTGGTACT GAGCAAAACC CCGCTAATCC TAATCCTTCT     600
CTTGAGGAGT CTCAGCCTCT TAATACTTTC ATGTTTCAGA ATAATAGGTT     650
CCGAAATAGG CAGGGGGCAT TAACTGTTTA TACGGGCACT GTTACTCAAG     700
GCACTGACCC CGTTAAAACT TATTACCAGT ACACTCCTGT ATCATCAAAA     750
GCCATGTATG ACGCTTACTG GAACGGTAAA TTCAGAGACT GCGCTTTCCA     800
TTCTGGCTTT AATGAGGATC CATTCGTTTG TGAATATCAA GGCCAATCGT     850
CTGACCTGCC TCAACCTCCT GTCAATGCTG GCGGCGGCTC TGGTGGTGGT     900
TCTGGTGGCG GCTCTGAGGG TGGTGGCTCT GAGGGTGGCG GTTCTGAGGG     950
```

| | | | | |
|---|---|---|---|---|
| TGGCGGCTCT | GAGGGAGGCG | GTTCCGGTGG | TGGCTCTGGT | TCCGGTGATT | 1000 |
| TTGATTATGA | AAAGATGGCA | AACGCTAATA | AGGGGGCTAT | GACCGAAAAT | 1050 |
| GCCGATGAAA | ACGCGCTACA | GTCTGACGCT | AAAGGCAAAC | TTGATTCTGT | 1100 |
| CGCTACTGAT | TACGGTGCTG | CTATCGATGG | TTTCATTGGT | GACGTTTCCG | 1150 |
| GCCTTGCTAA | TGGTAATGGT | GCTACTGGTG | ATTTGCTGG | CTCTAATTCC | 1200 |
| CAAATGGCTC | AAGTCGGTGA | CGGTGATAAT | TCACCTTTAA | TGAATAATTT | 1250 |
| CCGTCAATAT | TTACCTTCCC | TCCCTCAATC | GGTTGAATGT | CGCCCTTTTG | 1300 |
| TCTTTAGCGC | TGGTAAACCA | TATGAATTTT | CTATTGATTG | TGACAAAATA | 1350 |
| AACTTATTCC | GTGGTGTCTT | TGCGTTTCTT | TTATATGTTG | CCACCTTTAT | 1400 |
| GTATGTATTT | TCTACGTTTG | CTAACATACT | GCGTAATAAG | GAGTCTTAA | 1449 |

( 2 ) INFORMATION FOR SEQ ID NO:5:

( i ) SEQUENCE CHARACTERISTICS:
        ( A ) LENGTH:482 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

| Met | Lys | Lys | Leu | Leu | Phe | Ala | Ile | Pro | Leu | Val | Val | Pro | Phe | Tyr | Ser |
|---|---|---|---|---|---|---|---|---|---|---|---|---|---|---|---|
| 1 | | | | 5 | | | | | 10 | | | | | 15 | |
| Gly | Ala | Arg | Pro | Asp | Phe | Cys | Leu | Glu | Pro | Pro | Tyr | Thr | Gly | Pro | Cys |
| | | | 20 | | | | 25 | | | | | 30 | | | |
| Lys | Ala | Arg | Ile | Ile | Arg | Tyr | Phe | Tyr | Asn | Ala | Lys | Ala | Gly | Leu | Cys |
| | | 35 | | | | | 40 | | | | | 45 | | | |
| Gln | Thr | Phe | Val | Tyr | Gly | Gly | Cys | Arg | Ala | Lys | Arg | Asn | Asn | Phe | Lys |
| | 50 | | | | | 55 | | | | | 60 | | | | |
| Ser | Ala | Glu | Asp | Cys | Met | Arg | Thr | Cys | Gly | Gly | Ala | Ala | Glu | Thr | Val |
| 65 | | | | | 70 | | | | 75 | | | | | | 80 |
| Glu | Ser | Cys | Leu | Ala | Lys | Pro | His | Thr | Glu | Asn | Ser | Phe | Thr | Asn | Val |
| | | | | 85 | | | | | 90 | | | | | 95 | |
| Trp | Lys | Asp | Asp | Lys | Thr | Leu | Asp | Arg | Tyr | Ala | Asn | Tyr | Glu | Gly | Cys |
| | | | 100 | | | | | 105 | | | | | 110 | | |
| Leu | Trp | Asn | Ala | Thr | Gly | Val | Val | Cys | Thr | Gly | Asp | Glu | Thr | Gln |
| | | 115 | | | | | 120 | | | | | 125 | | |
| Cys | Tyr | Gly | Thr | Trp | Val | Pro | Ile | Gly | Leu | Ala | Ile | Pro | Glu | Asn | Glu |
| | 130 | | | | | 135 | | | | | 140 | | | | |
| Gly | Gly | Gly | Ser | Glu | Gly | Gly | Gly | Ser | Glu | Gly | Gly | Gly | Ser | Glu | Gly |
| 145 | | | | | 150 | | | | 155 | | | | | | 160 |
| Gly | Gly | Thr | Lys | Pro | Pro | Glu | Tyr | Gly | Asp | Thr | Pro | Ile | Pro | Gly | Tyr |
| | | | | 165 | | | | | 170 | | | | | 175 | |
| Thr | Tyr | Ile | Asn | Pro | Leu | Asp | Gly | Thr | Tyr | Pro | Pro | Gly | Thr | Glu | Gln |
| | | | 180 | | | | | 185 | | | | | 190 | | |
| Asn | Pro | Ala | Asn | Pro | Asn | Pro | Ser | Leu | Glu | Glu | Ser | Gln | Pro | Leu | Asn |
| | | | 195 | | | | 200 | | | | | 205 | | | |
| Thr | Phe | Met | Phe | Gln | Asn | Asn | Arg | Phe | Arg | Asn | Arg | Gln | Gly | Ala | Leu |
| | | 210 | | | | | 215 | | | | 220 | | | | |
| Thr | Val | Tyr | Thr | Gly | Thr | Val | Thr | Gln | Gly | Thr | Asp | Pro | Val | Lys | Thr |
| 225 | | | | | 230 | | | | 235 | | | | | | 240 |
| Tyr | Tyr | Gln | Tyr | Thr | Pro | Val | Ser | Ser | Lys | Ala | Met | Tyr | Asp | Ala | Tyr |
| | | | | 245 | | | | | 250 | | | | | 255 | |

| | | | | | | | | | | | | | | |
|---|---|---|---|---|---|---|---|---|---|---|---|---|---|---|
|Trp|Asn|Gly|Lys 260|Phe|Arg|Asp|Cys|Ala 265|Phe|His|Ser|Gly|Phe 270|Asn|Glu|
|Asp|Pro|Phe 275|Val|Cys|Glu|Tyr|Gln 280|Gly|Gln|Ser|Ser|Asp 285|Leu|Pro|Gln|
|Pro|Pro 290|Val|Asn|Ala|Gly|Gly 295|Gly|Ser|Gly|Gly|Gly 300|Ser|Gly|Gly|Gly|
|Ser 305|Glu|Gly|Gly|Gly|Ser 310|Glu|Gly|Gly|Gly|Ser 315|Glu|Gly|Gly|Gly|Ser 320|
|Glu|Gly|Gly|Gly|Ser 325|Gly|Gly|Gly|Ser 330|Gly|Ser|Gly|Asp|Phe|Asp 335|Tyr|
|Glu|Lys|Met|Ala 340|Asn|Ala|Asn|Lys|Gly 345|Ala|Met|Thr|Glu|Asn 350|Ala|Asp|
|Glu|Asn|Ala 355|Leu|Gln|Ser|Asp|Ala 360|Lys|Gly|Lys|Leu|Asp 365|Ser|Val|Ala|
|Thr|Asp 370|Tyr|Gly|Ala|Ala|Ile 375|Asp|Gly|Phe|Ile|Gly 380|Asp|Val|Ser|Gly|
|Leu 385|Ala|Asn|Gly|Asn|Gly 390|Ala|Thr|Gly|Asp|Phe 395|Ala|Gly|Ser|Asn|Ser 400|
|Gln|Met|Ala|Gln|Val 405|Gly|Asp|Gly|Asp|Asn 410|Ser|Pro|Leu|Met|Asn 415|Asn|
|Phe|Arg|Gln|Tyr 420|Leu|Pro|Ser|Leu|Pro 425|Gln|Ser|Val|Glu|Cys 430|Arg|Pro|
|Phe|Val|Phe 435|Ser|Ala|Gly|Lys|Pro 440|Tyr|Glu|Phe|Ser|Ile 445|Asp|Cys|Asp|
|Lys|Ile 450|Asn|Leu|Phe|Arg|Gly 455|Val|Phe|Ala|Phe|Leu 460|Leu|Tyr|Val|Ala|
|Thr 465|Phe|Met|Tyr|Val|Phe 470|Ser|Thr|Phe|Ala|Asn 475|Ile|Leu|Arg|Asn|Lys 480|
|Glu|Ser| | | | | | | | | | | | | | |

( 2 ) INFORMATION FOR SEQ ID NO:6:

( i ) SEQUENCE CHARACTERISTICS:
  ( A ) LENGTH:1455 bases
  ( B ) TYPE: nucleic acid
  ( C ) STRANDEDNESS: single
  ( D ) TOPOLOGY: linear ( i i ) MOLECULE TYPE:other nucleic acid
  ( A ) DESCRIPTION:synthetic DNA fragment ( x i ) SEQUENCE DESCRIPTION: SEQ ID NO:6:

```
GTGAAAAAAT  TATTATTCGC  AATTCCTTTA  GTTGTTCCTT  TCTATTCTGG       50

CGCCAAAGAA  GACTCTTGCC  AGCTGGGCTA  CTCGGCCGGT  CCCTGCATGG      100

GAATGACCAG  CAGGTATTTC  TATAATGGTA  CATCCATGGC  CTGTGAGACT      150

TTCCAGTACG  GCGGCTGCAT  GGGCAACGGT  AACAACTTCG  TCACAGAAAA      200

GGAGTGTCTG  CAGACCTGCC  GAACTGTGGG  CGCCGCTGAA  ACTGTTGAAA      250

GTTGTTTAGC  AAAACCCCAT  ACAGAAAATT  CATTTACTAA  CGTCTGGAAA      300

GACGACAAAA  CTTTAGATCG  TTACGCTAAC  TATGAGGGTT  GTCTGTGGAA      350

TGCTACAGGC  GTTGTAGTTT  GTACTGGTGA  CGAAACTCAG  TGTTACGGTA      400

CATGGGTTCC  TATTGGGCTT  GCTATCCCTG  AAAATGAGGG  TGGTGGCTCT      450

GAGGGTGGCG  GTTCTGAGGG  TGGCGGTTCT  GAGGGTGGCG  GTACTAAACC      500

TCCTGAGTAC  GGTGATACAC  CTATTCCGGG  CTATACTTAT  ATCAACCCTC      550
```

```
TCGACGGCAC TTATCCGCCT GGTACTGAGC AAAACCCCGC TAATCCTAAT    600

CCTTCTCTTG AGGAGTCTCA GCCTCTTAAT ACTTTCATGT TTCAGAATAA    650

TAGGTTCCGA AATAGGCAGG GGGCATTAAC TGTTTATACG GGCACTGTTA    700

CTCAAGGCAC TGACCCCGTT AAAACTTATT ACCAGTACAC TCCTGTATCA    750

TCAAAAGCCA TGTATGACGC TTACTGGAAC GGTAAATTCA GAGACTGCGC    800

TTTCCATTCT GGCTTTAATG AGGATCCATT CGTTTGTGAA TATCAAGGCC    850

AATCGTCTGA CCTGCCTCAA CCTCCTGTCA ATGCTGGCGG CGGCTCTGGT    900

GGTGGTTCTG GTGGCGGCTC TGAGGGTGGT GGCTCTGAGG GTGGCGGTTC    950

TGAGGGTGGC GGCTCTGAGG GAGGCGGTTC CGGTGGTGGC TCTGGTTCCG   1000

GTGATTTTGA TTATGAAAAG ATGGCAAACG CTAATAAGGG GGCTATGACC   1050

GAAAATGCCG ATGAAAACGC GCTACAGTCT GACGCTAAAG GCAAACTTGA   1100

TTCTGTCGCT ACTGATTACG GTGCTGCTAT CGATGGTTTC ATTGGTGACG   1150

TTTCCGGCCT TGCTAATGGT AATGGTGCTA CTGGTGATTT TGCTGGCTCT   1200

AATTCCCAAA TGGCTCAAGT CGGTGACGGT GATAATTCAC CTTTAATGAA   1250

TAATTTCCGT CAATATTTAC CTTCCCTCCC TCAATCGGTT GAATGTCGCC   1300

CTTTTGTCTT TAGCGCTGGT AAACCATATG AATTTTCTAT TGATTGTGAC   1350

AAAATAAACT TATTCCGTGG TGTCTTTGCG TTTCTTTTAT ATGTTGCCAC   1400

CTTTATGTAT GTATTTTCTA CGTTTGCTAA CATACTGCGT AATAAGGAGT   1450

CTTAA                                                    1455
```

(2) INFORMATION FOR SEQ ID NO:7:

(i) SEQUENCE CHARACTERISTICS:
        (A) LENGTH:484 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Lys Lys Leu Leu Phe Ala Ile Pro Leu Val Val Pro Phe Tyr Ser
 1               5                  10                  15

Gly Ala Lys Glu Asp Ser Cys Gln Leu Gly Tyr Ser Ala Gly Pro Cys
                20                  25                  30

Met Gly Met Thr Ser Arg Tyr Phe Tyr Asn Gly Thr Ser Met Ala Cys
            35                  40                  45

Glu Thr Phe Gln Tyr Gly Gly Cys Met Gly Asn Gly Asn Asn Phe Val
        50                  55                  60

Thr Glu Lys Glu Cys Leu Gln Thr Cys Arg Thr Val Gly Ala Ala Glu
65                  70                  75                  80

Thr Val Glu Ser Cys Leu Ala Lys Pro His Thr Glu Asn Ser Phe Thr
                85                  90                  95

Asn Val Trp Lys Asp Asp Lys Thr Leu Asp Arg Tyr Ala Asn Tyr Glu
                100                 105                 110

Gly Cys Leu Trp Asn Ala Thr Gly Val Val Val Cys Thr Gly Asp Glu
            115                 120                 125

Thr Gln Cys Tyr Gly Thr Trp Val Pro Ile Gly Leu Ala Ile Pro Glu
        130                 135                 140

Asn Glu Gly Gly Gly Ser Glu Gly Gly Gly Ser Glu Gly Gly Gly Ser
```

|     |     |     |     | 145 |     |     |     | 150 |     |     |     | 155 |     |     |     | 160 |
| --- | --- | --- | --- | --- | --- | --- | --- | --- | --- | --- | --- | --- | --- | --- | --- | --- |
| Glu | Gly | Gly | Gly | Thr | Lys | Pro | Pro | Glu | Tyr | Gly | Asp | Thr | Pro | Ile | Pro |
|     |     |     |     | 165 |     |     |     | 170 |     |     |     | 175 |     |     |     |
| Gly | Tyr | Thr | Tyr | Ile | Asn | Pro | Leu | Asp | Gly | Thr | Tyr | Pro | Pro | Gly | Thr |
|     |     |     | 180 |     |     |     |     | 185 |     |     |     |     | 190 |     |     |
| Glu | Gln | Asn | Pro | Ala | Asn | Pro | Asn | Pro | Ser | Leu | Glu | Glu | Ser | Gln | Pro |
|     |     | 195 |     |     |     |     | 200 |     |     |     |     | 205 |     |     |     |
| Leu | Asn | Thr | Phe | Met | Phe | Gln | Asn | Asn | Arg | Phe | Arg | Asn | Arg | Gln | Gly |
|     | 210 |     |     |     |     | 215 |     |     |     |     | 220 |     |     |     |     |
| Ala | Leu | Thr | Val | Tyr | Thr | Gly | Thr | Val | Thr | Gln | Gly | Thr | Asp | Pro | Val |
| 225 |     |     |     |     | 230 |     |     |     |     | 235 |     |     |     |     | 240 |
| Lys | Thr | Tyr | Tyr | Gln | Tyr | Thr | Pro | Val | Ser | Ser | Lys | Ala | Met | Tyr | Asp |
|     |     |     |     | 245 |     |     |     |     | 250 |     |     |     |     | 255 |     |
| Ala | Tyr | Trp | Asn | Gly | Lys | Phe | Arg | Asp | Cys | Ala | Phe | His | Ser | Gly | Phe |
|     |     |     | 260 |     |     |     |     | 265 |     |     |     |     | 270 |     |     |
| Asn | Glu | Asp | Pro | Phe | Val | Cys | Glu | Tyr | Gln | Gly | Gln | Ser | Ser | Asp | Leu |
|     |     | 275 |     |     |     |     |     | 280 |     |     |     |     | 285 |     |     |
| Pro | Gln | Pro | Pro | Val | Asn | Ala | Gly | Gly | Gly | Ser | Gly | Gly | Gly | Ser | Gly |
|     | 290 |     |     |     |     | 295 |     |     |     |     | 300 |     |     |     |     |
| Gly | Gly | Ser | Glu | Gly | Gly | Gly | Ser | Glu | Gly | Gly | Gly | Ser | Glu | Gly | Gly |
| 305 |     |     |     |     | 310 |     |     |     |     | 315 |     |     |     |     | 320 |
| Gly | Ser | Glu | Gly | Gly | Gly | Ser | Gly | Gly | Gly | Ser | Gly | Ser | Gly | Asp | Phe |
|     |     |     |     | 325 |     |     |     |     | 330 |     |     |     |     | 335 |     |
| Asp | Tyr | Glu | Lys | Met | Ala | Asn | Ala | Asn | Lys | Gly | Ala | Met | Thr | Glu | Asn |
|     |     |     | 340 |     |     |     |     | 345 |     |     |     |     | 350 |     |     |
| Ala | Asp | Glu | Asn | Ala | Leu | Gln | Ser | Asp | Ala | Lys | Gly | Lys | Leu | Asp | Ser |
|     |     | 355 |     |     |     |     | 360 |     |     |     |     | 365 |     |     |     |
| Val | Ala | Thr | Asp | Tyr | Gly | Ala | Ala | Ile | Asp | Gly | Phe | Ile | Gly | Asp | Val |
|     | 370 |     |     |     |     | 375 |     |     |     |     | 380 |     |     |     |     |
| Ser | Gly | Leu | Ala | Asn | Gly | Asn | Gly | Ala | Thr | Gly | Asp | Phe | Ala | Gly | Ser |
| 385 |     |     |     |     | 390 |     |     |     |     | 395 |     |     |     |     | 400 |
| Asn | Ser | Gln | Met | Ala | Gln | Val | Gly | Asp | Gly | Asp | Asn | Ser | Pro | Leu | Met |
|     |     |     |     | 405 |     |     |     |     | 410 |     |     |     |     | 415 |     |
| Asn | Asn | Phe | Arg | Gln | Tyr | Leu | Pro | Ser | Leu | Pro | Gln | Ser | Val | Glu | Cys |
|     |     |     | 420 |     |     |     |     | 425 |     |     |     |     | 430 |     |     |
| Arg | Pro | Phe | Val | Phe | Ser | Ala | Gly | Lys | Pro | Tyr | Glu | Phe | Ser | Ile | Asp |
|     |     | 435 |     |     |     |     | 440 |     |     |     |     | 445 |     |     |     |
| Cys | Asp | Lys | Ile | Asn | Leu | Phe | Arg | Gly | Val | Phe | Ala | Phe | Leu | Leu | Tyr |
|     | 450 |     |     |     |     | 455 |     |     |     |     | 460 |     |     |     |     |
| Val | Ala | Thr | Phe | Met | Tyr | Val | Phe | Ser | Thr | Phe | Ala | Asn | Ile | Leu | Arg |
| 465 |     |     |     |     | 470 |     |     |     |     | 475 |     |     |     |     | 480 |
| Asn | Lys | Glu | Ser |     |     |     |     |     |     |     |     |     |     |     |     |

( 2 ) INFORMATION FOR SEQ ID NO:8:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

| Lys | Glu | Asp | Ser | Cys | Gln | Leu | Gly | Tyr | Ser | Ala | Gly | Pro | Cys | Met | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

```
Met  Thr  Ser  Arg  Tyr  Phe  Tyr  Asn  Gly  Thr  Ser  Met  Ala  Cys  Glu  Thr
          20                       25                       30

Phe  Gln  Tyr  Gly  Gly  Cys  Met  Gly  Asn  Gly  Asn  Asn  Phe  Val  Thr  Glu
          35                       40                       45

Lys  Asp  Cys  Leu  Gln  Thr  Cys  Arg  Gly  Ala
          50                       55
```

( 2 ) INFORMATION FOR SEQ ID NO:9:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Lys  Glu  Asp  Ser  Cys  Gln  Leu  Gly  Tyr  Ser  Ala  Gly  Pro  Cys  Val  Ala
 1                  5                       10                      15

Met  Phe  Pro  Arg  Tyr  Phe  Tyr  Asn  Gly  Thr  Ser  Met  Ala  Cys  Glu  Thr
          20                       25                       30

Phe  Gln  Tyr  Gly  Gly  Cys  Met  Gly  Asn  Gly  Asn  Asn  Phe  Val  Thr  Glu
          35                       40                       45

Lys  Asp  Cys  Leu  Gln  Thr  Cys  Arg  Gly  Ala
          50                       55
```

( 2 ) INFORMATION FOR SEQ ID NO:10:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Arg  Pro  Asp  Phe  Cys  Gln  Leu  Gly  Tyr  Ser  Ala  Gly  Pro  Cys  Val  Ala
 1                  5                       10                      15

Met  Phe  Pro  Arg  Tyr  Phe  Tyr  Asn  Gly  Thr  Ser  Met  Ala  Cys  Glu  Thr
          20                       25                       30

Phe  Gln  Tyr  Gly  Gly  Cys  Met  Gly  Asn  Gly  Asn  Asn  Phe  Val  Thr  Glu
          35                       40                       45

Lys  Asp  Cys  Leu  Gln  Thr  Cys  Arg  Gly  Ala
          50                       55
```

( 2 ) INFORMATION FOR SEQ ID NO:11:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Arg  Pro  Asp  Phe  Cys  Gln  Leu  Gly  Tyr  Ser  Ala  Gly  Pro  Cys  Val  Ala
 1                  5                       10                      15

Met  Phe  Pro  Arg  Tyr  Phe  Tyr  Asn  Gly  Thr  Ser  Met  Ala  Cys  Glu  Thr
          20                       25                       30

Phe  Gln  Tyr  Gly  Gly  Cys  Met  Gly  Asn  Gly  Asn  Asn  Phe  Val  Thr  Glu
          35                       40                       45
```

```
Lys  Asp  Cys  Leu  Gln  Thr  Cys  Arg  Gly  Ala
     50                      55
```

( 2 ) INFORMATION FOR SEQ ID NO:12:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Arg  Pro  Asp  Phe  Cys  Gln  Leu  Gly  Tyr  Ser  Thr  Gly  Pro  Cys  Val  Ala
 1                    5                     10                      15

Met  Phe  Pro  Arg  Tyr  Phe  Tyr  Asn  Gly  Thr  Ser  Met  Ala  Cys  Glu  Thr
               20                    25                      30

Phe  Gln  Tyr  Gly  Gly  Cys  Met  Gly  Asn  Gly  Asn  Asn  Phe  Val  Thr  Glu
          35                    40                          45

Lys  Asp  Cys  Leu  Gln  Thr  Cys  Arg  Gly  Ala
     50                      55
```

( 2 ) INFORMATION FOR SEQ ID NO:13:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Arg  Pro  Asp  Phe  Cys  Gln  Leu  Gly  Tyr  Ser  Ala  Gly  Pro  Cys  Val  Gly
 1                    5                     10                      15

Met  Phe  Ser  Arg  Tyr  Phe  Tyr  Asn  Gly  Thr  Ser  Met  Ala  Cys  Gln  Thr
               20                    25                      30

Phe  Val  Tyr  Gly  Gly  Cys  Met  Gly  Asn  Gly  Asn  Asn  Phe  Val  Thr  Glu
          35                    40                          45

Lys  Asp  Cys  Leu  Gln  Thr  Cys  Arg  Gly  Ala
     50                      55
```

( 2 ) INFORMATION FOR SEQ ID NO:14:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Arg  Pro  Asp  Phe  Cys  Gln  Leu  Gly  Tyr  Ser  Ala  Gly  Pro  Cys  Ile  Gly
 1                    5                     10                      15

Met  Phe  Ser  Arg  Tyr  Phe  Tyr  Asn  Gly  Thr  Ser  Met  Ala  Cys  Glu  Thr
               20                    25                      30

Phe  Gln  Tyr  Gly  Gly  Cys  Met  Gly  Asn  Gly  Asn  Asn  Phe  Val  Thr  Glu
          35                    40                          45

Lys  Asp  Cys  Leu  Gln  Thr  Cys  Arg  Gly  Ala
     50                      55
```

( 2 ) INFORMATION FOR SEQ ID NO:15:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Lys Glu Asp Phe Cys Gln Leu Gly Tyr Ser Ala Gly Pro Cys Val Ala
 1               5                  10                  15

Met Phe Pro Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
            35                  40                  45

Lys Asp Cys Leu Gln Thr Cys Arg Gly Ala
            50                  55
```

( 2 ) INFORMATION FOR SEQ ID NO:16:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

```
Lys Pro Asp Ser Cys Gln Leu Gly Tyr Ser Ala Gly Pro Cys Val Ala
 1               5                  10                  15

Met Phe Pro Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
            35                  40                  45

Lys Asp Cys Leu Gln Thr Cys Arg Gly Ala
            50                  55
```

( 2 ) INFORMATION FOR SEQ ID NO:17:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

```
Arg Pro Asp Phe Cys Gln Leu Gly Tyr Ser Ala Gly Pro Cys Val Ala
 1               5                  10                  15

Met Phe Pro Arg Tyr Phe Tyr Asn Gly Thr Ser Met Ala Cys Glu Thr
            20                  25                  30

Phe Val Tyr Gly Gly Cys Met Gly Asn Gly Asn Asn Phe Val Thr Glu
            35                  40                  45

Lys Asp Cys Leu Gln Thr Cys Arg Gly Ala
            50                  55
```

( 2 ) INFORMATION FOR SEQ ID NO:18:

( i ) SEQUENCE CHARACTERISTICS:
        ( A ) LENGTH:58 amino acids
        ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:18:

| Arg | Pro | Asp | Phe | Cys | Gln | Leu | Gly | Tyr | Ser | Ala | Gly | Pro | Cys | Val | Ala |
|---|---|---|---|---|---|---|---|---|---|---|---|---|---|---|---|
| 1 | | | | 5 | | | | | 10 | | | | | 15 | |

| Met | Phe | Pro | Arg | Tyr | Phe | Tyr | Asn | Gly | Ala | Ser | Met | Ala | Cys | Gln | Thr |
|---|---|---|---|---|---|---|---|---|---|---|---|---|---|---|---|
| | | | 20 | | | | | 25 | | | | | 30 | | |

| Phe | Val | Tyr | Gly | Gly | Cys | Met | Gly | Asn | Gly | Asn | Asn | Phe | Val | Thr | Glu |
|---|---|---|---|---|---|---|---|---|---|---|---|---|---|---|---|
| | | 35 | | | | 40 | | | | | | 45 | | | |

| Lys | Asp | Cys | Leu | Gln | Thr | Cys | Arg | Gly | Ala |
|---|---|---|---|---|---|---|---|---|---|
| | 50 | | | | | 55 | | | |

( 2 ) INFORMATION FOR SEQ ID NO:19:

( i ) SEQUENCE CHARACTERISTICS:
( A ) LENGTH:56 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:19:

| Ala | Ala | Cys | Asn | Leu | Pro | Ile | Val | Arg | Gly | Pro | Cys | Ile | Ala | Phe | Phe |
|---|---|---|---|---|---|---|---|---|---|---|---|---|---|---|---|
| 1 | | | | 5 | | | | | 10 | | | | | 15 | |

| Pro | Arg | Trp | Ala | Phe | Asp | Ala | Val | Lys | Gly | Lys | Cys | Val | Leu | Phe | Pro |
|---|---|---|---|---|---|---|---|---|---|---|---|---|---|---|---|
| | | | 20 | | | | | 25 | | | | | 30 | | |

| Tyr | Gly | Gly | Cys | Gln | Gly | Asn | Gly | Asn | Lys | Phe | Tyr | Ser | Glu | Lys | Glu |
|---|---|---|---|---|---|---|---|---|---|---|---|---|---|---|---|
| | | 35 | | | | 40 | | | | | | 45 | | | |

| Cys | Arg | Glu | Tyr | Cys | Gly | Val | Pro |
|---|---|---|---|---|---|---|---|
| | 50 | | | | | 55 | |

( 2 ) INFORMATION FOR SEQ ID NO:20:

( i ) SEQUENCE CHARACTERISTICS:
( A ) LENGTH:56 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:20:

| Glu | Ala | Cys | Asn | Leu | Pro | Ile | Val | Arg | Gly | Pro | Cys | Ile | Ala | Phe | Phe |
|---|---|---|---|---|---|---|---|---|---|---|---|---|---|---|---|
| 1 | | | | 5 | | | | | 10 | | | | | 15 | |

| Pro | Arg | Trp | Ala | Phe | Asp | Ala | Val | Lys | Gly | Lys | Cys | Val | Leu | Phe | Pro |
|---|---|---|---|---|---|---|---|---|---|---|---|---|---|---|---|
| | | | 20 | | | | | 25 | | | | | 30 | | |

| Tyr | Gly | Gly | Cys | Gln | Gly | Asn | Gly | Asn | Lys | Phe | Tyr | Ser | Glu | Lys | Glu |
|---|---|---|---|---|---|---|---|---|---|---|---|---|---|---|---|
| | | 35 | | | | 40 | | | | | | 45 | | | |

| Cys | Arg | Glu | Tyr | Cys | Gly | Val | Pro |
|---|---|---|---|---|---|---|---|
| | 50 | | | | | 55 | |

( 2 ) INFORMATION FOR SEQ ID NO:21:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:21:

| Arg | Pro | Asp | Phe | Cys | Leu | Glu | Pro | Pro | Tyr | Thr | Gly | Pro | Cys | Lys | Ala |
|---|---|---|---|---|---|---|---|---|---|---|---|---|---|---|---|
| 1 | | | | 5 | | | | | 10 | | | | | 15 | |

| Arg | Ile | Ile | Arg | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Val | Tyr | Gly | Gly | Cys | Arg | Ala | Lys | Arg | Asn | Asn | Phe | Lys | Ser | Ala |
|---|---|---|---|---|---|---|---|---|---|---|---|---|---|---|---|
| | | 35 | | | | | 40 | | | | | 45 | | | |

| Glu | Asp | Cys | Met | Arg | Thr | Cys | Gly | Gly | Ala |
|---|---|---|---|---|---|---|---|---|---|
| 50 | | | | | | 55 | | | |

( 2 ) INFORMATION FOR SEQ ID NO:22:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

| Arg | Pro | Asp | Phe | Cys | Leu | Glu | Pro | Pro | Tyr | Thr | Gly | Pro | Cys | Val | Gly |
|---|---|---|---|---|---|---|---|---|---|---|---|---|---|---|---|
| 1 | | | | 5 | | | | | 10 | | | | | 15 | |

| Phe | Phe | Ser | Arg | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Val | Tyr | Gly | Gly | Cys | Met | Gly | Asn | Gly | Asn | Asn | Phe | Lys | Ser | Ala |
|---|---|---|---|---|---|---|---|---|---|---|---|---|---|---|---|
| | | 35 | | | | | 40 | | | | | 45 | | | |

| Glu | Asp | Cys | Met | Arg | Thr | Cys | Gly | Gly | Ala |
|---|---|---|---|---|---|---|---|---|---|
| 50 | | | | | | 55 | | | |

( 2 ) INFORMATION FOR SEQ ID NO:23:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:23:

| Arg | Pro | Asp | Phe | Cys | Leu | Glu | Pro | Pro | Tyr | Thr | Gly | Pro | Cys | Val | Gly |
|---|---|---|---|---|---|---|---|---|---|---|---|---|---|---|---|
| 1 | | | | 5 | | | | | 10 | | | | | 15 | |

| Phe | Phe | Gln | Arg | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Val | Tyr | Gly | Gly | Cys | Met | Gly | Asn | Gly | Asn | Asn | Phe | Lys | Ser | Ala |
|---|---|---|---|---|---|---|---|---|---|---|---|---|---|---|---|
| | | 35 | | | | | 40 | | | | | 45 | | | |

| Glu | Asp | Cys | Met | Arg | Thr | Cys | Gly | Gly | Ala |
|---|---|---|---|---|---|---|---|---|---|
| 50 | | | | | | 55 | | | |

( 2 ) INFORMATION FOR SEQ ID NO:24:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:24:

| Arg | Pro | Asp | Phe | Cys | Leu | Glu | Pro | Pro | Tyr | Thr | Gly | Pro | Cys | Val | Ala |
|---|---|---|---|---|---|---|---|---|---|---|---|---|---|---|---|
| 1 | | | | 5 | | | | | 10 | | | | | 15 | |

```
Ile  Phe  Pro  Arg  Tyr  Phe  Tyr  Asn  Ala  Lys  Ala  Gly  Leu  Cys  Gln  Thr
               20                  25                       30

Phe  Val  Tyr  Gly  Gly  Cys  Met  Gly  Asn  Gly  Asn  Asn  Phe  Lys  Ser  Ala
               35                  40                       45

Glu  Asp  Cys  Met  Arg  Thr  Cys  Gly  Gly  Ala
     50                  55
```

( 2 ) INFORMATION FOR SEQ ID NO:25:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

```
Arg  Pro  Asp  Phe  Cys  Leu  Glu  Pro  Pro  Tyr  Thr  Gly  Pro  Cys  Val  Ala
 1                   5                        10                       15

Phe  Phe  Lys  Arg  Ser  Phe  Tyr  Asn  Ala  Lys  Ala  Gly  Leu  Cys  Gln  Thr
               20                  25                       30

Phe  Val  Tyr  Gly  Gly  Cys  Met  Gly  Asn  Gly  Asn  Asn  Phe  Lys  Ser  Ala
               35                  40                       45

Glu  Asp  Cys  Met  Arg  Thr  Cys  Gly  Gly  Ala
     50                  55
```

( 2 ) INFORMATION FOR SEQ ID NO:26:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:26:

```
Arg  Pro  Asp  Phe  Cys  Leu  Glu  Pro  Pro  Tyr  Thr  Gly  Pro  Cys  Ile  Ala
 1                   5                        10                       15

Phe  Phe  Pro  Arg  Tyr  Phe  Tyr  Asn  Ala  Lys  Ala  Gly  Leu  Cys  Gln  Thr
               20                  25                       30

Phe  Val  Tyr  Gly  Gly  Cys  Met  Gly  Asn  Gly  Asn  Asn  Phe  Lys  Ser  Ala
               35                  40                       45

Glu  Asp  Cys  Met  Arg  Thr  Cys  Gly  Gly  Ala
     50                  55
```

( 2 ) INFORMATION FOR SEQ ID NO:27:

( i ) SEQUENCE CHARACTERISTICS:
        ( A ) LENGTH:62 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:27:

```
Glu  Ala  Glu  Ala  Arg  Pro  Asp  Phe  Cys  Leu  Glu  Pro  Pro  Tyr  Thr  Gly
 1                   5                        10                       15

Pro  Cys  Ile  Ala  Phe  Phe  Pro  Arg  Tyr  Phe  Tyr  Asn  Ala  Lys  Ala  Gly
               20                  25                       30

Leu  Cys  Gln  Thr  Phe  Val  Tyr  Gly  Gly  Cys  Met  Gly  Asn  Gly  Asn  Asn
               35                  40                       45
```

Phe Lys Ser Ala Glu Asp Cys Met Arg Thr Cys Gly Gly Ala
    50                  55                  60

( 2 ) INFORMATION FOR SEQ ID NO:28:

( i ) SEQUENCE CHARACTERISTICS:
      ( A ) LENGTH:58 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:28:

Arg Pro Asp Phe Cys Leu Glu Pro Pro Tyr Thr Gly Pro Cys Ile Ala
 1               5                  10                  15

Phe Phe Gln Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
         35                  40                  45

Glu Asp Cys Met Arg Thr Cys Gly Gly Ala
    50                  55

( 2 ) INFORMATION FOR SEQ ID NO:29:

( i ) SEQUENCE CHARACTERISTICS:
      ( A ) LENGTH:58 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:29:

Arg Pro Asp Phe Cys Leu Glu Pro Pro Tyr Thr Gly Pro Cys Ile Ala
 1               5                  10                  15

Leu Phe Lys Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
         35                  40                  45

Glu Asp Cys Met Arg Thr Cys Gly Gly Ala
    50                  55

( 2 ) INFORMATION FOR SEQ ID NO:30:

( i ) SEQUENCE CHARACTERISTICS:
      ( A ) LENGTH:58 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:30:

Arg Pro Asp Phe Cys Gln Leu Gly Tyr Ser Ala Gly Pro Cys Met Gly
 1               5                  10                  15

Met Thr Ser Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
         35                  40                  45

Lys Asp Cys Leu Gln Thr Cys Arg Gly Ala
    50                  55

( 2 ) INFORMATION FOR SEQ ID NO:31:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:31:

```
Arg Pro Asp Phe Cys Leu Glu Pro Pro Tyr Thr Gly Pro Cys Met Gly
 1               5                  10                  15
Phe Ser Lys Arg Tyr Phe Tyr Asn Ala Lys Ala Gly Leu Cys Gln Thr
             20                  25                  30
Phe Val Tyr Gly Gly Cys Arg Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO:32:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

```
Arg Pro Asp Phe Cys Leu Glu Pro Pro Tyr Thr Gly Pro Cys Met Ala
 1               5                  10                  15
Leu Phe Lys Arg Tyr Phe Tyr Asn Ala Lys Ala Gly Leu Cys Gln Thr
             20                  25                  30
Phe Val Tyr Gly Gly Cys Arg Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO:33:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:33:

```
Arg Pro Asp Phe Cys Leu Glu Pro Pro Asn Thr Gly Pro Cys Phe Ala
 1               5                  10                  15
Ile Thr Pro Arg Tyr Phe Tyr Asn Ala Lys Ala Gly Leu Cys Gln Thr
             20                  25                  30
Phe Val Tyr Gly Gly Cys Arg Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO:34:

( i ) SEQUENCE CHARACTERISTICS:
        ( A ) LENGTH:58 amino acids
        ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:34:

```
Arg Pro Asp Phe Cys Leu Glu Pro Pro Tyr Thr Gly Pro Cys Met Ala
 1               5                  10                  15
Leu Phe Gln Arg Tyr Phe Tyr Asn Ala Lys Ala Gly Leu Cys Gln Thr
             20                  25                  30
Phe Val Tyr Gly Gly Cys Arg Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO:35:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:35:

```
Arg Pro Asp Phe Cys Leu Glu Pro Pro Tyr Thr Gly Pro Cys Met Ala
 1               5                  10                  15
Ile Ser Pro Arg Tyr Phe Tyr Asn Ala Lys Ala Gly Leu Cys Gln Thr
             20                  25                  30
Phe Val Tyr Gly Gly Cys Arg Ala Lys Arg Asn Asn Phe Lys Ser Ala
         35                  40                  45
Glu Asp Cys Met Arg Thr Cys Gly Gly Ala
     50                  55
```

( 2 ) INFORMATION FOR SEQ ID NO:36:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:36:

```
Arg Pro Asp Phe Cys Leu Glu Pro Pro Tyr Thr Gly Pro Cys Val Ala
 1               5                  10                  15
Met Phe Pro Arg Tyr Phe Tyr Asn Ala Lys Ala Gly Leu Cys Gln Thr
             20                  25                  30
Phe Leu Tyr Gly Gly Cys Lys Gly Lys Gly Asn Asn Phe Lys Ser Ala
         35                  40                  45
Glu Asp Cys Met Arg Thr Cys Gly Gly Ala
     50                  55
```

( 2 ) INFORMATION FOR SEQ ID NO:37:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:37:

| Arg | Pro | Asp | Phe | Cys | Leu | Glu | Pro | Pro | Tyr | Thr | Gly | Pro | Cys | Val | Ala |
|---|---|---|---|---|---|---|---|---|---|---|---|---|---|---|---|
| 1 | | | | 5 | | | | | 10 | | | | | 15 | |

| Met | Phe | Pro | Arg | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Glu | Tyr | Gly | Gly | Cys | Trp | Ala | Lys | Gly | Asn | Asn | Phe | Lys | Ser | Ala |
|---|---|---|---|---|---|---|---|---|---|---|---|---|---|---|---|
| | | 35 | | | | | 40 | | | | | 45 | | | |

| Glu | Asp | Cys | Met | Arg | Thr | Cys | Gly | Gly | Ala |
|---|---|---|---|---|---|---|---|---|---|
| | 50 | | | | | 55 | | | |

( 2 ) INFORMATION FOR SEQ ID NO:38:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:38:

| Arg | Pro | Asp | Phe | Cys | Leu | Glu | Pro | Pro | Tyr | Thr | Gly | Pro | Cys | Val | Ala |
|---|---|---|---|---|---|---|---|---|---|---|---|---|---|---|---|
| 1 | | | | 5 | | | | | 10 | | | | | 15 | |

| Met | Phe | Pro | Arg | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Gly | Tyr | Ala | Gly | Cys | Arg | Ala | Lys | Gly | Asn | Asn | Phe | Lys | Ser | Ala |
|---|---|---|---|---|---|---|---|---|---|---|---|---|---|---|---|
| | | 35 | | | | | 40 | | | | | 45 | | | |

| Glu | Asp | Cys | Met | Arg | Thr | Cys | Gly | Gly | Ala |
|---|---|---|---|---|---|---|---|---|---|
| | 50 | | | | | 55 | | | |

( 2 ) INFORMATION FOR SEQ ID NO:39:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:39:

| Arg | Pro | Asp | Phe | Cys | Leu | Glu | Pro | Pro | Tyr | Thr | Gly | Pro | Cys | Val | Ala |
|---|---|---|---|---|---|---|---|---|---|---|---|---|---|---|---|
| 1 | | | | 5 | | | | | 10 | | | | | 15 | |

| Met | Phe | Pro | Arg | Tyr | Phe | Tyr | Asn | Ala | Lys | Ala | Gly | Leu | Cys | Gln | Thr |
|---|---|---|---|---|---|---|---|---|---|---|---|---|---|---|---|
| | | | 20 | | | | | 25 | | | | | 30 | | |

| Phe | Glu | Tyr | Gly | Gly | Cys | His | Ala | Glu | Gly | Asn | Asn | Phe | Lys | Ser | Ala |
|---|---|---|---|---|---|---|---|---|---|---|---|---|---|---|---|
| | | 35 | | | | | 40 | | | | | 45 | | | |

| Glu | Asp | Cys | Met | Arg | Thr | Cys | Gly | Gly | Ala |
|---|---|---|---|---|---|---|---|---|---|
| | 50 | | | | | 55 | | | |

( 2 ) INFORMATION FOR SEQ ID NO:40:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:40:

| Arg | Pro | Asp | Phe | Cys | Leu | Glu | Pro | Pro | Tyr | Thr | Gly | Pro | Cys | Val | Ala |
|---|---|---|---|---|---|---|---|---|---|---|---|---|---|---|---|
| 1 | | | | 5 | | | | | 10 | | | | | 15 | |

Met Phe Pro Arg Tyr Phe Tyr Asn Ala Lys Ala Gly Leu Cys Gln Thr
        20                  25                  30

Phe Leu Tyr Gly Gly Cys Trp Ala Gln Gly Asn Asn Phe Lys Ser Ala
        35                  40                  45

Glu Asp Cys Met Arg Thr Cys Gly Gly Ala
        50                  55

( 2 ) INFORMATION FOR SEQ ID NO:41:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:41:

Arg Pro Asp Phe Cys Leu Glu Pro Pro Tyr Thr Gly Pro Cys Val Ala
 1               5                  10                  15

Met Phe Pro Arg Tyr Phe Tyr Asn Ala Lys Ala Gly Leu Cys Gln Thr
        20                  25                  30

Phe Arg Tyr Gly Gly Cys Leu Ala Glu Gly Asn Asn Phe Lys Ser Ala
        35                  40                  45

Glu Asp Cys Met Arg Thr Cys Gly Gly Ala
        50                  55

( 2 ) INFORMATION FOR SEQ ID NO:42:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:42:

Arg Pro Asp Phe Cys Leu Glu Pro Pro Tyr Thr Gly Pro Cys Val Ala
 1               5                  10                  15

Met Phe Pro Arg Tyr Phe Tyr Asn Ala Lys Ala Gly Leu Cys Gln Thr
        20                  25                  30

Phe Asp Tyr Gly Gly Cys His Ala Asp Gly Asn Asn Phe Lys Ser Ala
        35                  40                  45

Glu Asp Cys Met Arg Thr Cys Gly Gly Ala
        50                  55

( 2 ) INFORMATION FOR SEQ ID NO:43:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:43:

Arg Pro Asp Phe Cys Leu Glu Pro Pro Tyr Thr Gly Pro Cys Val Ala
 1               5                  10                  15

Met Phe Pro Arg Tyr Phe Tyr Asn Ala Lys Ala Gly Leu Cys Gln Thr
        20                  25                  30

Phe Lys Tyr Gly Gly Cys Leu Ala His Gly Asn Asn Phe Lys Ser Ala
        35                  40                  45

```
Glu  Asp  Cys  Met  Arg  Thr  Cys  Gly  Gly  Ala
     50                      55
```

( 2 ) INFORMATION FOR SEQ ID NO:44:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:44:

```
Arg  Pro  Asp  Phe  Cys  Leu  Glu  Pro  Pro  Tyr  Thr  Gly  Pro  Cys  Val  Ala
 1                   5                        10                      15

Met  Phe  Pro  Arg  Tyr  Phe  Tyr  Asn  Ala  Lys  Ala  Gly  Leu  Cys  Gln  Thr
               20                       25                      30

Phe  Thr  Tyr  Gly  Gly  Cys  Trp  Ala  Asn  Gly  Asn  Asn  Phe  Lys  Ser  Ala
          35                  40                            45

Glu  Asp  Cys  Met  Arg  Thr  Cys  Gly  Gly  Ala
     50                      55
```

( 2 ) INFORMATION FOR SEQ ID NO:45:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:45:

```
Arg  Pro  Asp  Phe  Cys  Leu  Glu  Pro  Pro  Tyr  Thr  Gly  Pro  Cys  Val  Ala
 1                   5                        10                      15

Met  Phe  Pro  Arg  Tyr  Phe  Tyr  Asn  Ala  Lys  Ala  Gly  Leu  Cys  Gln  Thr
               20                       25                      30

Phe  Asn  Tyr  Gly  Gly  Cys  Glu  Gly  Lys  Gly  Asn  Asn  Phe  Lys  Ser  Ala
          35                  40                            45

Glu  Asp  Cys  Met  Arg  Thr  Cys  Gly  Gly  Ala
     50                      55
```

( 2 ) INFORMATION FOR SEQ ID NO:46:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:46:

```
Arg  Pro  Asp  Phe  Cys  Leu  Glu  Pro  Pro  Tyr  Thr  Gly  Pro  Cys  Val  Ala
 1                   5                        10                      15

Met  Phe  Pro  Arg  Tyr  Phe  Tyr  Asn  Ala  Lys  Ala  Gly  Leu  Cys  Gln  Thr
               20                       25                      30

Phe  Gln  Tyr  Gly  Gly  Cys  Glu  Gly  Tyr  Gly  Asn  Asn  Phe  Lys  Ser  Ala
          35                  40                            45

Glu  Asp  Cys  Met  Arg  Thr  Cys  Gly  Gly  Ala
     50                      55
```

( 2 ) INFORMATION FOR SEQ ID NO:47:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:47:

```
Arg  Pro  Asp  Phe  Cys  Leu  Glu  Pro  Pro  Tyr  Thr  Gly  Pro  Cys  Val  Ala
 1                   5                        10                       15

Met  Phe  Pro  Arg  Tyr  Phe  Tyr  Asn  Ala  Lys  Ala  Gly  Leu  Cys  Gln  Thr
                20                       25                       30

Phe  Gln  Tyr  Gly  Gly  Cys  Leu  Gly  Glu  Gly  Asn  Asn  Phe  Lys  Ser  Ala
           35                       40                       45

Glu  Asp  Cys  Met  Arg  Thr  Cys  Gly  Gly  Ala
     50                       55
```

( 2 ) INFORMATION FOR SEQ ID NO:48:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:48:

```
Arg  Pro  Asp  Phe  Cys  Leu  Glu  Pro  Pro  Tyr  Thr  Gly  Pro  Cys  Val  Ala
 1                   5                        10                       15

Met  Phe  Pro  Arg  Tyr  Phe  Tyr  Asn  Ala  Lys  Ala  Gly  Leu  Cys  Gln  Thr
                20                       25                       30

Phe  His  Tyr  Gly  Gly  Cys  Trp  Gly  Gln  Gly  Asn  Asn  Phe  Lys  Ser  Ala
           35                       40                       45

Glu  Asp  Cys  Met  Arg  Thr  Cys  Gly  Gly  Ala
     50                       55
```

( 2 ) INFORMATION FOR SEQ ID NO:49:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:49:

```
Arg  Pro  Asp  Phe  Cys  Leu  Glu  Pro  Pro  Tyr  Thr  Gly  Pro  Cys  Val  Ala
 1                   5                        10                       15

Met  Phe  Pro  Arg  Tyr  Phe  Tyr  Asn  Ala  Lys  Ala  Gly  Leu  Cys  Gln  Thr
                20                       25                       30

Phe  His  Tyr  Gly  Gly  Cys  Trp  Gly  Glu  Gly  Asn  Asn  Phe  Lys  Ser  Ala
           35                       40                       45

Glu  Asp  Cys  Met  Arg  Thr  Cys  Gly  Gly  Ala
     50                       55
```

( 2 ) INFORMATION FOR SEQ ID NO:50:

( i ) SEQUENCE CHARACTERISTICS:
        ( A ) LENGTH:58 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO:50:

```
Arg Pro Asp Phe Cys Leu Glu Pro Pro Tyr Thr Gly Pro Cys Val Ala
 1               5                  10                  15

Met Phe Pro Arg Tyr Phe Tyr Asn Ala Lys Ala Gly Leu Cys Gln Thr
            20                  25                  30

Phe Lys Tyr Gly Gly Cys Trp Gly Lys Gly Asn Asn Phe Lys Ser Ala
        35                  40                  45

Glu Asp Cys Met Arg Thr Cys Gly Gly Ala
    50                  55
```

(2) INFORMATION FOR SEQ ID NO:51:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:51:

```
Arg Pro Asp Phe Cys Leu Glu Pro Pro Tyr Thr Gly Pro Cys Val Ala
 1               5                  10                  15

Met Phe Pro Arg Tyr Phe Tyr Asn Ala Lys Ala Gly Leu Cys Gln Thr
            20                  25                  30

Phe Lys Tyr Gly Gly Cys His Gly Asn Gly Asn Asn Phe Lys Ser Ala
        35                  40                  45

Glu Asp Cys Met Arg Thr Cys Gly Gly Ala
    50                  55
```

(2) INFORMATION FOR SEQ ID NO:52:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:52:

```
Arg Pro Asp Phe Cys Leu Glu Pro Pro Tyr Thr Gly Pro Cys Val Ala
 1               5                  10                  15

Met Phe Pro Arg Tyr Phe Tyr Asn Ala Lys Ala Gly Leu Cys Gln Thr
            20                  25                  30

Phe Pro Tyr Gly Gly Cys Trp Ala Lys Gly Asn Asn Phe Lys Leu Ala
        35                  40                  45

Glu Asp Cys Met Arg Thr Cys Gly Gly Ala
    50                  55
```

(2) INFORMATION FOR SEQ ID NO:53:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: protein ( x i ) SEQUENCE DESCRIPTION: SEQ ID NO:53:

Arg Pro Asp Phe Cys Leu Glu Pro Pro Tyr Thr Gly Pro Cys Val Ala
1               5                   10                  15

Met Phe Pro Arg Tyr Phe Tyr Asn Ala Lys Ala Gly Leu Cys Gln Thr
            20                  25                  30

Phe Lys Tyr Gly Gly Cys Trp Gly His Gly Asn Asn Phe Lys Ser Ala
        35                  40                  45

Glu Asp Cys Met Arg Thr Cys Gly Gly Ala
50                      55

( 2 ) INFORMATION FOR SEQ ID NO:54:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:54:

Arg Pro Asp Phe Cys Leu Glu Pro Pro Tyr Thr Gly Pro Cys Val Ala
1               5                   10                  15

Met Phe Pro Arg Tyr Phe Tyr Asn Ala Lys Ala Gly Leu Cys Gln Thr
            20                  25                  30

Phe Asn Tyr Gly Gly Cys Trp Gly Lys Gly Asn Asn Phe Lys Ser Ala
        35                  40                  45

Glu Asp Cys Met Arg Thr Cys Gly Gly Ala
50                      55

( 2 ) INFORMATION FOR SEQ ID NO:55:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:55:

Arg Pro Asp Phe Cys Leu Glu Pro Pro Tyr Thr Gly Pro Cys Val Ala
1               5                   10                  15

Met Phe Pro Arg Tyr Phe Tyr Asn Ala Lys Ala Gly Leu Cys Gln Thr
            20                  25                  30

Phe Thr Tyr Gly Gly Cys Leu Gly His Gly Asn Asn Phe Lys Ser Ala
        35                  40                  45

Glu Asp Cys Met Arg Thr Cys Gly Gly Ala
50                      55

( 2 ) INFORMATION FOR SEQ ID NO:56:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:56:

Arg Pro Asp Phe Cys Leu Glu Pro Pro Tyr Thr Gly Pro Cys Val Ala
1               5                   10                  15

```
Met  Phe  Pro  Arg  Tyr  Phe  Tyr  Asn  Ala  Lys  Ala  Gly  Leu  Cys  Gln  Thr
               20                       25                         30

Phe  Thr  Tyr  Gly  Gly  Cys  Leu  Gly  Tyr  Gly  Asn  Asn  Phe  Lys  Ser  Ala
               35                       40                         45

Glu  Asp  Cys  Met  Arg  Thr  Cys  Gly  Gly  Ala
     50                       55
```

( 2 ) INFORMATION FOR SEQ ID NO:57:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:57:

```
Arg  Pro  Asp  Phe  Cys  Leu  Glu  Pro  Pro  Tyr  Thr  Gly  Pro  Cys  Val  Ala
 1                    5                        10                         15

Met  Phe  Pro  Arg  Tyr  Phe  Tyr  Asn  Ala  Lys  Ala  Gly  Leu  Cys  Gln  Thr
               20                       25                         30

Phe  Lys  Tyr  Gly  Gly  Cys  Trp  Ala  Glu  Gly  Asn  Asn  Phe  Lys  Ser  Ala
               35                       40                         45

Glu  Asp  Cys  Met  Arg  Thr  Cys  Gly  Gly  Ala
     50                       55
```

( 2 ) INFORMATION FOR SEQ ID NO:58:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:58:

```
Arg  Pro  Asp  Phe  Cys  Leu  Glu  Pro  Pro  Tyr  Thr  Gly  Pro  Cys  Val  Ala
 1                    5                        10                         15

Met  Phe  Pro  Arg  Tyr  Phe  Tyr  Asn  Ala  Lys  Ala  Gly  Leu  Cys  Gln  Thr
               20                       25                         30

Phe  Gly  Tyr  Gly  Gly  Cys  Trp  Gly  Glu  Gly  Asn  Asn  Phe  Lys  Ser  Ala
               35                       40                         45

Glu  Asp  Cys  Met  Arg  Thr  Cys  Gly  Gly  Ala
     50                       55
```

( 2 ) INFORMATION FOR SEQ ID NO:59:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:59:

```
Arg  Pro  Asp  Phe  Cys  Leu  Glu  Pro  Pro  Tyr  Thr  Gly  Pro  Cys  Val  Ala
 1                    5                        10                         15

Met  Phe  Pro  Arg  Tyr  Phe  Tyr  Asn  Ala  Lys  Ala  Gly  Leu  Cys  Gln  Thr
               20                       25                         30

Phe  Glu  Tyr  Gly  Gly  Cys  Trp  Ala  Asn  Gly  Asn  Asn  Phe  Lys  Ser  Ala
               35                       40                         45
```

```
Glu  Asp  Cys  Met  Arg  Thr  Cys  Gly  Gly  Ala
     50                  55
```

( 2 ) INFORMATION FOR SEQ ID NO:60:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:60:

```
Arg  Pro  Asp  Phe  Cys  Leu  Glu  Pro  Pro  Tyr  Thr  Gly  Pro  Cys  Val  Ala
 1                   5                        10                       15

Met  Phe  Pro  Arg  Tyr  Phe  Tyr  Asn  Ala  Lys  Ala  Gly  Leu  Cys  Gln  Thr
               20                       25                       30

Phe  Val  Tyr  Gly  Gly  Cys  His  Gly  Asp  Gly  Asn  Asn  Phe  Lys  Ser  Ala
          35                       40                       45

Glu  Asp  Cys  Met  Arg  Thr  Cys  Gly  Gly  Ala
     50                  55
```

( 2 ) INFORMATION FOR SEQ ID NO:61:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:61:

```
Arg  Pro  Asp  Phe  Cys  Leu  Glu  Pro  Pro  Tyr  Thr  Gly  Pro  Cys  Val  Ala
 1                   5                        10                       15

Met  Phe  Pro  Arg  Tyr  Phe  Tyr  Asn  Ala  Lys  Ala  Gly  Leu  Cys  Gln  Thr
               20                       25                       30

Phe  Met  Tyr  Gly  Gly  Cys  Gln  Gly  Lys  Gly  Asn  Asn  Phe  Lys  Ser  Ala
          35                       40                       45

Glu  Asp  Cys  Met  Arg  Thr  Cys  Gly  Gly  Ala
     50                  55
```

( 2 ) INFORMATION FOR SEQ ID NO:62:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:62:

```
Arg  Pro  Asp  Phe  Cys  Leu  Glu  Pro  Pro  Tyr  Thr  Gly  Pro  Cys  Val  Ala
 1                   5                        10                       15

Met  Phe  Pro  Arg  Tyr  Phe  Tyr  Asn  Ala  Lys  Ala  Gly  Leu  Cys  Gln  Thr
               20                       25                       30

Phe  Tyr  Tyr  Gly  Gly  Cys  Trp  Ala  Lys  Gly  Asn  Asn  Phe  Lys  Ser  Ala
          35                       40                       45

Glu  Asp  Cys  Met  Arg  Thr  Cys  Gly  Gly  Ala
     50                  55
```

( 2 ) INFORMATION FOR SEQ ID NO:63:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:63:

```
Arg Pro Asp Phe Cys Leu Glu Pro Pro Tyr Thr Gly Pro Cys Val Ala
 1               5                  10                  15
Met Phe Pro Arg Tyr Phe Tyr Asn Ala Lys Ala Gly Leu Cys Gln Thr
                20                  25                  30
Phe Met Tyr Gly Gly Cys Trp Gly Asp Gly Asn Asn Phe Lys Ser Ala
            35                  40                  45
Glu Asp Cys Met Arg Thr Cys Gly Gly Ala
        50                  55
```

( 2 ) INFORMATION FOR SEQ ID NO:64:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:64:

```
Arg Pro Asp Phe Cys Leu Glu Pro Pro Tyr Thr Gly Pro Cys Val Ala
 1               5                  10                  15
Met Phe Pro Arg Tyr Phe Tyr Asn Ala Lys Ala Gly Leu Cys Gln Thr
                20                  25                  30
Phe Thr Tyr Gly Gly Cys His Gly Asn Gly Asn Asn Phe Lys Ser Ala
            35                  40                  45
Glu Asp Cys Met Arg Thr Cys Gly Gly Ala
        50                  55
```

( 2 ) INFORMATION FOR SEQ ID NO:65:

( i ) SEQUENCE CHARACTERISTICS:
        ( A ) LENGTH:8157 bases
        ( B ) TYPE: nucleic acid
        ( C ) STRANDEDNESS: single
        ( D ) TOPOLOGY: CIRCULAR ( i i ) MOLECULE TYPE:other nucleic acid
        ( A ) DESCRIPTION: DNA plasmid ( x i ) SEQUENCE DESCRIPTION: SEQ ID NO:65:

```
AGATCGCGGC CGCGATCTAA CATCCAAAGA CGAAAGGTTG AATGAAACCT      50
TTTTGCCATC CGACATCCAC AGGTCCATTC TCACACATAA GTGCCAAACG     100
CAACAGGAGG GGATACACTA GCAGCAGACC GTTGCAAACG CAGGACCTCC     150
ACTCCTCTTC TCCTCAACAC CCACTTTTGC CATCGAAAAA CCAGCCCAGT     200
TATTGGGCTT GATTGGAGCT CGCTCATTCC AATTCCTTCT ATTAGGCTAC     250
TAACACCATG ACTTTATTAG CCTGTCTATC CTGGCCCCCC TGGCGAGGTC     300
ATGTTTGTTT ATTTCCGAAT GCAACAAGCT CCGCATTACA CCCGAACATC     350
ACTCCAGATG AGGGCTTTCT GAGTGTGGGG TCAAATAGTT TCATGTTCCC     400
AAATGGCCCA AAACTGACAG TTTAAACGCT GTCTTGGAAC CTAATATGAC     450
```

```
AAAAGCGTGA TCTCATCCAA GATGAACTAA GTTTGGTTCG TTGAAATGCT    500
AACGGCCAGT TGGTCAAAAA GAAACTTCCA AAAGTCGCCA TACCGTTTGT    550
CTTGTTTGGT ATTGATTGAC GAATGCTCAA AAATAATCTC ATTAATGCTT    600
AGCGCAGTCT CTCTATCGCT TCTGAACCCG GTGGCACCTG TGCCGAAACG    650
CAAATGGGGA ACAACCCGC TTTTTGGATG ATTATGCATT GTCCTCCACA     700
TTGTATGCTT CCAAGATTCT GGTGGGAATA CTGCTGATAG CCTAACGTTC    750
ATGATCAAAA TTTAACTGTT CTAACCCCTA CTTGACAGGC AATATATAAA    800
CAGAAGGAAG CTGCCCTGTC TTAAACCTTT TTTTTTATCA TCATTATTAG    850
CTTACTTTCA TAATTGCGAC TGGTTCCAAT TGACAAGCTT TTGATTTTAA    900
CGACTTTTAA CGACAACTTG AGAAGATCAA AAAACAACTA ATTATTCGAA    950
ACGAGGAATT CGCCTTAGAC ATGACTGTTC CTCAGTTCAA GTTGGGCATT   1000
ACGAGAAGAC CGGTCTTGCT AGATTCTAAT CAAGAGGATG TCAGAATGCC   1050
ATTTGCCTGA GAGATGCAGG CTTCATTTTT GATACTTTTT TATTTGTAAC   1100
CTATATAGTA TAGGATTTTT TTTGTCATTT TGTTTCTTCT CGTACGAGCT   1150
TGCTCCTGAT CAGCCTATCT CGCAGCTGAT GAATATCTTG TGGTAGGGGT   1200
TTGGAAAAAT CATTCGAGTT TGATGTTTTT CTTGGTATTT CCCACTCCTC   1250
TTCAGAGTAC AGAAGATTAA GTGAGAAGTT CGTTTGTGCA AGCTTATCGA   1300
TAAGCTTTAA TGCGGTAGTT TATCACAGTT AAATTGCTAA CGCAGTCAGG   1350
CACCGTGTAT GAAATCTAAC AATGCGCTCA TCGTCATCCT CGGCACCGTC   1400
ACCCTGGATG CTGTAGGCAT AGGCTTGGTT ATGCCGGTAC TGCCGGGCCT   1450
CTTGCGGGAT ATCGTCCATT CCGACAGCAT CGCCAGTCAC TATGGCGTGC   1500
TGCTAGCGCT ATATGCGTTG ATGCAATTTC TATGCGCACC CGTTCTCGGA   1550
GCACTGTCCG ACCGCTTTGG CCGCCGCCCA GTCCTGCTCG CTTCGCTACT   1600
TGGAGCCACT ATCGACTACG CGATCATGGC GACCACACCC GTCCTGTGGA   1650
TCTATCGAAT CTAAATGTAA GTTAAAATCT CTAAATAATT AAATAAGTCC   1700
CAGTTTCTCC ATACGAACCT TAACAGCATT GCGGTGAGCA TCTAGACCTT   1750
CAACAGCAGC CAGATCCATC ACTGCTTGGC CAATATGTTT CAGTCCCTCA   1800
GGAGTTACGT CTTGTGAAGT GATGAACTTC TGGAAGGTTG CAGTGTTAAC   1850
TCCGCTGTAT TGACGGGCAT ATCCGTACGT TGGCAAAGTG TGGTTGGTAC   1900
CGGAGGAGTA ATCTCCACAA CTCTCTGGAG AGTAGGCACC AACAAACACA   1950
GATCCAGCGT GTTGTACTTG ATCAACATAA GAAGAAGCAT TCTCGATTTG   2000
CAGGATCAAG TGTTCAGGAG CGTACTGATT GGACATTTCC AAAGCCTGCT   2050
CGTAGGTTGC AACCGATAGG GTTGTAGAGT GTGCAATACA CTTGCGTACA   2100
ATTTCAACCC TTGGCAACTG CACAGCTTGG TTGTGAACAG CATCTTCAAT   2150
TCTGGCAAGC TCCTTGTCTG TCATATCGAC AGCCAACAGA ATCACCTGGG   2200
AATCAATACC ATGTTCAGCT TGAGCAGAAG GTCTGAGGCA ACGAAATCTG   2250
GATCAGCGTA TTTATCAGCA ATAACTAGAA CTTCAGAAGG CCCAGCAGGC   2300
ATGTCAATAC TACACAGGGC TGATGTGTCA TTTTGAACCA TCATCTTGGC   2350
AGCAGTAACG AACTGGTTTC CTGGACCAAA TATTTGTCA CACTTAGGAA    2400
CAGTTTCTGT TCCGTAAGCC ATAGCAGCTA CTGCCTGGGC GCCTCCTGCT   2450
```

| | | | | | |
|---|---|---|---|---|---|
| AGCACGATAC | ACTTAGCACC | AACCTTGTGG | GCAACGTAGA | TGACTTCTGG | 2500 |
| GGTAAGGGTA | CCATCCTTCT | TAGGTGGAGA | TGCAAAAACA | ATTTCTTTGC | 2550 |
| AACCAGCAAC | TTTGGCAGGA | ACACCCAGCA | TCAGGGAAGT | GGAAGGCAGA | 2600 |
| ATTGCGGTTC | CACCAGGAAT | ATAGAGGCCA | ACTTTCTCAA | TAGGTCTTGC | 2650 |
| AAAACGAGAG | CAGACTACAC | CAGGGCAAGT | CTCAACTTGC | AACGTCTCCG | 2700 |
| TTAGTTGAGC | TTCATGGAAT | TTCCTGACGT | TATCTATAGA | GAGATCAATG | 2750 |
| GCTCTCTTAA | CGTTATCTGG | CAATTGCATA | AGTTCCTCTG | GAAAGGAGC | 2800 |
| TTCTAACACA | GGTGTCTTCA | AAGCGACTCC | ATCAAACTTG | GCAGTTAGTT | 2850 |
| CTAAAGGGC | TTTGTCACCA | TTTGACGAA | CATTGTCGAC | AATTGGTTTG | 2900 |
| ACTAATTCCA | TAATCTGTTC | CGTTTTCTGG | ATAGGACGAC | GAAGGGCATC | 2950 |
| TTCAATTTCT | TGTGAGGAGG | CCTTAGAAAC | GTCAATTTTG | CACAATTCAA | 3000 |
| TACGACCTTC | AGAAGGGACT | TCTTTAGGTT | TGGATTCTTC | TTTAGGTTGT | 3050 |
| TCCTTGGTGT | ATCCTGGCTT | GGCATCTCCT | TTCCTTCTAG | TGACCTTTAG | 3100 |
| GGACTTCATA | TCCAGGTTTC | TCTCCACCTC | GTCCAACGTC | ACACCGTACT | 3150 |
| TGGCACATCT | AACTAATGCA | AATAAAATA | AGTCAGCACA | TTCCCAGGCT | 3200 |
| ATATCTTCCT | TGGATTTAGC | TTCTGCAAGT | TCATCAGCTT | CCTCCCTAAT | 3250 |
| TTAGCGTTC | AACAAAACTT | CGTCGTCAAA | TAACCGTTTG | GTATAAGAAC | 3300 |
| CTTCTGGAGC | ATTGCTCTTA | CGATCCCACA | AGGTGCTTCC | ATGGCTCTAA | 3350 |
| GACCCTTTGA | TTGGCCAAAA | CAGGAAGTGC | GTTCCAAGTG | ACAGAAACCA | 3400 |
| ACACCTGTTT | GTTCAACCAC | AAATTTCAAG | CAGTCTCCAT | CACAATCCAA | 3450 |
| TTCGATACCC | AGCAACTTTT | GAGTTCGTCC | AGATGTAGCA | CCTTTATACC | 3500 |
| ACAAACCGTG | ACGACGAGAT | TGGTAGACTC | CAGTTTGTGT | CCTTATAGCC | 3550 |
| TCCGGAATAG | ACTTTTTGGA | CGAGTACACC | AGGCCCAACG | AGTAATTAGA | 3600 |
| AGAGTCAGCC | ACCAAAGTAG | TGAATAGACC | ATCGGGGCGG | TCAGTAGTCA | 3650 |
| AAGACGCCAA | CAAAATTTCA | CTGACAGGGA | ACTTTTTGAC | ATCTTCAGAA | 3700 |
| AGTTCGTATT | CAGTAGTCAA | TTGCCGAGCA | TCAATAATGG | GGATTATACC | 3750 |
| AGAAGCAACA | GTGGAAGTCA | CATCTACCAA | CTTTGCGGTC | TCAGAAAAAG | 3800 |
| CATAAACAGT | TCTACTACCG | CCATTAGTGA | AACTTTTCAA | ATCGCCCAGT | 3850 |
| GGAGAAGAAA | AAGGCACAGC | GATACTAGCA | TTAGCGGGCA | AGGATGCAAC | 3900 |
| TTTATCAACC | AGGGTCCTAT | AGATAACCCT | AGCGCCTGGG | ATCATCCTTT | 3950 |
| GGACAACTCT | TTCTGCCAAA | TCTAGGTCCA | AAATCACTTC | ATTGATACCA | 4000 |
| TTATACGGAT | GACTCAACTT | GCACATTAAC | TTGAAGCTCA | GTCGATTGAG | 4050 |
| TGAACTTGAT | CAGGTTGTGC | AGCTGGTCAG | CAGCATAGGG | AAACACGGCT | 4100 |
| TTTCCTACCA | AACTCAAGGA | ATTATCAAAC | TCTGCAACAC | TTGCGTATGC | 4150 |
| AGGTAGCAAG | GGAAATGTCA | TACTTGAAGT | CGGACAGTGA | GTGTAGTCTT | 4200 |
| GAGAAATTCT | GAAGCCGTAT | TTTTATTATC | AGTGAGTCAG | TCATCAGGAG | 4250 |
| ATCCTCTACG | CCGGACGCAT | CGTGGCCGGC | ATCACCGGCG | CCACAGGTGC | 4300 |
| GGTTGCTGGC | GCCTATATCG | CCGACATCAC | CGATGGGGAA | GATCGGGCTC | 4350 |
| GCCACTTCGG | GCTCATGAGC | GCTTGTTTCG | GCGTGGGTAT | GGTGGCAGGC | 4400 |
| CCCGTGGCCG | GGGGACTGTT | GGGCGCCATC | TCCTTGCATG | CACCATTCCT | 4450 |

```
TGCGGCGGCG GTGCTCAACG GCCTCAACCT ACTACTGGGC TGCTTCCTAA    4500
TGCAGGAGTC GCATAAGGGA GAGCGTCGAG TATCTATGAT TGGAAGTATG    4550
GGAATGGTGA TACCCGCATT CTTCAGTGTC TTGAGGTCTC CTATCAGATT    4600
ATGCCCAACT AAAGCAACCG GAGGAGGAGA TTTCATGGTA AATTTCTCTG    4650
ACTTTTGGTC ATCAGTAGAC TCGAACTGTG AGACTATCTC GGTTATGACA    4700
GCAGAAATGT CCTTCTTGGA GACAGTAAAT GAAGTCCCAC CAATAAAGAA    4750
ATCCTTGTTA TCAGGAACAA ACTTCTTGTT TCGAACTTTT TCGGTGCCTT    4800
GAACTATAAA ATGTAGAGTG GATATGTCGG GTAGGAATGG AGCGGGCAAA    4850
TGCTTACCTT CTGGACCTTC AAGAGGTATG TAGGGTTTGT AGATACTGAT    4900
GCCAACTTCA GTGACAACGT TGCTATTTCG TTCAAACCAT TCCGAATCCA    4950
GAGAAATCAA AGTTGTTTGT CTACTATTGA TCCAAGCCAG TGCGGTCTTG    5000
AAACTGACAA TAGTGTGCTC GTGTTTTGAG GTCATCTTTG TATGAATAAA    5050
TCTAGTCTTT GATCTAAATA ATCTTGACGA GCCAAGGCGA TAAATACCCA    5100
AATCTAAAAC TCTTTTAAAA CGTTAAAAGG ACAAGTATGT CTGCCTGTAT    5150
TAAACCCCAA ATCAGCTCGT AGTCTGATCC TCATCAACTT GAGGGGCACT    5200
ATCTTGTTTT AGAGAAATTT GCGGAGATGC GATATCGAGA AAAAGGTACG    5250
CTGATTTTAA ACGTGAAATT TATCTCAAGA TCGCGGCCGC GATCTCGAAT    5300
AATAACTGTT ATTTTCAGT GTTCCCGATC TGCGTCTATT TCACAATACC    5350
AACATGAGTC AGCTTATCGA TGATAAGCTG TCAAACATGA GAATTAATTC    5400
GATGATAAGC TGTCAAACAT GAGAAATCTT GAAGACGAAA GGGCCTCGTG    5450
ATACGCCTAT TTTTATAGGT TAATGTCATG ATAATAATGG TTTCTTAGAC    5500
GTCAGGTGGC ACTTTTCGGG GAAATGTGCG CGGAACCCCT ATTTGTTTAT    5550
TTTTCTAAAT ACATTCAAAT ATGTATCCGC TCATGAGACA ATAACCCTGA    5600
TAAATGCTTC AATAATATTG AAAAAGGAAG AGTATGAGTA TTCAACATTT    5650
CCGTGTCGCC CTTATTCCCT TTTTGCGGC ATTTTGCCTT CCTGTTTTTG    5700
CTCACCCAGA AACGCTGGTG AAAGTAAAAG ATGCTGAAGA TCAGTTGGGT    5750
GCACGAGTGG GTTACATCGA ACTGGATCTC AACAGCGGTA AGATCCTTGA    5800
GAGTTTTCGC CCCGAAGAAC GTTTTCCAAT GATGAGCACT TTTAAAGTTC    5850
TGCTATGTGG CGCGGTATTA TCCCGTGTTG ACGCCGGGCA AGAGCAACTC    5900
GGTCGCCGCA TACACTATTC TCAGAATGAC TTGGTTGAGT ACTCACCAGT    5950
CACAGAAAAG CATCTTACGG ATGGCATGAC AGTAAGAGAA TTATGCAGTG    6000
CTGCCATAAC CATGAGTGAT AACACTGCGG CCAACTTACT TCTGACAACG    6050
ATCGGAGGAC CGAAGGAGCT AACCGCTTTT TTGCACAACA TGGGGGATCA    6100
TGTAACTCGC CTTGATCGTT GGGAACCGGA GCTGAATGAA GCCATACCAA    6150
ACGACGAGCG TGACACCACG ATGCCTGCAG CAATGGCAAC AACGTTGCGC    6200
AAACTATTAA CTGGCGAACT ACTTACTCTA GCTTCCCGGC AACAATTAAT    6250
AGACTGGATG GAGGCGGATA AAGTTGCAGG ACCACTTCTG CGCTCGGCCC    6300
TTCCGGCTGG CTGGTTTATT GCTGATAAAT CTGGAGCCGG TGAGCGTGGG    6350
TCTCGCGGTA TCATTGCAGC ACTGGGGCCA GATGGTAAGC CCTCCCGTAT    6400
CGTAGTTATC TACACGACGG GGAGTCAGGC AACTATGGAT GAACGAAATA    6450
```

-continued

```
GACAGATCGC TGAGATAGGT GCCTCACTGA TTAAGCATTG GTAACTGTCA    6500
GACCAAGTTT ACTCATATAT ACTTTAGATT GATTTAAATT GTAAACGTTA    6550
ATATTTTGTT AAAATTCGCG TTAAATTTTT GTTAAATCAG CTCATTTTTT    6600
AACCAATAGG CCGAAATCGG CAAAATCCCT TATAAATCAA AGAATAGAC     6650
CGAGATAGGG TTGAGTGTTG TTCCAGTTTG GAACAAGAGT CCACTATTAA    6700
AGAACGTGGA CTCCAACGTC AAAGGGCGAA AAACCGTCTA TCAGGGCGAT    6750
GGCCCACTAC GTGAACCATC ACCCTAATCA AGTTTTTGG GGTCGAGGTG     6800
CCGTAAAGCA CTAAATCGGA ACCCTAAAGG GAGCCCCGA TTTAGAGCTT     6850
GACGGGGAAA GCCGGCGAAC GTGGCGAGAA AGGAAGGGAA GAAAGCGAAA    6900
GGAGCGGGCG CTAGGGCGCT GGCAAGTGTA GCGGTCACGC TGCGCGTAAC    6950
CACCACACCC GCCGCGCTTA ATGCGCCGCT ACAGGGCGCG TAAAAGGATC    7000
TAGGTGAAGA TCCTTTTTGA TAATCTCATG ACCAAAATCC CTTAACGTGA    7050
GTTTTCGTTC CACTGAGCGT CAGACCCCGT AGAAAAGATC AAAGGATCTT    7100
CTTGAGATCC TTTTTTTCTG CGCGTAATCT GCTGCTTGCA AACAAAAAAA    7150
CCACCGCTAC CAGCGGTGGT TTGTTTGCCG GATCAAGAGC TACCAACTCT    7200
TTTTCCGAAG GTAACTGGCT TCAGCAGAGC GCAGATACCA AATACTGTCC    7250
TTCTAGTGTA GCCGTAGTTA GGCCACCACT TCAAGAACTC TGTAGCACCG    7300
CCTACATACC TCGCTCTGCT AATCCTGTTA CCAGTGGCTG CTGCCAGTGG    7350
CGATAAGTCG TGTCTTACCG GGTTGGACTC AAGACGATAG TTACCGGATA    7400
AGGCGCAGCG GTCGGGCTGA ACGGGGGGTT CGTGCACACA GCCCAGCTTG    7450
GAGCGAACGA CCTACACCGA ACTGAGATAC CTACAGCGTG AGCATTGAGA    7500
AAGCGCCACG CTTCCCGAAG GGAGAAAGGC GGACAGGTAT CCGGTAAGCG    7550
GCAGGGTCGG AACAGGAGAG CGCACGAGGG AGCTTCCAGG GGGAAACGCC    7600
TGGTATCTTT ATAGTCCTGT CGGGTTTCGC CACCTCTGAC TTGAGCGTCG    7650
ATTTTTGTGA TGCTCGTCAG GGGGGCGGAG CCTATGGAAA AACGCCAGCA    7700
ACGCGGCCTT TTTACGGTTC CTGGCCTTTT GCTGGCCTTT TGCTCACATG    7750
TTCTTTCCTG CGTTATCCCC TGATTCTGTG GATAACCGTA TTACCGCCTT    7800
TGAGTGAGCT GATACCGCTC GCCGCAGCCG AACGACCGAG CGCAGCGAGT    7850
CAGTGAGCGA GGAAGCGGAA GAGCGCCTGA TGCGGTATTT TCTCCTTACG    7900
CATCTGTGCG GTATTTCACA CCGCATATGG TGCACTCTCA GTACAATCTG    7950
CTCTGATGCC GCATAGTTAA GCCAGTATAC ACTCCGCTAT CGCTACGTGA    8000
CTGGGTCATG GCTGCGCCCC GACACCCGCC AACACCCGCT GACGCGCCCT    8050
GACGGGCTTG TCTGCTCCCG GCATCCGCTT ACAGACAAGC TGTGACCGTC    8100
TCCGGGAGCT GCATGTGTCA GAGGTTTTCA CCGTCATCAC CGAAACGCGC    8150
GAGGCAG                                                   8157
```

( 2 ) INFORMATION FOR SEQ ID NO:66:

( i ) SEQUENCE CHARACTERISTICS:
        ( A ) LENGTH:8584 bases
        ( B ) TYPE: nucleic acid
        ( C ) STRANDEDNESS: single
        ( D ) TOPOLOGY: circular ( i i ) MOLECULE TYPE:other nucleic acid
    ( A ) DESCRIPTION: DNA plasmid ( x i ) SEQUENCE DESCRIPTION: SEQ ID NO:66:

| | | | | | |
|---|---|---|---|---|---|
| AGATCGCGGC | CGCGATCTAA | CATCCAAAGA | CGAAAGGTTG | AATGAAACCT | 50 |
| TTTTGCCATC | CGACATCCAC | AGGTCCATTC | TCACACATAA | GTGCCAAACG | 100 |
| CAACAGGAGG | GGATACACTA | GCAGCAGACC | GTTGCAAACG | CAGGACCTCC | 150 |
| ACTCCTCTTC | TCCTCAACAC | CCACTTTGC | CATCGAAAAA | CCAGCCCAGT | 200 |
| TATTGGGCTT | GATTGGAGCT | CGCTCATTCC | AATTCCTTCT | ATTAGGCTAC | 250 |
| TAACACCATG | ACTTTATTAG | CCTGTCTATC | CTGGCCCCCC | TGGCGAGGTC | 300 |
| ATGTTTGTTT | ATTTCCGAAT | GCAACAAGCT | CCGCATTACA | CCCGAACATC | 350 |
| ACTCCAGATG | AGGGCTTTCT | GAGTGTGGGG | TCAAATAGTT | TCATGTTCCC | 400 |
| AAATGGCCCA | AAACTGACAG | TTTAAACGCT | GTCTTGGAAC | CTAATATGAC | 450 |
| AAAAGCGTGA | TCTCATCCAA | GATGAACTAA | GTTTGGTTCG | TTGAAATGCT | 500 |
| AACGGCCAGT | TGGTCAAAAA | GAAACTTCCA | AAAGTCGCCA | TACCGTTTGT | 550 |
| CTTGTTTGGT | ATTGATTGAC | GAATGCTCAA | AAATAATCTC | ATTAATGCTT | 600 |
| AGCGCAGTCT | CTCTATCGCT | TCTGAACCCG | GTGGCACCTG | TGCCGAAACG | 650 |
| CAAATGGGGA | AACAACCCGC | TTTTTGGATG | ATTATGCATT | GTCCTCCACA | 700 |
| TTGTATGCTT | CCAAGATTCT | GGTGGGAATA | CTGCTGATAG | CCTAACGTTC | 750 |
| ATGATCAAAA | TTAACTGTT | CTAACCCCTA | CTTGACAGGC | AATATATAAA | 800 |
| CAGAAGGAAG | CTGCCCTGTC | TTAAACCTTT | TTTTTATCA | TCATTATTAG | 850 |
| CTTACTTTCA | TAATTGCGAC | TGGTTCCAAT | TGACAAGCTT | TTGATTTTAA | 900 |
| CGACTTTTAA | CGACAACTTG | AGAAGATCAA | AAAACAACTA | ATTATTCGAA | 950 |
| ACGATGAGAT | TCCCATCTAT | CTTCACTGCT | GTTTGTTCG | CTGCTTCCTC | 1000 |
| TGCTTTGGCT | GCTCCAGTTA | ACACCACTAC | TGAAGACGAG | ACTGCTCAAA | 1050 |
| TTCCTGCTGA | GGCTGTCATC | GGTTACTCTG | ACTTGGAAGG | TGACTTCGAC | 1100 |
| GTCGCTGTTT | TGCCATTCTC | TAACTCTACT | AACAACGGTT | TGTTGTTCAT | 1150 |
| CAACACTACC | ATCGCTTCTA | TCGCTGCTAA | GGAGGAAGGT | GTTTCCTTGG | 1200 |
| ACAAGAGAGC | TGCTTGTAAC | TTGCCAATCG | TCAGAGGTCC | ATGCATTGCT | 1250 |
| TTCTTCCCAA | GATGGGCTTT | CGACGCTGTT | AAGGGTAAGT | GCGTCTTGTT | 1300 |
| CCCATACGGT | GGTTGTCAAG | GTAACGGTAA | CAAGTTCTAC | TCTGAGAAGG | 1350 |
| AGTGTAGAGA | GTACTGTGGT | GTTCCATAGT | AAGAATTCGC | CTTAGACATG | 1400 |
| ACTGTTCCTC | AGTTCAAGTT | GGGCATTACG | AGAAGACCGG | TCTTGCTAGA | 1450 |
| TTCTAATCAA | GAGGATGTCA | GAATGCCATT | TGCCTGAGAG | ATGCAGGCTT | 1500 |
| CATTTTGAT | ACTTTTTAT | TTGTAACCTA | TATAGTATAG | GATTTTTTT | 1550 |
| GTCATTTGT | TTCTTCTCGT | ACGAGCTTGC | TCCTGATCAG | CCTATCTCGC | 1600 |
| AGCTGATGAA | TATCTTGTGG | TAGGGGTTTG | GGAAAATCAT | TCGAGTTTGA | 1650 |
| TGTTTTCTT | GGTATTTCCC | ACTCCTCTTC | AGAGTACAGA | AGATTAAGTG | 1700 |
| AGAAGTTCGT | TTGTGCAAGC | TTATCGATAA | GCTTAATGC | GGTAGTTTAT | 1750 |
| CACAGTTAAA | TTGCTAACGC | AGTCAGGCAC | CGTGTATGAA | ATCTAACAAT | 1800 |
| GCGCTCATCG | TCATCCTCGG | CACCGTCACC | CTGGATGCTG | TAGGCATAGG | 1850 |
| CTTGGTTATG | CCGGTACTGC | CGGGCCTCTT | GCGGGATATC | GTCCATTCCG | 1900 |

```
ACAGCATCGC CAGTCACTAT GGCGTGCTGC TAGCGCTATA TGCGTTGATG   1950
CAATTTCTAT GCGCACCCGT TCTCGGAGCA CTGTCCGACC GCTTTGGCCG   2000
CCGCCCAGTC CTGCTCGCTT CGCTACTTGG AGCCACTATC GACTACGCGA   2050
TCATGGCGAC CACACCCGTC CTGTGGATCT ATCGAATCTA AATGTAAGTT   2100
AAAATCTCTA AATAATTAAA TAAGTCCCAG TTTCTCCATA CGAACCTTAA   2150
CAGCATTGCG GTGAGCATCT AGACCTTCAA CAGCAGCCAG ATCCATCACT   2200
GCTTGGCCAA TATGTTTCAG TCCCTCAGGA GTTACGTCTT GTGAAGTGAT   2250
GAACTTCTGG AAGGTTGCAG TGTTAACTCC GCTGTATTGA CGGGCATATC   2300
CGTACGTTGG CAAAGTGTGG TTGGTACCGG AGGAGTAATC TCCACAACTC   2350
TCTGGAGAGT AGGCACCAAC AAACACAGAT CCAGCGTGTT GTACTTGATC   2400
AACATAAGAA GAAGCATTCT CGATTTGCAG GATCAAGTGT TCAGGAGCGT   2450
ACTGATTGGA CATTTCCAAA GCCTGCTCGT AGGTTGCAAC CGATAGGGTT   2500
GTAGAGTGTG CAATACACTT GCGTACAATT TCAACCCTTG CAACTGCAC    2550
AGCTTGGTTG TGAACAGCAT CTTCAATTCT GGCAAGCTCC TTGTCTGTCA   2600
TATCGACAGC CAACAGAATC ACCTGGGAAT CAATACCATG TTCAGCTTGA   2650
GCAGAAGGTC TGAGGCAACG AAATCTGGAT CAGCGTATTT ATCAGCAATA   2700
ACTAGAACTT CAGAAGGCCC AGCAGGCATG TCAATACTAC ACAGGGCTGA   2750
TGTGTCATTT TGAACCATCA TCTTGGCAGC AGTAACGAAC TGGTTTCCTG   2800
GACCAAATAT TTTGTCACAC TTAGGAACAG TTTCTGTTCC GTAAGCCATA   2850
GCAGCTACTG CCTGGGCGCC TCCTGCTAGC ACGATACACT TAGCACCAAC   2900
CTTGTGGGCA ACGTAGATGA CTTCTGGGGT AAGGGTACCA TCCTTCTTAG   2950
GTGGAGATGC AAAAACAATT TCTTTGCAAC CAGCAACTTT GGCAGGAACA   3000
CCCAGCATCA GGGAAGTGGA AGGCAGAATT GCGGTTCCAC CAGGAATATA   3050
GAGGCCAACT TTCTCAATAG GTCTTGCAAA ACGAGAGCAG ACTACACCAG   3100
GGCAAGTCTC AACTTGCAAC GTCTCCGTTA GTTGAGCTTC ATGGAATTTC   3150
CTGACGTTAT CTATAGAGAG ATCAATGGCT CTCTTAACGT TATCTGGCAA   3200
TTGCATAAGT TCCTCTGGGA AAGGAGCTTC TAACACAGGT GTCTTCAAAG   3250
CGACTCCATC AAACTTGGCA GTTAGTTCTA AAAGGGCTTT GTCACCATTT   3300
TGACGAACAT TGTCGACAAT TGGTTTGACT AATTCCATAA TCTGTTCCGT   3350
TTTCTGGATA GGACGACGAA GGGCATCTTC AATTTCTTGT GAGGAGGCCT   3400
TAGAAACGTC AATTTTGCAC AATTCAATAC GACCTTCAGA AGGGACTTCT   3450
TTAGGTTTGG ATTCTTCTTT AGGTTGTTCC TTGGTGTATC CTGGCTTGGC   3500
ATCTCCTTTC CTTCTAGTGA CCTTTAGGGA CTTCATATCC AGGTTTCTCT   3550
CCACCTCGTC CAACGTCACA CCGTACTTGG CACATCTAAC TAATGCAAAA   3600
TAAAATAAGT CAGCACATTC CCAGGCTATA TCTTCCTTGG ATTTAGCTTC   3650
TGCAAGTTCA TCAGCTTCCT CCCTAATTTT AGCGTTCAAC AAAACTTCGT   3700
CGTCAAATAA CCGTTGGTA TAAGAACCTT CTGGAGCATT GCTCTTACGA    3750
TCCCACAAGG TGCTTCCATG GCTCTAAGAC CCTTTGATTG GCCAAAACAG   3800
GAAGTGCGTT CCAAGTGACA GAAACCAACA CCTGTTTGTT CAACCACAAA   3850
TTTCAAGCAG TCTCCATCAC AATCCAATTC GATACCCAGC AACTTTTGAG   3900
```

```
TTCGTCCAGA TGTAGCACCT TTATACCACA AACCGTGACG ACGAGATTGG  3950
TAGACTCCAG TTTGTGTCCT TATAGCCTCC GGAATAGACT TTTTGGACGA  4000
GTACACCAGG CCCAACGAGT AATTAGAAGA GTCAGCCACC AAAGTAGTGA  4050
ATAGACCATC GGGGCGGTCA GTAGTCAAAG ACGCCAACAA AATTTCACTG  4100
ACAGGGAACT TTTTGACATC TTCAGAAAGT TCGTATTCAG TAGTCAATTG  4150
CCGAGCATCA ATAATGGGGA TTATACCAGA AGCAACAGTG GAAGTCACAT  4200
CTACCAACTT TGCGGTCTCA GAAAAAGCAT AAACAGTTCT ACTACCGCCA  4250
TTAGTGAAAC TTTTCAAATC GCCCAGTGGA GAAGAAAAAG GCACAGCGAT  4300
ACTAGCATTA GCGGGCAAGG ATGCAACTTT ATCAACCAGG GTCCTATAGA  4350
TAACCCTAGC GCCTGGGATC ATCCTTTGGA CAACTCTTTC TGCCAAATCT  4400
AGGTCCAAAA TCACTTCATT GATACCATTA TACGGATGAC TCAACTTGCA  4450
CATTAACTTG AAGCTCAGTC GATTGAGTGA ACTTGATCAG GTTGTGCAGC  4500
TGGTCAGCAG CATAGGGAAA CACGGCTTTT CCTACCAAAC TCAAGGAATT  4550
ATCAAACTCT GCAACACTTG CGTATGCAGG TAGCAAGGGA AATGTCATAC  4600
TTGAAGTCGG ACAGTGAGTG TAGTCTTGAG AAATTCTGAA GCCGTATTTT  4650
TATTATCAGT GAGTCAGTCA TCAGGAGATC CTCTACGCCG GACGCATCGT  4700
GGCCGGCATC ACCGGCGCCA CAGGTGCGGT TGCTGGCGCC TATATCGCCG  4750
ACATCACCGA TGGGGAAGAT CGGGCTCGCC ACTTCGGGCT CATGAGCGCT  4800
TGTTTCGGCG TGGGTATGGT GGCAGGCCCC GTGGCCGGGG GACTGTTGGG  4850
CGCCATCTCC TTGCATGCAC CATTCCTTGC GGCGGCGGTG CTCAACGGCC  4900
TCAACCTACT ACTGGGCTGC TTCCTAATGC AGGAGTCGCA TAAGGGAGAG  4950
CGTCGAGTAT CTATGATTGG AAGTATGGGA ATGGTGATAC CCGCATTCTT  5000
CAGTGTCTTG AGGTCTCCTA TCAGATTATG CCCAACTAAA GCAACCGGAG  5050
GAGGAGATTT CATGGTAAAT TTCTCTGACT TTTGGTCATC AGTAGACTCG  5100
AACTGTGAGA CTATCTCGGT TATGACAGCA GAAATGTCCT TCTTGGAGAC  5150
AGTAAATGAA GTCCCACCAA TAAAGAAATC CTTGTTATCA GGAACAAACT  5200
TCTTGTTTCG AACTTTTTCG GTGCCTTGAA CTATAAAATG TAGAGTGGAT  5250
ATGTCGGGTA GGAATGGAGC GGGCAAATGC TTACCTTCTG GACCTTCAAG  5300
AGGTATGTAG GGTTTGTAGA TACTGATGCC AACTTCAGTG ACAACGTTGC  5350
TATTTCGTTC AAACCATTCC GAATCCAGAG AAATCAAAGT TGTTTGTCTA  5400
CTATTGATCC AAGCCAGTGC GGTCTTGAAA CTGACAATAG TGTGCTCGTG  5450
TTTTGAGGTC ATCTTTGTAT GAATAAATCT AGTCTTTGAT CTAAATAATC  5500
TTGACGAGCC AAGGCGATAA ATACCCAAAT CTAAAACTCT TTTAAAACGT  5550
TAAAAGGACA AGTATGTCTG CCTGTATTAA ACCCCAAATC AGCTCGTAGT  5600
CTGATCCTCA TCAACTTGAG GGGCACTATC TTGTTTTAGA GAAATTTGCG  5650
GAGATGCGAT ATCGAGAAAA AGGTACGCTG ATTTTAAACG TGAAATTTAT  5700
CTCAAGATCG CGGCCGCGAT CTCGAATAAT AACTGTTATT TTTCAGTGTT  5750
CCCGATCTGC GTCTATTTCA CAATACCAAC ATGAGTCAGC TTATCGATGA  5800
TAAGCTGTCA AACATGAGAA TTAATTCGAT GATAAGCTGT CAAACATGAG  5850
AAATCTTGAA GACGAAAGGG CCTCGTGATA CGCCTATTTT TATAGGTTAA  5900
```

```
TGTCATGATA ATAATGGTTT CTTAGACGTC AGGTGGCACT TTTCGGGGAA    5950
ATGTGCGCGG AACCCCTATT TGTTTATTTT TCTAAATACA TTCAAATATG    6000
TATCCGCTCA TGAGACAATA ACCCTGATAA ATGCTTCAAT AATATTGAAA    6050
AAGGAAGAGT ATGAGTATTC AACATTCCG  TGTCGCCCTT ATTCCCTTTT    6100
TTGCGGCATT TTGCCTTCCT GTTTTGCTC  ACCCAGAAAC GCTGGTGAAA    6150
GTAAAAGATG CTGAAGATCA GTTGGGTGCA CGAGTGGGTT ACATCGAACT    6200
GGATCTCAAC AGCGGTAAGA TCCTTGAGAG TTTTCGCCCC GAAGAACGTT    6250
TTCCAATGAT GAGCACTTTT AAAGTTCTGC TATGTGGCGC GGTATTATCC    6300
CGTGTTGACG CCGGGCAAGA GCAACTCGGT CGCCGCATAC ACTATTCTCA    6350
GAATGACTTG GTTGAGTACT CACCAGTCAC AGAAAAGCAT CTTACGGATG    6400
GCATGACAGT AAGAGAATTA TGCAGTGCTG CCATAACCAT GAGTGATAAC    6450
ACTGCGGCCA ACTTACTTCT GACAACGATC GGAGGACCGA AGGAGCTAAC    6500
CGCTTTTTTG CACAACATGG GGGATCATGT AACTCGCCTT GATCGTTGGG    6550
AACCGGAGCT GAATGAAGCC ATACCAAACG ACGAGCGTGA CACCACGATG    6600
CCTGCAGCAA TGGCAACAAC GTTGCGCAAA CTATTAACTG GCGAACTACT    6650
TACTCTAGCT TCCCGGCAAC AATTAATAGA CTGGATGGAG GCGGATAAAG    6700
TTGCAGGACC ACTTCTGCGC TCGGCCCTTC CGGCTGGCTG GTTTATTGCT    6750
GATAAATCTG GAGCCGGTGA GCGTGGGTCT CGCGGTATCA TTGCAGCACT    6800
GGGGCCAGAT GGTAAGCCCT CCCGTATCGT AGTTATCTAC ACGACGGGGA    6850
GTCAGGCAAC TATGGATGAA CGAAATAGAC AGATCGCTGA GATAGGTGCC    6900
TCACTGATTA AGCATTGGTA ACTGTCAGAC CAAGTTTACT CATATATACT    6950
TTAGATTGAT TTAAATTGTA AACGTTAATA TTTTGTTAAA ATTCGCGTTA    7000
AATTTTTGTT AAATCAGCTC ATTTTTTAAC CAATAGGCCG AAATCGGCAA    7050
AATCCCTTAT AAATCAAAAG AATAGACCGA GATAGGGTTG AGTGTTGTTC    7100
CAGTTTGGAA CAAGAGTCCA CTATTAAAGA ACGTGGACTC CAACGTCAAA    7150
GGGCGAAAAA CCGTCTATCA GGGCGATGGC CCACTACGTG AACCATCACC    7200
CTAATCAAGT TTTTTGGGGT CGAGGTGCCG TAAAGCACTA AATCGGAACC    7250
CTAAAGGGAG CCCCCGATTT AGAGCTTGAC GGGGAAAGCC GGCGAACGTG    7300
GCGAGAAAGG AAGGGAAGAA AGCGAAAGGA GCGGGCGCTA GGGCGCTGGC    7350
AAGTGTAGCG GTCACGCTGC GCGTAACCAC CACACCCGCC GCGCTTAATG    7400
CGCCGCTACA GGGCGCGTAA AAGGATCTAG GTGAAGATCC TTTTTGATAA    7450
TCTCATGACC AAAATCCCTT AACGTGAGTT TTCGTTCCAC TGAGCGTCAG    7500
ACCCCGTAGA AAAGATCAAA GGATCTTCTT GAGATCCTTT TTTTCTGCGC    7550
GTAATCTGCT GCTTGCAAAC AAAAAAACCA CCGCTACCAG CGGTGGTTTG    7600
TTTGCCGGAT CAAGAGCTAC CAACTCTTTT TCCGAAGGTA ACTGGCTTCA    7650
GCAGAGCGCA GATACCAAAT ACTGTCCTTC TAGTGTAGCC GTAGTTAGGC    7700
CACCACTTCA AGAACTCTGT AGCACCGCCT ACATACCTCG CTCTGCTAAT    7750
CCTGTTACCA GTGGCTGCTG CCAGTGGCGA TAAGTCGTGT CTTACCGGGT    7800
TGGACTCAAG ACGATAGTTA CCGGATAAGG CGCAGCGGTC GGGCTGAACG    7850
GGGGGTTCGT GCACACAGCC CAGCTTGGAG CGAACGACCT ACACCGAACT    7900
```

```
GAGATACCTA   CAGCGTGAGC   ATTGAGAAAG   CGCCACGCTT   CCCGAAGGGA      7950

GAAAGGCGGA   CAGGTATCCG   GTAAGCGGCA   GGGTCGGAAC   AGGAGAGCGC      8000

ACGAGGGAGC   TTCCAGGGGG   AAACGCCTGG   TATCTTTATA   GTCCTGTCGG      8050

GTTTCGCCAC   CTCTGACTTG   AGCGTCGATT   TTTGTGATGC   TCGTCAGGGG      8100

GGCGGAGCCT   ATGGAAAAAC   GCCAGCAACG   CGGCCTTTTT   ACGGTTCCTG      8150

GCCTTTTGCT   GGCCTTTTGC   TCACATGTTC   TTTCCTGCGT   TATCCCCTGA      8200

TTCTGTGGAT   AACCGTATTA   CCGCCTTTGA   GTGAGCTGAT   ACCGCTCGCC      8250

GCAGCCGAAC   GACCGAGCGC   AGCGAGTCAG   TGAGCGAGGA   AGCGGAAGAG      8300

CGCCTGATGC   GGTATTTTCT   CCTTACGCAT   CTGTGCGGTA   TTTCACACCG      8350

CATATGGTGC   ACTCTCAGTA   CAATCTGCTC   TGATGCCGCA   TAGTTAAGCC      8400

AGTATACACT   CCGCTATCGC   TACGTGACTG   GGTCATGGCT   GCGCCCCGAC      8450

ACCCGCCAAC   ACCCGCTGAC   GCGCCCTGAC   GGGCTTGTCT   GCTCCCGGCA      8500

TCCGCTTACA   GACAAGCTGT   GACCGTCTCC   GGGAGCTGCA   TGTGTCAGAG      8550

GTTTTCACCG   TCATCACCGA   AACGCGCGAG   GCAG                          8584
```

( 2 ) INFORMATION FOR SEQ ID NO:67:

( i ) SEQUENCE CHARACTERISTICS:
        ( A ) LENGTH:141 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:67:

```
Met  Arg  Phe  Pro  Ser  Ile  Phe  Thr  Ala  Val  Leu  Phe  Ala  Ala  Ser  Ser
 1                   5                  10                          15

Ala  Leu  Ala  Ala  Pro  Val  Asn  Thr  Thr  Thr  Glu  Asp  Glu  Thr  Ala  Gln
                20                  25                          30

Ile  Pro  Ala  Glu  Ala  Val  Ile  Gly  Tyr  Ser  Asp  Leu  Glu  Gly  Asp  Phe
                35                  40                          45

Asp  Val  Ala  Val  Leu  Pro  Phe  Ser  Asn  Ser  Thr  Asn  Asn  Gly  Leu  Leu
         50                  55                          60

Phe  Ile  Asn  Thr  Thr  Ile  Ala  Ser  Ile  Ala  Ala  Lys  Glu  Glu  Gly  Val
 65                  70                          75                          80

Ser  Leu  Asp  Lys  Arg  Ala  Ala  Cys  Asn  Leu  Pro  Ile  Val  Arg  Gly  Pro
                85                  90                          95

Cys  Ile  Ala  Phe  Phe  Pro  Arg  Trp  Ala  Phe  Asp  Ala  Val  Lys  Gly  Lys
               100                 105                         110

Cys  Val  Leu  Phe  Pro  Tyr  Gly  Gly  Cys  Gln  Gly  Asn  Gly  Asn  Lys  Phe
               115                 120                         125

Tyr  Ser  Glu  Lys  Glu  Cys  Arg  Glu  Tyr  Cys  Gly  Val  Pro
               130                 135                         140
```

( 2 ) INFORMATION FOR SEQ ID NO:68:

( i ) SEQUENCE CHARACTERISTICS:
        ( A ) LENGTH:448 bases
        ( B ) TYPE: nucleic acid
        ( C ) STRANDEDNESS: single
        ( D ) TOPOLOGY: linear ( i i ) MOLECULE TYPE:other nucleic acid
        ( A ) DESCRIPTION:synthetic DNA fragment ( x i ) SEQUENCE DESCRIPTION: SEQ ID NO:68:

| | | | | | |
|---|---|---|---|---|---|
| TTCGAAACGA | TGAGATTCCC | ATCTATCTTC | ACTGCTGTTT | TGTTCGCTGC | 50 |
| TTCCTCTGCT | TTGGCTGCTC | CAGTTAACAC | CACTACTGAA | GACGAGACTG | 100 |
| CTCAAATTCC | TGCTGAGGCT | GTCATCGGTT | ACTCTGACTT | GGAAGGTGAC | 150 |
| TTCGACGTCG | CTGTTTTGCC | ATTCTCTAAC | TCTACTAACA | ACGGTTTGTT | 200 |
| GTTCATCAAC | ACTACCATCG | CTTCTATCGC | TGCTAAGGAG | GAAGGTGTTT | 250 |
| CCTTGGACAA | GAGAGAGGCT | TGTAACTTGC | CAATCGTCAG | AGGTCCATGC | 300 |
| ATTGCTTTCT | TCCCAAGATG | GGCTTTCGAC | GCTGTTAAGG | GTAAGTGCGT | 350 |
| CTTGTTCCCA | TACGGTGGTT | GTCAAGGTAA | CGGTAACAAG | TTCTACTCTG | 400 |
| AGAAGGAGTG | TAGAGAGTAC | TGTGGTGTTC | CATAGTAAGA | ATTCGCCT | 448 |

( 2 ) INFORMATION FOR SEQ ID NO:69:

( i ) SEQUENCE CHARACTERISTICS:
( A ) LENGTH:141 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:69:

```
Met Arg Phe Pro Ser Ile Phe Thr Ala Val Leu Phe Ala Ala Ser Ser
 1               5                  10                  15

Ala Leu Ala Ala Pro Val Asn Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Cys Asn Leu Pro Ile Val Arg Gly Pro
                85                  90                  95

Cys Ile Ala Phe Phe Pro Arg Trp Ala Phe Asp Ala Val Lys Gly Lys
               100                 105                 110

Cys Val Leu Phe Pro Tyr Gly Gly Cys Gln Gly Asn Gly Asn Lys Phe
           115                 120                 125

Tyr Ser Glu Lys Glu Cys Arg Glu Tyr Cys Gly Val Pro
       130                 135                 140
```

( 2 ) INFORMATION FOR SEQ ID NO:70:

( i ) SEQUENCE CHARACTERISTICS:
( A ) LENGTH:8590 bases
( B ) TYPE: nucleic acid
( C ) STRANDEDNESS: single
( D ) TOPOLOGY: circular ( i i ) MOLECULE TYPE:other nucleic acid
( A ) DESCRIPTION: DNA plasmid ( x i ) SEQUENCE DESCRIPTION: SEQ ID NO:70:

| | | | | | |
|---|---|---|---|---|---|
| AGATCGCGGC | CGCGATCTAA | CATCCAAAGA | CGAAAGGTTG | AATGAAACCT | 50 |
| TTTTGCCATC | CGACATCCAC | AGGTCCATTC | TCACACATAA | GTGCCAAACG | 100 |
| CAACAGGAGG | GGATACACTA | GCAGCAGACC | GTTGCAAACG | CAGGACCTCC | 150 |

```
ACTCCTCTTC  TCCTCAACAC  CCACTTTTGC  CATCGAAAAA  CCAGCCCAGT   200
TATTGGGCTT  GATTGGAGCT  CGCTCATTCC  AATTCCTTCT  ATTAGGCTAC   250
TAACACCATG  ACTTTATTAG  CCTGTCTATC  CTGGCCCCCC  TGGCGAGGTC   300
ATGTTTGTTT  ATTTCCGAAT  GCAACAAGCT  CCGCATTACA  CCCGAACATC   350
ACTCCAGATG  AGGGCTTTCT  GAGTGTGGGG  TCAAATAGTT  TCATGTTCCC   400
AAATGGCCCA  AAACTGACAG  TTTAAACGCT  GTCTTGGAAC  CTAATATGAC   450
AAAAGCGTGA  TCTCATCCAA  GATGAACTAA  GTTGGTTCG   TTGAAATGCT   500
AACGGCCAGT  TGGTCAAAAA  GAAACTTCCA  AAAGTCGCCA  TACCGTTTGT   550
CTTGTTTGGT  ATTGATTGAC  GAATGCTCAA  AAATAATCTC  ATTAATGCTT   600
AGCGCAGTCT  CTCTATCGCT  TCTGAACCCG  GTGGCACCTG  TGCCGAAACG   650
CAAATGGGGA  AACAACCCGC  TTTTTGGATG  ATTATGCATT  GTCCTCCACA   700
TTGTATGCTT  CCAAGATTCT  GGTGGGAATA  CTGCTGATAG  CCTAACGTTC   750
ATGATCAAAA  TTTAACTGTT  CTAACCCCTA  CTTGACAGGC  AATATATAAA   800
CAGAAGGAAG  CTGCCCTGTC  TTAAACCTTT  TTTTTTATCA  TCATTATTAG   850
CTTACTTTCA  TAATTGCGAC  TGGTTCCAAT  TGACAAGCTT  TTGATTTTAA   900
CGACTTTTAA  CGACAACTTG  AGAAGATCAA  AAAACAACTA  ATTATTCGAA   950
ACGATGAGAT  TCCCATCTAT  CTTCACTGCT  GTTTGTTCG   CTGCTTCCTC  1000
TGCTTTGGCT  GCTCCAGTTA  ACACCACTAC  TGAAGACGAG  ACTGCTCAAA  1050
TTCCTGCTGA  GGCTGTCATC  GGTTACTCTG  ACTTGGAAGG  TGACTTCGAC  1100
GTCGCTGTTT  TGCCATTCTC  TAACTCTACT  AACAACGGTT  TGTTGTTCAT  1150
CAACACTACC  ATCGCTTCTA  TCGCTGCTAA  GGAGGAAGGT  GTTTCCTTGG  1200
ACAAGAGAGC  TGCTTGTAAC  TTGCCAATCG  TCAGAGGTCC  ATGCATTGCT  1250
TTCTTCCCAA  GATGGGCTTT  CGACGCTGTT  AAGGGTAAGT  GCGTCTTGTT  1300
CCCATACGGT  GGTTGTCAAG  GTAACGGTAA  CAAGTTCTAC  TCTGAGAAGG  1350
AGTGTAGAGA  GTACTGTGGT  GTTCCATAGT  AAGAATTCGC  CTTAGACATG  1400
ACTGTTCCTC  AGTTCAAGTT  GGGCATTACG  AGAAGACCGG  TCTTGCTAGA  1450
TTCTAATCAA  GAGGATGTCA  GAATGCCATT  TGCCTGAGAG  ATGCAGGCTT  1500
CATTTTGAT   ACTTTTTAT   TTGTAACCTA  TATAGTATAG  GATTTTTTT   1550
GTCATTTGT   TTCTTCTCGT  ACGAGCTTGC  TCCTGATCAG  CCTATCTCGC  1600
AGCTGATGAA  TATCTTGTGG  TAGGGGTTTG  GGAAAATCAT  TCGAGTTTGA  1650
TGTTTTCTT   GGTATTTCCC  ACTCCTCTTC  AGAGTACAGA  AGATTAAGTG  1700
AGAAGTTCGT  TTGTGCAAGC  TTATCGATAA  GCTTAATGC   GGTAGTTTAT  1750
CACAGTTAAA  TTGCTAACGC  AGTCAGGCAC  CGTGTATGAA  ATCAACAAT   1800
GCGCTCATCG  TCATCCTCGG  CACCGTCACC  CTGGATGCTG  TAGGCATAGG  1850
CTTGGTTATG  CCGGTACTGC  CGGGCCTCTT  GCGGGATATC  GTCCATTCCG  1900
ACAGCATCGC  CAGTCACTAT  GGCGTGCTGC  TAGCGCTATA  TGCGTTGATG  1950
CAATTTCTAT  GCGCACCCGT  TCTCGGAGCA  CTGTCCGACC  GCTTTGGCCG  2000
CCGCCCAGTC  CTGCTCGCTT  CGCTACTTGG  AGCCACTATC  GACTACGCGA  2050
TCATGGCGAC  CACACCCGTC  CTGTGGATCT  ATCGAATCTA  AATGTAAGTT  2100
AAAATCTCTA  AATAATTAAA  TAAGTCCCAG  TTTCTCCATA  CGAACCTTAA  2150
```

```
CAGCATTGCG GTGAGCATCT AGACCTTCAA CAGCAGCCAG ATCCATCACT    2200
GCTTGGCCAA TATGTTTCAG TCCCTCAGGA GTTACGTCTT GTGAAGTGAT    2250
GAACTTCTGG AAGGTTGCAG TGTTAACTCC GCTGTATTGA CGGGCATATC    2300
CGTACGTTGG CAAAGTGTGG TTGGTACCGG AGGAGTAATC TCCACAACTC    2350
TCTGGAGAGT AGGCACCAAC AAACACAGAT CCAGCGTGTT GTACTTGATC    2400
AACATAAGAA GAAGCATTCT CGATTTGCAG GATCAAGTGT TCAGGAGCGT    2450
ACTGATTGGA CATTTCCAAA GCCTGCTCGT AGGTTGCAAC CGATAGGGTT    2500
GTAGAGTGTG CAATACACTT GCGTACAATT TCAACCCTTG GCAACTGCAC    2550
AGCTTGGTTG TGAACAGCAT CTTCAATTCT GGCAAGCTCC TTGTCTGTCA    2600
TATCGACAGC CAACAGAATC ACCTGGGAAT CAATACCATG TTCAGCTTGA    2650
GCAGAAGGTC TGAGGCAACG AAATCTGGAT CAGCGTATTT ATCAGCAATA    2700
ACTAGAACTT CAGAAGGCCC AGCAGGCATG TCAATACTAC ACAGGGCTGA    2750
TGTGTCATTT TGAACCATCA TCTTGGCAGC AGTAACGAAC TGGTTTCCTG    2800
GACCAAATAT TTTGTCACAC TTAGGAACAG TTTCTGTTCC GTAAGCCATA    2850
GCAGCTACTG CCTGGGCGCC TCCTGCTAGC ACGATACACT TAGCACCAAC    2900
CTTGTGGGCA ACGTAGATGA CTTCTGGGGT AAGGGTACCA TCCTTCTTAG    2950
GTGGAGATGC AAAAACAATT TCTTTGCAAC CAGCAACTTT GGCAGGAACA    3000
CCCAGCATCA GGGAAGTGGA AGGCAGAATT GCGGTTCCAC CAGGAATATA    3050
GAGGCCAACT TTCTCAATAG GTCTTGCAAA ACGAGAGCAG ACTACACCAG    3100
GGCAAGTCTC AACTTGCAAC GTCTCCGTTA GTTGAGCTTC ATGGAATTTC    3150
CTGACGTTAT CTATAGAGAG ATCAATGGCT CTCTTAACGT TATCTGGCAA    3200
TTGCATAAGT TCCTCTGGGA AGGAGCTTC TAACACAGGT GTCTTCAAAG     3250
CGACTCCATC AAACTTGGCA GTTAGTTCTA AAAGGGCTTT GTCACCATTT    3300
TGACGAACAT TGTCGACAAT TGGTTTGACT AATTCCATAA TCTGTTCCGT    3350
TTTCTGGATA GGACGACGAA GGGCATCTTC AATTTCTTGT GAGGAGGCCT    3400
TAGAAACGTC AATTTTGCAC AATTCAATAC GACCTTCAGA AGGGACTTCT    3450
TTAGGTTTGG ATTCTTCTTT AGGTTGTTCC TTGGTGTATC CTGGCTTGGC    3500
ATCTCCTTTC CTTCTAGTGA CCTTTAGGGA CTTCATATCC AGGTTTCTCT    3550
CCACCTCGTC CAACGTCACA CCGTACTTGG CACATCTAAC TAATGCAAAA    3600
TAAAATAAGT CAGCACATTC CCAGGCTATA TCTTCCTTGG ATTTAGCTTC    3650
TGCAAGTTCA TCAGCTTCCT CCCTAATTTT AGCGTTCAAC AAAACTTCGT    3700
CGTCAAATAA CCGTTTGGTA TAAGAACCTT CTGGAGCATT GCTCTTACGA    3750
TCCCACAAGG TGCTTCCATG GCTCTAAGAC CCTTTGATTG GCCAAAACAG    3800
GAAGTGCGTT CCAAGTGACA GAAACCAACA CCTGTTTGTT CAACCACAAA    3850
TTTCAAGCAG TCTCCATCAC AATCCAATTC GATACCCAGC AACTTTTGAG    3900
TTCGTCCAGA TGTAGCACCT TTATACCACA AACCGTGACG ACGAGATTGG    3950
TAGACTCCAG TTTGTGTCCT TATAGCCTCC GGAATAGACT TTTTGGACGA    4000
GTACACCAGG CCCAACGAGT AATTAGAAGA GTCAGCCACC AAAGTAGTGA    4050
ATAGACCATC GGGGCGGTCA GTAGTCAAAG ACGCCAACAA AATTTCACTG    4100
ACAGGGAACT TTTTGACATC TTCAGAAAGT TCGTATTCAG TAGTCAATTG    4150
```

```
CCGAGCATCA  ATAATGGGGA  TTATACCAGA  AGCAACAGTG  GAAGTCACAT  4200
CTACCAACTT  TGCGGTCTCA  GAAAAAGCAT  AAACAGTTCT  ACTACCGCCA  4250
TTAGTGAAAC  TTTTCAAATC  GCCCAGTGGA  GAAGAAAAAG  GCACAGCGAT  4300
ACTAGCATTA  GCGGGCAAGG  ATGCAACTTT  ATCAACCAGG  GTCCTATAGA  4350
TAACCCTAGC  GCCTGGGATC  ATCCTTTGGA  CAACTCTTTC  TGCCAAATCT  4400
AGGTCCAAAA  TCACTTCATT  GATACCATTA  TACGGATGAC  TCAACTTGCA  4450
CATTAACTTG  AAGCTCAGTC  GATTGAGTGA  ACTTGATCAG  GTTGTGCAGC  4500
TGGTCAGCAG  CATAGGGAAA  CACGGCTTTT  CCTACCAAAC  TCAAGGAATT  4550
ATCAAACTCT  GCAACACTTG  CGTATGCAGG  TAGCAAGGGA  AATGTCATAC  4600
TTGAAGTCGG  ACAGTGAGTG  TAGTCTTGAG  AAATTCTGAA  GCCGTATTTT  4650
TATTATCAGT  GAGTCAGTCA  TCAGGAGATC  CTCTACGCCG  GACGCATCGT  4700
GGCCGGCATC  ACCGGCGCCA  CAGGTGCGGT  TGCTGGCGCC  TATATCGCCG  4750
ACATCACCGA  TGGGGAAGAT  CGGGCTCGCC  ACTTCGGGCT  CATGAGCGCT  4800
TGTTTCGGCG  TGGGTATGGT  GGCAGGCCCC  GTGGCCGGGG  GACTGTTGGG  4850
CGCCATCTCC  TTGCATGCAC  CATTCCTTGC  GGCGGCGGTG  CTCAACGGCC  4900
TCAACCTACT  ACTGGGCTGC  TTCCTAATGC  AGGAGTCGCA  TAAGGGAGAG  4950
CGTCGAGTAT  CTATGATTGG  AAGTATGGGA  ATGGTGATAC  CCGCATTCTT  5000
CAGTGTCTTG  AGGTCTCCTA  TCAGATTATG  CCCAACTAAA  GCAACCGGAG  5050
GAGGAGATTT  CATGGTAAAT  TTCTCTGACT  TTTGGTCATC  AGTAGACTCG  5100
AACTGTGAGA  CTATCTCGGT  TATGACAGCA  GAAATGTCCT  TCTTGGAGAC  5150
AGTAAATGAA  GTCCCACCAA  TAAAGAAATC  CTTGTTATCA  GGAACAAACT  5200
TCTTGTTTCG  CGAACTTTTT  CGGTGCCTTG  AACTATAAAA  TGTAGAGTGG  5250
ATATGTCGGG  TAGGAATGGA  GCGGGCAAAT  GCTTACCTTC  TGGACCTTCA  5300
AGAGGTATGT  AGGGTTTGTA  GATACTGATG  CCAACTTCAG  TGACAACGTT  5350
GCTATTTCGT  TCAAACCATT  CCGAATCCAG  AGAAATCAAA  GTTGTTTGTC  5400
TACTATTGAT  CCAAGCCAGT  GCGGTCTTGA  AACTGACAAT  AGTGTGCTCG  5450
TGTTTTGAGG  TCATCTTTGT  ATGAATAAAT  CTAGTCTTTG  ATCTAAATAA  5500
TCTTGACGAG  CCAAGGCGAT  AAATACCCAA  ATCTAAAACT  CTTTTAAAAC  5550
GTTAAAAGGA  CAAGTATGTC  TGCCTGTATT  AAACCCCAAA  TCAGCTCGTA  5600
GTCTGATCCT  CATCAACTTG  AGGGGCACTA  TCTTGTTTTA  GAGAAATTTG  5650
CGGAGATGCG  ATATCGAGAA  AAAGGTACGC  TGATTTTAAA  CGTGAAATTT  5700
ATCTCAAGAT  CGCGGCCGCG  ATCTCGAATA  ATAACTGTTA  TTTTTCAGTG  5750
TTCCCGATCT  GCGTCTATTT  CACAATACCA  ACATGAGTCA  GCTTATCGAT  5800
GATAAGCTGT  CAAACATGAG  AATTAATTCG  ATGATAAGCT  GTCAAACATG  5850
AGAAATCTTG  AAGACGAAAG  GGCCTCGTGA  TACGCCTATT  TTTATAGGTT  5900
AATGTCATGA  TAATAATGGT  TTCTTAGACG  TACGTCAGGT  GGCACTTTTC  5950
GGGGAAATGT  GCGCGGAACC  CCTATTTGTT  TATTTTTCTA  AATACATTCA  6000
AATATGTATC  CGCTCATGAG  ACAATAACCC  TGATAAATGC  TTCAATAATA  6050
TTGAAAAAGG  AAGAGTATGA  GTATTCAACA  TTTCCGTGTC  GCCCTTATTC  6100
CCTTTTTTGC  GGCATTTTGC  CTTCCTGTTT  TTGCTCACCC  AGAAACGCTG  6150
```

```
GTGAAAGTAA AAGATGCTGA AGATCAGTTG GGTGCACGAG TGGGTTACAT      6200
CGAACTGGAT CTCAACAGCG GTAAGATCCT TGAGAGTTTT CGCCCCGAAG      6250
AACGTTTTCC AATGATGAGC ACTTTTAAAG TTCTGCTATG TGGCGCGGTA      6300
TTATCCCGTG TTGACGCCGG GCAAGAGCAA CTCGGTCGCC GCATACACTA      6350
TTCTCAGAAT GACTTGGTTG AGTACTCACC AGTCACAGAA AAGCATCTTA      6400
CGGATGGCAT GACAGTAAGA GAATTATGCA GTGCTGCCAT AACCATGAGT      6450
GATAACACTG CGGCCAACTT ACTTCTGACA ACGATCGGAG GACCGAAGGA      6500
GCTAACCGCT TTTTTGCACA ACATGGGGGA TCATGTAACT CGCCTTGATC      6550
GTTGGGAACC GGAGCTGAAT GAAGCCATAC CAAACGACGA GCGTGACACC      6600
ACGATGCCTG CAGCAATGGC AACAACGTTG CGCAAACTAT TAACTGGCGA      6650
ACTACTTACT CTAGCTTCCC GGCAACAATT AATAGACTGG ATGGAGGCGG      6700
ATAAAGTTGC AGGACCACTT CTGCGCTCGG CCCTTCCGGC TGGCTGGTTT      6750
ATTGCTGATA AATCTGGAGC CGGTGAGCGT GGGTCTCGCG GTATCATTGC      6800
AGCACTGGGG CCAGATGGTA AGCCCTCCCG TATCGTAGTT ATCTACACGA      6850
CGGGGAGTCA GGCAACTATG GATGAACGAA ATAGACAGAT CGCTGAGATA      6900
GGTGCCTCAC TGATTAAGCA TTGGTAACTG TCAGACCAAG TTTACTCATA      6950
TATACTTTAG ATTGATTTAA ATTGTAAACG TTAATATTTT GTTAAAATTC      7000
GCGTTAAATT TTTGTTAAAT CAGCTCATTT TTTAACCAAT AGGCCGAAAT      7050
CGGCAAAATC CCTTATAAAT CAAAAGAATA GACCGAGATA GGGTTGAGTG      7100
TTGTTCCAGT TTGGAACAAG AGTCCACTAT TAAAGAACGT GGACTCCAAC      7150
GTCAAAGGGC GAAAAACCGT CTATCAGGGC GATGGCCCAC TACGTGAACC      7200
ATCACCCTAA TCAAGTTTTT TGGGGTCGAG GTGCCGTAAA GCACTAAATC      7250
GGAACCCTAA AGGGAGCCCC CGATTTAGAG CTTGACGGGG AAAGCCGGCG      7300
AACGTGGCGA GAAAGGAAGG GAAGAAAGCG AAAGGAGCGG GCGCTAGGGC      7350
GCTGGCAAGT GTAGCGGTCA CGCTGCGCGT AACCACCACA CCCGCCGCGC      7400
TTAATGCGCC GCTACAGGGC GCGTAAAAGG ATCTAGGTGA AGATCCTTT       7450
TGATAATCTC ATGACCAAAA TCCCTTAACG TGAGTTTTCG TTCCACTGAG      7500
CGTCAGACCC CGTAGAAAAG ATCAAAGGAT CTTCTTGAGA TCCTTTTTTT      7550
CTGCGCGTAA TCTGCTGCTT GCAAACAAAA AAACCACCGC TACCAGCGGT      7600
GGTTTGTTTG CCGGATCAAG AGCTACCAAC TCTTTTTCCG AAGGTAACTG      7650
GCTTCAGCAG AGCGCAGATA CCAAATACTG TCCTTCTAGT GTAGCCGTAG      7700
TTAGGCCACC ACTTCAAGAA CTCTGTAGCA CCGCCTACAT ACCTCGCTCT      7750
GCTAATCCTG TTACCAGTGG CTGCTGCCAG TGGCGATAAG TCGTGTCTTA      7800
CCGGGTTGGA CTCAAGACGA TAGTTACCGG ATAAGGCGCA GCGGTCGGGC      7850
TGAACGGGGG GTTCGTGCAC ACAGCCCAGC TTGGAGCGAA CGACCTACAC      7900
CGAACTGAGA TACCTACAGC GTGAGCATTG AGAAAGCGCC ACGCTTCCCG      7950
AAGGGAGAAA GGCGGACAGG TATCCGGTAA GCGGCAGGGT CGGAACAGGA      8000
GAGCGCACGA GGGAGCTTCC AGGGGGAAAC GCCTGGTATC TTTATAGTCC      8050
TGTCGGGTTT CGCCACCTCT GACTTGAGCG TCGATTTTTG TGATGCTCGT      8100
CAGGGGGGCG GAGCCTATGG AAAAACGCCA GCAACGCGGC CTTTTTACGG      8150
```

```
TTCCTGGCCT    TTTGCTGGCC    TTTTGCTCAC    ATGTTCTTTC    CTGCGTTATC    8200

CCCTGATTCT    GTGGATAACC    GTATTACCGC    CTTTGAGTGA    GCTGATACCG    8250

CTCGCCGCAG    CCGAACGACC    GAGCGCAGCG    AGTCAGTGAG    CGAGGAAGCG    8300

GAAGAGCGCC    TGATGCGGTA    TTTTCTCCTT    ACGCATCTGT    GCGGTATTTC    8350

ACACCGCATA    TGGTGCACTC    TCAGTACAAT    CTGCTCTGAT    GCCGCATAGT    8400

TAAGCCAGTA    TACACTCCGC    TATCGCTACG    TGACTGGGTC    ATGGCTGCGC    8450

CCCGACACCC    GCCAACACCC    GCTGACGCGC    CCTGACGGGC    TTGTCTGCTC    8500

CCGGCATCCG    CTTACAGACA    AGCTGTGACC    GTCTCCGGGA    GCTGCATGTG    8550

TCAGAGGTTT    TCACCGTCAT    CACCGAAACG    CGCGAGGCAG                  8590
```

( 2 ) INFORMATION FOR SEQ ID NO:71:

( i ) SEQUENCE CHARACTERISTICS:
      ( A ) LENGTH:58 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:71:

```
Arg  Pro  Asp  Phe  Cys  Leu  Leu  Pro  Ala  Glu  Thr  Gly  Pro  Cys  Arg  Ala
  1                  5                           10                          15

Met  Ile  Pro  Arg  Phe  Tyr  Tyr  Asn  Ala  Lys  Ser  Gly  Lys  Cys  Glu  Pro
                 20                          25                          30

Phe  Ile  Tyr  Gly  Gly  Cys  Gly  Gly  Asn  Ala  Asn  Asn  Phe  Lys  Thr  Glu
              35                          40                          45

Glu  Glu  Cys  Arg  Arg  Thr  Cys  Gly  Gly  Ala
          50                          55
```

( 2 ) INFORMATION FOR SEQ ID NO:72:

( i ) SEQUENCE CHARACTERISTICS:
      ( A ) LENGTH:147 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:72:

```
Ala  Val  Leu  Pro  Gln  Glu  Glu  Gly  Ser  Gly  Gly  Gly  Gln  Leu  Val
  1                  5                           10                     15

Thr  Glu  Val  Thr  Lys  Lys  Glu  Asp  Ser  Cys  Gln  Leu  Gly  Tyr  Ser  Ala
                 20                          25                          30

Gly  Pro  Cys  Met  Gly  Met  Thr  Ser  Arg  Tyr  Phe  Tyr  Asn  Gly  Thr  Ser
              35                          40                          45

Met  Ala  Cys  Glu  Thr  Phe  Gln  Tyr  Gly  Gly  Cys  Met  Gly  Asn  Gly  Asn
          50                          55                          60

Asn  Phe  Val  Thr  Glu  Lys  Glu  Cys  Leu  Gln  Thr  Cys  Arg  Thr  Val  Ala
 65                          70                          75                 80

Ala  Cys  Asn  Leu  Pro  Ile  Val  Arg  Gly  Pro  Cys  Arg  Ala  Phe  Ile  Gln
                 85                          90                          95

Leu  Trp  Ala  Phe  Asp  Ala  Val  Lys  Gly  Lys  Cys  Val  Leu  Phe  Pro  Tyr
                100                         105                        110

Gly  Gly  Cys  Gln  Gly  Asn  Gly  Asn  Lys  Phe  Tyr  Ser  Glu  Lys  Glu  Cys
              115                         120                        125
```

```
Arg  Glu  Tyr  Cys  Gly  Val  Pro  Gly  Asp  Gly  Asp  Glu  Glu  Leu  Leu  Arg
     130            135                 140

Phe  Ser  Asn
145
```

( 2 ) INFORMATION FOR SEQ ID NO:73:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:73:

```
Val  Arg  Glu  Val  Cys  Ser  Glu  Gln  Ala  Glu  Thr  Gly  Pro  Cys  Arg  Ala
1              5                      10                      15

Met  Ile  Ser  Arg  Trp  Tyr  Phe  Asp  Val  Thr  Glu  Gly  Lys  Cys  Ala  Pro
          20                      25                      30

Phe  Phe  Tyr  Gly  Gly  Cys  Gly  Gly  Asn  Arg  Asn  Asn  Phe  Asp  Thr  Glu
          35                 40                           45

Glu  Tyr  Cys  Met  Ala  Val  Cys  Gly  Ser  Ala
     50                  55
```

( 2 ) INFORMATION FOR SEQ ID NO:74:

( i ) SEQUENCE CHARACTERISTICS:
( A ) LENGTH:59 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:74:

```
Arg  Asn  Arg  Glu  Val  Cys  Ser  Glu  Gln  Ala  Glu  Thr  Gly  Pro  Cys  Arg
1              5                      10                      15

Ala  Met  Ile  Ser  Arg  Trp  Tyr  Phe  Asp  Val  Thr  Glu  Gly  Lys  Cys  Ala
               20                      25                      30

Pro  Phe  Phe  Tyr  Gly  Gly  Cys  Gly  Gly  Asn  Arg  Asn  Asn  Phe  Asp  Thr
          35                      40                      45

Glu  Glu  Tyr  Cys  Met  Ala  Val  Cys  Gly  Ser  Ala
     50                       55
```

( 2 ) INFORMATION FOR SEQ ID NO:75:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:75:

```
Thr  Val  Ala  Ala  Cys  Asn  Leu  Pro  Ile  Val  Arg  Gly  Pro  Cys  Arg  Ala
1              5                      10                      15

Phe  Ile  Gln  Leu  Trp  Ala  Phe  Asp  Ala  Val  Lys  Gly  Lys  Cys  Val  Leu
          20                      25                      30

Phe  Pro  Tyr  Gly  Gly  Cys  Gln  Gly  Asn  Gly  Asn  Lys  Phe  Tyr  Ser  Glu
          35                      40                      45

Lys  Glu  Cys  Arg  Glu  Tyr  Cys  Gly  Val  Pro
```

( 2 ) INFORMATION FOR SEQ ID NO:76:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:76:

```
Lys Pro Asp Phe Cys Phe Leu Glu Glu Asp Pro Gly Ile Cys Arg Gly
 1               5                  10                  15
Tyr Ile Thr Arg Tyr Phe Tyr Asn Asn Gln Thr Lys Gln Cys Glu Arg
             20                  25                  30
Phe Lys Tyr Gly Gly Cys Leu Gly Asn Met Asn Asn Phe Glu Thr Leu
         35                  40                  45
Glu Glu Cys Lys Asn Ile Cys Glu Asp Gly
     50                  55
```

( 2 ) INFORMATION FOR SEQ ID NO:77:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:77:

```
Met His Ser Phe Cys Ala Phe Lys Ala Asp Asp Gly Pro Cys Lys Ala
 1               5                  10                  15
Ile Met Lys Arg Phe Phe Phe Asn Ile Phe Thr Arg Gln Cys Glu Glu
             20                  25                  30
Phe Ile Tyr Gly Gly Cys Glu Gly Asn Gln Asn Arg Phe Glu Ser Leu
         35                  40                  45
Glu Glu Cys Lys Lys Met Cys Thr Arg Asp
     50                  55
```

( 2 ) INFORMATION FOR SEQ ID NO:78:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:78:

```
Leu Pro Asn Val Cys Ala Phe Pro Met Glu Lys Gly Pro Cys Gln Thr
 1               5                  10                  15
Tyr Met Thr Arg Trp Phe Phe Asn Phe Glu Thr Gly Glu Cys Glu Leu
             20                  25                  30
Phe Ala Tyr Gly Gly Cys Gly Gly Asn Ser Asn Asn Phe Leu Arg Lys
         35                  40                  45
Glu Lys Cys Glu Lys Phe Cys Lys Phe Thr
     50                  55
```

( 2 ) INFORMATION FOR SEQ ID NO:79:

( i ) SEQUENCE CHARACTERISTICS:
    ( A ) LENGTH:58 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:79:

```
Glu Thr Asp Ile Cys Lys Leu Pro Lys Asp Glu Gly Thr Cys Arg Asp
 1               5                  10                  15
Phe Ile Leu Lys Trp Tyr Tyr Asp Pro Asn Thr Lys Ser Cys Ala Arg
                20                  25                  30
Phe Trp Tyr Gly Gly Cys Gly Gly Asn Glu Asn Lys Phe Gly Ser Gln
            35                  40                  45
Lys Glu Cys Glu Lys Val Cys Ala Pro Val
 50                  55
```

( 2 ) INFORMATION FOR SEQ ID NO:80:

( i ) SEQUENCE CHARACTERISTICS:
    ( A ) LENGTH:58 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:80:

```
Asn Ala Glu Ile Cys Leu Leu Pro Leu Asp Tyr Gly Pro Cys Arg Ala
 1               5                  10                  15
Leu Leu Leu Arg Tyr Tyr Tyr Asp Arg Tyr Thr Gln Ser Cys Arg Gln
                20                  25                  30
Phe Leu Tyr Gly Gly Cys Glu Gly Asn Ala Asn Asn Phe Tyr Thr Trp
            35                  40                  45
Glu Ala Cys Asp Asp Ala Cys Trp Arg Ile
 50                  55
```

( 2 ) INFORMATION FOR SEQ ID NO:81:

( i ) SEQUENCE CHARACTERISTICS:
    ( A ) LENGTH:61 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:81:

```
Val Pro Lys Val Cys Arg Leu Gln Val Ser Val Asp Asp Gln Cys Glu
 1               5                  10                  15
Gly Ser Thr Glu Lys Tyr Phe Phe Asn Leu Ser Ser Met Thr Cys Glu
                20                  25                  30
Lys Phe Phe Ser Gly Gly Cys His Arg Asn Arg Ile Glu Asn Arg Phe
            35                  40                  45
Pro Asp Glu Ala Thr Cys Met Gly Phe Cys Ala Pro Lys
 50                  55                  60
```

( 2 ) INFORMATION FOR SEQ ID NO:82:

( i ) SEQUENCE CHARACTERISTICS:
    ( A ) LENGTH:58 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:82:

| Ile | Pro | Ser | Phe | Cys | Tyr | Ser | Pro | Lys | Asp | Glu | Gly | Leu | Cys | Ser | Ala |
|---|---|---|---|---|---|---|---|---|---|---|---|---|---|---|---|
| 1 | | | | 5 | | | | | 10 | | | | | 15 | |

| Asn | Val | Thr | Arg | Tyr | Tyr | Phe | Asn | Pro | Arg | Tyr | Arg | Thr | Cys | Asp | Ala |
|---|---|---|---|---|---|---|---|---|---|---|---|---|---|---|---|
| | | | 20 | | | | | 25 | | | | | 30 | | |

| Phe | Thr | Tyr | Thr | Gly | Cys | Gly | Gly | Asn | Asp | Asn | Asn | Phe | Val | Ser | Arg |
|---|---|---|---|---|---|---|---|---|---|---|---|---|---|---|---|
| | | 35 | | | | | 40 | | | | | 45 | | | |

| Glu | Asp | Cys | Lys | Arg | Ala | Cys | Ala | Lys | Ala |
|---|---|---|---|---|---|---|---|---|---|
| | 50 | | | | | 55 | | | |

( 2 ) INFORMATION FOR SEQ ID NO:83:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:83:

| Lys | Pro | Asp | Phe | Cys | Phe | Leu | Glu | Glu | Asp | Pro | Gly | Ile | Cys | Val | Gly |
|---|---|---|---|---|---|---|---|---|---|---|---|---|---|---|---|
| 1 | | | | 5 | | | | | 10 | | | | | 15 | |

| Tyr | Phe | Thr | Arg | Tyr | Phe | Tyr | Asn | Asn | Gln | Thr | Lys | Gln | Cys | Glu | Arg |
|---|---|---|---|---|---|---|---|---|---|---|---|---|---|---|---|
| | | | 20 | | | | | 25 | | | | | 30 | | |

| Phe | Lys | Tyr | Gly | Gly | Cys | Leu | Gly | Asn | Met | Asn | Asn | Phe | Glu | Thr | Leu |
|---|---|---|---|---|---|---|---|---|---|---|---|---|---|---|---|
| | | 35 | | | | | 40 | | | | | 45 | | | |

| Glu | Glu | Cys | Lys | Asn | Ile | Cys | Glu | Asp | Gly |
|---|---|---|---|---|---|---|---|---|---|
| | 50 | | | | | 55 | | | |

( 2 ) INFORMATION FOR SEQ ID NO:84:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:84:

| Lys | Pro | Asp | Phe | Cys | Phe | Leu | Glu | Glu | Asp | Pro | Gly | Ile | Cys | Val | Gly |
|---|---|---|---|---|---|---|---|---|---|---|---|---|---|---|---|
| 1 | | | | 5 | | | | | 10 | | | | | 15 | |

| Phe | Phe | Thr | Arg | Tyr | Phe | Tyr | Asn | Asn | Gln | Thr | Lys | Gln | Cys | Glu | Arg |
|---|---|---|---|---|---|---|---|---|---|---|---|---|---|---|---|
| | | | 20 | | | | | 25 | | | | | 30 | | |

| Phe | Val | Tyr | Gly | Gly | Cys | Leu | Gly | Asn | Met | Asn | Asn | Phe | Glu | Thr | Leu |
|---|---|---|---|---|---|---|---|---|---|---|---|---|---|---|---|
| | | 35 | | | | | 40 | | | | | 45 | | | |

| Glu | Glu | Cys | Lys | Asn | Ile | Cys | Glu | Asp | Gly |
|---|---|---|---|---|---|---|---|---|---|
| | 50 | | | | | 55 | | | |

( 2 ) INFORMATION FOR SEQ ID NO:85:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:85:

```
Lys  Pro  Asp  Phe  Cys  Phe  Leu  Glu  Glu  Asp  Pro  Gly  Ile  Cys  Val  Gly
 1              5                        10                      15

Phe  Phe  Thr  Arg  Tyr  Phe  Tyr  Asn  Ala  Gln  Thr  Lys  Gln  Cys  Glu  Arg
               20                        25                      30

Phe  Val  Tyr  Gly  Gly  Cys  Leu  Gly  Asn  Met  Asn  Asn  Phe  Glu  Thr  Leu
          35                        40                            45

Glu  Glu  Cys  Lys  Asn  Ile  Cys  Glu  Asp  Gly
          50                   55
```

( 2 ) INFORMATION FOR SEQ ID NO:86:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:86:

```
Lys  Pro  Asp  Phe  Cys  Phe  Leu  Glu  Glu  Asp  Pro  Gly  Pro  Cys  Val  Gly
 1              5                        10                      15

Phe  Phe  Gln  Arg  Tyr  Phe  Tyr  Asn  Ala  Gln  Thr  Lys  Gln  Cys  Glu  Arg
               20                        25                      30

Phe  Val  Tyr  Gly  Gly  Cys  Gln  Gly  Asn  Met  Asn  Asn  Phe  Glu  Thr  Leu
          35                        40                            45

Glu  Glu  Cys  Lys  Asn  Ile  Cys  Glu  Asp  Gly
          50                   55
```

( 2 ) INFORMATION FOR SEQ ID NO:87:

( i ) SEQUENCE CHARACTERISTICS:
        ( A ) LENGTH:56 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:87:

```
Asp  Phe  Cys  Phe  Leu  Glu  Glu  Asp  Pro  Gly  Pro  Cys  Val  Gly  Phe  Phe
 1              5                        10                      15

Thr  Arg  Tyr  Phe  Tyr  Asn  Asn  Gln  Thr  Lys  Gln  Cys  Glu  Arg  Phe  Val
               20                        25                      30

Tyr  Gly  Gly  Cys  Gln  Gly  Asn  Met  Asn  Asn  Phe  Glu  Thr  Leu  Glu  Glu
          35                        40                            45

Cys  Lys  Asn  Ile  Cys  Glu  Asp  Gly
          50                   55
```

( 2 ) INFORMATION FOR SEQ ID NO:88:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:88:

```
Gly  Pro  Ser  Trp  Cys  Leu  Thr  Pro  Ala  Asp  Arg  Gly  Leu  Cys  Val  Ala
 1              5                        10                      15

Asn  Phe  Asn  Arg  Phe  Tyr  Tyr  Asn  Ser  Val  Ile  Gly  Lys  Cys  Arg  Pro
               20                        25                      30
```

```
Phe Lys Tyr Ser Gly Cys Gly Gly Asn Glu Asn Asn Phe Thr Ser Lys
        35                  40                  45

Gln Glu Cys Leu Arg Ala Cys Lys Lys Gly
 50                  55
```

( 2 ) INFORMATION FOR SEQ ID NO:89:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:89:

```
Gly Pro Ser Trp Cys Leu Thr Pro Ala Asp Arg Gly Leu Cys Val Ala
 1               5                  10                  15

Phe Phe Asn Arg Phe Tyr Tyr Asn Ser Val Ile Gly Lys Cys Arg Pro
            20                  25                  30

Phe Lys Tyr Ser Gly Cys Gly Gly Asn Glu Asn Asn Phe Lys Ser Lys
        35                  40                  45

Gln Glu Cys Leu Arg Ala Cys Lys Lys Gly
 50                  55
```

( 2 ) INFORMATION FOR SEQ ID NO:90:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:90:

```
Gly Pro Ser Trp Cys Leu Thr Pro Ala Val Arg Gly Pro Cys Val Ala
 1               5                  10                  15

Phe Phe Asn Arg Phe Tyr Tyr Asn Ser Val Ile Gly Lys Cys Arg Pro
            20                  25                  30

Phe Val Tyr Gly Gly Cys Gly Gly Asn Glu Asn Asn Phe Lys Ser Lys
        35                  40                  45

Gln Glu Cys Leu Arg Ala Cys Lys Lys Gly
 50                  55
```

( 2 ) INFORMATION FOR SEQ ID NO:91:

( i ) SEQUENCE CHARACTERISTICS:
        ( A ) LENGTH:61 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:91:

```
Gln Asp His Pro Lys Phe Cys Tyr Leu Pro Ala Asp Pro Gly Arg Cys
 1               5                  10                  15

Lys Ala His Ile Pro Arg Phe Tyr Tyr Asp Ser Ala Ser Asn Lys Cys
            20                  25                  30

Asn Lys Phe Ile Tyr Gly Gly Cys Pro Gly Asn Ala Asn Asn Phe Lys
        35                  40                  45

Thr Trp Asp Glu Cys Arg Gln Thr Cys Gly Ala Ser Ala
```

( 2 ) INFORMATION FOR SEQ ID NO:92:

( i ) SEQUENCE CHARACTERISTICS:
        ( A ) LENGTH:65 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:92:

```
Arg Asp Arg Pro Lys Phe Cys Tyr Leu Pro Ala Asp Pro Gly Arg Cys
 1               5                  10                  15
Leu Ala Tyr Met Pro Arg Phe Tyr Tyr Asn Pro Ala Ser Asn Lys Cys
            20                  25                  30
Glu Lys Phe Ile Tyr Gly Gly Cys Arg Gly Asn Ala Asn Asn Phe Lys
        35                  40                  45
Thr Trp Asp Glu Cys Arg His Thr Cys Val Ala Ser Gly Ile Gln Pro
    50                  55                  60
Arg
65
```

( 2 ) INFORMATION FOR SEQ ID NO:93:

( i ) SEQUENCE CHARACTERISTICS:
        ( A ) LENGTH:61 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:93:

```
Phe Cys Tyr Leu Pro Asp Asp Pro Gly Val Cys Lys Ala His Ile Pro
 1               5                  10                  15
Arg Phe Tyr Tyr Asn Pro Ala Ser Asn Lys Cys Lys Asn Phe Ile Tyr
            20                  25                  30
Gly Gly Cys Gly Gly Asn Ala Asn Asn Phe Glu Thr Arg Ala Glu Cys
        35                  40                  45
Arg His Thr Cys Val Ala Ser Gly Lys Gly Gly Pro Arg
    50                  55                  60
```

( 2 ) INFORMATION FOR SEQ ID NO:94:

( i ) SEQUENCE CHARACTERISTICS:
        ( A ) LENGTH:57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:94:

```
Arg Pro Asp Phe Cys Glu Leu Pro Ala Glu Thr Gly Leu Cys Lys Ala
 1               5                  10                  15
Tyr Ile Arg Ser Phe His Tyr Asn Leu Ala Ala Gln Gln Cys Leu Gln
            20                  25                  30
Phe Ile Tyr Gly Gly Cys Gly Gly Asn Ala Asn Arg Phe Lys Thr Ile
        35                  40                  45
Asp Glu Cys Arg Arg Thr Cys Val Gly
    50                  55
```

( 2 ) INFORMATION FOR SEQ ID NO:95:

( i ) SEQUENCE CHARACTERISTICS:
        ( A ) LENGTH:60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:95:

```
His  Asp  Arg  Pro  Thr  Phe  Cys  Asn  Leu  Pro  Pro  Glu  Ser  Gly  Arg  Cys
 1                   5                        10                       15
Arg  Gly  His  Ile  Arg  Arg  Ile  Tyr  Tyr  Asn  Leu  Glu  Ser  Asn  Lys  Cys
              20                        25                       30
Lys  Val  Phe  Phe  Tyr  Gly  Gly  Cys  Gly  Gly  Asn  Ala  Asn  Asn  Phe  Glu
              35                        40                       45
Thr  Arg  Asp  Glu  Cys  Arg  Glu  Thr  Cys  Gly  Gly  Lys
              50                        55                       60
```

( 2 ) INFORMATION FOR SEQ ID NO:96:

( i ) SEQUENCE CHARACTERISTICS:
        ( A ) LENGTH:65 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:96:

```
Lys  Asn  Arg  Pro  Thr  Phe  Cys  Asn  Leu  Leu  Pro  Glu  Thr  Gly  Arg  Cys
 1                   5                        10                       15
Asn  Ala  Leu  Ile  Pro  Ala  Phe  Tyr  Tyr  Asn  Ser  His  Leu  His  Lys  Cys
              20                        25                       30
Gln  Lys  Phe  Asn  Tyr  Gly  Gly  Cys  Gly  Gly  Asn  Ala  Asn  Asn  Phe  Lys
              35                        40                       45
Thr  Ile  Asp  Glu  Cys  Gln  Arg  Thr  Cys  Ala  Ala  Lys  Tyr  Gly  Arg  Ser
              50                        55                       60
Ser
65
```

( 2 ) INFORMATION FOR SEQ ID NO:97:

( i ) SEQUENCE CHARACTERISTICS:
        ( A ) LENGTH:62 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:97:

```
Ile  Asn  Gly  Asp  Cys  Glu  Leu  Pro  Lys  Val  Val  Gly  Pro  Cys  Arg  Ala
 1                   5                        10                       15
Arg  Phe  Pro  Arg  Tyr  Tyr  Tyr  Asn  Ser  Ser  Ser  Lys  Arg  Cys  Glu  Lys
              20                        25                       30
Phe  Ile  Tyr  Gly  Gly  Cys  Gly  Gly  Asn  Ala  Asn  Asn  Phe  His  Thr  Leu
              35                        40                       45
Glu  Glu  Cys  Glu  Lys  Val  Cys  Gly  Val  Arg  Ser  Val  Gly  Arg
              50                        55                       60
```

( 2 ) INFORMATION FOR SEQ ID NO:98:

( i ) SEQUENCE CHARACTERISTICS:
        ( A ) LENGTH:62 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:98:

```
Glu Val Cys Ser Glu Gln Ala Glu Thr Gly Pro Cys Arg Ala Met Ile
 1               5                  10                 15

Ser Arg Trp Tyr Phe Asp Val Thr Glu Gly Lys Cys Ala Pro Phe Phe
            20                  25                 30

Tyr Gly Gly Cys Gly Gly Asn Arg Asn Asn Phe Asp Thr Glu Glu Tyr
        35                  40                  45

Cys Met Ala Val Cys Gly Ser Val Met Ser Gln Ser Leu Arg
    50                  55                  60
```

( 2 ) INFORMATION FOR SEQ ID NO:99:

( i ) SEQUENCE CHARACTERISTICS:
        ( A ) LENGTH:57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:99:

```
Arg Pro Arg Phe Cys Glu Leu Pro Ala Glu Thr Gly Leu Cys Lys Ala
 1               5                  10                 15

Arg Ile Arg Ser Phe His Tyr Asn Arg Ala Ala Gln Gln Cys Leu Glu
            20                  25                 30

Phe Ile Tyr Gly Gly Cys Gly Gly Asn Ala Asn Arg Phe Lys Thr Ile
        35                  40                  45

Asp Glu Cys His Arg Thr Cys Val Gly
    50                  55
```

( 2 ) INFORMATION FOR SEQ ID NO:100:

( i ) SEQUENCE CHARACTERISTICS:
        ( A ) LENGTH:69 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:100:

```
Ser Val Glu Glu Val Val Arg Glu Val Cys Ser Glu Gln Ala Glu Thr
 1               5                  10                 15

Gly Pro Cys Arg Ala Met Ile Ser Arg Trp Tyr Phe Asp Val Thr Glu
            20                  25                 30

Gly Lys Cys Val Pro Phe Phe Tyr Gly Gly Cys Gly Gly Asn Arg Asn
        35                  40                  45

Asn Phe Asp Thr Glu Glu Tyr Cys Met Ala Val Cys Gly Ser Val Ser
    50                  55                  60

Thr Gln Ser Leu Leu
65
```

( 2 ) INFORMATION FOR SEQ ID NO:101:

( i ) SEQUENCE CHARACTERISTICS:
  ( A ) LENGTH: 65 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:101:

```
Val Val Arg Glu Val Cys Ser Glu Gln Ala Glu Thr Gly Pro Cys Arg
 1               5                  10                  15

Ala Met Ile Ser Arg Trp Tyr Phe Asp Val Thr Glu Gly Lys Cys Ala
            20                  25                  30

Pro Phe Phe Tyr Gly Gly Cys Gly Gly Asn Arg Asn Asn Phe Asp Thr
            35                  40                  45

Glu Glu Tyr Cys Met Ala Val Cys Gly Ser Val Met Ser Gln Ser Leu
        50                  55                  60

Arg
65
```

( 2 ) INFORMATION FOR SEQ ID NO:102:

( i ) SEQUENCE CHARACTERISTICS:
    ( A ) LENGTH: 57 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:102:

```
Ala Ala Lys Tyr Cys Lys Leu Pro Leu Arg Ile Gly Pro Cys Lys Arg
 1               5                  10                  15

Lys Ile Pro Ser Phe Tyr Tyr Lys Trp Lys Ala Lys Gln Cys Leu Pro
            20                  25                  30

Phe Asp Tyr Ser Gly Cys Gly Gly Asn Ala Asn Arg Phe Lys Thr Ile
            35                  40                  45

Glu Glu Cys Arg Arg Thr Cys Val Gly
        50                  55
```

( 2 ) INFORMATION FOR SEQ ID NO:103:

( i ) SEQUENCE CHARACTERISTICS:
    ( A ) LENGTH: 57 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:103:

```
Ala Ala Lys Tyr Cys Lys Leu Pro Val Arg Tyr Gly Pro Cys Lys Lys
 1               5                  10                  15

Lys Phe Pro Ser Phe Tyr Tyr Asn Trp Lys Ala Lys Gln Cys Leu Pro
            20                  25                  30

Phe Asn Tyr Ser Gly Cys Gly Gly Asn Ala Asn Arg Phe Lys Thr Ile
            35                  40                  45

Glu Glu Cys Arg Arg Thr Cys Val Gly
        50                  55
```

( 2 ) INFORMATION FOR SEQ ID NO:104:

( i ) SEQUENCE CHARACTERISTICS:
   ( A ) LENGTH: 57 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:104:

```
Ala  Ala  Lys  Tyr  Cys  Lys  Leu  Pro  Val  Arg  Tyr  Gly  Pro  Cys  Lys  Lys
 1                  5                        10                      15

Lys  Ile  Pro  Ser  Phe  Tyr  Tyr  Lys  Trp  Lys  Ala  Lys  Gln  Cys  Leu  Pro
               20                       25                      30

Phe  Asp  Tyr  Ser  Gly  Cys  Gly  Gly  Asn  Ala  Asn  Arg  Phe  Lys  Thr  Ile
          35                       40                      45

Glu  Glu  Cys  Arg  Arg  Thr  Cys  Val  Gly
 50                            55
```

( 2 ) INFORMATION FOR SEQ ID NO:105:

( i ) SEQUENCE CHARACTERISTICS:
      ( A ) LENGTH: 58 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:105:

```
Arg  Pro  Asp  Phe  Cys  Leu  Glu  Pro  Pro  Tyr  Thr  Gly  Pro  Cys  Lys  Ala
 1                  5                        10                      15

Arg  Ile  Ile  Arg  Tyr  Phe  Tyr  Asn  Ala  Lys  Ala  Gly  Leu  Cys  Gln  Pro
               20                       25                      30

Phe  Val  Tyr  Gly  Gly  Cys  Arg  Ala  Lys  Arg  Asn  Asn  Phe  Lys  Ser  Ser
          35                       40                      45

Glu  Asp  Cys  Met  Arg  Thr  Cys  Gly  Gly  Ala
 50                            55
```

( 2 ) INFORMATION FOR SEQ ID NO:106:

( i ) SEQUENCE CHARACTERISTICS:
      ( A ) LENGTH: 59 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:106:

```
Leu  Gln  His  Arg  Thr  Phe  Cys  Lys  Leu  Pro  Ala  Glu  Pro  Gly  Pro  Cys
 1                  5                        10                      15

Lys  Ala  Ser  Ile  Pro  Ala  Phe  Tyr  Tyr  Asn  Trp  Ala  Ala  Lys  Lys  Cys
               20                       25                      30

Gln  Leu  Phe  His  Tyr  Gly  Gly  Cys  Lys  Gly  Asn  Ala  Asn  Arg  Phe  Ser
          35                       40                      45

Thr  Ile  Glu  Lys  Cys  Arg  His  Ala  Cys  Val  Gly
 50                            55
```

( 2 ) INFORMATION FOR SEQ ID NO:107:

( i ) SEQUENCE CHARACTERISTICS:
      ( A ) LENGTH: 69 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:107:

| Ser | Val | Glu | Glu | Val | Val | Arg | Glu | Val | Cys | Ser | Glu | Gln | Ala | Glu | Thr |
|---|---|---|---|---|---|---|---|---|---|---|---|---|---|---|---|
| 1 | | | | 5 | | | | | 10 | | | | | 15 | |

| Gly | Pro | Cys | Arg | Ala | Met | Ile | Ser | Arg | Trp | Tyr | Phe | Asp | Val | Thr | Glu |
|---|---|---|---|---|---|---|---|---|---|---|---|---|---|---|---|
| | | | 20 | | | | | 25 | | | | | 30 | | |

| Gly | Lys | Cys | Ala | Pro | Phe | Phe | Tyr | Gly | Gly | Cys | Gly | Gly | Asn | Arg | Asn |
|---|---|---|---|---|---|---|---|---|---|---|---|---|---|---|---|
| | | 35 | | | | | 40 | | | | | 45 | | | |

| Asn | Phe | Asp | Thr | Glu | Glu | Tyr | Cys | Met | Ala | Val | Cys | Gly | Ser | Val | Ser |
|---|---|---|---|---|---|---|---|---|---|---|---|---|---|---|---|
| | 50 | | | | | 55 | | | | | 60 | | | | |

| Ser | Gln | Ser | Leu | Leu |
|---|---|---|---|---|
| 65 | | | | |

( 2 ) INFORMATION FOR SEQ ID NO:108:

( i ) SEQUENCE CHARACTERISTICS:
( A ) LENGTH:57 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:108:

| Arg | Pro | Gly | Phe | Cys | Glu | Leu | Pro | Ala | Ala | Lys | Gly | Leu | Cys | Lys | Ala |
|---|---|---|---|---|---|---|---|---|---|---|---|---|---|---|---|
| 1 | | | | 5 | | | | | 10 | | | | | 15 | |

| His | Lys | Pro | Ala | Phe | Tyr | Tyr | Asn | Lys | Asp | Ser | His | Arg | Cys | Gln | Lys |
|---|---|---|---|---|---|---|---|---|---|---|---|---|---|---|---|
| | | | 20 | | | | | 25 | | | | | 30 | | |

| Phe | Ile | Tyr | Gly | Gly | Cys | Gly | Gly | Asn | Ala | Asn | Arg | Phe | Arg | Thr | Ile |
|---|---|---|---|---|---|---|---|---|---|---|---|---|---|---|---|
| | | | 35 | | | | | 40 | | | | | 45 | | |

| Asp | Glu | Cys | Asn | Arg | Thr | Cys | Val | Gly |
|---|---|---|---|---|---|---|---|---|
| | 50 | | | | | 55 | | |

( 2 ) INFORMATION FOR SEQ ID NO:109:

( i ) SEQUENCE CHARACTERISTICS:
( A ) LENGTH:60 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:109:

| His | Asp | Arg | Pro | Thr | Phe | Cys | Asn | Leu | Ala | Pro | Glu | Ser | Gly | Arg | Cys |
|---|---|---|---|---|---|---|---|---|---|---|---|---|---|---|---|
| 1 | | | | 5 | | | | | 10 | | | | | 15 | |

| Arg | Gly | His | Leu | Arg | Arg | Ile | Tyr | Tyr | Asn | Leu | Glu | Ser | Asn | Lys | Cys |
|---|---|---|---|---|---|---|---|---|---|---|---|---|---|---|---|
| | | | 20 | | | | | 25 | | | | | 30 | | |

| Lys | Val | Phe | Phe | Tyr | Gly | Gly | Cys | Gly | Gly | Asn | Ala | Asn | Asn | Phe | Glu |
|---|---|---|---|---|---|---|---|---|---|---|---|---|---|---|---|
| | | | 35 | | | | | 40 | | | | | 45 | | |

| Thr | Arg | Asp | Glu | Cys | Arg | Glu | Thr | Cys | Gly | Gly | Lys |
|---|---|---|---|---|---|---|---|---|---|---|---|
| | 50 | | | | | 55 | | | | | 60 |

( 2 ) INFORMATION FOR SEQ ID NO:110:

( i ) SEQUENCE CHARACTERISTICS:
( A ) LENGTH:58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:110:

| Arg | Pro | Asp | Phe | Cys | Leu | Glu | Pro | Pro | Tyr | Thr | Gly | Pro | Cys | Lys | Ala |
|1||||5|||||10|||||15||

| Arg | Met | Ile | Arg | Tyr | Phe | Tyr | Asn | Ala | Lys | Ala | Gly | Leu | Cys | Gln | Pro |
||||20|||||25|||||30|||

| Phe | Val | Tyr | Gly | Gly | Cys | Arg | Ala | Lys | Arg | Asn | Asn | Phe | Lys | Ser | Ala |
|||35|||||40|||||45||||

| Glu | Asp | Cys | Met | Arg | Thr | Cys | Gly | Gly | Ala |
|||50|||||55|||

( 2 ) INFORMATION FOR SEQ ID NO:111:

( i ) SEQUENCE CHARACTERISTICS:
       ( A ) LENGTH:59 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:111:

| Glx | Arg | Pro | Asp | Phe | Cys | Leu | Glu | Pro | Pro | Tyr | Thr | Gly | Pro | Cys | Lys |
|1||||5|||||10|||||15|

| Ala | Arg | Met | Ile | Arg | Tyr | Phe | Tyr | Asn | Ala | Lys | Ala | Gly | Leu | Cys | Gln |
||||20|||||25|||||30||

| Pro | Phe | Val | Tyr | Gly | Gly | Cys | Arg | Ala | Lys | Ser | Asn | Asn | Phe | Lys | Ser |
|||35|||||40|||||45|||

| Ala | Glu | Asp | Cys | Met | Arg | Thr | Cys | Gly | Gly | Ala |
|||50|||||55|||

( 2 ) INFORMATION FOR SEQ ID NO:112:

( i ) SEQUENCE CHARACTERISTICS:
       ( A ) LENGTH:60 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:112:

| Thr | Glu | Arg | Pro | Asp | Phe | Cys | Leu | Glu | Pro | Pro | Tyr | Thr | Gly | Pro | Cys |
|1||||5|||||10|||||15|

| Lys | Ala | Ala | Met | Ile | Arg | Tyr | Phe | Tyr | Asn | Ala | Lys | Ala | Gly | Phe | Cys |
||||20|||||25|||||30|

| Glu | Thr | Phe | Val | Tyr | Gly | Gly | Cys | Arg | Ala | Lys | Ser | Asn | Asn | Phe | Lys |
|||35|||||40|||||45||

| Ser | Ala | Glu | Asp | Cys | Met | Arg | Thr | Cys | Gly | Gly | Ala |
|||50|||||55||||60|

( 2 ) INFORMATION FOR SEQ ID NO:113:

( i ) SEQUENCE CHARACTERISTICS:
       ( A ) LENGTH:66 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:113:

| Gln | Gly | Asp | Lys | Arg | Asp | Ile | Cys | Arg | Leu | Pro | Pro | Glu | Gln | Gly | Pro |
|1||||5|||||10|||||15|

Cys Lys Gly Arg Ile Pro Arg Tyr Phe Tyr Asn Pro Ala Ser Arg Met
              20                  25                  30

Cys Glu Ser Phe Ile Tyr Gly Gly Cys Lys Gly Asn Lys Asn Asn Phe
              35                  40                  45

Lys Thr Lys Ala Glu Cys Val Arg Ala Cys Arg Pro Pro Glu Arg Pro
       50                  55                  60

Gly Val
 65

( 2 ) INFORMATION FOR SEQ ID NO:114:

( i ) SEQUENCE CHARACTERISTICS:
        ( A ) LENGTH:69 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:114:

Gln Ala Lys Ala Gln Arg Pro Asp Phe Cys Leu Glu Pro Pro Tyr Thr
 1                5                  10                  15

Gly Pro Cys Lys Ala Arg Ile Ile Arg Tyr Phe Tyr Asn Ala Lys Ala
              20                  25                  30

Gly Leu Cys Gln Thr Phe Val Tyr Gly Gly Cys Arg Ala Lys Arg Asn
              35                  40                  45

Asn Phe Lys Ser Ala Glu Asp Cys Met Arg Thr Cys Gly Gly Ala Ile
       50                  55                  60

Gly Pro Trp Glu Asn
 65

( 2 ) INFORMATION FOR SEQ ID NO:115:

( i ) SEQUENCE CHARACTERISTICS:
        ( A ) LENGTH:69 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:115:

Gln Ala Lys Ala Gln Arg Pro Asp Phe Cys Leu Glu Pro Pro Tyr Thr
 1                5                  10                  15

Gly Pro Cys Lys Ala Lys Met Ile Arg Tyr Phe Tyr Asn Ala Lys Ala
              20                  25                  30

Gly Phe Cys Glu Thr Phe Val Tyr Gly Gly Cys Lys Ala Lys Ser Asn
              35                  40                  45

Asn Phe Arg Ser Ala Glu Asp Cys Met Arg Thr Cys Gly Gly Ala Ile
       50                  55                  60

Gly Pro Arg Glu Asn
 65

( 2 ) INFORMATION FOR SEQ ID NO:116:

( i ) SEQUENCE CHARACTERISTICS:
        ( A ) LENGTH:58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:116:

| Gln | Gly | Arg | Pro | Ser | Phe | Cys | Asn | Leu | Pro | Ala | Glu | Thr | Gly | Pro | Cys |
|---|---|---|---|---|---|---|---|---|---|---|---|---|---|---|---|
| 1 | | | | 5 | | | | | 10 | | | | | 15 | |

| Lys | Ala | Ser | Phe | Arg | Gln | Tyr | Tyr | Tyr | Asn | Ser | Lys | Ser | Gly | Gly | Cys |
|---|---|---|---|---|---|---|---|---|---|---|---|---|---|---|---|
| | | | 20 | | | | | 25 | | | | | 30 | | |

| Gln | Gln | Phe | Ile | Tyr | Gly | Gly | Cys | Arg | Gly | Asn | Gln | Asn | Arg | Phe | Asp |
|---|---|---|---|---|---|---|---|---|---|---|---|---|---|---|---|
| | | 35 | | | | | 40 | | | | | 45 | | | |

| Thr | Thr | Gln | Gln | Cys | Gln | Gly | Val | Cys | Val |
|---|---|---|---|---|---|---|---|---|---|
| | 50 | | | | | 55 | | | |

( 2 ) INFORMATION FOR SEQ ID NO:117:

( i ) SEQUENCE CHARACTERISTICS:
        ( A ) LENGTH:57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:117:

| Arg | Pro | Tyr | Ala | Cys | Glu | Leu | Ile | Val | Ala | Ala | Gly | Pro | Cys | Met | Phe |
|---|---|---|---|---|---|---|---|---|---|---|---|---|---|---|---|
| 1 | | | | 5 | | | | | 10 | | | | | 15 | |

| Phe | Ile | Ser | Ala | Phe | Tyr | Tyr | Ser | Lys | Gly | Ala | Asn | Lys | Cys | Tyr | Pro |
|---|---|---|---|---|---|---|---|---|---|---|---|---|---|---|---|
| | | | 20 | | | | | 25 | | | | | 30 | | |

| Phe | Thr | Tyr | Ser | Gly | Cys | Arg | Gly | Asn | Ala | Asn | Arg | Phe | Lys | Thr | Ile |
|---|---|---|---|---|---|---|---|---|---|---|---|---|---|---|---|
| | | 35 | | | | | 40 | | | | | 45 | | | |

| Glu | Glu | Cys | Arg | Arg | Thr | Cys | Val | Val |
|---|---|---|---|---|---|---|---|---|
| | 50 | | | | | 55 | | |

( 2 ) INFORMATION FOR SEQ ID NO:118:

( i ) SEQUENCE CHARACTERISTICS:
        ( A ) LENGTH:59 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:118:

| Gln | Pro | Arg | Arg | Lys | Leu | Cys | Ile | Leu | His | Arg | Asn | Pro | Gly | Arg | Cys |
|---|---|---|---|---|---|---|---|---|---|---|---|---|---|---|---|
| 1 | | | | 5 | | | | | 10 | | | | | 15 | |

| Tyr | Asp | Lys | Ile | Pro | Ala | Phe | Tyr | Tyr | Asn | Gln | Lys | Lys | Lys | Gln | Cys |
|---|---|---|---|---|---|---|---|---|---|---|---|---|---|---|---|
| | | | 20 | | | | | 25 | | | | | 30 | | |

| Glu | Arg | Phe | Asp | Trp | Ser | Gly | Cys | Gly | Gly | Asn | Ser | Asn | Arg | Phe | Lys |
|---|---|---|---|---|---|---|---|---|---|---|---|---|---|---|---|
| | | 35 | | | | | 40 | | | | | 45 | | | |

| Thr | Ile | Glu | Glu | Cys | Arg | Arg | Thr | Cys | Ile | Gly |
|---|---|---|---|---|---|---|---|---|---|---|
| | 50 | | | | | 55 | | | | |

( 2 ) INFORMATION FOR SEQ ID NO:119:

( i ) SEQUENCE CHARACTERISTICS:
        ( A ) LENGTH:59 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:119:

| Gln | Pro | Arg | Arg | Lys | Leu | Cys | Ile | Leu | His | Arg | Asn | Pro | Gly | Arg | Cys |
|---|---|---|---|---|---|---|---|---|---|---|---|---|---|---|---|
| 1 | | | | 5 | | | | | 10 | | | | | 15 | |

```
Tyr Asp Lys Ile Pro Ala Phe Tyr Tyr Asn Gln Lys Lys Lys Gln Cys
            20                  25                  30

Glu Gly Phe Thr Trp Ser Gly Cys Gly Gly Asn Ser Asn Arg Phe Lys
            35                  40                  45

Thr Ile Glu Glu Cys Arg Arg Thr Cys Ile Gly
            50                  55
```

( 2 ) INFORMATION FOR SEQ ID NO:120:

( i ) SEQUENCE CHARACTERISTICS:
        ( A ) LENGTH:64 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:120:

```
Glu Val Val Arg Glu Val Cys Ser Glu Gln Ala Glu Thr Gly Pro Cys
 1               5                  10                  15

Arg Ala Met Ile Ser Arg Trp Tyr Tyr Asp Val Thr Glu Ser Lys Cys
            20                  25                  30

Ala Gln Phe Ile Tyr Gly Gly Cys Gly Gly Asn Arg Asn Asn Phe Glu
            35                  40                  45

Ser Asp Asp Tyr Cys Met Ala Val Cys Gly Ser Val Ile Pro Ala Thr
            50                  55                  60
```

( 2 ) INFORMATION FOR SEQ ID NO:121:

( i ) SEQUENCE CHARACTERISTICS:
        ( A ) LENGTH:60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:121:

```
Gln Pro Leu Arg Lys Leu Cys Ile Leu His Arg Asn Pro Gly Arg Cys
 1               5                  10                  15

Tyr Gln Lys Ile Pro Ala Phe Tyr Tyr Asn Gln Lys Lys Lys Gln Cys
            20                  25                  30

Glx Gly Phe Thr Trp Ser Gly Cys Gly Gly Asn Ser Asn Arg Phe Lys
            35                  40                  45

Thr Ile Glu Glu Cys Arg Arg Thr Cys Ile Arg Lys
            50                  55                  60
```

( 2 ) INFORMATION FOR SEQ ID NO:122:

( i ) SEQUENCE CHARACTERISTICS:
        ( A ) LENGTH:60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:122:

```
Trp Gln Pro Pro Trp Tyr Cys Lys Glu Pro Val Arg Ile Gly Ser Cys
 1               5                  10                  15

Lys Lys Gln Phe Ser Ser Phe Tyr Phe Lys Trp Thr Ala Lys Lys Cys
            20                  25                  30

Leu Pro Phe Leu Phe Ser Gly Cys Gly Gly Asn Ala Asn Arg Phe Gln
            35                  40                  45
```

```
Thr  Ile  Gly  Glu  Cys  Arg  Lys  Lys  Cys  Leu  Gly  Lys
      50                  55                       60
```

( 2 ) INFORMATION FOR SEQ ID NO:123:

( i ) SEQUENCE CHARACTERISTICS:
        ( A ) LENGTH:67 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:123:

```
Phe  Gln  Thr  Pro  Pro  Asp  Leu  Cys  Gln  Leu  Pro  Gln  Ala  Arg  Gly  Pro
 1                    5                     10                      15

Cys  Lys  Ala  Ala  Leu  Leu  Arg  Tyr  Phe  Tyr  Asn  Ser  Thr  Ser  Asn  Ala
              20                      25                      30

Cys  Glu  Pro  Phe  Thr  Tyr  Gly  Gly  Cys  Gln  Gly  Asn  Asn  Asn  Asn  Phe
         35                      40                          45

Glu  Thr  Thr  Glu  Met  Cys  Leu  Arg  Ile  Cys  Glu  Pro  Pro  Gln  Gln  Thr
      50                  55                       60

Asp  Lys  Ser
 65
```

( 2 ) INFORMATION FOR SEQ ID NO:124:

( i ) SEQUENCE CHARACTERISTICS:
        ( A ) LENGTH:69 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:124:

```
Thr  Phe  Gln  Lys  Gly  Lys  Pro  Asp  Phe  Cys  Phe  Leu  Glu  Glu  Asp  Pro
 1                    5                     10                      15

Gly  Ile  Cys  Arg  Gly  Tyr  Ile  Thr  Arg  Tyr  Phe  Tyr  Asn  Asn  Gln  Ser
              20                      25                      30

Lys  Gln  Cys  Glu  Arg  Phe  Lys  Tyr  Gly  Gly  Cys  Leu  Gly  Asn  Leu  Asn
         35                      40                          45

Asn  Phe  Glu  Ser  Leu  Glu  Glu  Cys  Lys  Asn  Thr  Cys  Glu  Asn  Pro  Thr
      50                  55                       60

Ser  Asp  Phe  Gln  Val
 65
```

( 2 ) INFORMATION FOR SEQ ID NO:125:

( i ) SEQUENCE CHARACTERISTICS:
        ( A ) LENGTH:69 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:125:

```
Arg  Trp  Ala  Phe  His  Gly  Pro  Ser  Trp  Cys  Leu  Pro  Pro  Ala  Asp  Arg
 1                    5                     10                      15

Gly  Leu  Cys  Gln  Ala  Asn  Glu  Ile  Arg  Phe  Phe  Tyr  Asn  Ala  Ile  Ile
              20                      25                      30

Gly  Lys  Cys  Arg  Pro  Phe  Lys  Tyr  Ser  Gly  Cys  Gly  Gly  Asn  Glu  Asn
```

```
                       35                       40                       45
Asn  Phe  Thr  Ser  Lys  Lys  Ala  Cys  Ile  Thr  Ala  Cys  Lys  Lys  Gly  Phe
          50                       55                       60

Ile  Pro  Lys  Ser  Ile
 65
```

( 2 ) INFORMATION FOR SEQ ID NO:126:

( i ) SEQUENCE CHARACTERISTICS:
        ( A ) LENGTH:57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:126:

```
Val  Asp  Lys  Ser  Ala  Cys  Leu  Gln  Pro  Lys  Glu  Val  Gly  Pro  Cys  Arg
 1                   5                        10                      15

Lys  Ser  Asp  Phe  Val  Phe  Phe  Tyr  Asn  Ala  Asp  Thr  Lys  Ala  Cys  Glu
               20                       25                      30

Glu  Phe  Leu  Tyr  Gly  Gly  Cys  Arg  Gly  Asn  Asp  Asn  Arg  Phe  Asn  Thr
          35                       40                       45

Lys  Glu  Glu  Cys  Glu  Lys  Leu  Cys  Leu
          50                       55
```

( 2 ) INFORMATION FOR SEQ ID NO:127:

( i ) SEQUENCE CHARACTERISTICS:
        ( A ) LENGTH:65 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:127:

```
Arg  Thr  Val  Gln  Ala  Cys  Asn  Leu  Pro  Ile  Val  Arg  Gly  Pro  Cys  Arg
 1                   5                        10                      15

Ala  Gly  Ile  Glu  Leu  Trp  Ala  Phe  Asp  Ala  Val  Lys  Gly  Lys  Cys  Val
               20                       25                      30

Arg  Phe  Ile  Tyr  Gly  Gly  Cys  Asn  Gly  Asn  Gly  Asn  Gln  Phe  Tyr  Ser
          35                       40                       45

Gln  Lys  Glu  Cys  Lys  Glu  Tyr  Cys  Gly  Ile  Pro  Gly  Glu  Ala  Asp  Glu
          50                       55                       60

Glu
 65
```

( 2 ) INFORMATION FOR SEQ ID NO:128:

( i ) SEQUENCE CHARACTERISTICS:
        ( A ) LENGTH:60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:128:

```
Lys  Glu  Asp  Ser  Cys  Gln  Leu  Gly  Tyr  Ser  Gln  Gly  Pro  Cys  Leu  Gly
 1                   5                        10                      15

Met  Phe  Lys  Arg  Tyr  Phe  Tyr  Asn  Gly  Thr  Ser  Met  Ala  Cys  Glu  Thr
               20                       25                      30
```

```
Phe  Tyr  Tyr  Gly  Gly  Cys  Met  Gly  Asn  Gly  Asn  Asn  Phe  Pro  Ser  Glu
          35                      40                      45

Lys  Glu  Cys  Leu  Gln  Thr  Cys  Arg  Thr  Val  Gln  Ala
     50                      55                      60
```

( 2 ) INFORMATION FOR SEQ ID NO:129:

( i ) SEQUENCE CHARACTERISTICS:
        ( A ) LENGTH:60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:129:

```
Lys  Glu  Asp  Ser  Cys  Gln  Leu  Gly  Tyr  Ser  Gln  Gly  Pro  Cys  Leu  Gly
 1                  5                      10                      15

Met  Ile  Lys  Arg  Tyr  Phe  Tyr  Asn  Gly  Ser  Ser  Met  Ala  Cys  Glu  Thr
          20                      25                      30

Phe  His  Tyr  Gly  Gly  Cys  Met  Gly  Asn  Gly  Asn  Asn  Phe  Val  Ser  Gln
          35                      40                      45

Lys  Glu  Cys  Leu  Gln  Thr  Cys  Arg  Thr  Val  Ser  Ala
     50                      55                      60
```

( 2 ) INFORMATION FOR SEQ ID NO:130:

( i ) SEQUENCE CHARACTERISTICS:
        ( A ) LENGTH:56 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:130:

```
Lys  Glu  Asp  Ser  Cys  Glu  Leu  Gly  Tyr  Ser  Gln  Gly  Pro  Cys  Leu  Gly
 1                  5                      10                      15

Met  Ile  Lys  Arg  Tyr  Phe  Tyr  Asn  Gly  Ser  Ser  Met  Ala  Cys  Glu  Thr
          20                      25                      30

Phe  His  Tyr  Gly  Gly  Cys  Met  Gly  Asn  Gly  Asn  Asn  Phe  Val  Ser  Gln
          35                      40                      45

Lys  Glu  Cys  Leu  Gln  Thr  Cys  Arg
     50                      55
```

( 2 ) INFORMATION FOR SEQ ID NO:131:

( i ) SEQUENCE CHARACTERISTICS:
        ( A ) LENGTH:69 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:131:

```
Pro  Leu  Gln  Lys  Pro  Thr  His  Ser  Phe  Cys  Ala  Met  Lys  Val  Asp  Asp
 1                  5                      10                      15

Gly  Pro  Cys  Arg  Ala  Tyr  Ile  Lys  Arg  Phe  Phe  Phe  Asn  Ile  Leu  Thr
          20                      25                      30

His  Gln  Cys  Glu  Glu  Phe  Ile  Tyr  Gly  Gly  Cys  Glu  Gly  Asn  Glu  Asn
          35                      40                      45

Arg  Phe  Glu  Ser  Leu  Glu  Glu  Cys  Lys  Glu  Lys  Cys  Ala  Arg  Asp  Tyr
```

5 0                                  5 5                                  6 0

Pro  Lys  Met  Thr  Thr
     6 5

( 2 ) INFORMATION FOR SEQ ID NO:132:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:132:

Lys  Glu  Asp  Ser  Cys  Gln  Leu  Asp  His  Ala  Gln  Gly  Pro  Cys  Leu  Gly
 1                    5                        1 0                    1 5

Met  Ile  Ser  Arg  Tyr  Phe  Tyr  Asn  Gly  Thr  Ser  Met  Ala  Cys  Glu  Thr
               2 0                        2 5                    3 0

Phe  Gln  Tyr  Gly  Gly  Cys  Leu  Gly  Asn  Gly  Asn  Asn  Phe  Ala  Ser  Gln
          3 5                        4 0                        4 5

Lys  Glu  Cys  Leu  Gln  Thr  Cys  Arg  Thr  Val  Ala  Ala
          5 0                        5 5                        6 0

( 2 ) INFORMATION FOR SEQ ID NO:133:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:133:

Arg  Thr  Val  Ala  Ala  Cys  Asn  Leu  Pro  Ile  Val  Gln  Gly  Pro  Cys  Arg
 1                    5                        1 0                    1 5

Ala  Phe  Ile  Arg  Leu  Trp  Ala  Phe  Asp  Ala  Ala  Gln  Gly  Lys  Cys  Val
               2 0                        2 5                    3 0

Leu  Phe  Thr  Tyr  Gly  Gly  Cys  Arg  Gly  Asn  Gly  Asn  Lys  Phe  Tyr  Ser
          3 5                        4 0                        4 5

Gln  Lys  Glu  Cys  Lys  Glu  Tyr  Cys  Gly  Ile  Pro  Gly  Asp  Gly  Asp  Glu
          5 0                        5 5                        6 0

Glu
 6 5

( 2 ) INFORMATION FOR SEQ ID NO:134:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:134:

Xaa  Xaa  Xaa  Xaa  Cys  Xaa  Xaa  Xaa  Xaa  Xaa  Xaa  Gly  Pro  Cys  Xaa  Xaa
 1                    5                        1 0                    1 5

Xaa  Phe  Xaa  Arg  Xaa  Xaa  Xaa  Xaa  Xaa  Xaa  Xaa  Xaa  Xaa  Cys  Xaa  Xaa
               2 0                        2 5                    3 0

Phe  Xaa  Tyr  Gly  Gly  Cys  Xaa  Xaa  Xaa  Gly  Asn  Xaa  Phe  Xaa  Xaa  Xaa
          3 5                        4 0                        4 5

```
Xaa  Xaa  Cys  Xaa  Xaa  Xaa  Cys  Xaa  Xaa  Xaa
     50                      55
```

( 2 ) INFORMATION FOR SEQ ID NO:135:

( i ) SEQUENCE CHARACTERISTICS:
        ( A ) LENGTH:249 bases
        ( B ) TYPE: nucleic acid
        ( C ) STRANDEDNESS: single
        ( D ) TOPOLOGY: linear ( i i ) MOLECULE TYPE:other nucleic acid
        ( A ) DESCRIPTION:synthetic DNA fragment ( x i ) SEQUENCE DESCRIPTION: SEQ ID NO:135:

```
ATGAAGAAGC  TTCTCTTCGC  CATTCCTCTG  GTGGTACCTT  TCTATTCCGG        50

CGCCAAGCCT  GACTTCTGCT  TCCTCGAGGA  GGATCCCGGG  ATTTGCCGCG       100

GTTATATTAC  GCGTTATTTC  TATAATAACC  AGACTAAGCA  ATGTGAGCGG       150

TTCAAGTATG  GTGGTTGCCT  AGGTAATATG  AACAACTTCG  AGACTCTAGA       200

AGAGTGTAAG  AACATATGTG  AGGATGGTGG  TGCTGAGACT  GTTGAGTCT        249
```

( 2 ) INFORMATION FOR SEQ ID NO:136:

( i ) SEQUENCE CHARACTERISTICS:
        ( A ) LENGTH:83 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:136:

```
Met  Lys  Lys  Leu  Leu  Phe  Ala  Ile  Pro  Leu  Val  Val  Pro  Phe  Tyr  Ser
 1              5                        10                           15

Gly  Ala  Lys  Pro  Asp  Phe  Cys  Phe  Leu  Glu  Glu  Asp  Pro  Gly  Ile  Cys
               20                  25                        30

Arg  Gly  Tyr  Ile  Thr  Arg  Tyr  Phe  Tyr  Asn  Asn  Gln  Thr  Lys  Gln  Cys
          35                       40                       45

Glu  Arg  Phe  Lys  Tyr  Gly  Gly  Cys  Leu  Gly  Asn  Met  Asn  Asn  Phe  Glu
     50                       55                       60

Thr  Leu  Glu  Glu  Cys  Lys  Asn  Ile  Cys  Glu  Asp  Gly  Gly  Ala  Glu  Thr
65                       70                       75                        80

Val  Glu  Ser
```

( 2 ) INFORMATION FOR SEQ ID NO:137:

( i ) SEQUENCE CHARACTERISTICS:
        ( A ) LENGTH:189 bases
        ( B ) TYPE: nucleic acid
        ( C ) STRANDEDNESS: single
        ( D ) TOPOLOGY: linear ( i i ) MOLECULE TYPE:other nucleic acid
        ( A ) DESCRIPTION:synthetic DNA fragment ( x i ) SEQUENCE DESCRIPTION: SEQ ID NO:137:

```
GCGGCCGAGA  TGCATTCCTT  CTGCGCTTTC  AAAGCTGATG  ACGGTCCGTG        50

TAAAGCTATC  ATGAAACGTT  TCTTCTTCAA  CATTTTCACG  CGTCAGTGCG       100

AGGAATTCAT  TTACGGTGGT  TGTGAAGGTA  ACCAGAACCG  GTTCGAATCT       150

CTAGAGGAAT  GTAAGAAGAT  GTGCACTCGT  GACGGCGCC                    189
```

(2) INFORMATION FOR SEQ ID NO:138:

(i) SEQUENCE CHARACTERISTICS:
        (A) LENGTH:63 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:138:

```
Ala Ala Glu Met His Ser Phe Cys Ala Phe Lys Ala Asp Asp Gly Pro
 1               5                  10                 15
Cys Lys Ala Ile Met Lys Arg Phe Phe Phe Asn Ile Phe Thr Arg Gln
            20                  25                 30
Cys Glu Glu Phe Ile Tyr Gly Gly Cys Glu Gly Asn Gln Asn Arg Phe
            35              40                 45
Glu Ser Leu Glu Glu Cys Lys Lys Met Cys Thr Arg Asp Gly Ala
        50              55              60
```

(2) INFORMATION FOR SEQ ID NO:139:

(i) SEQUENCE CHARACTERISTICS:
        (A) LENGTH:189 bases
        (B) TYPE: nucleic acid
        (C) STRANDEDNESS: single
        (D) TOPOLOGY: linear (ii) MOLECULE TYPE:other nucleic acid
        (A) DESCRIPTION:synthetic DNA fragment (xi) SEQUENCE DESCRIPTION: SEQ ID NO:139:

```
GCGGCCGAGA TGCATTCCTT CTGCGCTTTC AAAGCTNRTR VSGGTCNTTG         50
TRTTGSTNTC TTCMNSCGTT DSTTCTTCAA CATTTTCACG CGTCAGTGCS        100
WGVHATTCVH ATACGGTGGT TGTVHGGSTA ACSRGAACCG GTTCGAATCT        150
CTAGAGGAAT GTAAGAAGAT GTGCACTCGT GACGGCGCC                    189
```

(2) INFORMATION FOR SEQ ID NO:140:

(i) SEQUENCE CHARACTERISTICS:
        (A) LENGTH:63 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:140:

```
Ala Ala Glu Met His Ser Phe Cys Ala Phe Lys Ala Xaa Xaa Gly Xaa
 1               5                  10                 15
Cys Xaa Xaa Xaa Phe Xaa Arg Xaa Phe Phe Asn Ile Phe Thr Arg Gln
            20                  25                 30
Cys Xaa Xaa Phe Xaa Tyr Gly Gly Cys Xaa Xaa Asn Xaa Asn Arg Phe
            35              40                 45
Glu Ser Leu Glu Glu Cys Lys Lys Met Cys Thr Arg Asp Gly Ala
        50              55              60
```

(2) INFORMATION FOR SEQ ID NO:141:

(i) SEQUENCE CHARACTERISTICS:
        (A) LENGTH:201 bases
        (B) TYPE: nucleic acid
        (C) STRANDEDNESS: single
        (D) TOPOLOGY: linear ( i i ) MOLECULE TYPE:other nucleic acid
    ( A ) DESCRIPTION:synthetic DNA fragment ( x i ) SEQUENCE DESCRIPTION: SEQ ID NO:141:

| | | | | | |
|---|---|---|---|---|---|
| GGCGCCAAGC | CTGACTTCTG | CTTCCTCGAG | GAGNRTVVSG | GGMNTTGCRT | 50 |
| TGSTNWTTTT | MNSCGTTDST | TCTATAATAA | CCAGGCTAAG | CAATGTSWGV | 100 |
| NATTCVHATA | TGGTGGTTGC | VHGGSTAATV | BGAACAACTT | CGAGACTCTA | 150 |
| GAAGAGTGTA | AGAACATATG | TGAGGATGGT | GGTGCTGAGA | CTGTTGAGTC | 200 |
| T | | | | | 201 |

( 2 ) INFORMATION FOR SEQ ID NO:142:

( i ) SEQUENCE CHARACTERISTICS:
    ( A ) LENGTH:67 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:142:

| | | | | | | | | | | | | | | |
|---|---|---|---|---|---|---|---|---|---|---|---|---|---|---|
| Gly | Ala | Lys | Pro | Asp | Phe | Cys | Phe | Leu | Glu | Glu | Xaa | Xaa | Gly | Xaa | Cys |
| 1 | | | | 5 | | | | | 10 | | | | | 15 | |
| Xaa | Xaa | Xaa | Phe | Xaa | Arg | Xaa | Phe | Tyr | Asn | Asn | Gln | Ala | Lys | Gln | Cys |
| | | | 20 | | | | | 25 | | | | | 30 | | |
| Xaa | Arg | Phe | Xaa | Tyr | Gly | Gly | Cys | Xaa | Xaa | Asn | Xaa | Asn | Asn | Phe | Glu |
| | | 35 | | | | | 40 | | | | | 45 | | | |
| Thr | Leu | Glu | Glu | Cys | Lys | Asn | Ile | Cys | Glu | Asp | Gly | Gly | Ala | Glu | Thr |
| | 50 | | | | | 55 | | | | | 60 | | | | |
| Val | Glu | Ser | | | | | | | | | | | | | |
| 65 | | | | | | | | | | | | | | | |

( 2 ) INFORMATION FOR SEQ ID NO:143:

( i ) SEQUENCE CHARACTERISTICS:
    ( A ) LENGTH:234 bases
    ( B ) TYPE: nucleic acid
    ( C ) STRANDEDNESS: single
    ( D ) TOPOLOGY: linear ( i i ) MOLECULE TYPE:other nucleic acid
    ( A ) DESCRIPTION:synthetic DNA fragment ( x i ) SEQUENCE DESCRIPTION: SEQ ID NO:143:

| | | | | | |
|---|---|---|---|---|---|
| ATGAAGAAGC | TTCTCTTCGC | CATTCCTCTG | GTGGTACCTT | TCTATTCCGG | 50 |
| TGCTGGGCCC | TCTTGGTGCC | TTACGCCGGC | NGACCGCGGT | CTCTGCAGAG | 100 |
| CTAATGAGAA | TCGTTTCTAC | TACAACTCGA | GTATTGGTAA | GTGCAGACCT | 150 |
| TTTAAATATT | CTGGTTGTGG | TGGCAATGAG | AATAATTTCG | AATCTAAGCA | 200 |
| AGAGTGCCTG | CGCGCATGCA | AGAAGGGTGG | CGCC | | 234 |

( 2 ) INFORMATION FOR SEQ ID NO:144:

( i ) SEQUENCE CHARACTERISTICS:
    ( A ) LENGTH:78 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:144:

Met Lys Lys Leu Leu Phe Ala Ile Pro Leu Val Val Pro Phe Tyr Ser
1               5               10              15

Gly Ala Gly Pro Ser Trp Cys Leu Thr Pro Ala Asp Arg Gly Leu Cys
            20              25              30

Arg Ala Asn Glu Asn Arg Phe Tyr Tyr Asn Ser Ser Ile Gly Lys Cys
            35              40              45

Arg Pro Phe Lys Tyr Ser Gly Cys Gly Gly Asn Glu Asn Asn Phe Glu
        50              55              60

Ser Lys Gln Glu Cys Leu Arg Ala Cys Lys Lys Gly Gly Ala
65              70              75

( 2 ) INFORMATION FOR SEQ ID NO:145:

( i ) SEQUENCE CHARACTERISTICS:
        ( A ) LENGTH:180 bases
        ( B ) TYPE: nucleic acid
        ( C ) STRANDEDNESS: single
        ( D ) TOPOLOGY: linear ( i i ) MOLECULE TYPE:other nucleic acid
        ( A ) DESCRIPTION:synthetic DNA fragment ( x i ) SEQUENCE DESCRIPTION: SEQ ID NO:145:

GGGCCCTCTT GGTGCCTTAC GCCGGCNNRT VVSGGTMNTT GCRTTGSTNW      50

TTTTMNSCGT TDSTACTACA ACTCGAGTAT TGGTAAGTGC SDGVNATTTV     100

HATATRGTGG TTGTVNGGST AATVBGAATA ATTTCGAATC TAAGCAAGAG     150

TGCCTGCGCG CATGCAAGAA GGGTGGCGCC                          180

( 2 ) INFORMATION FOR SEQ ID NO:146:

( i ) SEQUENCE CHARACTERISTICS:
        ( A ) LENGTH:60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:146:

Gly Pro Ser Trp Cys Leu Thr Pro Ala Xaa Xaa Gly Xaa Cys Xaa Xaa
1               5               10              15

Xaa Phe Xaa Arg Xaa Tyr Tyr Asn Ser Ser Ile Gly Lys Cys Xaa Xaa
            20              25              30

Phe Xaa Tyr Xaa Gly Cys Xaa Xaa Asn Xaa Asn Asn Phe Glu Ser Lys
            35              40              45

Gln Glu Cys Leu Arg Ala Cys Lys Lys Gly Gly Ala
        50              55              60

( 2 ) INFORMATION FOR SEQ ID NO:147:

( i ) SEQUENCE CHARACTERISTICS:
        ( A ) LENGTH:61 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:147:

Ile Ala Ala Cys Asn Leu Pro Ile Val Gln Gly Pro Cys Arg Ala Gly
1               5               10              15

Ala Glu Leu Leu Ala Phe Asp Ala Ala Gln Gly Lys Cys Ile Gln Phe

```
                            20                          25                              30
Ile  Tyr  Gly  Gly  Cys  Lys  Gly  Asn  Asn  Asn  Lys  Phe  Tyr  Ser  Glu  Pro
               35                          40                     45

Lys  Cys  Lys  Trp  Tyr  Cys  Gly  Val  Pro  Gly  Asp  Gly  Tyr
     50                         55                    60
```

( 2 ) INFORMATION FOR SEQ ID NO:148:

( i ) SEQUENCE CHARACTERISTICS:
        ( A ) LENGTH:61 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:148:

```
Ile  Ala  Ala  Cys  Asn  Leu  Pro  Ile  Val  Gln  Gly  Pro  Cys  Arg  Ala  Phe
1                   5                        10                         15

Ala  Glu  Leu  Leu  Ala  Phe  Asp  Ala  Ala  Gln  Gly  Lys  Cys  Ile  Gln  Phe
               20                       25                         30

Ile  Tyr  Gly  Gly  Cys  Lys  Gly  Asn  Asn  Asn  Lys  Phe  Tyr  Ser  Glu  Pro
               35                          40                     45

Lys  Cys  Lys  Trp  Tyr  Cys  Gly  Val  Pro  Gly  Asp  Gly  Tyr
     50                         55                    60
```

( 2 ) INFORMATION FOR SEQ ID NO:149:

( i ) SEQUENCE CHARACTERISTICS:
        ( A ) LENGTH:65 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:149:

```
Arg  Thr  Val  Ser  Ala  Cys  Ser  Leu  Pro  Ile  Val  Gln  Gly  Pro  Cys  Arg
1                   5                        10                         15

Ala  Phe  Ile  Arg  Leu  Trp  Ala  Phe  Asp  Ala  Ala  Gln  Gly  Lys  Cys  Val
               20                       25                         30

Leu  Phe  Asn  Tyr  Gly  Gly  Cys  Gln  Gly  Asn  Gly  Asn  Lys  Phe  Tyr  Ser
               35                       40                         45

Gln  Lys  Glu  Cys  Lys  Glu  Tyr  Cys  Gly  Val  Pro  Gly  Glu  Glu  Asp  Glu
     50                         55                         60

Glu
65
```

( 2 ) INFORMATION FOR SEQ ID NO:150:

( i ) SEQUENCE CHARACTERISTICS:
        ( A ) LENGTH:61 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:150:

```
Thr  Glu  Arg  Gly  Phe  Leu  Asp  Cys  Thr  Ser  Pro  Pro  Val  Thr  Gly  Pro
1                   5                        10                         15

Cys  Arg  Ala  Gly  Phe  Lys  Arg  Tyr  Asn  Tyr  Asn  Thr  Arg  Thr  Lys  Gln
               20                       25                         30
```

```
Cys Glu Pro Phe Lys Tyr Gly Gly Cys Lys Gly Asn Gly Asn Arg Tyr
         35              40              45

Lys Ser Glu Gln Asp Cys Leu Asp Ala Cys Ser Gly Phe
 50              55                      60
```

( 2 ) INFORMATION FOR SEQ ID NO:151:

( i ) SEQUENCE CHARACTERISTICS:
        ( A ) LENGTH:56 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:151:

```
Gly Ser Ile Cys Leu Glu Pro Lys Val Val Gly Pro Cys Thr Ala Tyr
 1               5                   10                  15

Phe Pro Arg Phe Tyr Phe Asp Ser Glu Thr Gly Lys Cys Thr Pro Phe
             20              25                  30

Ile Tyr Gly Gly Cys Glu Gly Asn Ser Tyr Val Asp Glu Lys Leu His
         35              40                  45

Ala Cys Arg Ala Ile Cys Arg Ala
 50              55
```

( 2 ) INFORMATION FOR SEQ ID NO:152:

( i ) SEQUENCE CHARACTERISTICS:
        ( A ) LENGTH:65 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:152:

```
Arg Thr Val Glu Ala Cys Asn Leu Pro Ile Val Gln Gly Pro Cys Arg
 1               5                   10                  15

Ala Phe Ile Gln Leu Trp Ala Phe Asp Ala Val Lys Gly Lys Cys Val
             20              25                  30

Arg Phe Ser Tyr Gly Gly Cys Lys Gly Asn Gly Asn Lys Phe Tyr Ser
         35              40                  45

Gln Lys Glu Cys Lys Glu Tyr Cys Gly Ile Pro Gly Glu Ala Asp Glu
 50              55                  60

Arg
 65
```

( 2 ) INFORMATION FOR SEQ ID NO:153:

( i ) SEQUENCE CHARACTERISTICS:
        ( A ) LENGTH:60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:153:

```
Lys Ala Asp Ser Cys Gln Leu Asp Tyr Ser Gln Gly Pro Cys Leu Gly
 1               5                   10                  15

Leu Phe Lys Arg Tyr Phe Tyr Asn Gly Thr Ser Met Ala Cys Glu Thr
             20              25                  30
```

```
Phe  Leu  Tyr  Gly  Gly  Cys  Met  Gly  Asn  Leu  Asn  Asn  Phe  Leu  Ser  Gln
              35                      40                          45

Lys  Glu  Cys  Leu  Gln  Thr  Cys  Arg  Thr  Val  Glu  Ala
         50                      55                      60
```

( 2 ) INFORMATION FOR SEQ ID NO:154:

( i ) SEQUENCE CHARACTERISTICS:
        ( A ) LENGTH:62 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:154:

```
Asp  Lys  Pro  Thr  Thr  Lys  Pro  Ile  Cys  Glu  Gln  Ala  Phe  Gly  Asn  Ser
 1                    5                      10                         15

Gly  Pro  Cys  Phe  Ala  Tyr  Ile  Lys  Leu  Tyr  Ser  Tyr  Asn  Gln  Lys  Thr
              20                      25                      30

Lys  Lys  Cys  Glu  Glu  Phe  Ile  Tyr  Gly  Gly  Cys  Lys  Gly  Asn  Asp  Asn
              35                      40                      45

Arg  Phe  Asp  Thr  Leu  Ala  Glu  Cys  Glu  Gln  Lys  Cys  Ile  Lys
         50                      55                      60
```

( 2 ) INFORMATION FOR SEQ ID NO:155:

( i ) SEQUENCE CHARACTERISTICS:
        ( A ) LENGTH:62 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:155:

```
Asp  Lys  Pro  Thr  Thr  Lys  Pro  Ile  Cys  Glu  Gln  Ala  Phe  Gly  Asn  Ser
 1                    5                      10                         15

Gly  Pro  Cys  Phe  Ala  Tyr  Ile  Lys  Leu  Tyr  Ser  Tyr  Asn  Gln  Lys  Thr
              20                      25                      30

Lys  Lys  Cys  Glu  Glu  Phe  Ile  Tyr  Gly  Gly  Cys  Gln  Gly  Asn  Asp  Asn
              35                      40                      45

Arg  Phe  Ile  Thr  Leu  Ala  Glu  Cys  Glu  Gln  Lys  Cys  Ile  Lys
         50                      55                      60
```

( 2 ) INFORMATION FOR SEQ ID NO:156:

( i ) SEQUENCE CHARACTERISTICS:
        ( A ) LENGTH:57 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:156:

```
Arg  Pro  Arg  Phe  Cys  Glu  Leu  Ala  Pro  Ser  Ala  Gly  Ser  Cys  Phe  Gly
 1                    5                      10                         15

Phe  Val  Ser  Ser  Tyr  Tyr  Tyr  Asn  Arg  Tyr  Ser  Asn  Thr  Cys  His  Ser
              20                      25                      30

Phe  Thr  Tyr  Ser  Gly  Cys  Gly  Lys  Asn  Ala  Asn  Arg  Phe  Arg  Thr  Ile
              35                      40                      45

Asp  Glu  Cys  Asn  Arg  Thr  Cys  Val  Val
         50                      55
```

( 2 ) INFORMATION FOR SEQ ID NO:157:

( i ) SEQUENCE CHARACTERISTICS:
        ( A ) LENGTH:69 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:157:

```
Glu Gly Pro Glu Asn Val Met Asp Ile Cys Leu Leu Gln Lys Glu Glu
 1               5                  10                  15
Gly Thr Cys Arg Asp Phe Val Leu Lys Trp His Tyr Asp Leu Lys Thr
                20                  25                  30
Lys Ser Cys Ala Arg Phe Trp Tyr Gly Gly Cys Gly Gly Asn Glu Asn
                35                  40                  45
Arg Phe Asn Thr Gln Lys Glu Cys Glu Lys Ala Cys Ser Pro Gly Asn
                50                  55                  60
Ile Ser Pro Gly Val
65
```

( 2 ) INFORMATION FOR SEQ ID NO:158:

( i ) SEQUENCE CHARACTERISTICS:
        ( A ) LENGTH:60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:158:

```
Arg Gln Arg His Arg Asp Cys Asp Lys Pro Pro Asp Lys Gly Asn Cys
 1               5                  10                  15
Gly Pro Val Arg Ala Phe Tyr Tyr Asp Thr Arg Leu Lys Thr Cys Lys
                20                  25                  30
Ala Phe Gln Tyr Arg Gly Cys Asp Gly Asp His Gly Asn Phe Lys Thr
                35                  40                  45
Glu Thr Leu Cys Arg Cys Glu Cys Leu Val Tyr Pro
                50                  55                  60
```

( 2 ) INFORMATION FOR SEQ ID NO:159:

( i ) SEQUENCE CHARACTERISTICS:
        ( A ) LENGTH:63 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:159:

```
Asp Glu Pro Thr Thr Asp Leu Pro Ile Cys Glu Gln Ala Phe Gly Asp
 1               5                  10                  15
Ala Gly Leu Cys Phe Gly Tyr Met Lys Leu Tyr Ser Tyr Asn Gln Glu
                20                  25                  30
Thr Lys Asn Cys Glu Glu Phe Ile Tyr Gly Gly Cys Gln Gly Asn Asp
                35                  40                  45
Asn Arg Phe Ser Thr Leu Ala Glu Cys Glu Gln Lys Cys Ile Asn
                50                  55                  60
```

( 2 ) INFORMATION FOR SEQ ID NO:160:

( i ) SEQUENCE CHARACTERISTICS:
        ( A ) LENGTH:60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:160:

```
Arg Lys Arg His Pro Asp Cys Asp Lys Pro Pro Asp Thr Lys Ile Cys
 1               5                  10                  15
Gln Thr Val Arg Ala Phe Tyr Tyr Lys Pro Ser Ala Lys Arg Cys Val
             20                  25                  30
Gln Phe Arg Tyr Gly Gly Cys Asp Gly Asp His Gly Asn Phe Lys Ser
             35                  40                  45
Asp His Leu Cys Arg Cys Glu Cys Glu Leu Tyr Arg
             50                  55                  60
```

( 2 ) INFORMATION FOR SEQ ID NO:161:

( i ) SEQUENCE CHARACTERISTICS:
        ( A ) LENGTH:59 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:161:

```
Arg Gln Arg His Arg Asp Cys Asp Lys Pro Asp Lys Gly Asn Cys
 1               5                  10                  15
Gly Pro Val Arg Ala Phe Tyr Tyr Asp Thr Arg Leu Lys Thr Cys Lys
             20                  25                  30
Ala Phe Gln Tyr Arg Gly Cys Asp Gly Asp His Gly Asn Phe Lys Ser
             35                  40                  45
Asp His Leu Cys Arg Cys Glu Cys Glu Leu Tyr
             50                  55
```

( 2 ) INFORMATION FOR SEQ ID NO:162:

( i ) SEQUENCE CHARACTERISTICS:
        ( A ) LENGTH:62 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:162:

```
Lys Asn Pro Glu Cys Gly Glu Pro His Ser Leu Asp Gly Ser Pro Asn
 1               5                  10                  15
Gly Ile Ser Cys Arg Gly Tyr Phe Pro Ser Trp Ser Tyr Asn Pro Asp
             20                  25                  30
Ala Gln Gln Cys Val Ser Phe Val Tyr Gly Gly Cys Gly Gly Asn Asn
             35                  40                  45
Asn Arg Phe Gly Ser Gln Asn Glu Cys Glu Glu Arg Cys Ile
             50                  55                  60
```

( 2 ) INFORMATION FOR SEQ ID NO:163:

( i ) SEQUENCE CHARACTERISTICS:
        ( A ) LENGTH:4 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO:163:

Arg Pro Asp Phe
 1

(2) INFORMATION FOR SEQ ID NO:164:

(i) SEQUENCE CHARACTERISTICS:
(A) LENGTH:8 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:164:

Glu Ala Glu Ala Arg Pro Asp Phe
 1               5

(2) INFORMATION FOR SEQ ID NO:165:

(i) SEQUENCE CHARACTERISTICS:
(A) LENGTH:4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:165:

Lys Glu Asp Ser
 1

(2) INFORMATION FOR SEQ ID NO:166:

(i) SEQUENCE CHARACTERISTICS:
(A) LENGTH:4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:166:

Lys Glu Asp Phe
 1

(2) INFORMATION FOR SEQ ID NO:167:

(i) SEQUENCE CHARACTERISTICS:
(A) LENGTH:4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:167:

Lys Pro Asp Ser
 1

(2) INFORMATION FOR SEQ ID NO:168:

(i) SEQUENCE CHARACTERISTICS:
(A) LENGTH:4 amino acids
(B) TYPE: amino acid (C) STRANDEDNESS: single
(D) TOPOLOGY: linear (ii) MOLECULE TYPE: protein (xi) SEQUENCE DESCRIPTION: SEQ ID NO:168:

Thr Val Ala Ala
 1

(2) INFORMATION FOR SEQ ID NO:169:

(i) SEQUENCE CHARACTERISTICS:
(A) LENGTH: 2 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:169:

Ala Ala
 1

(2) INFORMATION FOR SEQ ID NO:170:

(i) SEQUENCE CHARACTERISTICS:
(A) LENGTH: 2 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:170:

Glu Ala
 1

(2) INFORMATION FOR SEQ ID NO:171:

(i) SEQUENCE CHARACTERISTICS:
(A) LENGTH: 2 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:171:

Asp Phe
 1

(2) INFORMATION FOR SEQ ID NO:172:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:172:

Tyr Thr Gly Pro
 1

(2) INFORMATION FOR SEQ ID NO:173:

(i) SEQUENCE CHARACTERISTICS:
(A) LENGTH: 4 amino acids
(B) TYPE: amino acid ( C ) STRANDEDNESS: single
            ( D ) TOPOLOGY: linear ( i i ) MOLECULE TYPE: protein ( x i ) SEQUENCE DESCRIPTION: SEQ ID NO:173:

Ser Ala Gly Pro
 1

( 2 ) INFORMATION FOR SEQ ID NO:174:

( i ) SEQUENCE CHARACTERISTICS:
            ( A ) LENGTH:4 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:174:

Ser Thr Gly Pro
 1

( 2 ) INFORMATION FOR SEQ ID NO:175:

( i ) SEQUENCE CHARACTERISTICS:
            ( A ) LENGTH:4 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:175:

Val Arg Gly Pro
 1

( 2 ) INFORMATION FOR SEQ ID NO:176:

( i ) SEQUENCE CHARACTERISTICS:
            ( A ) LENGTH:7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:176:

Val Ala Met Phe Pro Arg Tyr
 1               5

( 2 ) INFORMATION FOR SEQ ID NO:177:

( i ) SEQUENCE CHARACTERISTICS:
            ( A ) LENGTH:7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:177:

Val Gly Phe Phe Ser Arg Tyr
 1               5

( 2 ) INFORMATION FOR SEQ ID NO:178:

( i ) SEQUENCE CHARACTERISTICS:
            ( A ) LENGTH:7 amino acids
            ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:178:

Val Gly Phe Phe Gln Arg Tyr
1               5

( 2 ) INFORMATION FOR SEQ ID NO:179:

( i ) SEQUENCE CHARACTERISTICS:
( A ) LENGTH:7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:179:

Val Ala Ile Phe Pro Arg Tyr
1               5

( 2 ) INFORMATION FOR SEQ ID NO:180:

( i ) SEQUENCE CHARACTERISTICS:
( A ) LENGTH:7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:180:

Val Ala Phe Phe Lys Arg Ser
1               5

( 2 ) INFORMATION FOR SEQ ID NO:181:

( i ) SEQUENCE CHARACTERISTICS:
( A ) LENGTH:7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:181:

Ile Ala Phe Phe Pro Arg Tyr
1               5

( 2 ) INFORMATION FOR SEQ ID NO:182:

( i ) SEQUENCE CHARACTERISTICS:
( A ) LENGTH:7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:182:

Ile Ala Phe Phe Gln Arg Tyr
1               5

( 2 ) INFORMATION FOR SEQ ID NO:183:

( i ) SEQUENCE CHARACTERISTICS:
( A ) LENGTH:7 amino acids
( B ) TYPE: amino acid ( C ) STRANDEDNESS: single
            ( D ) TOPOLOGY: linear ( i i ) MOLECULE TYPE: protein ( x i ) SEQUENCE DESCRIPTION: SEQ ID NO:183:

Ile Ala Leu Phe Lys Arg Tyr
 1               5

( 2 ) INFORMATION FOR SEQ ID NO:184:

( i ) SEQUENCE CHARACTERISTICS:
            ( A ) LENGTH:7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:184:

Ile Gly Met Phe Ser Arg Tyr
 1               5

( 2 ) INFORMATION FOR SEQ ID NO:185:

( i ) SEQUENCE CHARACTERISTICS:
            ( A ) LENGTH:7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:185:

Ile Ala Phe Phe Pro Arg Trp
 1               5

( 2 ) INFORMATION FOR SEQ ID NO:186:

( i ) SEQUENCE CHARACTERISTICS:
            ( A ) LENGTH:7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:186:

Val Ala Phe Phe Pro Arg Trp
 1               5

( 2 ) INFORMATION FOR SEQ ID NO:187:

( i ) SEQUENCE CHARACTERISTICS:
            ( A ) LENGTH:7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:187:

Val Ala Ile Phe Pro Arg Trp
 1               5

( 2 ) INFORMATION FOR SEQ ID NO:188:

( i ) SEQUENCE CHARACTERISTICS:
            ( A ) LENGTH:7 amino acids
            ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:188:

Val Ala Phe Phe Pro Arg Trp
1               5

( 2 ) INFORMATION FOR SEQ ID NO:189:

( i ) SEQUENCE CHARACTERISTICS:
( A ) LENGTH:7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:189:

Val Gly Phe Phe Ser Arg Trp
1               5

( 2 ) INFORMATION FOR SEQ ID NO:190:

( i ) SEQUENCE CHARACTERISTICS:
( A ) LENGTH:7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:190:

Val Ala Met Phe Pro Arg Trp
1               5

( 2 ) INFORMATION FOR SEQ ID NO:191:

( i ) SEQUENCE CHARACTERISTICS:
( A ) LENGTH:7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:191:

Val Ala Phe Phe Pro Arg Phe
1               5

( 2 ) INFORMATION FOR SEQ ID NO:192:

( i ) SEQUENCE CHARACTERISTICS:
( A ) LENGTH:7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:192:

Val Gly Phe Phe Ser Arg Phe
1               5

( 2 ) INFORMATION FOR SEQ ID NO:193:

( i ) SEQUENCE CHARACTERISTICS:
( A ) LENGTH:7 amino acids
( B ) TYPE: amino acid (C) STRANDEDNESS: single
        (D) TOPOLOGY: linear (ii) MOLECULE TYPE: protein (xi) SEQUENCE DESCRIPTION: SEQ ID NO:193:

Val Ala Met Phe Pro Arg Phe
 1               5

(2) INFORMATION FOR SEQ ID NO:194:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:194:

Gln Thr Phe Val Tyr
 1               5

(2) INFORMATION FOR SEQ ID NO:195:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:195:

Val Leu Phe Pro Tyr
 1               5

(2) INFORMATION FOR SEQ ID NO:196:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:196:

Glu Thr Phe Gln Tyr
 1               5

(2) INFORMATION FOR SEQ ID NO:197:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:197:

Gln Thr Phe Val Tyr
 1               5

(2) INFORMATION FOR SEQ ID NO:198:

(i) SEQUENCE CHARACTERISTICS:
        (A) LENGTH: 5 amino acids
        (B) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:198:

Glu Thr Phe Val Tyr
1               5

( 2 ) INFORMATION FOR SEQ ID NO:199:

( i ) SEQUENCE CHARACTERISTICS:
( A ) LENGTH:5 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:199:

Val Leu Phe Pro Tyr
1               5

( 2 ) INFORMATION FOR SEQ ID NO:200:

( i ) SEQUENCE CHARACTERISTICS:
( A ) LENGTH:5 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:200:

Gln Thr Phe Leu Tyr
1               5

( 2 ) INFORMATION FOR SEQ ID NO:201:

( i ) SEQUENCE CHARACTERISTICS:
( A ) LENGTH:5 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:201:

Gln Thr Phe Glu Tyr
1               5

( 2 ) INFORMATION FOR SEQ ID NO:202:

( i ) SEQUENCE CHARACTERISTICS:
( A ) LENGTH:5 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:202:

Gln Thr Phe Gly Tyr
1               5

( 2 ) INFORMATION FOR SEQ ID NO:203:

( i ) SEQUENCE CHARACTERISTICS:
( A ) LENGTH:5 amino acids
( B ) TYPE: amino acid

```
            ( C ) STRANDEDNESS: single
            ( D ) TOPOLOGY: linear ( i i ) MOLECULE TYPE: protein ( x i ) SEQUENCE DESCRIPTION: SEQ ID NO:203:

Gln  Thr  Phe  Arg  Tyr
 1                    5

( 2 ) INFORMATION FOR SEQ ID NO:204:

( i ) SEQUENCE CHARACTERISTICS:
            ( A ) LENGTH:5 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:204:

Gln  Thr  Phe  Asp  Tyr
 1                    5

( 2 ) INFORMATION FOR SEQ ID NO:205:

( i ) SEQUENCE CHARACTERISTICS:
            ( A ) LENGTH:5 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:205:

Gln  Thr  Phe  Lys  Tyr
 1                    5

( 2 ) INFORMATION FOR SEQ ID NO:206:

( i ) SEQUENCE CHARACTERISTICS:
            ( A ) LENGTH:5 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:206:

Gln  Thr  Phe  Thr  Tyr
 1                    5

( 2 ) INFORMATION FOR SEQ ID NO:207:

( i ) SEQUENCE CHARACTERISTICS:
            ( A ) LENGTH:5 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:207:

Gln  Thr  Phe  Asn  Tyr
 1                    5

( 2 ) INFORMATION FOR SEQ ID NO:208:

( i ) SEQUENCE CHARACTERISTICS:
            ( A ) LENGTH:5 amino acids
            ( B ) TYPE: amino acid
```

( C ) STRANDEDNESS: single
( D ) TOPOLOGY: linear ( i i ) MOLECULE TYPE: protein ( x i ) SEQUENCE DESCRIPTION: SEQ ID NO:208:

Gln Thr Phe Gln Tyr
1               5

( 2 ) INFORMATION FOR SEQ ID NO:209:

( i ) SEQUENCE CHARACTERISTICS:
( A ) LENGTH:5 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:209:

Gln Thr Phe His Tyr
1               5

( 2 ) INFORMATION FOR SEQ ID NO:210:

( i ) SEQUENCE CHARACTERISTICS:
( A ) LENGTH:5 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:210:

Gln Thr Phe Pro Tyr
1               5

( 2 ) INFORMATION FOR SEQ ID NO:211:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:211:

Met Gly Asn Gly
1

( 2 ) INFORMATION FOR SEQ ID NO:212:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:212:

Gln Gly Asn Gly
1

( 2 ) INFORMATION FOR SEQ ID NO:213:

( i ) SEQUENCE CHARACTERISTICS:
( A ) LENGTH:4 amino acids
( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:213:

Lys Gly Lys Gly
1

( 2 ) INFORMATION FOR SEQ ID NO:214:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:214:

Trp Ala Lys Gly
1

( 2 ) INFORMATION FOR SEQ ID NO:215:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:215:

Arg Ala Lys Gly
1

( 2 ) INFORMATION FOR SEQ ID NO:216:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:216:

His Ala Glu Gly
1

( 2 ) INFORMATION FOR SEQ ID NO:217:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:217:

Trp Ala Gln Gly
1

( 2 ) INFORMATION FOR SEQ ID NO:218:

( i ) SEQUENCE CHARACTERISTICS:
( A ) LENGTH:4 amino acids
( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:218:

Leu Ala Glu Gly
1

( 2 ) INFORMATION FOR SEQ ID NO:219:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:219:

His Ala Asp Gly
1

( 2 ) INFORMATION FOR SEQ ID NO:220:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:220:

Leu Ala His Gly
1

( 2 ) INFORMATION FOR SEQ ID NO:221:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:221:

Trp Ala Asn Gly
1

( 2 ) INFORMATION FOR SEQ ID NO:222:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:222:

Glu Gly Lys Gly
1

( 2 ) INFORMATION FOR SEQ ID NO:223:

( i ) SEQUENCE CHARACTERISTICS:
( A ) LENGTH:4 amino acids
( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:223:

Glu Gly Tyr Gly
1

( 2 ) INFORMATION FOR SEQ ID NO:224:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:224:

Leu Gly Glu Gly
1

( 2 ) INFORMATION FOR SEQ ID NO:225:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:225:

Trp Gly Gln Gly
1

( 2 ) INFORMATION FOR SEQ ID NO:226:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:226:

Trp Gly Glu Gly
1

( 2 ) INFORMATION FOR SEQ ID NO:227:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:227:

Trp Gly Lys Gly
1

( 2 ) INFORMATION FOR SEQ ID NO:228:

( i ) SEQUENCE CHARACTERISTICS:
( A ) LENGTH:4 amino acids
( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:228:

His Gly Asn Gly
 1

( 2 ) INFORMATION FOR SEQ ID NO:229:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:229:

Trp Gly His Gly
 1

( 2 ) INFORMATION FOR SEQ ID NO:230:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:230:

Leu Gly His Gly
 1

( 2 ) INFORMATION FOR SEQ ID NO:231:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:231:

Leu Gly Tyr Gly
 1

( 2 ) INFORMATION FOR SEQ ID NO:232:

( i ) SEQUENCE CHARACTERISTICS:
( A ) LENGTH:4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:232:

Trp Ala Glu Gly
 1

( 2 ) INFORMATION FOR SEQ ID NO:233:

( i ) SEQUENCE CHARACTERISTICS:
( A ) LENGTH:4 amino acids
( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:233:

```
His  Gly  Asp  Gly
 1
```

( 2 ) INFORMATION FOR SEQ ID NO:234:

( i ) SEQUENCE CHARACTERISTICS:
    ( A ) LENGTH:51 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:234:

```
Cys  Xaa  Xaa  Xaa  Xaa  Xaa  Xaa  Gly  Xaa  Cys  Xaa  Xaa  Xaa  Xaa  Xaa  Xaa
 1                    5                         10                            15

Xaa  Xaa  Tyr  Xaa  Xaa  Xaa  Xaa  Xaa  Xaa  Cys  Xaa  Xaa  Phe  Xaa  Tyr  Xaa
              20                         25                       30

Gly  Cys  Xaa  Xaa  Xaa  Xaa  Asn  Xaa  Phe  Xaa  Xaa  Xaa  Xaa  Xaa  Cys  Xaa
           35                       40                      45

Xaa  Xaa  Cys
 50
```